US007674888B2

(12) United States Patent
Perron et al.

(10) Patent No.: US 7,674,888 B2
(45) Date of Patent: *Mar. 9, 2010

(54) VIRAL MATERIAL AND NUCLEOTIDE FRAGMENTS ASSOCIATED WITH MULTIPLE SCLEROSIS, FOR DIAGNOSTIC, PROPHYLACTIC AND THERAPEUTIC PURPOSES

(75) Inventors: Herve Perron, Lyons (FR); Frederic Beseme, Villefontaine (FR); Frederic Bedin, Lyons (FR); Glaucia Paranhos-Baccala, Lyons (FR); Florence Komurian-Pradel, Saint Cyr au Mont d'Or (FR); Colette Jolivet-Reynaud, Bron (FR); Bernard Mandrand, Villeurbanne (FR); Jeremy Alexander Garson, Guildford (GB); Philip William Tuke, London (GB)

(73) Assignee: Biomerieux, Marcy l'Etoile (FR)

( * ) Notice: Subject to any disclaimer, the term of this patent is extended or adjusted under 35 U.S.C. 154(b) by 626 days.

This patent is subject to a terminal disclaimer.

(21) Appl. No.: 11/581,030

(22) Filed: Oct. 16, 2006

(65) Prior Publication Data

US 2007/0031452 A1 Feb. 8, 2007

Related U.S. Application Data

(60) Division of application No. 10/114,104, filed on Apr. 3, 2002, now abandoned, which is a division of application No. 08/979,847, filed on Nov. 26, 1997, now Pat. No. 6,582,703, which is a continuation-in-part of application No. 08/756,429, filed on Nov. 26, 1996, now abandoned.

(51) Int. Cl.
*C07H 21/02* (2006.01)

(52) U.S. Cl. ................... 536/23.1; 435/235.1; 530/300; 530/350

(58) Field of Classification Search ................. 536/23.1
See application file for complete search history.

(56) References Cited

U.S. PATENT DOCUMENTS

| | | | |
|---|---|---|---|
| 4,311,686 | A | 1/1982 | Angers et al. |
| 4,346,074 | A | 8/1982 | Gilmour et al. |
| 4,388,298 | A | 6/1983 | Nazerian et al. |
| 4,396,600 | A | 8/1983 | Messineo et al. |
| 4,520,113 | A | 5/1985 | Gallo et al. |
| 4,647,773 | A | 3/1987 | Gallo et al. |
| 4,708,818 | A | 11/1987 | Montagnier et al. |
| 4,900,553 | A | 2/1990 | Silver et al. |
| 5,158,976 | A | 10/1992 | Rosenberg |
| 5,219,837 | A | 6/1993 | Cohen et al. |
| 5,225,352 | A | 7/1993 | Zanetta et al. |
| 5,585,262 | A | 12/1996 | Perron et al. |
| 5,650,318 | A | 7/1997 | Perron et al. |
| 5,728,540 | A | 3/1998 | Perron et al. |
| 5,800,980 | A | 9/1998 | Perron et al. |
| 5,871,745 | A | 2/1999 | Perron et al. |
| 5,871,996 | A | 2/1999 | Perron et al. |
| 5,876,954 | A | 3/1999 | Perron et al. |
| 5,925,555 | A | 7/1999 | Perron et al. |
| 5,962,217 | A | 10/1999 | Perron et al. |
| 6,001,987 | A | 12/1999 | Perron et al. |
| 6,071,736 | A | 6/2000 | Perron et al. |
| 6,184,025 | B1 | 2/2001 | Perron et al. |
| 6,291,225 | B1 | 9/2001 | Perron et al. |
| 6,342,383 | B1 | 1/2002 | Perron et al. |

FOREIGN PATENT DOCUMENTS

| | | |
|---|---|---|
| EP | 0 222 310 | 5/1987 |
| EP | 0 326 395 | 8/1989 |
| WO | 93/07259 | 4/1993 |
| WO | 93/20188 | 10/1993 |
| WO | WO 93/23550 | 11/1993 |
| WO | WO 94/28138 | 12/1994 |
| WO | WO 95/21256 | 8/1995 |

OTHER PUBLICATIONS

La Mantia et al., Nucleic Acids Research 1991, 19, 1513-1520.*

P. Challoner et al., "Plaque-Associated Expression of Human Herpesvirus 6 in Multiple Sclerosis", *Proc. Natl., Acad. Sci. USA*, vol. 92, pp. 7440-7444, Aug. 1995.

S. Haahr et al., "Increased Risk of Multiple Sclerosis After Late Epstein-Barr Virus Infection", *Acta Neurol Scand*, Suppl. 169 pp. 70-75, 1997.

K. Takeuchi, "Expression of Human Endogenous Retroviruses in Rheumatoid Arthritis" (Abstract only), *Hokkaido Igaku Zasshi:*, vol. 69: No. 4, pp. 821-835, 1994.

P. Gaudin et al., "Infrequency of Detection of Particle-Associated MSRV/HERV~W RNA in the Synovial Fluid of Patients with Rheumatoid Arthritis", *Rheumatology*, vol. 39, pp. 950-954, 2000.

(Continued)

*Primary Examiner*—Mary E Mosher
*Assistant Examiner*—Myron G Hill
(74) *Attorney, Agent, or Firm*—Oliff & Berridge, PLC

(57) ABSTRACT

The invention provides viral material and nucleotide fragments associated with multiple sclerosis and/or rheumatoid arthritis for use in method of diagnosis, prophylaxis, and therapy.

5 Claims, 70 Drawing Sheets

OTHER PUBLICATIONS

Acha-Orbea et al., "M1s—A Retrovirus Exploits the Immune System", *Immunology Today*, vol. 12, No. 10, 1991, pp. 356-361.
Asai et al., "J. of Neurochem", vol. 59, No. 1, pp. 307-317, 1992.
*ATCC Catalogue of Cell Lines and Hybridomas*, Sixth Edition, 1988, pp. 165 and 344-355.
C.R.M. Bangham et al., "PCR Analysis of DNA from Multiple Sclerosis Patients for the Presence of HTLV-I", *Science*, vol. 246, Nov. 10, 1989, pp. 821-824.
R. Baccala et al., "Genomically Imposed and Somatically Modified Human Thymocyte vb Gene Repertoires", *Proc. Natl. Acad. Sci.*, vol. 88, pp. 2908, 1991.
J. Bai et al., "Unique Long Terminal repeat U3 Sequences Distinguish Exogenous Jaagsiekte Sheep Retroviruses Associated with Ovine Pulmonary Carcinoma from Endogenous Loci in the Sheep Genome", *J. Virol.*, vol. 70, pp. 3159-3168, (1996).
Barna et al., "Human Astrocytes Proliferate in Response to Tumor Necrosis Factor Alpha", *J. Neuroimmunol.*, 30 (1990), pp. 239-243.
Beck et al., "Increased Production of Interferon Gamma and Tumor Necrosis Factor Precedes Clinical Manifestation in Multiple Sclerosis: Do Cytokines Trigger Off Exacerbations?", *Acta Neurol. Scand.*, 1988: 78, pp. 318-323.
J. I. Bell et al., "Multiple Loci for Multiple Sclerosis", *Nature Genetics*, vol. 13, pp. 377-378, (1996).
Bergamini et al., "Multiple Sclerosis. I. The Immune Pathogenetic Hypothesis", *Riv. Neurol.*, vol. 59, No. 5, Oct. 1989, pp. 176-190.
T. Bergström et al., "Isolation of Herpes Virus Type 1 During First Attack of Multiple Sclerosis.", *Annales Neurology*, vol. 26, pp. 283-285, (1989).
Bernton et al., "No Direct Neuronotoxicity by HIV-1 Virions or Culture Fluids from HIV-1 Infected T Cells or Monocytes", *Aids Research and Human Retroviruses*, vol. 8, No. 4, 1992, pp. 495-503.
Birnbaum et al., "Spinal Fluid Lymphocytes from a SubGroup of Multiple Sclerosis Patients Respond to Mycobacterial Antigens", *Ann. Neurol.*, vol. 34, No. 1, Jul. 1993, pp. 18-24.
Bjare, "Serum-Free Cell Culture", *Pharmac. Ther.*, vol. 53, 1992, pp. 355-374.
C. Bosgiraud et al., "Ultrastructural Study on Visna Virus in Sheep Plexus Choroid Cells", *Biological Abstracts*, vol. 83, No. 7, 1987.
D. Ross Boswell et al., "Sequence comparison and alignment: the measurement and interpretation of sequence similarity", *Computational Molecular Biology, Sources and Methods for Sequence Analysis*, pp. 161-178.
Boyle et al., "Cellular Immune Response in Multiple Sclerosis Plaques", *American Journal of Pathology*, vol. 137, No. 3, Sep. 1990, pp. 575-584.
Bradford, A Rapid and Sensitive Method for the Quantitation of Microgram Quantities of Protein Utilizing the Principle of Protein-Dye Binding, *Anal. Biochem.*, 72, 1976, pp. 248-254.
Brocke et al., "Induction of Relapsing Paralysis in Experimental Autoimmune Encephalomyelitis by Bacterial Superantigen", *Nature*, vol. 365, Oct. 14, 1993, pp. 642-644.
Calder, et al., "MS: A Localized Immune Disease of the Central Nervous System", *Immunology Today*, vol. 10, No. 3, 1989, pp. 99-103.
Carp et al., "Viral Etiology of Multiple Sclerosis", *Prog. Med. Virol.*, vol. 24, pp. 158-177, 1978.
Charcot, "Histologie de la sclerose en plaques [Histology of Multiple Sclerosis]", Gaz. Hop. (Paris), 1868; 41, 554-66.
Chomczynski et al., "Single-Step Method of RNA Isolation by Acid Guanidinium Thiocyanate-Phenol-Chloroform Extraction", *Anal. Biochem.*, 1987, vol. 162, pp. 156-159.
Cole et al., "The Mycoplasma Arthritidis T-Cell Mitogen, MAM: A Model Superantigen", *Immunology Today*, vol. 12, No. 8, 1991, pp. 271-276.
Cook et al., "Multiple Sclerosis and Distemper in Iceland 1966-1978", *Acta Neurol. Scandinav.* 61, 1980, pp. 244-251.
Dalgleish et al., "Do Human T-Lymphotrophic Viruses (HTLVs) and Other Enveloped Viruses Induce Autoimmunity in Multiple Sclerosis?", *Neuropath. App. Neurobiol.*, 1987, 13, pp. 241-250.
A. N. Davison et al., "Biosynthesis of Myelin and Neurotoxic Factors in the Serum of Multiple Sclerosis Patients", *Advances in Experimental Medicine and Biology*, vol. 100, pp. 19-25, 1978.
De Keyser, "Autoimmunity in Multiple Sclerosis", *Neurology*, 38, Mar. 1988, pp. 371-374.
S. Dhib-Jalbut et al., "Measles Virus Polypeptide-Specific Antibody Profile in Multiple Sclerosis", *Neurology*, vol. 40, pp. 430-435, (1990).
Dunn et al., "A Novel Method to Map Transcripts: Evidence for Homology Between an Adenovirus mRNA and Discrete Multiple Regions of the Viral Genome", *Cell*, vol. 12, Sep. 1977, pp. 23-36.
Ebers et al., "The Geography of MS Reflects Genetic Susceptibility", *Neurology*, 36, Apr. 1986, Suppl. 1, p. 108.
Elian et al., "Multiple Sclerosis Among United Kingdom-Born Children of Immigrants from the Indian Subcontinent, Africa and the West Indies", *J Neurol Neurosurg Psychiat*, 1990; 53, pp. 906-911.
Escourolle et al., "Principales Donnees Morphologiques Approches Physiopathologiques et Etiologiques de la Sclerose en Plaques [Principal Morphological Data, Physiopathological and Etiological Approaches to Multiple Sclerosis]", *La Reveue du Praticien*, Paris, 1980; 30, pp. 2047-2053.
E. J. Field, "Immunological Treatment for Multiple Sclerosis", *The Lancet*, Jun. 3, 1989, p. 1272.
Frohman et al., "Rapid Production of Full-Length cDNAs from Rare Transcripts: Amplification Using a Single Gene-Specific Oligonucleotide Primer", *Proc. Natl. Acad. Sci. USA*, 1988, vol. 85, pp. 8998-9002.
Medline Abstract of Fu et al., "Rabies virus nucleoprotein expressed in and purified from insect cells is efficacious as a vaccine," Proc Natl Acad Sci USA 88: 2001-05 (1991).
Galiana et al., "Establishment of Permanent Astroglial Cell Lines, Able to Differentiate in Vitro, From Transgenic Mice Carrying the Polyoma Virus Large T Gene: An Alternative Approach to Brain Cell Immortalization", *Journal of Neuroscience Research*, 1990; 26: pp. 269-277.
M. B. Gardner et al., "Congenital Transmission of Murine Leukaemia Virus from Wild Mice Prone to Development of Lymphoma and Paralysis", *J. Natl. Cancer Inst.*, vol. 62, pp. 63-69, (1979).
M. B. Gardner, "Genetic resistance to a Retroviral Neurologic Disease in Wild Mice, in Retrovirus Infections of the Nervous System", *Oldstone M.B.A. and Koprowsky H. Eds. Current Topice in Microbiology and Immunology*, No. 160, pp. 3-10, (Springer-Verlag, Berlin, 1990).
Gay, "Is Multiple Sclerosis Caused by an Oral Spirochaete", *The Lancet*, Jul. 12, 1986, pp. 75-77.
A. Gessain et al., "Intrathecal Synthesis of Antibodies to Human T Lymphotropic Virus Type I and the Presence of IgG Oligoclonal Bands in the Cerebrospinal Fluid of Patients with Endemic Tropical Spastic Paraparesis", *The Journal of Infectious Diseases*, vol. 157, No. 6, Jun. 1988, pp. 1226-1234.
A. Gessain et al., Antibodies to Human T-Lymphotrophic Virus type-I in Patients with Tropical Spastic Paraparesis, *Lancet*, vol. 2, pp. 407-410, (1985).
Giulian et al., "The Envelope Glycoprotein of Human Immunodeficiency Virus Type 1 Stimulates Release of Neurotoxins from Monocytes", *Proc. Natl. Acad. Sci. USA*, vol. 90, 1993, pp. 2769-2773.
D. Giulian et al., "Secretion of Neurotoxins by Mononuclear Phagocytes Infected with HIV-1", *Science*, vol. 250, Dec. 14, 1990, pp. 1593-1596.
Gonzalez-Scarano et al., "Multiple Sclerosis Disease Activity Correlates with Gadolinium-Enhanced Magnetic Resonance Imaging", *Annals of Neurology*, vol. 21, No. 3, Mar. 1987, pp. 300-306.
F. Gonzalez-Scarano et al., "Sequence Similarities Between Human Immunodeficiency Virus gp41 and Paramyxovirus Fusion Proteins.", *AIDS Res. Hum. Retrov.*, vol. 3, pp. 245-252, (1987).
R. Gonzales-Quintial et al., *J. Clin. Invest.*, vol. 97, No. 5, pp. 1335-1343, 1996.
S.J. Greenberg et al., "Detection of sequences homologous to human retroviral DNA in multiple sclerosis by gene amplification", *Proc. Natl. Acad. Sci. USA*, vol. 86, Apr. 1989, pp. 2878-2882.

S. Haahr et al., "A Putative New Retrovirus Associated with Multiple Sclerosis and the Possible Involvement of Epstein-Barr Virus in this Disease", *NY Acad. Science*, vol. 724, pp. 148-156, 1994.
S. Haahr et al., "Is Multiple Sclerosis Caused by a Dual Infection with Retrovirus and Epstein-Barr Virus?", *Neuroepidemiology*, vol. 11, pp. 299-303, (1992).
S. Haahr et al., "Just Another Dubious Virus in Cells from a Patient with Multiple Sclerosis?", *The Lancet*, vol. 337, Apr. 6, 1991, pp. 863-864.
A. T. Haase, "Pathogenesis of Lentivirus Infections", *Nature*, vol. 322, Jul. 10, 1986, pp. 130-136.
Haegert et al. HLA-DRβ, -DQα, and -DQβ Restriction Fragment Length Polymorphisms in Multiple Sclerosis, *J. Neurosci. Res.*, 1989; 23, pp. 46-54.
S.L. Hauser et al., "Analysis of Human T-lymphotropic virus sequences in multiple sclerosis tissue", *Nature*, vol. 322, Jul. 10, 1986, pp. 176-178.
Hauw et al., "Aspects Anatomo-Pathologiques de la Sclerose en Plaques [Anatomopathological Aspects of Multiple Sclerosis]", *La Sclerose en Plaques* [*Multiple Sclerosis*], 9-47 (Rascol et al. eds., 1980).
Hirayama et al., "Serum-Mediated Oligodendrocyte Cytotoxicity in Multiple Sclerosis Patients and Controls", *Neurology* 1986, vol. 36, pp. 276-278.
Hoffman et al., "Handbook of Clinical Neurology, 12; Viral Diseases", R.R. McKendall, ed., Elsevier Science Publishing, Amsterdam, 1989, pp. 453-466.
Huang, "Defective Interfering Viruses", *Fundamental Virology*, Fields et al., eds., 1986, pp. 101-117.
Huck et al., "J. of Neurosei", vol. 4, No. 10, pp. 2650-2657, 1984.
A. W. Hugin et al., "A Virus-Encoded Superantigen in a Retrovirus-Induced Immunodeficiency Syndrome of Mice", *Science*, vol. 252, pp. 424-427, (1991).
James, "Multiple Sclerosis or Blood-Brain Barrier Disease", *The Lancet*, Jan. 7, 1989, p. 46.
Medline abstract of Jarrett et al., "Studies on vaccination against papillomaviruses: a comparison of purified virus, tumour extract and transformed cells in prophylactic vaccination," Vet Rec 126: 449-52 (1990).
Jervis et al., "Experimental Allergic Encephalomyelitis", *J. Neuropathol. Exp. Neurol.*, 1948; 7, pp. 309-320.
D. Johnson et al., "Quantitation of the Myelin-Associated Glycoprotein in Human Nervous Tissue from Controls and Multiple Sclerosis Patients", *Journal of Neurochemistry*, vol. 46, No. 4, 1986, pp. 1086-1093.
Johnson, "Viral Aspects of Multiple Sclerosis", *Handbook of Clinical Neurology*, vol. 3(47): Demyelinating Diseases, 1985, pp. 319-336.
R.T. Johnson, "Nononcogenic Retrovirus Infections as Models for Chronic and Relapsing Human Diseases: Introduction", *Reviews of Infectious Diseases*, vol. 7, No. 1, Jan.-Feb. 1985, pp. 66-67.
Juntunen et al. "Multiple Sclerosis and Occupational Exposure to Chemicals: A Co-Twin Study of a Nationwide Series of Twins", *Br. J. Int. Med.*, 1989; 46: pp. 417-419.
Karpas et al., "Lack of evidence for involvement of known human retroviruses in multiple sclerosis", *Nature*, vol. 322, Jul. 10, 1986, pp. 177-178.
Kent et al., "Cerebral Blood Flow, Cerebral Metabolism and Blood-Brain Barrier," *Handbook of Clinical Neurology*, vol. 56(12), 1989, pp. 79-91.
H. Koprowski et al., "Multiple sclerosis and human T-cell lymphotropic retroviruses", *Nature*, vol. 318, Nov. 14, 1985, pp. 154-160.
G. La Mantia et al., "Identification of New Human Repetitive Sequences: Characterization of the Corresponding cDNAs and their Expression in Embryonal Carcinoma Cells", *Nucleic Acids Research*, vol. 17, No. 15, 5913-5922, (1989).
G. La Mantia et al., "Identification and Characterization of Novel Human Endogenous Retroviral Sequences Prefentially Expressed in Undifferentiated Embryonal Carcinoma Cells", *Nucleic Acids Res.*, 1991, vol. 19, No. 7, pp. 1513-1520.
H. Lassmann et al., "Chronic Relapsing Experimental Allergic Encephalomyelitis-Clinicopathological Comparison with Multiple Sclerosis", Arch Neurol, vol. 36, Aug. 1979, pp. 490-497.
Medline abstract of Leao, "Tuberculosis: new strategies for the development of diagnostic tests and vaccines," Braz J Med Biol Res 26: 827-33 (1993).
Levi et al., Human Immunodeficiency Coat Protein gp120 Inhibits the β-adrenergic Regulation of Astroglial and Microglial Functions, *Proc. Natl. Acad. Sci. USA*, vol. 90, Feb. 1993, pp. 1541-1545.
Levine et al., "Conversion of Lytic to Persistent Alphavirus Infection by the bcl-2 Cellular Oncogene", *Nature*, vol. 361, Feb. 25, 1993, pp. 739-742.
Y.S. Lie et al., Journal of Virology, vol. 38, No. 12, Dec. 1994, pp. 7840-7849, "Chinese hamster ovary cells contain transcriptionally active full length type C provirises".
Linial et al., "Retroviral RNA Packaging: Sequence Requirements and Implications", in *Current Topics in Microbiology and Immunobiology. Retroviruses, Strategies of Replication*, Swanstrom et al., eds., vol. 157, 1990, pp. 125-152.
R. Lisak et al., "In Vitro Cell-Mediated Immunity of Cerebrospinal-Fluid Lymphocytes to Myelin Basic Protein in Primary Demyelinating Diseases", *The New England Journal of Medicine*, vol. 297, No. 16, Oct. 20, 1977, pp. 850-853.
Lo et al, "Newly Discovered Mycoplasma Isolated from Patients Infected with HIV", *The Lancet*, vol. 338, Dec. 7, 1991, pp. 1415-1418.
Lori et al., "Viral DNA Carried by Human Immunodeficiency Virus Type 1 Virions", *J. Virol.*, vol. 66, No. 8, Aug. 1992, pp. 5067-5074.
F. Mallet et al., "Continuous RT-PCR and taq DNA Polymerase: Characterization and Comparison to Uncoupled Procedures", *Biotechniques*, vol. 18, pp. 678-687, 1985.
Mallet et al., "Enzyme-Linked Oligosorbent Assay for Detection of Polymerase Chain Reaction-Amplified Human Immunodeficiency Virus Type I", *J. Clin. Microbiol.*, Jun. 1993, vol. 31, No. 6, pp. 1444-1449.
Marie, "Sclerose en Plaques et Maladies Infectieuses [Multiple Sclerosis and Infectious Diseases]", *Le Progres Medical*, 1884; 12, pp. 287-289.
P. Marrack et al., "A Maternally Inherited Superantigen Encoded by a Mammary Tumor Virus", *Nature*, vol. 349, pp. 524-526, (1991).
McDonald, "The Mystery of the Origin of Multiple Sclerosis", *J. Neurol. Neurosurg. Psych.*, 1986; 49, pp. 113-123.
J. Merregaert et al., "Nucleotide Sequence of a Radiation Leukemia Virus Genome", *Virology*, vol. 158, No. 1, pp. 88-102, (1987).
Meyerhans et al., "Temporal Fluctuations in HIV Quasispecies in Vivo Are Not Reflected by Sequential HIV Isolations", *Cell*, vol. 58, Sep. 8, 1989, pp. 901-910.
J.D. Mosca et al., "Activation of human immunodeficiency virus by herpesvirus infection: Identification of a region within the long terminal repeat that responds to a trans-acting factor encoded by herpes simplex virus 1", *Proceedings of the National Academy of Sciences of USA*, vol. 84, No. 21, Nov. 1987, pp. 7408-7412.
Mosmann, "Rapid Colorimetric Assay for Cellular Growth and Survival: Application to Proliferation and Cytotoxicity Assays", *Journal of Immunological Methods*, 65, 1983, pp. 55-63.
O. Narayan et al., "Lentiviral Diseases of Sheep and Goats: Chronic Pneumonia Leukoencephalomyelitis, and Arthritis", *Reviews of Infectious Diseases*, vol. 7, No. 1, Jan.-Feb. 1985, pp. 89-98.
N. Nathanson et al., "Experimental Visna in Icelandic Sheep: The Prototype Lentiviral Infection", *Reviews of Infectious Diseases*, vol. 7, No. 1, Jan.-Feb. 1985, pp. 75-82.
Newell et al., "Ligation of Major Histocompatibility Complex Class II Molecules Mediates Apoptotic Cell Death in Resting B Lymphocytes", *Proc. Natl. Acad. Sci. USA*, vol. 90, Nov. 1993, pp. 10459-10463.
Nielsen et al., "Sequence-Selective Recognition of DNA by Strand Displacement with a Thymine-Substituted Polyamide", *Science*, vol. 254, pp. 1497-1500.
Norby, "Viral Antibodies in Multiple Sclerosis", *Prog. Med. Virol.*, vol. 24 1978, pp. 1-39 (1978).
M. Ohta et al., "Sera from Ptients with Multiple Sclerosis React with Human T Cell Lymphotropic Virus-I Gag Proteins but not Env Proteins—Western Blotting Analysis", The Journal of Immunology, vol. 137, No. 11, Dec. 1, 1986, pp. 3440-3443.
Medline abstract of Orlandi et al., "Characterization of the 175-kilodalton erythrocyte binding antigen of Plasmodium falciparum," Mol Biochem Parasitol 40: 285-94 (1990).
Ostrove et al., "Activation of the Human Innumodeficiency Virus by Herpes Simplex Virus Type 1", J Virol 61(12), Dec. 1987, pp. 3726-3732.
M. Palmarini, "The Exogenous Form of Jaagsiekte Retrovirus is Specifically Associated with a contagious Lung Cancer of Sheet", *J. Virol*, vol. 70, pp. 1618-1623, (1996).
J.L. Pablos et al., "A novel retroviral POL sequence is present in patients with rheumatoid arthritis", & American College of Rheumatology 57th Annual Scientific Meeting, Nov. 7-11, 1993 San Antonio, Texas, USA, *Arthritis and Rheumatism*, vol. 36, No. 9 supl. 1993, p. S55, Abstract No. 102.
Medline abstract of Pei et al., "Identification, purification, and characterization of major antigenic proteins of Campylobacter jejuni," J Biol Chem 266: 16363-69 (1991).
H. Perron et al., "Isolations of an Unknown Retrovirus from CSF, Blood and Brain Cells of Patients with Multiple Sclerosis", in *Current concepts in Multiple Sclerosis*, Wietholter et al., eds., 1991, Elsevier publ., pp. 111-116.
H. Perron et al., "Leptomeningeal cell line from multiple sclerosis with reverse transcriptase activity and viral particles", *Res. Virol.*, Nov. 1989, vol. 140(6), pp. 551-561.
H. Perron et al., "Leptomeningeal cell line from multiple sclerosis with reverse transcriptase activity and viral particles", Biological Abstracts, vol. 89, No. 9, May 1, 1990.
H. Perron et al., "Isolation of Retrovirus from Patients with Multiple Sclerosis", *The Lancet*, vol. 337, No. 8745, Apr. 6, 1991, pp. 862-863.
H. Perron et al., "Antibody to Reverse Transcriptase of Human Retrovirus in Multiple Sclerosis", Biological Abstracts, vol. 93, No. 6, Mar. 15, 1992.
H. Perron et al., "Herpes simplex virus ICPO and ICP4 immediate early proteins strongly enhance expression of a retrovirus harboured by a leptomeningeal cell line from a patient with multiple sclerosis", The Journal of General Virology, vol. 74, No. 1, Jan. 1993, pp. 65-72.
H. Perron et al., "Retrovirus Isolation from Patients with Multiple Sclerosis: Epiphenomenon or Causative Factor?", *AIDS Research and Human Retroviruses*, vol. 8, No. 5, May 1992, p. 922.
H. Perron et al., "In Vitro Transmission and Antigenicity of a Retrovirus Isolated from a Multiple Sclerosis Patient", *Res. Virol.*, vol. 143, No. 5, 1992, pp. 337-350.
Perron et al., "Retroviral Reactivation by Herpesviruses in MS: Serological Arguments", Current Concepts in Multiple Sclerosis 1991, pp. 331-332.
A. Plaza et al., Theofilopoulos, A.N. New Human vβ 12DD Genes and Polymorphic Variants. J. Imm; vol. 147, No. 12, pp. 4360-4365, 1991.
Poirier et al., "La Barrier Hemato-Encephalique. Donnees Morphologiques [The Blood-Brain Barrier. Morphological Data]", *La Revue de Medecine Interne*, vol. IV, No. 2, Jun. 1983, pp. 131-144.
J. L. Portis, "Wild Mouse Retrovirus: Pathogenesis in Retrovirus Infections in the Nervous System". Oldstone M.B.A. and Koprowsky H. Eds. Current topics in microbiology and immunology, n°160, pp. 11-27, (Springer-Verlag, Berlin, 1990).
C.M. Poser et al., "New Diagnostic Criteria for Multiple Sclerosis: Guidelines for Research Protocols, in "The Diagnosis of Multiple Sclerosis"", *Thieme Stratton Inc.*, pp. 225-229, 1984.
D.N., Posnet, "Do Superantigens Play a Role in Autoimmunity?", *Semin. Immunol.*, vol. 5, pp. 65-72, 1993.
Prineas, "The Neuropathology of Multiple Sclerosis", *Handbook of Clinical Neurology*, vol. 3 (47), 1985, pp. 213-257.
Prineas et al., "Multiple Sclerosis: Remyelination of Nascent Lesions", *Annals of Neurology*, vol. 33, No. 2, Feb. 1993, pp. 137-151.
Prineas, "Pathology of the Early Lesion in Multiple Sclerosis", *Human Pathology*, vol. 6, No. 5, Sep. 1975, pp. 531-554.
Prineas et al., "Macrophages, Lymphocytes, and Plasma Cells in the Perivascular Compartment in Chronic Multiple Sclerosis", *Laboratory Investigation*, vol. 38, No. 4, 1978, pp. 409-421.
Ransohoff et al., "Heat-Shock Proteins and Autoimmunity: Implications for Multiple Sclerosis", *Annals of Neurology*, vol. 34, No. 1, Jul. 1993, pp. 5-7.
Rapoport, *Blood-Brain Barrier in Physiology and Medicine*, 129 (1976).
E.P. Reddy et al., "Amplification and Molecular Cloning of HTLV-I Sequences from DNA of Multiple Sclerosis Patients", *Science*, vol. 243, Jan. 27, 1989, pp. 529-533.
S. S. Rhee et al., "A single Amino Acid Substitution Within the Matrix Protein of a D-Type Retrovirus Converts Its Morphogenesis to that of a C-Type Retrovirus", Cell 63, pp. 77-86, (1990).
Riise et al., "Clustering of Residence of Multiple Sclerosis Patients at Age 13 to 20 Years in Hordaland, Norway", *Am J Epidemiol* 1991, vol. 133, No. 9, pp. 932-939.
Robbins et al., "Production of Cytotoxic Factor for Oligodendrocytes by Stimulated Astrocytes", *The Journal of Immunology*, vol. 139, No. 8, Oct. 15, 1987, pp. 2593-2597.
Rosati et al., "Incidence of Multiple Sclerosis in the Town of Sassari, Sardinia, 1965 to 1985: Evidence for Increasing Occurrence of the Disease", *Neurology* 38 (Mar. 1988), pp. 384-388.
Rudge, "Does a Retrovirally Encoded Superantigen Cause Multiple Sclerosis?", *J. Neurology Neurosurgery & Psychiatry* 1991, vol. 54, pp. 853-855.
Medline abstract of Rumschlag et al., "Immunologic characterization of a 35-kilodalton recombinant antigen of Mycobacterium tuberculosis," J Clin Microbiol 28: 591-95 (1990).
Medline abstract of Sakulramrung et al., "Antigenic and immunogenic characteristics of subcellular fractions and whole cells of a rough *E. coli* 0111 (J5) mutant," Immunobiology 169: 372-88 (1985).
Selmaj, et al., "Tumor Necrosis Factor Mediates Myelin and Oligodendrocyte Damage In Vitro", *Annals of Neurology*, vol. 23, No. 4, Apr. 1988, pp. 339-346.
Shih et al., "Detection of MUltiple, Novel Reverse Transcriptase Coding Sequences in Human Nucleic Acids: Relation to Primate Retroviruses", *J. Virol.*, Jan. 1989, vol. 63, No. 1, pp. 64-75.
Silberberg et al., "Tissue Culture Demyelination by Normal Human Serum", *Annals of Neurology*, vol. 15, No. 6, Jun. 1994, pp. 575-580.
M. Sommerlund et al., "Retrovirus-like particles ina n Epstein-Barr virus-producing cell line derived from a patient with chronic progressive myelopathy", *Acta Neurol Scand*, 1993: 87: pp. 71-76.
P. Sonigo et al., "Nucleotide Sequence of Mason-Pfizer Monkey Virus: An immunosuppressive D-Type Retrovirus", Cell 45, pp. 375-385, (1986).
Southern, "Detection of Specific Sequences Among DNA Fragments Separated by Gel Electrophoresis", *J. Mol. Biol.*, 1975, vol. 98, pp. 503-517.
Suzumura et al., "Serum Cytotoxicity to Oligodendrocytes in Multiple Sclerosis and Controls: Assessment by $^{51}Cr$ Release Assay", *J. Neuroimmunol.*, 11 (1986), pp. 137-147.
Traugott, "Multiple Sclerosis: Relevance of Class I and Class II MHC-Expressing Cells to Lesion Development", *Journal of Neuroimmunology*, 16, 1987, pp. 283-302.
Waksman, "Mechanisms in Multiple Sclerosis", *Nature*, vol. 318, Nov. 14, 1985, pp. 104-105.
K.G. Warren et al., "Diagnostic Value of Cerebrospinal Fluid Anti-Myelin Basic Protein in Patients with Multiple Sclerosis", Annals of Neurology, vol. 20, No. 1, Jul. 1986, pp. 20-25.
Williams et al., "Molecular Regulation of Apoptosis: Genetic Controls on Cell Death", *Cell*, vol. 74, Sep. 10, 1993, pp. 777-779.
Wienfield et al., "Stress Proteins, Autoimmunity, and Autoimmune Disease", *Current Topics in Microbiology and Immunology*, vol. 167, Springer-Verlag, Berlin, 1991, pp. 161-189.
D. L. Wilkinson et al., "Evidence for a functional subclass of the RTLV-H family of human endogenous retrovirus-like sequences", *J. Virol.*, vol. 67, pp. 2981-2989, (1993).
Wollinsky et al., "Liquorpherese bei 10 Patienten mit Multipler Sklerose [Fluid Phoresis in 10 Patients With Multiple Sclerosis]", *Verhandlungen der Deutschen Gesellschaft fur Neurologie*, vol. 7, 1992, pp. 444-445.
Woodland, et al., "An Endogenous Retrovirus Mediating Deletion of αβ T cells?", *Nature*, vol. 349, Feb. 7, 1991, pp. 529-530.

* cited by examiner

FIG. 1

| | | | | | | |
|---|---|---|---|---|---|---|
| Consensus | GTTTAGGGAT | ANCCCTCATC | TCTTTGGTCA | GGTACTGGCC | CAAGATCTAG | 50 |
| Consensus | GCCACTTCTC | AGGTCCAGSN | ACTCTGTYCC | TTCAG | 85 | |

(POL MSRV-1B)

| | | | | | | |
|---|---|---|---|---|---|---|
| Consensus | GTTCAGGGAT | AGCCCCCATC | TATTTGGCCA | GGCACTAGCT | CAATACTTGA | 50 |
| Consensus | GCCAGTTCTC | ATACCTGGAC | AYTCTYGTCC | TTCGGT | 86 | |

(POL MSRV-1B)

| | | | | | | |
|---|---|---|---|---|---|---|
| Consensus | GTTCARRGAT | AGCCCCCATC | TATTTGGCCW | RGYATTAGCC | CAAGACTTGA | 50 |
| Consensus | GYCAATTCTC | ATACCTGGAC | ACTCTTGTCC | TTYRG | 85 | |

(POL MSRV-1B)

| | | | | | | |
|---|---|---|---|---|---|---|
| Consensus | GTTCAGGGAT | AGCTCCCATC | TATTTGGCCT | GGCATTAACC | CGAGACTTAA | 50 |
| Consensus | GCCAGTTCTY | ATACGTGGAC | ACTCTTGTCC | TTTGG | 85 | |

(POL MSRV-1B)

| | | | | | |
|---|---|---|---|---|---|
| Consensus | GTGTTGCCAC | AGGGGTTTAR | RGATANCYCY | CATCTMTTTG | GYCWRGYAYT |
| Consensus | RRCYCRAKAY | YTRRGYCAVT | TCTYAKRYSY | RGSNAYTCTB | KYCCTTYRGT |
| Consensus | ACATGGATGA | C | | | |

FIG. 2

CONSENSUS A

```
GTTTAGGGATAGCCC   TCATCTCTTTGGTCA   GGTACTGGCCCAAGA   TCTAGGCCACTTCTC   60
V - G - P         S S L W S         G T G P R         S R P L L
 F R D S P         H L F G Q         V L A Q D         L G H F S
  L G I A L         I S L V R         Y W P K I         - A T S Q

AGGTCCAGGCACTCT   GTTCCTTCAG                                           85
R S R H S         V P S
 G P G T L         F L Q
  V Q A L C         S F
```

CONSENSUS B

```
GTTCAGGGATAGCCC   CCATCTATTTGGCCA   GGCACTAGCTCAATA   CTTGAGCCAGTTCTC   60
V Q G - P         P S I W P         G T S S I         L E P V L
 F R D S P         H L F G Q         A L A Q Y         L S Q F S
  S G I A P         I Y L A R         H - L N T         - A S S H

ATACCTGGACACTCT   TGTCCTTCGGT                                          86
I P G H S         C P S
 Y L D T L         V L R
  T W T L L         S F G
```

CONSENSUS C

```
GTTCAGGGATAGCCC   CCATCTATTTGGCCA   GGCATTAGCCCAAGA   CTTGAGTCAATTCTC   60
V Q G - P         P S I W P         G I S P R         L E S I L
 F R D S P         H L F G Q         A L A Q D         L S Q F S
  S G I A P         I Y L A R         H - P K T         - V N S H

ATACCTGGACACTCT   TGTCCTTCAG                                           85
I P G H S         C P S
 Y L D T L         V L Q
  T W T L L         S F
```

CONSENSUS D

```
GTTCAGGGATAGCTC   CCATCTATTTGGCCT   GGCATTAACCCGAGA   CTTAAGCCAGTTCTC   60
V Q G - L         P S I W P         G I N P R         L K P V L
 F R D S S         H L F G L         A L T R D         L S Q F S
  S G I A P         I Y L A W         H - P E T         - A S S H

ATACGTGGACACTCT   TGTCCTTTGG                                           85
I R G H S         C P L
 Y V D T L         V L W
  T W T L L         S F
```

FIG. 3

| | | | | | | |
|---|---|---|---|---|---|---|
| Consensus | TTGGATCCAG | TGYTGCCACA | GGGCGCTGAA | GCCTATCGCG | TGCAGTTGCC | 50 |
| Consensus | GGATGCCGCC | TATAGCCTCT | ACGTGGATGA | CCTSCTGAAG | CTTGAG | 96 |

FIG. 6

| | | | | | |
|---|---|---|---|---|---|
| CAAGCCACCC | AAGAACTCTT | AAATTTCCTC | ACTACCTGTG | GCTACAAGGT | 50 |
| TTCCAAACCA | AAGGCTCAGC | TCTGCTCACA | GGAGATTAGA | TACTTAGGGT | 100 |
| TAAAATTATC | CAAAGGCACC | AGGGGCCTCA | GTGAGGAACG | TATCCAGCCT | 150 |
| ATACTGGGTT | ATCCTCATCC | CAAAACCCTA | AAGCAACTAA | GAGGGTTCCT | 200 |
| TAGCATGATC | AGGTTTCTGC | CGAAAACAAG | ATTCCCAGGT | ACAACCAAAA | 250 |
| TAGCCAGACC | ATTATATACA | CTAATTAAGG | AAACTCAGAA | AGCCAATACC | 300 |
| TATTTAGTAA | GATGGACACC | TAAACAGAAG | GCTTTCCAGG | CCCTAAAGAA | 350 |
| GGCCCTAACC | CAAGCCCCAG | TGTTCAGCTT | GCCAACAGGG | CAAGATTTTT | 400 |
| CTTTATATGG | CACAGAAAAA | ACAGGAATCG | CTCTAGGAGT | CCTTACACAG | 450 |
| GTCCGAGGGA | TGAGCTTGCA | ACCCGTGGCA | TACCTGAATA | AGGAAATTGA | 500 |
| TGTAGTGGCA | AAGGGTTGGC | CTCATNGTTT | ATGGGTAATG | GNGGCAGTAG | 550 |
| CAGTCTNAGT | ATCTGAAGCA | GTTAAAATAA | TACAGGGAAG | AGATCTTNCT | 600 |
| GTGTGGACAT | CTCATGATGT | GAACGGCATA | CTCACTGCTA | AAGGAGACTT | 650 |
| GTGGTTGTCA | GACAACCATT | TACTTAANTA | TCAGGCTCTA | TTACTTGAAG | 700 |
| AGCCAGTGCT | GNGACTGCGC | ACTTGTGCAA | CTCTTAAACC | C | 741 |

FIG. 7

TCAGGGATAGCCCCCATCTATTTGGCCAGGCATTAGCCCAAGACTTGAGTC

AATTCTCATACCTGGACACTCTTGTCCTTCAGTACATGGATGATTTACTTT

TAGTCGCCCGTTCAGAAACCTTGTGCCATCAAGCCACCCAAGAACTCTTAA

CTTTCCTCACTACCTGTGGCTACAAGGTTTCCAAACCAAAGGCTCGGCTCT

GCTCACAGGAGATTAGATACTNAGGGCTAAAATTATCCAAAGGCACCAGG

GCCCTCAGTGAGGAACGTATCCAGCCTATACTGGCTTATCCTCATCCCAAA

ACCCTAAAGCAACTAAGAGGGTTCCTTGGCATAACAGGTTTCTGCCGAAA

ACAGATTCCCAGGTACASCCCAATAGCCAGACCATTATATACACTAATTA

NGGAAACTCAGAAAGCCAATACCTATTTAGTAAGATGGACACCTACAGAA

GTGGCTTTCCAGGCCCTAAAGAAGGCCCTAACCCAAGCCCCAGTGTTCAGC

TTGCCAACAGGGCAAGATTTTTCTTTATATGCCACAGAAAAAACAGGAAT

AGCTCTAGGAGTCCTTACGCAGGTCTCAGGGATGAGCTTGCAACCCGTGGT

ATACCTGAGTAAGGAAATTGATGTAGTGGCAAAGGGTT

FIG. 8

```
              10         20         30          40         50         60          70
               *          *          *           *          *          *           *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L  R>
___a___a___a___a___a___a___a___a___TRANSLATION OF F11-1 (A)____a___a___a___a___a___a___a___a___>

         80         90        100        110        120        130        140
          *          *          *          *          *          *          *
ATT ATC AAT GAG GCT GTT GTT CCT CTA TAC CCA GCT GTA CCT AAC CCT TAT ACA GTG CTT TCC CAA ATA CCA
 I   I   N   E   A   V   V   P   L   Y   P   A   V   P   N   P   Y   T   V   L   S   Q   I  P>
___a___a___a___a___a___a___a___a___TRANSLATION OF F11-1 (A)____a___a___a___a___a___a___a___a___>

     150        160        170        180        190        200        210
      *          *          *          *          *          *          *
GAG GAA GCA GAG TGG TTT ACA GTC CTG GAC CTT AAG GAT GCC TTT TTC TGC ATC CCT GTA CGT CCT GAC TCT
 E   E   A   E   W   F   T   V   L   D   L   K   D   A   F   F   C   I   P   V   R   P   D  S>
___a___a___a___a___a___a___a___a___TRANSLATION OF F11-1 (A)____a___a___a___a___a___a___a___a___>

    220        230        240        250        260        270        280
     *          *          *          *          *          *          *
CAA TTC TTG TTT GCC TTT GAA GAT CCT TTG AAC CCA ACG TCT CAA CTC ACC TGG ACT GTT|TTA CCC CAA GGG
 Q   F   L   F   A   F   E   D   P   L   N   P   T   S   Q   L   T   W   T   V   L   P   Q  G>
___a___a___a___a___a___a___a___a___TRANSLATION OF F11-1 (A)____a___a___a___a___a___a___a___a___>

 290
  *
TTC AAG GGA|
 F   K  G> |
___a___a___>|
```

FIG. 9a

```
        10          20          30          40          50          60          70
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R>
___a___a___a___a___a___a___a___TRANSLATION OF MSRV-1 POL *  (A)___a___a___a___a___a___a___a___>

     80          90         100         110         120         130         140
ATT ATC AAT GAG GCT GTT GTT CCT CTA TAC CCA GCT GTA CCT AAC CCT TAT ACA GTG CTT TCC CAA ATA CCA
 I   I   N   E   A   V   V   P   L   Y   P   A   V   P   N   P   Y   T   V   L   S   Q   I   P>
___a___a___a___a___a___a___a___TRANSLATION OF MSRV-1 POL *  (A)___a___a___a___a___a___a___a___>

    150         160         170    A    180|        190         200         210
GAG GAA GCA GAG TGG TTT ACA GTC CTG GAC CTT AAG|GAT GCC TTT TTC TGC ATC CCT GTA CGT CCT GAC TCT
 E   E   A   E   W   F   T   V   L   D   L   K | D   A   F   F   C   I   P   V   R   P   D   S>
___a___a___a___a___a___a___a___TRANSLATION OF MSRV-1 POL *  (A)___a___a___a___a___a___a___a___>

   220         230         240         250         260         270         280
CAA TTC TTG TTT GCC TTT GAA GAT CCT TTG AAC CCA ACG TCT CAA CTC ACC TGG ACT|GTT TTA CCC CAA GGG|
 Q   F   L   F   A   F   E   D   P   L   N   P   T   S   Q   L   T   W   T | V   L   P   Q   G>|
___a___a___a___a___a___a___a___TRANSLATION OF MSRV-1 POL *  (A)___a___a___a___a___a___a___a___>

290         300         310         320         330|   B    340         350         360
TTC AGG GAT AGC CCC CAT CTA TTT GGC CAG GCA TTA GCC CAA|GAC TTG AGT CAA TTC TCA TAC CTG GAC ACT
 F   R   D   S   P   H   L   F   G   Q   A   L   A   Q | D   L   S   Q   F   S   Y   L   D   T>
___a___a___a___a___a___a___a___TRANSLATION OF MSRV-1 POL *  (A)___a___a___a___a___a___a___a___>

         370         380         390         400         410         420         430
CTT GTC CTT CAG|TAC ATG GAT GAT|TTA CTT TTA GTC GCC CGT TCA GAA ACC TTG TGC CAT CAA GCC ACC CAA
 L   V   L   Q | Y   M   D   D | L   L   L   V   A   R   S   E   T   L   C   H   Q   A   T   Q>
___a___a___a___a___a___a___a___TRANSLATION OF MSRV-1 POL *  (A)___a___a___a___a___a___a___a___>

     440         450         460         470         480         490         500
GAA CTC TTA ACT TTC CTC ACT ACC TGT GGC TAC AAG GTT TCC AAA CCA AAG GCT CGG CTC TGC TCA CAG GAG
 E   L   L   T   F   L   T   T   C   G   Y   K   V   S   K   P   K   A   R   L   C   S   Q   E>
___a___a___a___a___a___a___a___TRANSLATION OF MSRV-1 POL *  (A)___a___a___a___a___a___a___a___>

    510         520         530         540         550         560         570
ATT AGA TAC TNA GGG CTA AAA TTA TCC AAA GGC ACC AGG GCC CTC AGT GAG GAA CGT ATC CAG CCT ATA CTG
 I   R   Y   X   G   L   K   L   S   K   G   T   R   A   L   S   E   E   R   I   Q   P   I   L>
___a___a___a___a___a___a___a___TRANSLATION OF MSRV-1 POL *  (A)___a___a___a___a___a___a___a___>

   580         590         600         610         620         630         640
GCT TAT CCT CAT CCC AAA ACC CTA AAG CAA CTA AGA GGG TTC CTT GGC ATA ACA GGT TTC TGC CGA AAA CAG
 A   Y   P   H   P   K   T   L   K   Q   L   R   G   F   L   G   I   T   G   F   C   R   K   Q>
___a___a___a___a___a___a___a___TRANSLATION OF MSRV-1 POL *  (A)___a___a___a___a___a___a___a___>

650         660         670         680         690         700         710         720
ATT CCC AGG TAC ASC CCA ATA GCC AGA CCA TTA TAT ACA CTA ATT ANG GAA ACT CAG AAA GCC AAT ACC TAT
 I   P   R   Y   X   P   I   A   R   P   L   Y   T   L   I   X   E   T   Q   K   A   N   T   Y>
___a___a___a___a___a___a___a___TRANSLATION OF MSRV-1 POL *  (A)___a___a___a___a___a___a___a___>

         730         740         750         760         770         780         790
TTA GTA AGA TGG ACA CCT ACA GAA GTG GCT TTC CAG GCC CTA AAG AAG GCC CTA ACC CAA GCC CCA GTG TTC
 L   V   R   W   T   P   T   E   V   A   F   Q   A   L   K   K   A   L   T   Q   A   P   V   F>
___a___a___a___a___a___a___a___TRANSLATION OF MSRV-1 POL *  (A)___a___a___a___a___a___a___a___>

     800         810         820         830         840         850         860
AGC TTG CCA ACA GGG CAA GAT TTT TCT TTA TAT GCC ACA GAA AAA ACA GGA ATA GCT CTA GGA GTC CTT ACG
 S   L   P   T   G   Q   D   F   S   L   Y   A   T   E   K   T   G   I   A   L   G   V   L   T>
___a___a___a___a___a___a___a___TRANSLATION OF MSRV-1 POL *  (A)___a___a___a___a___a___a___a___>

    870         880         890         900         910         920         930
CAG GTC TCA GGG ATG AGC TTG CAA CCC GTG GTA TAC CTG AGT AAG GAA ATT GAT GTA GTG GCA AAG GGT TGG
 Q   V   S   G   M   S   L   Q   P   V   V   Y   L   S   K   E   I   D   V   V   A   K   G   W>
___a___a___a___a___a___a___a___TRANSLATION OF MSRV-1 POL *  (A)___a___a___a___a___a___a___a___>

   940         950         960         970         980         990        1000
CCT CAT NGT TTA TGG GTA ATG GNG GCA GTA GCA GTC TNA GTA TCT GAA GCA GTT AAA ATA ATA CAG GGA AGA
 P   H   X   L   W   V   M   X   A   V   A   V   X   V   S   E   A   V   K   I   I   Q   G   R>
___a___a___a___a___a___a___a___TRANSLATION OF MSRV-1 POL *  (A)___a___a___a___a___a___a___a___>

1010        1020        1030        1040        1050        1060        1070        1080
GAT CTT NCT GTG TGG ACA TCT CAT GAT GTG AAC GGC ATA CTC ACT GCT AAA GGA GAC TTG TGG TTG TCA GAC
 D   L   X   V   W   T   S   H   D   V   N   G   I   L   T   A   K   G   D   L   W   L   S   D>
___a___a___a___a___a___a___a___TRANSLATION OF MSRV-1 POL *  (A)___a___a___a___a___a___a___a___>
```

FIG. 9b

```
              1090           1100           1110            1120           1130           1140            1150
                *              *              *               *              *              *               *
AAC CAT TTA CTT AAN TAT CAG GCT CTA TTA CTT GAA GAG CCA GTG CTG NGA CTG CGC ACT TGT GCA ACT CTT
 N   H   L   L   X   Y   Q   A   L   L   L   E   E   P   V   L   X   L   R   T   C   A   T   L>
___a___a___a___a___a___a___a___TRANSLATION OF MSRV-1 POL *  (A)____a___a___a___a___a___a___a___>
AAA CCC
 K   P>
___a___>
```

FIG. 13

GTGCTGATTGGTGTATTTACAATCCTTTATCTAATCCGAAATGCCCATGTTG
CAATATGGAAAGAAAGGGAGTTCCTAACCTCTGGGGGAACCCCCATTAAA
TACCACAAGTAAATCATGGAGTTATTGCACACAGTGCAAAAACTCAAGGA
GGTGGAAGTCTTACACTGCCAAAGCCATCAGAAAAGGGAAGAGGGGAGAA
GAGCAGCATAAGTGGCTACAGAGGCAAGGAAAGACTAGCAGAAAGGAAA
GAGAGAAAGAGACAGAAAGTCAGAGAGAGAGAGAGGAAGAGACAGAGCA
CAAAGAGGGAGTCAGAGAGAGAGAGAGACAGAGAGTCAGAGAGAAGGAA
AGAGAGAGAGGAAGAGACAAAGAATGAATCAAACAGAGAGACAGAAAGT
CAGAGAGAGAGAGAGAGAGGAAGAGACAGAGAAAAAGAGGGAGTCAGAA
AAAGAGAGACCAAAGAAGAAGTCCAAAGAGAAAGAAAGAGAGATGGAAG
TAGTAAAGGAAAAACAGTGTACCCTATTCCTTTAAAAGCCGGGGTAAATTT
AAAACCTATAATTGATAACTGAAGGTCTTCTCTGTAACCCTGTAACACTCC
AATACCACCTTGTTGTCAAGTGTAAACAAGGGCGTAGCCCAAAAGCACTG
AGGCCACTAACAACCCATAGCCTTCCTATCAAAATTCCTTAACCCAGCAGG
TTTCCTAACAGGGGATCTAAATCTTAATTAATTACCATACAATGGTCCAAC
CAGACTTAGGAGGAATTCCCTTCAGGACGGGAAGATAGATGCTTCCTCCCA
GGCGATTAAGGGAGAAAGACACAATGGGTATTCAGTAAGTGCCAAGGGGA
ACACTTGTAGAAGCAAAGTTAGGAAAATTGCCAAATAATTGGTTTGCTCAA
GAGTTGTTTGCACTCAGCCAAACCTTGAAGTACTTGCAGAATCAGAAAGGA
GCCATCTATACCAATTCTAAGTTAATATGGACTGAAGGAGGTTTTATTAAT
ACCAAAGAGAAATTAAAATCCCAAACTTATAAGGTTTTCAACCAAAGTAA
AGTTTGCTAAAAGTTAACAGCGTAACATGTATTATCCTACTACCACACACT
CTCAAAGGATTTCTCAGACAGTTTGCAAGAAATAATGATATCTATCCTTAC
TCTACAATCCCAAATAGACTCTTTGGCAGCAGTGACTCTCCAAAACCGTCA
AGGCCTAGACCTCCTCACTGCTGAGAAAGGAGGACTCTGCACCTTCTTAAG
GGAAGAGTGTTGTCTTTACACTAACCAGTCAGGGATAGTATGAGATGCTGC
CCGGCATTTACAGAAAAAGGCTTCTGAAATCAGACAACGCCTTTCAAATTC
CTATACCAACCTCTGGAGTTGGGCAACATGGTTTCTTCCCTTTCTATGTCCC
ATGGCTGCCATCTTGCTATTACTCGCCTTTGGGCCCTGTATTTTTAACCTCC
TTGTCAAATTTGTTTCTTCTAGGATCGAGGCCATCAAGCTACAGATGGTCTT
ACAAATGGAACCCCAAATGAGCTCAACTATCAACTTCTACTGAGGACCCCT
AGACCAACCCCCTGGCCCTTTCACTGGCCTAAAGAGTTCCCCTCTGGAGGA
CACTACCACTGCAGGGCCCCATCTTTGCCCCTATCCAGAAGGAAGTAGCTA
GAGCAGTCATTGCCCAATTCCCAAGAGCAGCTGGGGTGTCCCGTTTAGAGT
GGGGATTGAGAGGTGAAGCCAGCTGGACTTCTGGGTCGGGTGGGGACTTG
GAGAACTTTTGTGTCTAGCTAAAGGATTGTAAATGCAACAATCAGTGCTCT
GTGTCTAGCTAAAGGATTGTAAATACACCAATCAGCAC

FIG. 15

GGCTGCTAAAGGAGACTTGTGGTTGTCAGACAATCGCCTACTTAGGTACCA
GGCCTTATTACTTGAGGGACTGGTGCTTCAGATGCGCACTTGTGCAGCTCT
TAACCCAAACTTATGCTGCCCAGAAGGATCTTTTAGAGGTCCCCTTAGCCA
ACCCTGACCTCAACCTATATATATACTGATGGAAGTTCGTTTGTAGAAAAG
GGATTACAAAGGGNAGGATATNCCATAGGTTAGTGATAAAGCAGTACTTG
AAAGTAAGCCTCTTCCCCCCAGGGACCAGCGCCCCCGTTAGCAGAACTAGT
GGCACTGACCCCGAGCCTTAGAACTTGGAAAGGGAGGAGGATAAATGTGT
ATACAGATAGCAAGTATGCTTATCTAATCCGAAATGCCCATGTTG

FIG. 16

TCAGGGATAGCCCCCATCTATTTGGTCAGGCACTGGCCCAAGATCTAGGGA
CATGCCACTTTTAAGAGCCATTTCTCAAGTCCAGGTACTCTGGTCCTTCGGT
ATGTGGATGATTTACTTTTGGCTACCAGTTCAGTAGCCTCATGCCAGCAGG
CTACTCTAGATCTCTTGAACTTTCTAGCTAATCAAGGGTACAAGGCATCTA
GGTTGAAGGCCCAGCTTTGCCTACAGCAGGTCAAATATCTAGGCCTAATCT
TAGCCAGAGGGACCAGGGCACTCAGCAAGGAACAAATACAGCCTATACTG
GCTTATCCTCACCCTAAGACATTAAAACAGTTGCGGGGGTTCCTTGGAATC
ACTGGCTTTTTGGTGACTATGGATTCCCAGATACAGCAAGATTGGCAGGCC
CCTCTATACTGTAATCAAGGAGACTCACGAGGGCAAGTACTCATCTAGTAG
AATGGGAACTAGGGACAGAAACAGCCTTCAAAACCTTAAAGCAGGCCCTA
GTACAATCTCCAGCTTTAAGCCTTCCCACAGGACAAAACTTCTCTTTATAC
ATCACAGAGAGGGCAGAGATAGCTCTTGGTGTCCTTATTCAGACTCATGGG
ACTACCCCACAACCAGTGGCACACCTAAGTAAGGAAATTGATGTAGTAGC
AAAAGGCTGGCCTCACTGTTTATGGGTAGCTGTGGTGGTGGCTGTCTTAGT
GTCAGAAGCTATCAAAATAATACAAGGAAAGGATCTCACTGTCTGGACTA
CTCATGATGTAATGGCATACTAGGTGCCAAAAGAAGTTTATGGGTATCAGA
CAACCACCTGCTTAGATACCAGGGACTACTCCTGGAGGATTGGGCTTCAAG
TGCGTTTTTTGTGGCCTCAACCCTGCCACTTTTCCTCCAGAGGATGGAGAG
CCGCTTGAGCATGCTTGCCAACAGGTTGTAGGCCAGAATTATTCCACCCGA
GATGATCTCTTAGAGTACCCTTAGCTAATCCTGACCTTAACCTATATACCA
ATGGAAGTTCATTTGTGGAAAACGGGATATGAAGGGCAGGTTATGTCATAG
TTAGTGATGTAATCATACTTGCAAGTAAGCCTCTTACCCCAGGGGCCAGCA
CTCAGTTAGCAGAACTAGTCACACTTACCTTAACCTTAGAACTGGGAAAGG
GAAAAAGAATAAATATGTATACAGATAGTAAGTATGCTTATCTAATCCTAC
ATGCCCATGCTGCAATATGGAAGGAAAGGGAGTTCCTAACCCCTGGGGGA
ACCCCCATTAAATACCACAAGGYAAATCATGGAGTTATTGCACGCAGTGC
AAAAACTCAAGGAGGTGGCAGTCTTACACTGCCGAAGCYATCAAAAAGGG
GAAGGAGAGGGGAGAACAGCAGCATAAGTGGTTGGCAGAGGCAGTGAAA
GACCAGCAGAGAGAAGGAGAGAGACAACGTCAACGACAGAAGGAAAGAA
GAGGAGGAGACAGAGAGGAAGAGACAGAGAGACAGTTAGTCCAAGAGAG
AGACAGAGAGAGGAAGAGACAGACAGAAAGTCCAAGAGAGAAGGAAAGA
GAGGAAGAGACCAAGGAGTCCNAGAGAGAGAAAGAGATAGAAGTAGTAA
AGAAAAAACATTGTACCCTATTCCTTTAAAAGCCGGGGTATATTTAAAACC
TATAATTGATAATTGAGTTCTTGCACCCTCCTCCAGGGGATYGCTGGGAGG
AAACCCTCAACCGATATGTGAAAATTGTGGGTCGTCCCTATGTCTCAATTA
CCAGCCAATACCCCCTTGTTTTAGTGTGAACGAGGGTGTAGAGCGCAGAC
AGGGAGACCTCTGACAATCCATACCCTTCCTATCCAAAATCCTTAACCCAG
CAGGTTTTCTAAAAGGGGATCTAAATCTTAATTAATTACCATACAAAGGTC
AAACCAGATCTAGGAGGAACTTCCTTCAGGACAGGATGATAGATGGTTCCT
CCCAGGCGATTAAAGAAAATAAAAAGACACATGGGCAGCCAGTAAGTGAT
AAGGGAACACTAGTAGAAGCAGTTAGGAGAAGTTGCCTAATAATTGGTCT
ACTCCAAATGTGTGAGTTGTTCGCACTCAGCCCAAATCTTAAAGTACTTAC
AGAATTAGGGAGGAGCCATTTACACCAATTCTAAGTTAATATGGACTGGAT
GAGGTTTTATTAATAGCGAAGGAGAATTAAATCCTAAACTNACAAGGTTTT
CAACTAAAGTAAATTTTACTAAAAGCTAACAGTGTAACATGCATTATCCTA
CTACAACACACTCTCANAGGATTCCTCAGACAGTTTACAAGAAATAACAA
AATCTATCTGGTAAGGATAGTAACTACAATCCCAAATACATTCTTTGGCAG
CAGTGACTCTC

FIG. 17

TCAGGGATAGCCCCCATCTATTTGATCAGGCACTAGCCCAAGATCTAGGCC
ACTTCTGAAGTCCAGGCATTCTAGTCCTTCAGTATGTGGATGATTTACTTTT
GGCTACCAGTTTGGAAGCCTCATGCCAGCAGGCTACTTGAGATCTCTTGAA
CTTTCTAGCTAATCAAGGGTGTATGGCATCTAAATTGAAAGTCCAGCTCTG
CCTACAACAAGTCAAATATCTAGGCCTAATCTTAGATAGAAGAACCAGGG
CCCTCAGCAAGGAATGAATAAAGCCTATGCTGGCTTATCGGCACCCTAAGA
CATTAAAACAATTGTGGGGGTTCCTTGGAATCACTGGCTTTTGCCGACTAT
GGATCCCTGGATAGAGTGAGATAGCCAGGCCCCCTCTATTACTCTTATCAA
GGAGACCCAGAGGGCAAATACTTATCTAGTATTATGGGNACCAGAGGCAG
AAAAAGCCTTCCAAACCTTAAAGGAGACCCTAGTACAAGCTCCAGCTTTAA
GCCTTCCCACAGGACAAANCTTCTCTTTATATGTCACAGAGAGAGCAGGAA
TAGCTCCTGGAGTCCTTACTCAGACTTTTGGACGACCCCACGGCCAGTGGC
RTACCTAAGTAAGGAAATTGATGTAGTAGCAAAAGGCTGGCCTCACTGTTT
ATGGGTAGTTGCGGCTGTGGCAGTCTTACTGTCAAAGGCTATCAAAATAAT
ACAAGGAAAGGATTTCACTATCTGGACTACTCATGAGGAAAATGGCATATT
AGGTGCCAAAGGAAGTTTTTGGCTATCAGACAACCACCTGCTCAGATTCCA
GGCACTACTGATTGAGAGACCAGTGCTTTAAATATGTATGTGTGTGTGTGG
CCCTCAACCCTGCCACTGTTCTCCCAGAAGATGGAGAACCAATGAAGCATT
ACTGTCAACAAATTAGAGTCCAGAGTTATGCTGCCTGAGAGGATCTCTTAG
AAGTCCCCTTAGCTAATCCTGACCTTAACCTATATGCTGATGGAAGTTCAC
TTGTGGAGAATGGGATACGAAAAGCACATTATGCCATAGTTAGTGAGGTA
ACAGTACTTGAAAGTAAGCCTATTCCCCCATGGACCAGAGCCCAGTTAGCA
GAACTAGTGGCACTTACCCAAGCCTTAGAACTAGGAAAGGGAAAAATAAT
AAATGTGTATACAGATAGCAAGTATGCTTATCTAATCCTACATGCCCATGC
TGCAGTATGGAAAGAAAGGGAGTTCCTAACCTCTGGGGGAACCCCCATTA
AATACCACAAGGCAAATCATGGAGTTATTGCATGTAGTGCAAAACCTCAA
GTAGGTGGCAGTTTTACACTGCCTGAAGCTATGGGGAAGGAGAGAGGAGA
ACAGCAGCATAAGTGGCTAGCAGAGGCAGCGAAAGACTAGCAGAGAGGA
GAGGTAGGGGAAAGACAGAAAGTCAAAGAAAAGAAGTCAAAGACAGACA
GAGAAAGAGACAGAGGGAGCCAGAGAGAAAGAAAAGAGAGAACGAAAGA
GACAGAATGTCAAAGAACAGAAGAGAGAGGCAGCGCCAGAAGAGTTAAG
AAAGTGAGAAAGAGAGATGGAAATAGTAAAGAAAAAACAGTGTACCCTAT
TCCTTTAAAAGCCAGGGTAAATTTAAAACGTATAATTTTATAATTGGAAGG
TCTTCTCCATAACCCTATAACATTAAAATACCACCTTGTTGTCAGTGTAAAC
AAGAGCATAGCCCAAAAGCACTGAGGCCACTGACAACCCATAGCCTTCCT
ATCAAAAATCCTTAACTCTGCAGGTTTCCTAACAGGGGATCTAAATCTCAA
CTAATCACCATACAATGGTCCGACCAGACCTAGGAGCGACTCCCCTCAGG
ACAGAAGGATGGATGGTTCCTCCCAGGCCATTAAGGGAAAGAGACACAAT
GGGTATTCAGTAAGTGATAAGGGAACTCTTGTAGAAGCAGTTAGGAAGATT
GCCTAATATTTGGTCTGCTCAAATGTGCCAGCTGTTTGCACTCAGCTAAAC
CTTAAATTACTTACAGAATTAGGAAGGAGCCATCTATACCAATTCTGAGTT
AATATGAGCTGAACAAGTTCTTATTAATAGCAAAGAATCATTGAAATCTCA
AACTTGCAAAGTTTTCAACAAAAGTAAAGTTTGCTGAAAGTTAGCAGTGTA
ACATGTATTATCCTAACTTCTAATCTTGTGGAAATCAGACCCTATCAGTGC
CCCTCAAAGCTGAAGTCCATCAGCATATGGCCATACAACTAATACCCCTAT
TTATAGGGTTAGGAATGGCCACTGCTACAGGAATGGGAGTAACAGGTTTAT
CTACTTCATTATCCTATTACCACACACTCTTAAAGGATTTCTCAGACAGTTT
ACAAGAAATAACAAAATCTATCCTTACTCTNTARTCCCAAATAGRTTCTTT
GGCAGCAGTGACTCTC

FIG. 23

| | | | | | | |
|---|---|---|---|---|---|---|
| 1 | TTCCTGAGTT | CTTGCACTAA | CCTCAAATGA | GAGAAGTGCC | GCCATAACTG | CAACCCAAGA |
| 61 | GTTTGGCGAT | CCCTGGTATC | TCAGTCAGGT | CAATGACAGG | ATGACAACAG | AGGAAAGATA |
| 121 | ATGATTCCCC | ACAGGCCAGC | AGGCAGTTCC | CAGTGTAGAC | CCTCATTAGG | ACACAGAATC |
| 181 | AGAACATGGA | GATTGGTGCC | GCAGACATTT | GCTAACTTGC | GTGCTAGAAG | GACTAAGGAA |
| 241 | AACTAGGAAG | ATATGAATTA | TTCAATGATG | TCCACTATAA | CACAGGGGAA | AGGAAGAAAA |
| 301 | TCCTACTGCC | TTTCTGGAGA | GACTAAGGGA | GGCATTGAGG | AAGCATACCA | GGCAAGTGGA |
| 361 | CATTGGAGGC | TCTGGAAAAG | GGAAAAGTTG | GGAAAAGTAT | ATGTCTAATA | GGGCTTGCTT |
| 421 | CCAGTGTGGT | CTACAAGGAC | ACTTTAAAAA | AGATTGTCCA | ATAGAAATAA | GCCACCACCT |
| 481 | CGTCCATGCC | CCTTATGTCA | AGGGAATCAC | TGGAAGGCCC | ACTGCCCCAG | GGGATGAAGG |
| 541 | TCCTCTGAGT | CAGAAGCCAC | TAACCAGATG | ATCCAGCAGC | AGGACTGAGG | GTGCCCGGGG |
| 601 | CAAGCGCCAG | CCCATGCCAT | CACCCTCACA | GAGCCCCAGG | TATGCTTGAC | CATTGAGGGT |
| 661 | CAGAAGGGTA | CTGTCTCCTG | GACACTGGCG | GGCCTTCTCA | GTCTTACTTT | CCTGTCCTGG |
| 721 | ACAACTGTCC | TCCAGATCTG | TCACTGTCCG | AGGGGTCCTA | GGACAGCCAG | TCACTAGATA |
| 781 | CTTCTCCCAG | CCACTAAGTT | GTGACTGGGG | AACTTTACTC | TTCCACATGC | TTTTCTAATT |
| 841 | ATGCCTGAAA | GCCCCACTCT | CTTGTTAGGG | GAGAGACATT | CTAGCAAAAG | CAGGGGCCAT |
| 901 | TATACATGTG | AATATAGGAG | AAGGAACAAC | TGTTTGTTGT | CCCCTGCTTG | AGGAAGGAAT |
| 961 | TAATCCTGAA | GTCCGGGCAA | CAGAAGGACA | ATATGGACAA | GCAAAGAATG | CCCGTCCTGT |
| 1021 | TCAAGTTAAA | CTAAAGGATT | CCACCTCCTT | TCCCTACCAA | AGGCAGTACC | CCCTCAGACC |
| 1081 | CGAGACCCAA | CAAGAACTCC | AAAAGATTGT | AAAGGACCTA | AAAGCCCAAG | GCCTAGTAAA |
| 1141 | ACCAAGCAAT | AGCCCTTGCA | AGACTCCAAT | TTTAGGAGTA | AGGAAACCCA | ACGGAC |

FIG. 27a

```
ATG ATC CAG CAG CAG GAC NGA GGG TGC CCG GGG CAA GCG CCA GCC CAT GCC ATC ACC CTC ACA GAG CCC CAG GTA TGC TTG ACC ATT GAG 90
M   I   Q   Q   Q   D   X   G   C   P   G   Q   A   P   A   H   A   I   T   L   T   E   P   Q   V   C   L   T   I   E

GGT CAG AAG GGT NAC TGT CTC CTG GAC ACT GGC GGN GCC TTC TCA GTC TTA CTT TCC TGT CCT GGA CAA CTG TCC TCC AGA TCT GTC ACT 180
G   Q   K   G   X   C   L   L   D   T   G   G   A   F   S   V   L   L   S   C   P   G   Q   L   S   S   R   S   V   T

GTC CGA CGG GTC CTA GGA CAG CCA GTC ACT AGA TAC TTC TCC CAG CCA CTA AGT TGT GAC TGG GGA ACT TTA CTC TTC CCA CAT GCT TTT 270
V   R   G   V   L   G   Q   P   V   T   R   Y   F   S   Q   P   L   S   C   D   W   G   T   L   L   F   P   H   A   F

CTA ATT ATG CCT GAA AGC CCC ACT CTC TTG TTG GGG AGA GAC ATT CTA GCA AAA GCA GGG GCC ATT ATA CAT GTG AAT ATA GGA GAA GGA 360
L   I   M   P   E   S   P   T   L   L   L   G   R   D   I   L   A   K   A   G   A   I   I   H   V   N   I   G   E   G

ACA ACT GTT TGT TGT CCC CTG CTT GAG GAA GGA ATT AAT CCT GAA GTC CGG GCA ACA GAA GGA CAA TAT GGA CAA GCA AAG AAT GCC CGT 450
T   T   V   C   C   P   L   L   E   E   G   I   N   P   E   V   R   A   T   E   G   Q   Y   G   Q   A   K   N   A   R

CCT GTT CAA GTT AAA CTA AAG GAT TCC ACC TCC TTT CCC TAC CAA AGG CAG TAC CCC CTC AGA CCC GAG ACC CAA CAA GAA CTC CAA AAG 540
P   V   Q   V   K   L   K   D   S   T   S   F   P   Y   Q   R   Q   Y   P   L   R   P   E   T   Q   Q   E   L   Q   K

ATT GTA AAG GAC CTA AAA GCC CAA GGC CTA GTA AAA CCA AGC AAT AGC CCT TGC AAG ACT CCA ATT TTA GGA GTA AGG AAA CCC AAC GGA 630
I   V   K   D   L   K   A   Q   G   L   V   K   P   S   N   S   P   C   K   T   P   I   L   G   V   R   K   P   N   G

CAG TGG AGG TTA GTG CAA GAA CTC AGG ATT ATC AAT GAG GCT GTT GTT CCT CTA TAC CCA GCT GTA CCT AAC CCT TAT ACA GTG CTT TCC 720
Q   W   R   L   V   Q   E   L   R   I   I   N   E   A   V   V   P   L   Y   P   A   V   P   N   P   Y   T   V   L   S

CAA ATA CCA GAG GAA GCA GAG TGG TTT ACA GTC CTG GAC CTT AAG GAT GCC TTT TTC TGC ATC CCT GTA CGT CCT GAC TCT CAA TTC TTG 810
Q   I   P   E   E   A   E   W   F   T   V   L   D   L   K   D   A   F   F   C   I   P   V   R   P   D   S   Q   F   L

TTT GCC TTT GAA GAT CCT TTG AAC CCA ACG TCT CAA CTC ACC TGG ACT GTT TTA CCC CAA GGG TTC AGG GAT AGC CCC CAT CTA TTT GGC 900
F   A   F   E   D   P   L   N   P   T   S   Q   L   T   W   T   V   L   P   Q   G   F   R   D   S   P   H   L   F   G

CAG GCA TTA GCC CAA GAC TTG AGT CAA TTC TCA TAC CTG GAC ACT CTT GTC CTT CAG TAC ATG GAT GAT TTA CTT TTA GTC GCC CGT TCA 990
Q   A   L   A   Q   D   L   S   Q   F   S   Y   L   D   T   L   V   L   Q   Y   M   D   D   L   L   L   V   A   R   S

GAA ACC TTG TGC CAT CAA GCC ACC CAA GAA CTC TTA ACT TTC CTC ACT ACC TGT GGC TAC AAG GTT TCC AAA CCA AAG GCT CGG CTC TGC 1080
E   T   L   C   H   Q   A   T   Q   E   L   L   T   F   L   T   T   C   G   Y   K   V   S   K   P   K   A   R   L   C
```

FIG. 27b

```
TCA CAG GAG ATT AGA TAC TNA GGG CTA AAA TTA TCC AAA GGC ACC AGG GCC CTC AGT GAG GAA CGT ATC CAG CCT ATA CTG GCT TAT CCT 1170
S   Q   E   I   R   Y   X   G   L   K   L   S   K   G   T   R   A   L   S   E   E   R   I   Q   P   I   L   A   Y   P

CAT CCC AAA ACC CTA AAG CAA CTA AGA GGG TTC CTT GGC ATA ACA GGT TTC TGC CGA AAA CAG ATT CCC AGG TAC ASC CCA ATA GCC AGA 1260
H   P   K   T   L   K   Q   L   R   G   F   L   G   I   T   G   F   C   R   K   Q   I   P   R   Y   X   P   I   A   R

CCA TTA TAT ACA CTA ATT ANG GAA ACT CAG AAA GCC AAT ACC TAT TTA GTA AGA TGG ACA CCT ACA GAA GTG GCT TTC CAG GCC CTA AAG 1350
P   L   Y   T   L   I   X   E   T   Q   K   A   N   T   Y   L   V   R   W   T   P   T   E   V   A   F   Q   A   L   K

AAG GCC CTA ACC CAA GCC CCA GTG TTC AGC TTG CCA ACA GGG CAA GAT TTT TCT TTA TAT GCC ACA GAA AAA ACA GGA ATA GCT CTA GGA 1440
K   A   L   T   Q   A   P   V   F   S   L   P   T   G   Q   D   F   S   L   Y   A   T   E   K   T   G   I   A   L   G

GTC CTT ACG CAG GTC TCA GGG ATG AGC TTG CAA CCC GTG GTA TAC CTG AGT AAG GAA ATT GAT GTA GTG GCA AAG GGT TGG CCT CAT NGT 1530
V   L   T   Q   V   S   G   M   S   L   Q   P   V   V   Y   L   S   K   E   I   D   V   V   A   K   G   W   P   H   X

TTA TGG GTA ATG GNG GCA GTA GCA GTC TNA GTA TCT GAA GCA GTT AAA ATA ATA CAG GGA AGA GAT CTT NCT GTG TGG ACA TCT CAT GAT 1620
L   W   V   M   X   A   V   A   V   X   V   S   E   A   V   K   I   I   Q   G   R   D   L   X   V   W   T   S   H   D

GTG AAC GGC ATA CTC ACT GCT AAA GGA GAC TTG TGG TTG TCA GAC AAC CAT TTA CTT AAN TAT CAG GCT CTA TTA CTT GAA GAG CCA GTG 1710
V   N   G   I   L   T   A   K   G   D   L   W   L   S   D   N   H   L   L   X   Y   Q   A   L   L   L   E   E   P   V

CTG NGA CTG CGC ACT TGT GCA ACT CTT AAA CCC AAA CTT ATG CTG CCC AGA AGG ATC TTT NTA GAG GTC CCC TTA GCC AAC CCT GAC CTC 1800
L   X   L   R   T   C   A   T   L   K   P   K   L   M   L   P   R   R   I   F   X   E   V   P   L   A   N   P   D   L

AAC TAT ATA TAT ACT GAT GGA AGT TCG TTT GTA GAA AAG GGA TTA CAA AGG GNA GGA TAT NCC ATA GGT GTT AGT GAT AAA GCA GTA CTT 1890
N   Y   I   Y   T   D   G   S   S   F   V   E   K   G   L   Q   R   X   G   Y   X   I   G   V   S   D   K   A   V   L

GAA AGT AAG CCT CTT CCC CCC CAG GGA CCA GCG CCC CCG TTA GCA GAA CTA GTG GCA CTG ACC CCG CGA GCC TTA GAA CTT TGG AAA GGG 1980
E   S   K   P   L   P   P   Q   G   P   A   P   P   L   A   E   L   V   A   L   T   P   R   A   L   E   L   W   K   G

AGG AGG ATA AAT GTG TAT ACA GAT AGC AAG TAT GCT TAT CTA ATC CGA AAT GCC CAT GTT GTT TAT CTA ATC CGA AAT GCC CAT GTT GCA 2070
R   R   I   N   V   Y   T   D   S   K   Y   A   Y   L   I   R   N   A   H   V   V   Y   L   I   R   N   A   H   V   A

ATA TGG AAA GAA AGG GAG TTC CTA ACC TCT GGG GGA ACC CCC ATT AAA TAC CAC AAG TTA ATC ATG GAG TTA TTG CAC ACA GTG CAA AAA 2160
I   W   K   E   R   E   F   L   T   S   G   G   T   P   I   K   Y   H   K   L   I   M   E   L   L   H   T   V   Q   K
```

FIG. 27c

```
CTC AAG GAG GTG GAA GTC TTA CAC TGC CAA AGC CAT CAG AAA AGG GAA AGG GGA GAA GAG CAG CAT AAG TGG CTA CAG AGG CAA GGA AAG 2250
L   K   E   V   E   V   L   H   C   Q   S   H   Q   K   R   E   R   G   E   E   Q   H   K   W   L   Q   R   Q   G   K

ACT AGC AGA AAG GAA AGA GAG AAA GAG ACA GAA AGT CAG AGA GAG AGA GAG GAA GAG ACA GAG CAC AAA GAG GGA GTC AGA GAG AGA GAG 2340
T   S   R   K   E   R   E   K   E   T   E   S   Q   R   E   R   E   E   E   T   E   H   K   E   G   V   R   E   R   E

AGA CAG AGA GTC AGA GAG AAG GAA AGA GAG AGA GGA AGA GAC AAA GAA TGA                                                     2391
R   Q   R   V   R   E   K   E   R   E   R   G   R   D   K   E
```

FIG. 28

GATGCCTTTTTCTGCATCCCTGTACGTCCTGACTCTCAATTCTTGTTTGCCTTTGAAG
ATCCTTTGAACCCAACGTCTCAACTCACCTGGACTGTTTTACCCCAAGGGTTCAGGGA
TAGCCCCATCTATTTGGCCAGGCATTAGCCCAAGATGCCTTTTGCATCCCTGTACGTG
ACTCTCAATTCTTGTTTGCCTTTGCCTTTGAAGATGCTTTGAACCCAACGTCTCAACT
CACCTGGACTGTTTTACGCCAAGGGTTCAGGGATAGCCCCCATCTATTTGGC
CAGGCATTAGCCCAA

Asp-Ala-Phe-Phe-Cys-Ile-Pro-Val-Arg-Pro-Asp-Ser-Gln-Phe-
Leu-Phe-Ala-Phe-Glu-Asp-Pro-Leu-Asn-Pro-Thr-Ser-Gln-Leu-
Thr-Trp-Thr-Val-Leu-Pro-Gln-Gly-Phe-Arg-Asp-Ser-Pro-His-
Leu-Phe-Gly-Gln-Ala-Leu-Ala-Gln

FIG. 34

Cys-Ile-Pro-Val-Arg-Pro-Asp-Ser-Gln-Phe-Leu

Val-Leu-Pro-Gln-Gly-Phe-Arg-Asp-Ser-Pro-His-Leu-Phe-Gly-
Gln-Ala-Leu-Ala

Leu-Phe-Ala-Phe-Glu-Asp-Pro-Leu

Phe-Ala-Phe-Glu-Asp-Pro-Leu-Asn

FIG. 35

```
         10         20         30         40         50
 1234567890 1234567890 1234567890 1234567890 1234567890
 CTTCCCCAAC TAATAAGGAC CCCCCTTTCA ACCCAAACAG TCCAAAAGGA     50
 L  P  Q  L   I  R  T   P  L  S  T  Q  T  V   Q  K  D
  F  P  N   .  .  G  P   P  F  Q   P  K  Q   S  K  R  T
   S  P  T   N  K  D   P  P  F  N   P  N  S   P  K  G

 CATAGACAAA GGAGTAAACA ATGAACCAAA GAGTGCCAAT ATTCCCTGGT    100
  I  D  K   G  V  N  N   E  P  K   S  A  N   I  P  W  L
  .  T  K    E  .  T   M  N  Q  R   V  P  I   F  P  G
 H  R  Q  R   S  K  Q   .  T  K   E  C  Q  Y   S  L  V

 TATGCACCCT CCAAGCGGTG GGAGAAGAAT TCGGCCCAGC CAGAGTGCAT    150
   C  T  L   Q  A  V   G  E  E  F   G  P  A   R  V  H
 Y  A  P  S   K  R  W   E  K  N   S  A  Q  P   E  C  M
  M  H  P   P  S  G  G   R  R  I   R  P  S   Q  S  A  C

 GTACCTTTTT CTCTCTCACA CTTGAAGCAA ATTAAAATAG ACNTAGGTNA    200
 V  P  F  S   L  S  H   L  K  Q   I  K  I  D   X  G  X
  Y  L  F   L  S  H  T   .  S  K   L  K  .   T  .  V  N
   T  F  F   S  L  T   L  E  A  N   .  N  R   X  R  X

 ATTNTCAGAT AGCCCTGATG GYTATATTGA TGTTTTACAA GGATTAGGAC    250
  X  S  D   S  P  D  G   Y  I  D   V  L  Q   G  L  G  Q
  X  Q  I   A  L  M   X  I  L  M   F  Y  K   D  .  D
 I  X  R  .   P  .  W   L  Y  .   C  F  T  R   I  R  T

 AATCCTTTGA TCTGACATGG AGAGATATAA TATTACTGCT AAATCAGACG    300
  S  F  D   L  T  W   R  D  I  I   L  L  L   N  Q  T
 N  P  L  I   .  H  G   E  I  .   Y  Y  C  .   I  R  R
  I  L  .   S  D  M  E   R  Y  N   I  T  A   K  S  D  A

 CTAACCTCAA ATGAGAGAAG TGCTGCCATA ACTGGAGCCC GAGAGTTTGG    350
 L  T  S  N   E  R  S   A  A  I   T  G  A  R   E  F  G
  .  P  Q   M  R  E  V   L  P  .   L  E  P   E  S  L  A
  N  L  K   .  E  K   C  C  H  N   W  S  P   R  V  W

 CAATCTCTGG TATCTCAGTC AGGTCAATGA TAGGATGACA ACGGAGGAAA    400
  N  L  W   Y  L  S  Q   V  N  D   R  M  T   T  E  E  R
  I  S  G   I  S  V   R  S  M  I   G  .  Q   R  R  K
 Q  S  L  V   S  Q  S   G  Q  .   .  D  D  N   G  G  K

 GAGAACGATT CCCCACAGGG CAGCAGGCAG TTCCCAGTGT AGCTCCTCAT    450
  E  R  F   P  T  G   Q  Q  A  V   P  S  V   A  P  H
 E  N  D  S   P  Q  G   S  R  Q   F  P  V  .   L  L  I
  R  T  I   P  H  R  A   A  G  S   S  Q  C   S  S  S  L

 TGGGACACAG AATCAGAACA TGGAGATTGG TGCCGCAGAC ATTTA          495
 W  D  T  E   S  E  H   G  D  W   C  R  R  H   L
  G  T  Q   N  Q  N  M   E  I  G   A  A  D   I
  G  H  R   I  R  T   W  R  L  V   P  Q  T   F
```

FIG. 36

| 10<br>1234567890 | 20<br>1234567890 | 30<br>1234567890 | 40<br>1234567890 | 50<br>1234567890 | |
|---|---|---|---|---|---|
| CTTCCCCAAC | TAATAAGGAC | CCCCCTTTCA | ACCCAAACAG | TCCAAAAGGA | 50 |
| L P Q L | I R T | P L S | T Q T V | Q K D | |
| CATAGACAAA | GGAGTAAACA | ATGAACCAAA | GAGTGCCAAT | ATTCCCTGGT | 100 |
| I D K | G V N N | E P K | S A N | I P W L | |
| TATGCACCCT | CCAAGCGGTG | GGAGAAGAAT | TCGGCCCAGC | CAGAGTGCAT | 150 |
| C T L | Q A V | G E E F | G P A | R V H | |
| GTACCTTTTT | CTCTCTCACA | CTTGAAGCAA | ATTAAAATAG | ACCTAGGTAA | 200 |
| V P F S | L S H | L K Q | I K I D | L G K | |
| ATTCTCAGAT | AGCCCTGATG | GYTATATTGA | TGTTTTACAA | GGATTAGGAC | 250 |
| F S D | S P D G | Y I D | V L Q | G L G Q | |
| AATCCTTTGA | TCTGACATGG | AGAGATATAA | TATTACTGCT | AAATCAGACG | 300 |
| S F D | L T W | R D I I | L L L | N Q T | |
| CTAACCTCAA | ATGAGAGAAG | TGCTGCCATA | ACTGGAGCCC | GAGAGTTTGG | 350 |
| L T S N | E R S | A A I | T G A R | E F G | |
| CAATCTCTGG | TATCTCAGTC | AGGTCAATGA | TAGGATGACA | ACGGAGGAAA | 400 |
| N L W | Y L S Q | V N D | R M T | T E E R | |
| GAGAACGATT | CCCCACAGGG | CAGCAGGCAG | TTCCCAGTGT | AGCTCCTCAT | 450 |
| E R F | P T G | Q Q A V | P S V | A P H | |
| TGGGACACAG | AATCAGAACA | TGGAGATTGG | TGCCGCAGAC | ATTTACAACT | 500 |
| W D T E | S E H | G D W | C R R H | L Q L | |
| TGCGTGCTAN | AAGGACTNAG | GAAAACTAGG | AAGACTANGA | ATTATTCAAN | 550 |
| A C X | K D X G | K L G | R L X | I I Q X | |
| GATGTCCACT | ANNACACAGG | GGAAAGGAAG | AAAATCCTAC | TGCCTTTCTG | 600 |
| C P L | X H R | G K E E | N P T | A F L | |
| GAGAGACTAA | GGGAGGCATT | GAGGAAGCAT | ACCAGGCAAG | TGGACATTGG | 650 |
| E R L R | E A L | R K H | T R Q V | D I G | |
| AGGCTCTGGA | AAAGGGAAAA | GTTGGGCAAA | TTATATGCCT | AATAGGGCTT | 700 |
| G S G | K G K S | W A N | Y M P | N R A C | |
| GCTTCCAGTG | CAGTCTACAA | GGACGCTTTA | GAAAAGATTG | TCCAAGTAGA | 750 |
| F Q C | S L Q | G R F R | K D C | P S R | |
| AATAAGCCGC | CCCTCGTCCA | TGCCCCTTAT | GTCAAGGGAA | TCACTGGAAG | 800 |
| N K P P | L V H | A P Y | V K G I | T G R | |
| GCCTACTGCC | CCAGGGGACG | AAGGTCCTCT | GAGTCAGAAG | CCACTAACCT | 850 |
| P T A | P G D E | G P L | S Q K | P L T . | |
| GA | | | | | 852 |

FIG. 38a

```
        10          20          30          40          50
1234567890  1234567890  1234567890  1234567890  1234567890
AAGGAAACTC  AGAAAGCCAA  TACCCATTTA  GTAAGATGGA  CACCAGAAGC    50
K  E  T  Q   K  A  N     T  H  L     V  R  W  T   P  E  A
 R  K  L    R  K  P  I   P  I  .     .  D  G    H  Q  K  Q
  G  N  S    E  S  Q    Y  P  F  S    K  M  D    T  R  S

AGAAGCAGCT  TTCCAGGCCC  TAAAGAAATC  CCTAACCCAA  GCCCCAGTGT   100
 E  A  A    F  Q  A  L   K  K  S     L  T  Q    A  P  V  L
  K  Q  L    S  R  P    .  R  N  P   .  P  K     P  Q  C
R  S  S  F   P  G  P    K  E  I     P  N  P  S   P  S  V

TAAGCTTGCC  AACGGGGCAA  GACTTTTCTT  TATATGTCAC  AGAAAAACAG   150
 S  L  P    T  G  Q     D  F  S  L   Y  V  T     E  K  Q
  A  C  Q    R  G  K     T  F  L    Y  M  S  Q   K  N  R
K  L  A     N  G  A  R   L  F  F     I  C  H    R  K  T  G

GAATAGCTCT  AGGAGTCCTT  ACACAGGTCC  AAGGGACAAG  CTTGCAACCT   200
E  .  L  .   E  S  L     H  R  S    K  G  Q  A   C  N  L
 N  S  S    R  S  P  Y    T  G  P    R  D  K    L  A  T  C
  I  A  L    G  V  L    T  Q  V  Q    G  T  S    L  Q  P

GTGGCATACC  TGAGTAAGGA  AACTGATGTA  NTGGCAAAGG  GTTGGCCTCA   250
W  H  T     .  V  R  K   L  M  X    W  Q  R     V  G  L  I
 G  I  P    E  .  G     N  .  C  X   G  K  G     L  A  S
V  A  Y  L   S  K  E    T  D  V     X  A  K  G   W  P  H

TTGTTTACAG  GTAGGGCAGC  AGTAGCAGTC  TTAGTTTCTG  AAACAGTTAA   300
 V  Y  R    .  G  S     S  S  S  L   S  F  .     N  S  .
L  F  T  G   R  A  A    V  A  V     L  V  S  E   T  V  K
 C  L  Q    V  G  Q  Q   .  Q  S     .  F  L    K  Q  L  K

AATAATACAG  GGAAGAGATC  TTACTGTGTG  GACATCTCAT  GATGTGAACG   350
N  N  T  G   K  R  S     Y  C  V    D  I  S  .   C  E  R
 I  I  Q    G  R  D  L    T  V  W    T  S  H    D  V  N  G
 .  Y  R     E  E  I    L  L  C  G   H  L  M     M  .  T

GCATACTCAC  TGCTAAAGAG  GACTTGTGGC  TGTCAGACAA  CCATTTACTT   400
 H  T  H    C  .  R  G   L  V  A     V  R  Q    P  F  T
  I  L  T    A  K  E    D  L  W  L    S  D  N    H  L  L
A  Y  S  L   L  K  R     T  C  G    C  Q  T  T   I  Y  L

AAATAGCAGG  TTCTATTACT  TGAAGTGCCA  GTGCTGCGAC  TGCACATTTG   450
 I  A  G     S  I  T    .  S  A  S   A  A  T     A  H  L
K  .  Q  V   L  L  L     E  V  P    V  L  R  L   H  I  C
 N  S  R    F  Y  Y  L   K  C  Q     C  C  D    C  T  F  V

TGCAACTCTT  AACCCAGCCA  CATTTCTTCC  AGACAATGAA  GAAAAGATAG   500
C  N  S  .   P  S  H     I  S  S    R  Q  .  R   K  D  R
 A  T  L    N  P  A  T    F  L  P    D  N  E     E  K  I  E
  Q  L  L    T  Q  P    H  F  F  Q    T  M  K     K  R  .
```

FIG. 38b

| 10<br>1234567890 | 20<br>1234567890 | 30<br>1234567890 | 40<br>1234567890 | 50<br>1234567890 | |
|---|---|---|---|---|---|
| AACATAACTG | TCAACAAGTA | ATTGCTCAAA | CCTATGCTGC | TCGAGGGGAC | 550 |
| T . L | S T S N | C S N | L C C | S R G P | |
| H N C | Q Q V | I A Q T | Y A A | R G D | |
| N I T V | N K . | L L K | P M L L | E G T | |
| CTTCTAGAGG | TTCCCTTGAC | TGATCCCGAC | CTCAACTTGT | ATACTGATGG | 600 |
| S R G | S L D | . S R P | Q L V | Y . W | |
| L L E V | P L T | D P D | L N L Y | T D G | |
| F . R | F P . L | I P T | S T C | I L M E | |
| AAGTTCCTTG | GCAGAAAAAG | GACTTTGAAA | AGCGGGGTAT | GCAGTGATCA | 650 |
| K F L G | R K R | T L K | S G V C | S D Q | |
| S S L | A E K G | L . K | A G Y | A V I S | |
| V P W | Q K K | D F E K | R G M | Q . S | |
| GTGATAATGG | AATACTTGAA | AGTAATCGCC | TCACTCCAGG | AACTAGTGCT | 700 |
| . . W | N T . K | . S P | H S R | N . C S | |
| D N G | I L E | S N R L | T P G | T S A | |
| V I M E | Y L K | V I A | S L Q E | L V L | |
| CACCTGGCAG | AACTAATAGC | CCTCACTTGG | GCACTAGAAT | TAGGAGAAGG | 750 |
| P G R | T N S | P H L G | T R I | R R R | |
| H L A E | L I A | L T W | A L E L | G E G | |
| T W Q | N . . P | S L G | H . N | . E K E | |
| AAAAAGGGTA | AATATATATT | CAGACTCTAA | GTATGCTTAC | CTAGTCCTCC | 800 |
| K K G K | Y I F | R L . | V C L P | S P P | |
| K R V | N I Y S | D S K | Y A Y | L V L H | |
| K G . | I Y I | Q T L S | M L T | . S S | |
| ATGCCCATGC | AGCAATATGG | AGAGAGAGGG | AATTCCTAAC | TTCTGAGGGA | 850 |
| C P C | S N M E | R E G | I P N | F . G N | |
| A H A | A I W | R E R E | F L T | S E G | |
| M P M Q | Q Y G | E R G | N S . L | L R E | |
| ACACCTATCA | ACCATCAGGG | AAGCCATTAG | GAGATTATTA | TTGGCTGTAC | 900 |
| T Y Q | P S G | K P L G | D Y Y | W L Y | |
| T P I N | H Q G | S H . | E I I I | G C T | |
| H L S | T I R E | A I R | R L L | L A V Q | |
| AGAAACCTAA | AGAGGTGGCA | GTCTTACACT | GCCAGGGTCA | TCAGGAAGAA | 950 |
| R N L K | R W Q | S Y T | A R V I | R K K | |
| E T . | R G G S | L T L | P G S | S G R R | |
| K P K | E V A | V L H C | Q G H | Q E E | |
| GAGGAAAGGG | AAATAGAAGG | CAATCGCCAA | GCGGATATTG | AAGCAAAAAA | 1000 |
| R K G | K . K A | I A K | R I L | K Q K K | |
| G K G | N R R | Q S P S | G Y . | S K K | |
| E E R E | I E G | N R Q | A D I E | A K K | |

FIG. 38c

```
         10          20          30          40          50
 1234567890  1234567890  1234567890  1234567890  1234567890
 AGCCGCAAGG  CAGGACTCTC  CATTAGAAAT  GCTTATAGAA  GGACCCCTAG      1050
  P  Q  G     R  T  L    H  .  K  C    L  .  K    D  P  .
 S  R  K  A    G  L  S    I  R  N    A  Y  R  R    T  P  S
  A  A  R    Q  D  S  P    L  E  M    L  I  E    G  P  L  V

 TATGGGGTAA  TCCCCTCTGG  GAAACCAAGC  CCCAGTACTC  AGCAGGAAAA      1100
 Y  G  V  I    P  S  G    K  P  S    P  S  T  Q    Q  E  K
  M  G  .    S  P  L  G    N  Q  A    P  V  L    S  R  K  N
   W  G  N    P  L  W    E  T  K  P    Q  Y  S    A  G  K

 ATAGAATAGG  AAACCTCACA  AGGACATACT  TTCCTCCCCT  CCAGATGGCT      1150
 .  N  R    K  P  H  K    D  I  L    S  S  P    P  D  G  .
  R  I  G    N  L  T    R  T  Y  F    P  P  L    Q  M  A
 I  E  .  E    T  S  Q    G  H  T    F  L  P  S    R  W  L

 AGCCACTGAG  GAAGGAA                                             1167
  P  L  R    K  E
 S  H  .  G    R
  A  T  E    E  G
```

FIG. 39a

| 10 | 20 | 30 | 40 | 50 | |
|---|---|---|---|---|---|
| 1234567890 | 1234567890 | 1234567890 | 1234567890 | 1234567890 | |
| AACTTGCGTG | CTAGAAGGAC | TAAGGAAAAC | TAGGAAGACT | ATGAATTATT | 50 |
| N L R A | R R T | K E N | . E D Y | E L F | |
| T C V | L E G L | R K T | R K T | M N Y S | |
| L A C | . K D | . G K L | G R L | . I I | |
| CAATGATGTC | CACTATAACA | CAGGGGAAAG | GAAGAAAATC | CTACTGCCTT | 100 |
| N D V | H Y N T | G E R | K K I | L L P F | |
| M M S | T I T | Q G K G | R K S | Y C L | |
| Q . C P | L . H | R G K | E E N P | T A F | |
| TCTGGAGAGA | CTAAGGGAGG | CATTGAGGAA | GCATACCAGG | CAAGTGGACA | 150 |
| W R D | . G R | H . G S | I P G | K W T | |
| S G E T | K G G | I E E | A Y Q A | S G H | |
| L E R | L R E A | L R K | H T R | Q V D I | |
| TTGGAGGCTC | TGGAAAAGGG | AAAAGTTGGG | CAAATTGAAT | GCCTAATAGG | 200 |
| L E A L | E K G | K V G | Q I E C | L I G | |
| W R L | W K R E | K L G | K L N | A . . G | |
| G G S | G K G | K S W A | N . M | P N R | |
| GCTTGCTTCC | AGTGCAGTCT | ACAAGGACGC | TTTAGAAAAG | ATTGTCCAAG | 250 |
| L A S | S A V Y | K D A | L E K | I V Q V | |
| L L P | V Q S | T R T L | . K R | L S K | |
| A C F Q | C S L | Q G R | F R K D | C P S | |
| TAGAAATAAG | CCGCCCCTCG | TCCATGCCCC | TTATGTCAAG | GGAATCACTG | 300 |
| E I S | R P S | S M P L | M S R | E S L | |
| . K . A | A P R | P C P | L C Q G | N H W | |
| R N K | P P L V | H A P | Y V K | G I T G | |
| GAAGGCCTAC | TGCCCCAGGG | GACGAAGGTC | CTCTGAGTCA | GAAGCCACTA | 350 |
| E G L L | P Q G | T K V | L . V R | S H . | |
| K A Y | C P R G | R R S | S E S | E A T N | |
| R P T | A P G | D E G P | L S Q | K P L | |
| ACCTGATGAT | CCAGCAGCAG | GACTGAGGGT | GCCCGGGGCA | AGTGCCAGCC | 400 |
| P D D | P A A G | L R V | P G A | S A S P | |
| L M I | Q Q Q | D . G C | P G Q | V P A | |
| T . . S | S S R | T E G | A R G K | C Q P | |
| CATGCCATCA | CCCTCAGAGC | CCCGGGTATG | TTTGACCATT | GAGAGCCAGG | 450 |
| C H H | P Q S | P G Y V | . P L | R A R | |
| H A I T | L R A | P G M | F D H | E P G | |
| M P S | P S E P | R V C | L T I | E S Q E | |
| AAGTTAACTG | TCTCCTGGAC | ACTGGCGCAG | CCTTCTCAGT | CTTACTTTCC | 500 |
| K L T V | S W T | L A Q | P S Q S | Y F P | |
| S . L | S P G H | W R S | L L S | L T F L | |
| V N C | L L D | T G A A | F S V | L L S | |

FIG. 39b

```
         10         20         30         40         50
1234567890 1234567890 1234567890 1234567890 1234567890
TGTCCCAGAC AATTGTCCTC CAGATCTGTC ACTATCCGAG GGGTCCTAAG    550
 V  P  D   N  C  P  P   D  L  S   L  S  E   G  S  .  D
  S  Q  T   I  V  L   Q  I  C  H   Y  P  R   G  P  K
C  P  R  Q  L  S  S   R  S  V   T  I  R  G   V  L  R

ACAGCCAGTC ACTACATACT TCTCTCAGCC ACTAAGTTGT GACTGGGGAA    600
 S  Q  S   L  H  T   S  L  S  H   .  V  V   T  G  E
T  A  S  H  Y  I  L   L  S  A   T  K  L  .   L  G  N
 Q  P  V   T  T  Y  F  S  Q  P   L  S  C   D  W  G  T

CTTTACTCTT TTCACATGCT TTTCTAATTA TGCCTGAAAG CCCCACTCCC    650
L  Y  S  F  H  M  L   F  .  L   C  L  K  A   P  L  P
 F  T  L   F  T  C  F  S  N  Y   A  .  K   P  H  S  L
  L  L  F   S  H  A   F  L  I  M   P  E  S   P  T  P

TTGTTAGGGA GAGACATTTT AGCAAAAGCA GGGGCCATTA TACACCTGAA    700
 C  .  G   E  T  F  .   Q  K  Q   G  P  L   Y  T  .  T
 V  R  E   R  H  F   S  K  S  R   G  H  Y   T  P  E
L  L  G  R  D  I  L   A  K  A   G  A  I  I   H  L  N

CATAGGAAAA GGAATACCCA TTTGCTGTCC CCTGCTTGAG GAAGGAATTA    750
 .  E  K   E  Y  P   F  A  V  P   C  L  R   K  E  L
H  R  K  R  N  T  H   L  L  S   P  A  .  G   R  N  .
 I  G  K   G  I  P  I  C  C  P   L  L  E   E  G  I  N

ATCCTGAAGT CTGGGCAATA GAAGGACAAT ATGGACAAGC AAAGAATGCC    800
I  L  K  S  G  Q  .   K  D  N   M  D  K  Q   R  M  P
 S  .  S   L  G  N  R  R  T  I   W  T  S   K  E  C  P
  P  E  V   W  A  I   E  G  Q  Y  G  Q  A   K  N  A

CGTCCTGTTC AAGTTAAACT AAAGGATTCT GCCTCCTTTC CCTACCAAAG    850
V  L  F    K  L  N  .  R  I  L   P  P  F   P  T  K  G
 S  C  S   S  .  T   K  G  F  C   L  L  S   L  P  K
R  P  V  Q  V  K  L   K  D  S   A  S  F  P   Y  Q  R

GAAGTACCCT CTTAGACCCG AGGCCCTACA AGGACTCAAA AGATTGTTAA    900
 S  T  L   L  D  P   R  P  Y  K   D  S  K   D  C  .
E  V  P  S  .  T  R   G  P  T   R  T  Q  K   I  V  K
 K  Y  P   L  R  P  E  A  L  Q   G  L  K   R  L  L  R

GGACCTAAAA GCCCAAGGCC TAGTAAAACC ATGCAGTAGC CCCTGCAATA    950
G  P  K  S  P  R  P   S  K  T   M  Q  .  P   L  Q  Y
 D  L  K   A  Q  G  L  V  K  P   C  S  S   P  C  N  T
  T  .  K   P  K  A   .  .  N  H  A  V  A   P  A  I

CTCCAATTTT AGGAGTAAGG AAACCCAACG GACAGTGGAG GTTAGTGCAA   1000
 S  N  F   R  S  K  E   T  Q  R   T  V  E   V  S  A  R
 P  I  L   G  V  R   K  P  N  G   Q  W  R   L  V  Q
L  Q  F  .  E  .  G   N  P  T   D  S  G  G   .  C  K
```

FIG. 39c

| 10<br>1234567890 | 20<br>1234567890 | 30<br>1234567890 | 40<br>1234567890 | 50<br>1234567890 | |
|---|---|---|---|---|---|
| GATCTCAGGA | TTATTAATGA | GGCTGTTTTT | CCTCTATACC | CAGCTGTATC | 1050 |
| S Q D | Y . . | G C F S | S I P | S C I | |
| D L R I | I N E | A V F | P L Y P | A V S | |
| I S G | L L M R | L F F | L Y T | Q L Y L | |
| TAGCCCTTAT | ACTCTGCTTT | CCCTAATACC | AGAGGAAGCA | GAGTAGTTTA | 1100 |
| . P L Y | S A F | P N T | R G S R | V V Y | |
| S P Y | T L L S | L I P | E E A | E . F T | |
| A L I | L C F | P . Y Q | R K Q | S S L | |
| CAGTCCTGGA | CCTTAAGGAT | GCCTCTTTCT | GCATCCCTGT | ACATCCTGAT | 1150 |
| S P G | P . G C | L F L | H P C | T S . F | |
| V L D | L K D | A S F C | I P V | H P D | |
| Q S W T | L R M | P L S | A S L Y | I L I | |
| TCTCAATTCT | TGTTTGTCTT | TGAAGATCCT | TTGAACCCAA | TGTCTCAATT | 1200 |
| S I L | V C L | . R S F | E P N | V S I | |
| S Q F L | F V F | E D P | L N P M | S Q F | |
| L N S | C L S L | K I L | . T Q | C L N S | |
| CACCTGGACT | GTTTTACCCC | AGGGGTTCCG | GGATAGCCCC | CATCTATTTG | 1250 |
| H L D C | F T P | G V P | G . P P | S I W | |
| T W T | V L P Q | G F R | D S P | H L F G | |
| P G L | F Y P | R G S G | I A P | I Y L | |
| GCCAGGCATT | AGCCCAAGAC | TTGAGCCAAT | TCTCATACCT | GGACATCTTG | 1300 |
| P G I | S P R L | E P I | L I P | G H L V | |
| Q A L | A Q D | L S Q F | S Y L | D I L | |
| A R H . | P K T | . A N | S H T W | T S C | |
| TCCTTCGGTA | TGGGATGATT | TAATTTTAGC | CACCCGTTCA | GAAACCTTGT | 1350 |
| L R Y | G M I | . F . P | P V Q | K P C | |
| S F G M | G . F | N F S | H P F R | N L V | |
| P S V | W D D L | I L A | T R S | E T L C | |
| GCCATCAAGC | CACCCAAGCG | TTCTTAAATT | TCCTCACTCC | GTGTGGCTAC | 1400 |
| A I K P | P K R | S . I | S S L R | V A T | |
| P S S | H P S V | L K F | P H S | V W L Q | |
| H Q A | T Q A | F L N F | L T P | C G Y | |
| AAGGTTTCCA | AACCAAAGGC | TCAGCTCTGC | TCACAGCAGG | TTAAATACTT | 1450 |
| R F P | N Q R L | S S A | H S R | L N T . | |
| G F Q | T K G | S A L L | T A G | . I L | |
| K V S K | P K A | Q L C | S Q Q V | K Y L | |
| AGGGTTAAAA | TTATCCAAAG | GCACCAGGGC | CCTCTGTGAG | GAATGTATCC | 1500 |
| G . N | Y P K | A P G P | S V R | N V S | |
| R V K I | I Q R | H Q G | P L . G | M Y P | |
| G L K | L S K G | T R A | L C E | E C I Q | |

FIG. 39d

```
          10         20         30         40         50
 1234567890 1234567890 1234567890 1234567890 1234567890
 AACCTGTACT GGCTTATCTT CATCCCAAAA CCCTAAAGCA ACTAAGAAGG        1550
 N  L  Y  W   L  I  F   I  P  K   P  .  S  N    .  E  G
  T  C  T   G  L  S  S   S  Q  N   P  K  A   T  K  K  V
   P  V  L   A  Y  L   H  P  K  T   L  K  Q   L  R  R

 TCCTTGGCAT AACAGGTTTC TGCCGAA                                 1577
  P  W  H   N  R  F  L   P
   L  G  I   T  G  F   C  R
 S  L  A  .   Q  V  S   A  E
```

FIG. 40

| 10<br>1234567890 | 20<br>1234567890 | 30<br>1234567890 | 40<br>1234567890 | 50<br>1234567890 | |
|---|---|---|---|---|---|
| TCCAGCAGCA<br>S S S R | GGACTGAGGG<br>T E G | TGCCCGGGGC<br>A R G | AAGTGCCAGC<br>K C Q P | CCATGCCATC<br>M P S | 50 |
| ACCCTCAGAG<br>P S E | CCCCGGGTAT<br>P R V C | GTTTGACCAT<br>L T I | TGAGAGCCAG<br>E S Q | GAAGTTAACT<br>E V N C | 100 |
| GTCTCCTGGA<br>L L D | CACTGGCGCA<br>T G A | GCCTTCTCAG<br>A F S V | TCTTACTTTC<br>L L S | CTGTCCCAGA<br>C P R | 150 |
| CAATTGTCCT<br>Q L S S | CCAGATCTGT<br>R S V | CACTATCCGA<br>T I R | GGGGTCCTAA<br>G V L R | GACAGCCAGT<br>Q P V | 200 |
| CACTACATAC<br>T T Y | TTCTCTCAGC<br>F S Q P | CACTAAGTTG<br>L S C | TGACTGGGGA<br>D W G | ACTTTACTCT<br>T L L F | 250 |
| TTTCACATGC<br>S H A | TTTTCTAATT<br>F L I | ATGCCTGAAA<br>M P E S | GCCCCACTCC<br>P T P | CTTGTTAGGG<br>L L G | 300 |
| AGAGACATTT<br>R D I L | TAGCAAAAGC<br>A K A | AGGGGCCATT<br>G A I | ATACACCTGA<br>I H L N | ACATAGGAAA<br>I G K | 350 |
| AGGAATACCC<br>G I P | ATTTGCTGTC<br>I C C P | CCCTGCTTGA<br>L L E | GGAAGGAATT<br>E G I | AATCCTGAAG<br>N P E V | 400 |
| TCTGGGCAAT<br>W A I | AGAAGGACAA<br>E G Q | TATGGACAAG<br>Y G Q A | CAAAGAATGC<br>K N A | CCGTCCTGTT<br>R P V | 450 |
| CAAGTTAAAC<br>Q V K L | TAAAGGATTC<br>K D S | TGCCTCCTTT<br>A S F | CCCTACCAAA<br>P Y Q R | GGAAGTACCC<br>K Y P | 500 |
| TCTTAGACCC<br>L R P | GAGGCCCTAC<br>E A L Q | AAGGACTCAA<br>G L K | AAGATTGTTA<br>R L L | AGGACCT<br>R T | 547 |

FIG. 44

```
                  c g  a
PAN-UO      5'-ıtggaaagtgttacccc-3' (SEQ ID NO: 187)

PAN-UI      5'-ıagtgttaccccaagg-3' (SEQ ID NO: 188)
                 c g  a  g

                                                                                  c      g g
PAN-DI                                                    (SEQ ID NO: 189) 3'-atgtacctactgtacgac¬-5

                                                      (SEQ ID NO: 190)
HTLV-1      tggaaagtactaccccaagg  gtttaaaaatagtcccaccctgttcgaaatgcagctggcccatatcctgcagcccattcggcaagctttcccccaatgcactattcttcag  tacatggatgacattctc
            W K V L P Q G  F K N S P T L F E M Q L A H I L Q P I R Q A F P Q C T I L Q  Y M D D I L

                                                      (SEQ ID NO: 191)
HIV-1       tacaatgtgcttccacaggg  atggaaaggatcaccagcaatattccaaagtagcatgacaaaaatcttagagccttttaaaaaacaaaatccagacatagttatctatcaa  tacatggatgatttgtat
            Y N V L P Q G  W K G S P A I F Q S S M T K I L E P F K K Q N P D I V I Y Q  Y M D D L Y

                                                      (SEQ ID NO: 192)
MoMLV       tggaccagactccccacaggg  tttcaaaaacagtcccaccctgtttgatgaggcactgcacagagacctagcagacttccggatccagcacccagacttgatcctgctacag  tacgtggatgacttactg
            W T R L P Q G  F K N S P T L F D E A L H R D L A D F R I Q H P D L I L L Q  Y V D D L L

                                                      (SEQ ID NO: 193)
MPMV        tggaaggttttaccacaagg  tatggccaacagtcctaccttatgtcaaaaatatgtggccacagccatacataaggttagacatgcctggaaacaaatgtatattatacat  tacatggatgacatccta
            W K V L P Q G  M A N S P T L C Q K Y V A T A I H K V R H A W K Q M Y I I H  Y M D D I L

                                                      (SEQ ID NO: 194)
ERV9        tggatggtcttgccccaagg  gtttagggatagccctcatctgtttggtcaggccctagccaaagatctaggccacttctcaagtccaggc------actctggtccttcaa  tatgtggatgatttactt
            W M V L P Q G  F R D S P H L F G Q A L A K D L G H F S S P G - - T L V L Q  Y V D D L L

                                                      (SEQ ID NO: 195)
MSRV-cpol                         gttcagggatagcccccatctatttggccaggcattagcccaagacttgagccaattctcatacctggac------actcttgtccttcag
                                   F R D S P H L F G Q A L A Q D L S Q F S Y L D - - T L V L Q
                                     K                           Y                        R
                                                                                          W

DpV1                                 Perox-5'-catctitttggicaggcaitagc-3'

CpV1B                                                      5'-cttgagccagttctcatacctgga-3' (SEQ ID NO: 197)
```

FIG 48A

```
           10         20         30         40         50
  1234567890 1234567890 1234567890 1234567890 1234567890
  ATGATCCAGC AGCAGGACNG AGGGTGCCCG GGGCAAGCGC CAGCCCATGC     50
  M  I  Q  Q   Q  D  X  G  C  P  G  Q  A  P   A  H  A

  CATCACCCTC ACAGAGCCCC AGGTATGCTT GACCATTGAG GGTCAGAAGG    100
   I  T  L   T  E  P  Q   V  C  L   T  I  E   G  Q  K  G

  GTNACTGTCT CCTGGACACT GGCGGNGCCT TCTCAGTCTT ACTTTCCTGT    150
   X  C  L   L  D  T   G  G  A  F   S  V  L   L  S  C

  CCTGGACAAC TGTCCTCCAG ATCTGTCACT GTCCGAGGGG TCCTAGGACA    200
  P  G  Q  L   S  S  R   S  V  T   V  R  G  V   L  G  Q

  GCCAGTCACT AGATACTTCT CCCAGCCACT AAGTTGTGAC TGGGGAACTT    250
   P  V  T   R  Y  F  S   Q  P  L   S  C  D   W  G  T  L

  TACTCTTCCC ACATGCTTTT CTAATTATGC CTGAAAGCCC CACTCTCTTG    300
   L  F  P   H  A  F   L  I  M  P   E  S  P   T  L  L

  TTGGGGAGAG ACATTCTAGC AAAAGCAGGG GCCATTATAC ATGTGAATAT    350
  L  G  R  D   I  L  A   K  A  G   A  I  I  H   V  N  I

  AGGAGAAGGA ACAACTGTTT GTTGTCCCCT GCTTGAGGAA GGAATTAATC    400
   G  E  G   T  T  V  C   C  P  L   L  E  E   G  I  N  P

  CTGAAGTCCG GGCAACAGAA GGACAATATG GACAAGCAAA GAATGCCCGT    450
   E  V  R   A  T  E   G  Q  Y  G   Q  A  K   N  A  R

  CCTGTTCAAG TTAAACTAAA GGATTCCACC TCCTTTCCCT ACCAAAGGCA    500
  P  V  Q  V   K  L  K   D  S  T   S  F  P  Y   Q  R  Q
```

FIG 48B

```
           10         20         30         40         50
   1234567890 1234567890 1234567890 1234567890 1234567890
   GTACCCCCTC AGACCCGAGA CCCAACAAGA ACTCCAAAAG ATTGTAAAGG   550
    Y  P  L  R  P  E  T  Q  Q  E  L  Q  K  I  V  K  D

   ACCTAAAAGC CCAAGGCCTA GTAAAACCAA GCAATAGCCC TTGCAAGACT   600
     L  K  A  Q  G  L  V  K  P  S  N  S  P  C  K  T

   CCAATTTTAG GAGTAAGGAA ACCCAACGGA CAGTGGAGGT TAGTGCAAGA   650
   P  I  L  G  V  R  K  P  N  G  Q  W  R  L  V  Q  E

   ACTCAGGATT ATCAATGAGG CTGTTGTTCC TCTATACCCA GCTGTACCTA   700
    L  R  I  I  N  E  A  V  V  P  L  Y  P  A  V  P  N

   ACCCTTATAC AGTGCTTTCC CAAATACCAG AGGAAGCAGA GTGGTTTACA   750
     P  Y  T  V  L  S  Q  I  P  E  E  A  E  W  F  T

   GTCCTGGACC TTAAGGATGC CTTTTTCTGC ATCCCTGTAC GTCCTGACTC   800
   V  L  D  L  K  D  A  F  F  C  I  P  V  R  P  D  S

   TCAATTCTTG TTTGCCTTTG AAGATCCTTT GAACCCAACG TCTCAACTCA   850
    Q  F  L  F  A  F  E  D  P  L  N  P  T  S  Q  L  T

   CCTGGACTGT TTTACCCCAA GGGTTCAGGG ATAGCCCCCA TCTATTTGGC   900
     W  T  V  L  P  Q  G  F  R  D  S  P  H  L  F  G

   CAGGCATTAG CCCAAGACTT GAGTCAATTC TCATACCTGG ACACTCTTGT   950
   Q  A  L  A  Q  D  L  S  Q  F  S  Y  L  D  T  L  V

   CCTTCAGTAC ATGGATGATT TACTTTTAGT CGCCCGTTCA GAAACCTTGT  1000
    L  Q  Y  M  D  D  L  L  L  V  A  R  S  E  T  L  C
```

FIG 48C

```
         10         20         30         40         50
 1234567890 1234567890 1234567890 1234567890 1234567890
GCCATCAAGC CACCCAAGAA CTCTTAACTT TCCTCACTAC CTGTGGCTAC    1050
  H  Q  A   T  Q  E  L  L  T  F   L  T  T  C  G  Y

AAGGTTTCCA AACCAAAGGC TCGGCTCTGC TCACAGGAGA TTAGATACTN    1100
K  V  S  K  P  K  A  R  L  C  S  Q  E  I   R  Y  X

AGGGCTAAAA TTATCCAAAG GCACCAGGGC CCTCAGTGAG GAACGTATCC    1150
 G  L  K  L  S  K  G  T  R  A  L  S  E  E  R  I  Q

AGCCTATACT GGCTTATCCT CATCCCAAAA CCCTAAAGCA ACTAAGAGGG    1200
  P  I  L  A  Y  P  H  P  K  T  L  K  Q  L  R  G

TTCCTTGGCA TAACAGGTTT CTGCCGAAAA CAGATTCCCA GGTACASCCC    1250
F  L  G  I  T  G  F  C  R  K  Q  I  P  R  Y  X  P

AATAGCCAGA CCATTATATA CACTAATTAN GGAAACTCAG AAAGCCAATA    1300
  I  A  R  P  L  Y  T  L  I  X  E  T  Q  K  A  N  T

CCTATTTAGT AAGATGGACA CCTACAGAAG TGGCTTTCCA GGCCCTAAAG    1350
  Y  L  V  R  W  T  P  T  E  V  A  F  Q  A  L  K

AAGGCCCTAA CCCAAGCCCC AGTGTTCAGC TTGCCAACAG GGCAAGATTT    1400
K  A  L  T  Q  A  P  V  F  S  L  P  T  G  Q  D  F

TTCTTTATAT GCCACAGAAA AAACAGGAAT AGCTCTAGGA GTCCTTACGC    1450
 S  L  Y  A  T  E  K  T  G  I  A  L  G  V  L  T  Q

AGGTCTCAGG GATGAGCTTG CAACCCGTGG TATACCTGAG TAAGGAAATT    1500
  V  S  G  M  S  L  Q  P  V  V  Y  L  S  K  E  I
```

FIG 48D

```
          10         20         30         40         50
1234567890 1234567890 1234567890 1234567890 1234567890
GATGTAGTGG CAAAGGGTTG GCCTCATNGT TTATGGGTAA TGGNGGCAGT    1550
D  V  V  A   K  G  W   P  H  X   L  W  V  M   X  A  V

AGCAGTCTNA GTATCTGAAG CAGTTAAAAT AATACAGGGA AGAGATCTTN    1600
 A  V  X   V  S  E  A   V  K  I   I  Q  G   R  D  L  X

CTGTGTGGAC ATCTCATGAT GTGAACGGCA TACTSRCTGC TAAAGGAGAC    1650
 V  W  T   S  H  D   V  N  G  I   L  X  A   K  G  D

TTGTGGTTGT CAGACAACCA TTTACTTAAN TAYCAGGCYY TATTACTTGA    1700
L  W  L  S   D  N  H   L  L  X   Y  Q  A  L   L  L  E

AGAGCCAGTG CTGNGACTGC GCACTTGTCC AACTCTTAAA CCCAAACTTA    1750
 E  P  V   L  X  L  R   T  C  P   T  L  K   P  K  L  M

TGCTGCCCAG AAGGATCTTT NTAGAGGTCC CCTTAGCCAA CCCTGACCTC    1800
 L  P  R   R  I  F   X  E  V  P   L  A  N   P  D  L

AACTATATAT ATACTGATGG AAGTTCGTTT GTAGAAAAGG GATTACAAAG    1850
N  Y  I  Y   T  D  G   S  S  F   V  E  K  G   L  Q  R

GGNAGGATAT NCCATAGGTG TTAGTGATAA AGCAGTACTT GAAAGTAAGC    1900
 X  G  Y   X  I  G  V   S  D  K   A  V  L   E  S  K  P

CTCTTCCCCC CCAGGGACCA GCGCCCCCGT TAGCAGAACT AGTGGCACTG    1950
 L  P  P   Q  G  P   A  P  P  L   A  E  L   V  A  L

ACCCCGCGAG CCTTAGAACT TTGGAAAGGG AGGAGGATAA ATGTGTATAC    2000
T  P  R  A   L  E  L   W  K  G   R  R  I  N   V  Y  T
```

FIG 48E

```
         10         20         30         40         50
1234567890 1234567890 1234567890 1234567890 1234567890
AGATAGCAAG TATGCTTATC TAATCCGAAA TGCCCATGTT GCAATATGGA    2050
 D  S  K  Y  A  Y  L  I  R  N  A  H  V  A  I  W  K

AAGAAAGGGA GTTCCTAACC TCTGGGGGAA CCCCCATTAA ATACCACAAG    2100
  E  R  E  F  L  T  S  G  G  T  P  I  K  Y  H  K

TTAATCATGG AGTTATTGCA CACAGTGCAA AAACTCAAGG AGGTGGAAGT    2150
L  I  M  E  L  L  H  T  V  Q  K  L  K  E  V  E  V

CTTACACTGC CAAAGCCATC AGAAAAGGGA AAGAGGGGAA GAGCAGCATA    2200
 L  H  C  Q  S  H  Q  K  R  E  R  G  E  E  Q  H  K

AGTGGCTACA GAGGCAAGGA AAGACTAGCA GAAAGGAAAG AGAGAAAGAG    2250
  W  L  Q  R  Q  G  K  T  S  R  K  E  R  E  K  E

ACAGAAAGTC AGAGAGAGAG AGAGGAAGAG ACAGAGCACA AAGAGGGAGT    2300
T  E  S  Q  R  E  R  E  E  E  T  E  H  K  E  G  V

CAGAGAGAGA GAGAGACAGA GAGTCAGAGA GAAGGAAAGA GAGAGAGGAA    2350
 R  E  R  E  R  Q  R  V  R  E  K  E  R  E  R  G  R

GAGACAAAGA ATGA                                           2364
  D  K  E  .
```

FIG 49A

```
Complement of 8/46-7 propre     GACTTGAGCC AGTCCTCATA CCTGGACATT CTTGTTCATC AGTATAGGGA   50
1 /46-7 propre                  GACTTGAGCC AGTCCTCATA CCTGGACATT CTTGTTCCTC AGTATGGGGA   50
Complement of c15 propre 46-7   GACTTGAGCC AGTCCTCATA CCTGGACATT CTTGTTCCTC AGTATGGGGA   50
Consensus                       GACTTGAGCC AGTCCTCATA CCTGGACATT CTTGTTCMTC AGTATRGGGA   50

Complement of 8/46-7 propre     TGATTTAATT ATAGCCACCC ATTCAGAAAC CTTGTGGCAT CAAGCCACCC   100
1 /46-7 propre                  TGACTTAATT ATAGCCACCC ATTCAGAAAC CTTGTGGCAT CAAGCCACCC   100
Complement of c15 propre 46-7   TGATTTAATT ATAGCCACCC ATTCAGAAAC CTTGTGGCAC CAAGCCACCC   100
Consensus                       TGAMTTAATT ATAGCCACCC ATTCAGAAAC CTTGTGGCAY CAAGCCACCC   100

Complement of 8/46-7 propre     AAGTGCTCTT AAATTTCCTC GCTACCTGTG GCTCCAAACA AAGGGCTCAG   150
1 /46-7 propre                  AAGCGCTCTT AAATTTCCTT GCTACCTGTG GCTCCAAACA AAAGGCTCAC   150
Complement of c15 propre 46-7   AAGCGCTCTT AAATTTCCTC GCTACCTGTG GCTCCAAACA AAAGGCTCAG   150
Consensus                       AAGYGCTCTT AAATTTCCTY GCTACCTGTG GCTCCAAACA AARGGCTCAS   150

Complement of 8/46-7 propre     CTCTGCTCAC AGCAGGTTAA ATACTTAGGG CTAAAATTAT CCAAAGTCGC   200
1 /46-7 propre                  CTCTGCTCAC ACCAGGTTAA ATACTTAGGG CTAAAATTAT CCAAAGTCAC   200
Complement of c15 propre 46-7   CTCTGCTCAC AGCAGGTTAA ATACTTAGGG CTAAAATTAT CCAAAGTCAC   200
Consensus                       CTCTGCTCAC ASCAGGTTAA ATACTTAGGG CTAAAATTAT CCAAAGTCRC   200

Complement of 8/46-7 propre     CAGGGCCCTC AGAGAGGAAC GTATCCAGCG TATACTGGAT TATCCACATC   250
1 /46-7 propre                  CAGGGCCCTC AGAGAGGAAC GTATCCAGCG TATACTGGCT TATCCCCATC   250
Complement of c15 propre 46-7   CAGGGCCCTC AGAGAGGAAC GTATCCAGCG TATACTGGCT TATCCCCATC   250
Consensus                       CAGGGCCCTC AGAGAGGAAC GTATCCAGCG TATACTGGMT TATCCMCATC   250

Complement of 8/46-7 propre     CCAAAACCAT AAAGCAACTA AGAGGGTTCC TTGGCATAAC AGCCTTCTGC   300
1 /46-7 propre                  CCATAACCCT AAAGCAACTA AGAGGGTTCC TTGGCATATC AGCCTTCTGC   300
Complement of c15 propre 46-7   CCAAAACCCT AAAGCAACTA AGAAGGTTCC TTGGCATAAC AGCCTTCTGC   300
Consensus                       CCAWAACCMT AAAGCAACTA AGARGGTTCC TTGGCATAWC AGCCTTCTGC   300

Complement of 8/46-7 propre     CGAATATGGA TTCCCTGATA CAGTGAAATA GCCAGGCCAT TATGTACATT   350
1 /46-7 propre                  CGAATATGGA TTCCCGGATA CAGTGAAATA GCCAGGCCAT TATGTACATT   350
Complement of c15 propre 46-7   CGAATATGGA TTCCCAGATA CAGCGAAATA GCCAGGCCAT TATGTACATT   350
Consensus                       CGAATATGGA TTCCCVGATA CAGYGAAATA GCCAGGCCAT TATGTACATT   350

Complement of 8/46-7 propre     AGTTAAGGAA ACTCAGAAAG CCAATACCCA TATAGTAAGA TGGACACCTG   400
1 /46-7 propre                  AATTAAGGAA ACTCAGAAAG CCAATACCCA TATAGTAAGA TGGACACCTG   400
Complement of c15 propre 46-7   ATCTAAGGAA ACTCAGAAAG CCAATACCCA TATAGTAAGA TGGACACCTG   400
Consensus                       ADYTAAGGAA ACTCAGAAAG CCAATACCCA TATAGTAAGA TGGACACCTG   400

Complement of 8/46-7 propre     ACACAGAAGT GGCTTTCCAG GCCCTAAAG   429
1 /46-7 propre                  AAACAGAAGT GGCTTTCCAG GCCCTAAAG   429
Complement of c15 propre 46-7   AAACAGAAGT GGCTTTCCAG GCCCTAAAG   429
Consensus                       AMACAGAAGT GGCTTTCCAG GCCCTAAAG   429
```

FIG 49B

```
Trans of 1 /46-7 pr    (8)   DLSQSSYLDI LVLQYGDDLI IATHSETLWH QATQALLNFL ATCGSKQKAH   50
Trans of Complement-2  (5)   DLSQSSYLDI LVLQYRDDLI IATHSETLWH QATQVLLNFL ATCGSKQRAQ   50
Trans of Complement          DLSQSSYLDI LVEQYGDDLI IATHSETLWH QATQALLNFL ATCGSKQRAQ   50
Consensus                    DLSQSSYLDI LVLQYGDDLI IATHSETLWH QATQALLNFL ATCGSKQKAQ   50

Trans of 1 /46-7 pr          LCSHQVKYLG LKLSKVIRAL REERIQRILA YPHPITLKQL RGFLGISAFC  100
Trans of Complement-2        LCSQQVKYLG LKLSKVARAL REERIQRILD YPHPKTIKQL RGFLGIIAFC  100
Trans of Complement          LCSQQVKYLG LKLSKVIRAL REERIQRILA YPHPKTLKQL RRFLGIIAFC  100
Consensus                    LCSQQVKYLG LKLSKVIRAL REERIQRILA YPHPKTLKQL RGFLGIIAFC  100

Trans of 1 /46-7 pr          RIWIPGYSEI ARPLCTLIKE TQKANTHIVR WTPETEVAFQ ALK          143
Trans of Complement-2        RIWIPRYSEI ARPLCTLMKE TQKANTHIVR WTPETEVAFQ ALK          143
Trans of Complement          RIWIPRYSEI ARPLCTLSKE TQKANTHIVR WTPETEVAFQ ALK          143
Consensus                    RIWIPRYSEI ARPLCTL.KE TQKANTHIVR WTPETEVAFQ ALK          143
```

FIG 50B

```
Trans of c143 propr          DLSQSSYLDK LVLRYMDDLL LATHSETLCH QATQALLNFL ATCGYKVSKP   50
Trans of 42/68-1 pr          DLSQSSYLDT LVLRYMDDLL LATHSETLCH QATQALLNFL ATCGYKVSKP   50
Trans of 41/68-1 pr          DLSQSSYLDT LVLRYMDDLL LATHSETLCH QATQALLNFL ATCGYKVSKP   50
Consensus                    DLSQSSYLDT LVLRYMDDLL LATHSETLCH QATQALLNFL ATCGYKVSKP   50

Trans of c143 propr          KAQLCSQQVK YLGLKLSKGT RTLSEERIQP ILGYPHPKTL KQLTAFLGIT  100
Trans of 42/68-1 pr          KAQLCSQQVK YLGLKLSKGT RTLSEERIQP ILGYPHPKTL KQLTAFLGIT  100
Trans of 41/68-1 pr          KAQLCSQQVK YLGLKLSKGT RTLSEERIQP ILGYPHPKTL KQLTAFLGIT  100
Consensus                    KAQLCSQQVK YLGLKLSKGT RTLSEERIQP ILGYPHPKTL KQLTAFLGIT  100

Trans of c143 propr          GFCQIWIPRY SKIARPLNTR IKETQKANTH LVRWTSEAEV AFQALK       146
Trans of 42/68-1 pr          GFCQIWIPRY SKVARPLNTR IKETQKASTH LVRWTHEAEV AFQALK       146
Trans of 41/68-1 pr          GFCQIWIPRY SKIARPLNTR IKETQKANTH LVRWTHEAEV AFQALK       146
Consensus                    GFCQIWIPRY SKIARPLNTR IKETQKANTH LVRWTHEAEV AFQALK       146
```

FIG 50A

| | | |
|---|---|---|
| 41/68-1 propre | GACTTGAGCC AGTCCTCATA CCTGGACACT CTTGTCCTTC GGTACATGGA | 50 |
| c143 propre 68-1 | GACTTGAGCC AGTCATCATA CCTGGACAAT CTTGTCCTTC GGTACATGGA | 50 |
| 42/68-1 propre | GACTTGAGCC AGTCCTCATA CCTGGACACT CTTGTCCTTC GGTACATGGA | 50 |
| Consensus | GACTTGAGCC AGTCMTCATA CCTGGACAMT CTTGTCCTTC GGTACATGGA | 50 |
| 41/68-1 propre | TGATTTACTT TTAGCCACCC ATTCAGAAAC CTTGTGCCAT CAAGCCACCC | 100 |
| c143 propre 68-1 | TGATTTACTT TTAGCCACCC ATTCAGAAAC CTTGTGCCAT CAAGCCACCC | 100 |
| 42/68-1 propre | TGATTTACTT TTAGCCACCC ATTCAGAAAC CTTGTGCCAT CAAGCCACCC | 100 |
| Consensus | TGATTTACTT TTAGCCACCC ATTCAGAAAC CTTGTGCCAT CAAGCCACCC | 100 |
| 41/68-1 propre | AAGCACTCTT AAATTTCCTT GCTACCTGTG GCTACAAGGT TTCCAAACCA | 150 |
| c143 propre 68-1 | AAGCACTCTT AAATTTCCTT GCTACCTGTG GCTACAAGGT TTCCAAACCA | 150 |
| 42/68-1 propre | AAGCACTCTT AAATTTCCTT GCTACCTGTG GCTACAAGGT TTCCAAACCA | 150 |
| Consensus | AAGCACTCTT AAATTTCCTT GCTACCTGTG GCTACAAGGT TTCCAAACCA | 150 |
| 41/68-1 propre | AAGGCTCAGC TCTGCTCACA GCAGGTTAAA TACTTAGGGC TAAAATTATC | 200 |
| c143 propre 68-1 | AAGGCTCAGC TCTGCTCACA GCAGGTTAAA TACTTAGGGC TAAAATTATC | 200 |
| 42/68-1 propre | AAGGCTCAGC TCTGCTCACA GCAGGTTAAA TACTTAGGGC TAAAATTATC | 200 |
| Consensus | AAGGCTCAGC TCTGCTCACA GCAGGTTAAA TACTTAGGGC TAAAATTATC | 200 |
| 41/68-1 propre | CAAAGGCACC AGAACCCTCA GTGAGGAACG TATCCAGCCT ATACTGGGTT | 250 |
| c143 propre 68-1 | CAAAGGCACC AGAACCCTCA GTGAGGAACG TATCCAGCCT ATACTGGGTT | 250 |
| 42/68-1 propre | CAAAGGCACC AGAACCCTCA GTGAGGAACG TATCCAGCCT ATACTGGGTT | 250 |
| Consensus | CAAAGGCACC AGAACCCTCA GTGAGGAACG TATCCAGCCT ATACTGGGTT | 250 |
| 41/68-1 propre | ATCCTCATCC CAAAACCCTA AAGCAACTAA CAGCGTTCCT TGGCATAACA | 300 |
| c143 propre 68-1 | ATCCTCATCC CAAAACCCTA AAGCAACTAA CAGCGTTCCT TGGCATAACA | 300 |
| 42/68-1 propre | ATCCTCATCC CAAAACCCTA AAGCAACTAA CAGCGTTCCT TGGCATAACA | 300 |
| Consensus | ATCCTCATCC CAAAACCCTA AAGCAACTAA CAGCGTTCCT TGGCATAACA | 300 |
| 41/68-1 propre | GGTTTCTGCC AAATATGGAT TCCCAGGTAC AGCAAGATAG CCAGACCATT | 350 |
| c143 propre 68-1 | GGTTTCTGCC AAATATGGAT TCCCAGGTAC AGCAAAATAG CCAGACCATT | 350 |
| 42/68-1 propre | GGTTTCTGCC AAATATGGAT TCCCAGGTAC AGCAAAGTAG CCAGACCATT | 350 |
| Consensus | GGTTTCTGCC AAATATGGAT TCCCAGGTAC AGCAARRTAG CCAGACCATT | 350 |
| 41/68-1 propre | AAATACACGA ATTAAGGAAA CTCAAAAAGC CAATACCCAT TTAGTAAGAT | 400 |
| c143 propre 68-1 | AAATACACGA ATTAAGGAAA CTCAAAAAGC CAATACCCAT TTAGTAAGAT | 400 |
| 42/68-1 propre | AAATACACGA ATTAAGGAAA CTCAAAAAGC CAGTACCCAT TTAGTAAGAT | 400 |
| Consensus | AAATACACGA ATTAAGGAAA CTCAAAAAGC CARTACCCAT TTAGTAAGAT | 400 |
| 41/68-1 propre | GGACACCTGA AGCAGAAGTG GCTTTCCAGG CCCTAAAG | 438 |
| c143 propre 68-1 | GGACAACTGA AGCAGAAGTG GCTTTCCAGG CCCTAAAG | 438 |
| 42/68-1 propre | GGACACCTGA AGCAGAAGTG GCTTTCCAGG CCCTAAAG | 438 |
| Consensus | GGACAMCTGA AGCAGAAGTG GCTTTCCAGG CCCTAAAG | 438 |

FIG 51A

```
MSRV pol          ATTATGCCTG AAAGCCCCAC TCCCTTGTTA GGGAGAGACA TTTTAGCAAA    50
cons ADN 1,5,8    ---------- ---------- ---------- ---------- ----------
Consensus         ATTATGCCTG AAAGCCCCAC TCCCTTGTTA GGGAGAGACA TTTTAGCAAA    50

MSRV pol          AGCAGGGGCC ATTATACACC TGAACATAGG AAAAGGAATA CCCATTTGCT   100
cons ADN 1,5,8    ---------- ---------- ---------- ---------- ----------
Consensus         AGCAGGGGCC ATTATACACC TGAACATAGG AAAAGGAATA CCCATTTGCT   100

MSRV pol          GTCCCCTGCT TGAGGAAGGA ATTAATCCTG AAGTCTGGGC AATAGAAGGA   150
cons ADN 1,5,8    ---------- ---------- ---------- ---------- ----------
Consensus         GTCCCCTGCT TGAGGAAGGA ATTAATCCTG AAGTCTGGGC AATAGAAGGA   150

MSRV pol          CAATATGGAC AAGCAAAGAA TGCCCGTCCT GTTCAAGTTA AACTAAAGGA   200
cons ADN 1,5,8    ---------- ---------- ---------- ---------- ----------
Consensus         CAATATGGAC AAGCAAAGAA TGCCCGTCCT GTTCAAGTTA AACTAAAGGA   200

MSRV pol          TTCTGCCTCC TTTCCCTACC AAAGGAAGTA CCCTCTTAGA CCCGAGGCCC   250
cons ADN 1,5,8    ---------- ---------- ---------- ---------- ----------
Consensus         TTCTGCCTCC TTTCCCTACC AAAGGAAGTA CCCTCTTAGA CCCGAGGCCC   250

MSRV pol          TACAAGGANC TCAAAAGATT GTTAAGGACC TAAAAGCCCA AGGCCTAGTA   300
cons ADN 1,5,8    ---------- ---------- ---------- ---------- ----------
Consensus         TACAAGGANC TCAAAAGATT GTTAAGGACC TAAAAGCCCA AGGCCTAGTA   300

MSRV pol          AAACCATGCA GTAGCCCCTG CAATACTCCA ATTTTAGGAG TAAGGAAACC   350
cons ADN 1,5,8    ---------- ---------- ---------- ---------- ----------
Consensus         AAACCATGCA GTAGCCCCTG CAATACTCCA ATTTTAGGAG TAAGGAAACC   350

MSRV pol          CAACGGACAG TGGAGGTTAG TGCAAGATCT CAGGATTATT AATGAGGCTG   400
cons ADN 1,5,8    ---------- ---------- ---------- ---------- ----------
Consensus         CAACGGACAG TGGAGGTTAG TGCAAGATCT CAGGATTATT AATGAGGCTG   400

MSRV pol          TTTTTCCTCT ATACCCAGCT GTATCTAGCC CTTATACTCT GCTTTCCCTA   450
cons ADN 1,5,8    ---------- ---------- ---------- ---------- ----------
Consensus         TTTTTCCTCT ATACCCAGCT GTATCTAGCC CTTATACTCT GCTTTCCCTA   450

MSRV pol          ATACCAGAGG AAGCAGAGTG GTTTACAGTC CTGGACCTTA AGGATGCCTT   500
cons ADN 1,5,8    ---------- ---------- ---------- ---------- ----------
Consensus         ATACCAGAGG AAGCAGAGTG GTTTACAGTC CTGGACCTTA AGGATGCCTT   500

MSRV pol          TTTCTGCATC CCTGTACGTC CTGACTCTCA ATTCTTGTTT GCCTTTGAAG   550
cons ADN 1,5,8    ---------- ---------- ---------- ---------- ----------
Consensus         TTTCTGCATC CCTGTACGTC CTGACTCTCA ATTCTTGTTT GCCTTTGAAG   550

MSRV pol          ATCCTTTGAA CCCAACGTCT CAACTCACCT GGACTGTTTT ACCCCAAGGG   600
cons ADN 1,5,8    ---------- ---------- ---------- ---------- ----------
Consensus         ATCCTTTGAA CCCAACGTCT CAACTCACCT GGACTGTTTT ACCCCAAGGG   600

MSRV pol          TTCAGGGATA GCCCCCATCT ATTTGGCCAG GCATTAGCCC AAGACTTGAG   650
cons ADN 1,5,8    ---------- ---------- ---------- ---------- --GACTTGAG     8
Consensus         TTCAGGGATA GCCCCCATCT ATTTGGCCAG GCATTAGCCC AAGACTTGAG   650

MSRV pol          TCAATTCTCA TACCTGGACA TTCTTGTTCT TCAGTACGTG GATGATTTAC   700
cons ADN 1,5,8    CCAGTTCTCA TACCTGGACA TTCTTGTTCY TCAGTATRCG GATGAYTTAA    58
Consensus         YCARTYCTCA TACCTGGACA TTCTTGTTCY TCAGTAYRRG GATGAYTTAM   700

MSRV pol          TTTTAGTCCC CCCTTCAGAA ACCTTGTGCC AACAAGCCAC CCAAGAACTC   750
cons ADN 1,5,8    TTATAGCCAC CCATTCAGAA ACCTTGTGGC AACAAGCCAC CCAAGYGCTC   108
Consensus         TTWTAGMCMC CCMTTCAGAA ACCTTGTGSC AACAAGCCAC CCAAGRRCTC   750

MSRV pol          TTAACTTTCC TCACTACCTG TGGCTACAAG GTTTCCAAAC CAAAGGCTCG   800
cons ADN 1,5,8    TTAAATTTCC TYGCTACCTG TGGCT----- ----CCAAAC AAAAGGCTCA   149
Consensus         TTAAMTTTCC TYRCTACCTG TGGCTACAAG GTTTCCAAAC MAAAGGCTCR   800
```

FIG 51 B

MSRV pol GCTCTGCTCA CAGGAGGTTA GATACTTAGG GCTAAAATTA TCCAAAGGCA 850
cons ADN 1,5,8 SCTCTGCTCA CASCAGTTTA AATACTTAGG GCTAAAATTA TCCAAAGTCR 199
Consensus SCTCTGCTCA CASSAGKTTA RATACTTAGG GCTAAAATTA TCCAAAGKCR 850

MSRV pol CCAGGGCCCT CAGTGAGGAA CGTATCCAGC CTATACTGGC TTATCCTCAT 900
cons ADN 1,5,8 CCAGGGCCCT CAGAGAGGAA CGTATCCAGC GTATACTGGM TTATCCACAT 249
Consensus CCAGGGCCCT CAGWGAGGAA CGTATCCAGC STATACTGGM TTATCCMCAT 900

MSRV pol CCCAAAACCC TAAAGCAACT AAGAGGGTTC CTTGGCATAA CAGGTTTCTG 950
cons ADN 1,5,8 CCCATAACCM TAAAGCAACT AAGAAGGTTC CTTGGCATAT CAGCCTTCTG 299
Consensus CCCAWAACCM TAAAGCAACT AAGARGGTTC CTTGGCATAW CAGSYTTCTG 950

MSRV pol CCGAAAACAG ATTCCCAGGT ACACCCCAAT AGCCAGACCA TTATATACAC 1000
cons ADN 1,5,8 CCGAATATGG ATTCCCGGAT ACAGYGAAAT AGCCAGGCCA TTATGTACAT 349
Consensus CCGAAWAYRG ATTCCCVGRT ACASYSMAAT AGCCAGRCCA TTATRTACAY 1000

MSRV pol TAATTAGGGA AACTCAGAAA GCCAATACCT ATTTAGTAAG ATGGACACCT 1050
cons ADN 1,5,8 TADYTAAGGA AACTCAGAAA GCCAATACCC ATATAGTAAG ATGGACACCT 399
Consensus TADYTARGGA AACTCAGAAA GCCAATACCY ATWTAGTAAG ATGGACACCT 1050

MSRV pol ---ACAGAAG TGGCTTTCCA GGCCCTAAAG AAGGCCCTAA CCCAAGCCCC 1097
cons ADN 1,5,8 GARACAGAAG TGGCTTTCCA GGCCCTAAAG ---------- ---------- 429
Consensus GARACAGAAG TGGCTTTCCA GGCCCTAAAG AAGGCCCTAA CCCAAGCCCC 1100

MSRV pol AGTGTTCAGC TTGCCAACAG GGCAAGATTT TTCTTTATAT GCCACAGAAA 1147
cons ADN 1,5,8 ---------- ---------- ---------- ---------- ---------- 429
Consensus AGTGTTCAGC TTGCCAACAG GGCAAGATTT TTCTTTATAT GCCACAGAAA 1150

MSRV pol AAACAGGAAT AGCTCTAGGA GTCCTTACGC AGGTCTCAGG GATGAGCTTG 1197
cons ADN 1,5,8 ---------- ---------- ---------- ---------- ---------- 429
Consensus AAACAGGAAT AGCTCTAGGA GTCCTTACGC AGGTCTCAGG GATGAGCTTG 1200

MSRV pol CAACCCGTGG TATACCTGAG TAAGGAAATT GATGTAGTGG CAAAGGGTTG 1247
cons ADN 1,5,8 ---------- ---------- ---------- ---------- ---------- 429
Consensus CAACCCGTGG TATACCTGAG TAAGGAAATT GATGTAGTGG CAAAGGGTTG 1250

MSRV pol GCCTCATTGT TTATGGGTAA TGGCGGCAGT AGCAGTCTTA GTATCTGAAG 1297
cons ADN 1,5,8 ---------- ---------- ---------- ---------- ---------- 429
Consensus GCCTCATTGT TTATGGGTAA TGGCGGCAGT AGCAGTCTTA GTATCTGAAG 1300

MSRV pol CAGTTAAAAT AATACAGGGA AGAGATCTTA CTGTGTGGAC ATCTCATGAT 1347
cons ADN 1,5,8 ---------- ---------- ---------- ---------- ---------- 429
Consensus CAGTTAAAAT AATACAGGGA AGAGATCTTA CTGTGTGGAC ATCTCATGAT 1350

MSRV pol GTGAACGGCA TACTCACTGC TAAAGGAGAC TTGTGGTTGT CAGACAACCA 1397
cons ADN 1,5,8 ---------- ---------- ---------- ---------- ---------- 429
Consensus GTGAACGGCA TACTCACTGC TAAAGGAGAC TTGTGGTTGT CAGACAACCA 1400

MSRV pol TTTACTTAAT TATCAGGCTC TATTACTTGA AGAGCCAGTG CTGAGACTGC 1447
cons ADN 1,5,8 ---------- ---------- ---------- ---------- ---------- 429
Consensus TTTACTTAAT TATCAGGCTC TATTACTTGA AGAGCCAGTG CTGAGACTGC 1450

MSRV pol GCACTTGTGC AACTCTTAAA CCCGCCACAT TTCTTCCAGA CAATGAAGAA 1497
cons ADN 1,5,8 ---------- ---------- ---------- ---------- ---------- 429
Consensus GCACTTGTGC AACTCTTAAA CCCGCCACAT TTCTTCCAGA CAATGAAGAA 1500

MSRV pol AAGATAGAAC ATAACTGTCA ACAAGTAATT GCTCAAACCT ATGCTGCTCG 1547
cons ADN 1,5,8 ---------- ---------- ---------- ---------- ---------- 429
Consensus AAGATAGAAC ATAACTGTCA ACAAGTAATT GCTCAAACCT ATGCTGCTCG 1550

MSRV pol AGGGGACCTT CTAGAGGTTC CCTTGACTGA TCCCGACCTC AACTTGTATA 1597
cons ADN 1,5,8 ---------- ---------- ---------- ---------- ---------- 429
Consensus AGGGGACCTT CTAGAGGTTC CCTTGACTGA TCCCGACCTC AACTTGTATA 1600

FIG 51C

```
Trans of MSRV pol   IMPESPTPLL GRDILAKAGA IIHLNIGKGI PICCPLLEEG INPEVWAIEG   50
cons prot 1,5,8     ---------- ---------- ---------- ---------- ----------
Consensus           .......... .......... .......... .......... ..........   50

Trans of MSRV pol   QYGQAKNARP VQVKLKDSAS FPYQRKYPLR PEALQGXQKI VKDLKAQGLV  100
cons prot 1,5,8     ---------- ---------- ---------- ---------- ----------
Consensus           .......... .......... .......... .......... ..........  100

Trans of MSRV pol   KPCSSPCNTP ILGVRKPNGQ WRLVQDLRII NEAVFPLYPA VSSPYTLLSL  150
cons prot 1,5,8     ---------- ---------- ---------- ---------- ----------
Consensus           .......... .......... .......... .......... ..........  150

Trans of MSRV pol   IPEEAEWFTV LDLKDAFFCI PVRPDSQFLF AFEDPLNPTS QLTWTVLPQG  200
cons prot 1,5,8     ---------- ---------- ---------- ---------- ----------
Consensus           .......... .......... .......... .......... ..........  200

Trans of MSRV pol   FRDSPHLFGQ ALAQDLSQGS YLDHLVLQYV DDLLLVARSE TLQHQATQSL  250
cons prot 1,5,8     ---------- ----DLSQSS YLDHLVLQYG DDLIIATHSE TLWHQATQAL   36
Consensus           .......... ....DLSQ.S YLD.LVLQY. DDL.....SE TL.HQATQ.L  250

Trans of MSRV pol   LIFLITCGHK VSKEKARLCS QEIRYLGLKL SKGTRALSEE RIQSILAYPH  300
cons prot 1,5,8     LNFLATCGSK ---QKAQLCS QQVKYLGLKL SKVTRALREE RIQRILAYPH   83
Consensus           L.FL.TCG.K ...KA.LCS Q...YLGLKL SK.TRAL.EE RIQ.ILAYPH  300

Trans of MSRV pol   PKTLKQLRGF LGTTGFCRKQ IPRYTEIARP LYTLIRETQK ANTYLVRWTP  350
cons prot 1,5,8     PKTLKQLRGF LGITRFCRIW IPRYSEIARP LYTLKKETQK ANTHIVRWTP  133
Consensus           PKTLKQLRGF LGTT.FCR.. IPRY..IARP L.TL..ETQK ANT..VRWTP  350

Trans of MSRV pol   -TEVAFQALK KALTQAPVFS LPTGQDFSLY ATEKTGIALG VLTQVSGMSL  399
cons prot 1,5,8     ETEVAFQALK ---------- ---------- ---------- ----------  143
Consensus           .TEVAFQALK .......... .......... .......... ..........  400

Trans of MSRV pol   QPVVYLSKEI DVVAKGWPHC LWVMAAVAVL VSEAVKIIQG RDLTVWTSHD  449
cons prot 1,5,8     ---------- ---------- ---------- ---------- ----------  143
Consensus           .......... .......... .......... .......... ..........  450

Trans of MSRV pol   VNGILTAKGD LWLSDNHLLN YQALLLEEPV LRLRTCATLK PATFLPDNEE  499
cons prot 1,5,8     ---------- ---------- ---------- ---------- ----------  143
Consensus           .......... .......... .......... .......... ..........  500

Trans of MSRV pol   KIEHNCQQVI AQTYAARGDL LEVPLTDPDL NLYTDGSSLA EKGLRKAGYA  549
cons prot 1,5,8     ---------- ---------- ---------- ---------- ----------  143
Consensus           .......... .......... .......... .......... ..........  550

Trans of MSRV pol   VISDNGILES NRLTPGTSAH LAELIALTWA LELGEGKRVN IYSDSKYAYL  599
cons prot 1,5,8     ---------- ---------- ---------- ---------- ----------  143
Consensus           .......... .......... .......... .......... ..........  600

Trans of MSRV pol   VLHAHAAIWR EREFLTSEGT PINHQEAIRR LLLAVQKPKE VAVLHCQGHQ  649
cons prot 1,5,8     ---------- ---------- ---------- ---------- ----------  143
Consensus           .......... .......... .......... .......... ..........  650

Trans of MSRV pol   EEEERETEGN RQADIEAKKA ARQDSPLEML IEGP                   683
cons prot 1,5,8     ---------- ---------- ---------- ----                   143
Consensus           .......... .......... .......... ....                   684
```

FIG 52 A

```
MSRV pol           ATTATGCCTG AAAGCCCCAC TCCCTTGTTA GGGAGAGACA TTTTAGCAAA    50
cons ADN 41,42,43  ---------- ---------- ---------- ---------- ----------
Consensus          ATTATGCCTG AAAGCCCCAC TCCCTTGTTA GGGAGAGACA TTTTAGCAAA    50

MSRV pol           AGCAGGGGCC ATTATACACC TGAACATAGG AAAAGGAATA CCCATTTGCT   100
cons ADN 41,42,43  ---------- ---------- ---------- ---------- ----------
Consensus          AGCAGGGGCC ATTATACACC TGAACATAGG AAAAGGAATA CCCATTTGCT   100

MSRV pol           GTCCCCTGCT TGAGGAAGGA ATTAATCCTG AAGTCTGGGC AATAGAAGGA   150
cons ADN 41,42,43  ---------- ---------- ---------- ---------- ----------
Consensus          GTCCCCTGCT TGAGGAAGGA ATTAATCCTG AAGTCTGGGC AATAGAAGGA   150

MSRV pol           CAATATGGAC AAGCAAAGAA TGCCCGTCCT GTTCAAGTTA AACTAAAGGA   200
cons ADN 41,42,43  ---------- ---------- ---------- ---------- ----------
Consensus          CAATATGGAC AAGCAAAGAA TGCCCGTCCT GTTCAAGTTA AACTAAAGGA   200

MSRV pol           TTCTGCCTCC TTTCCCTACC AAAGGAAGTA CCCTCTTAGA CCCGAGGCCC   250
cons ADN 41,42,43  ---------- ---------- ---------- ---------- ----------
Consensus          TTCTGCCTCC TTTCCCTACC AAAGGAAGTA CCCTCTTAGA CCCGAGGCCC   250

MSRV pol           TACAAGGANC TCAAAAGATT GTTAAGGACC TAAAAGCCCA AGGCCTAGTA   300
cons ADN 41,42,43  ---------- ---------- ---------- ---------- ----------
Consensus          TACAAGGANC TCAAAAGATT GTTAAGGACC TAAAAGCCCA AGGCCTAGTA   300

MSRV pol           AAACCATGCA GTAGCCCCTG CAATACTCCA ATTTTAGGAG TAAGGAAACC   350
cons ADN 41,42,43  ---------- ---------- ---------- ---------- ----------
Consensus          AAACCATGCA GTAGCCCCTG CAATACTCCA ATTTTAGGAG TAAGGAAACC   350

MSRV pol           CAACGGACAG TGGAGGTTAG TGCAAGATCT CAGGATTATT AATGAGGCTG   400
cons ADN 41,42,43  ---------- ---------- ---------- ---------- ----------
Consensus          CAACGGACAG TGGAGGTTAG TGCAAGATCT CAGGATTATT AATGAGGCTG   400

MSRV pol           TTTTTCCTCT ATACCCAGCT GTATCTAGCC CTTATACTCT GCTTTCCCTA   450
cons ADN 41,42,43  ---------- ---------- ---------- ---------- ----------
Consensus          TTTTTCCTCT ATACCCAGCT GTATCTAGCC CTTATACTCT GCTTTCCCTA   450

MSRV pol           ATACCAGAGG AAGCAGAGTG GTTTACAGTC CTGGACCTTA AGGATGCCTT   500
cons ADN 41,42,43  ---------- ---------- ---------- ---------- ----------
Consensus          ATACCAGAGG AAGCAGAGTG GTTTACAGTC CTGGACCTTA AGGATGCCTT   500

MSRV pol           TTTCTGCATC CCTGTACGTC CTGACTCTCA ATTCTTGTTT GCCTTTGAAG   550
cons ADN 41,42,43  ---------- ---------- ---------- ---------- ----------
Consensus          TTTCTGCATC CCTGTACGTC CTGACTCTCA ATTCTTGTTT GCCTTTGAAG   550

MSRV pol           ATCCTTTGAA CCCAACGTCT CAACTCACCT GGACTGTTTT ACCCCAAGGG   600
cons ADN 41,42,43  ---------- ---------- ---------- ---------- ----------
Consensus          ATCCTTTGAA CCCAACGTCT CAACTCACCT GGACTGTTTT ACCCCAAGGG   600

MSRV pol           TTCAGGGATA GCCCCCATCT ATTTGGCCAG GCATTAGCCC AAGACTTGAG   650
cons ADN 41,42,43  ---------- ---------- ---------- ---------- --GACTTGAG     8
Consensus          TTCAGGGATA GCCCCCATCT ATTTGGCCAG GCATTAGCCC AAGACTTGAG   650

MSRV pol           TCAGTTCTCA TACCTGGACA CTCTTGTCCT TCAGTACGTG GATGATTTAC   700
cons ADN 41,42,43  CCAATCTTCA TACCTGGACA ATCTTGTCCT TCGGTACATG GATGATTTAC    58
Consensus          YCARTYYTCA TACCTGGACA MTCTTGTCCT TCRGTACRTG GATGATTTAC   700

MSRV pol           TTTTAGCCGC CCGTTCAGAA ACCTTGTGCC ATCAAGCCAC CCAAGCACTC   750
cons ADN 41,42,43  TTTTAGACAC CCATTCAGAA ACCTTGTGCC ATCAAGCCAC CCAAGAACTC   108
Consensus          TTTTAGMCRC CCRTTCAGAA ACCTTGTGCC ATCAAGCCAC CCAAGMACTC   750

MSRV pol           TTAACTTTCC TCACTACCTG TGGCTACAAG GTTTCCAAAC CAAAGGCTCG   800
cons ADN 41,42,43  TTAAATTTCC TTGCTACCTG TGGCTACAAG GTTTCCAAAC CAAAGGCTCA   158
Consensus          TTAAMTTTCC TYRCTACCTG TGGCTACAAG GTTTCCAAAC CAAAGGCTCR   800
```

FIG 52 B

```
MSRV pol             GCTCTGCTCA CAGGAGATTA GATACTTAGG GCTAAAATTA TCCAAAGGCA   850
cons ADN 41,42,43    GCTCTGCTCA CAGCAGGTTA AATACTTAGG GCTAAAATTA TCCAAAGGCA   208
Consensus            GCTCTGCTCA CAGSAGRTTA RATACTTAGG GCTAAAATTA TCCAAAGGCA   850

MSRV pol             CCAGGGCCCT CAGTGAGGAA CGTATCCAGC CTATACTGGC TTATCCTCAT   900
cons ADN 41,42,43    CCAGAACCCT CAGTGAGGAA CGTATCCAGC CTATACTGGG TTATCCTCAT   258
Consensus            CCAGRRCCCT CAGTGAGGAA CGTATCCAGC CTATACTGGS TTATCCTCAT   900

MSRV pol             CCCAAAACCC TAAAGCAACT AAGAGGGTTC CTTGGCATAA CAGGTTTCTG   950
cons ADN 41,42,43    CCCAAAACCC TAAAGCAACT AACAGCGTTC CTTGGCATAA CAGGTTTCTG   308
Consensus            CCCAAAACCC TAAAGCAACT AASAGSGTTC CTTGGCATAA CAGGTTTCTG   950

MSRV pol             CCGAAAACAG ATTCCCAGGT ACAGCCCAAT AGCCAGACCA TTATATACAC  1000
cons ADN 41,42,43    CCAAATATGG ATTCCCAGGT ACACCAARRT AGCCAGACCA TTAAATACAC   358
Consensus            CCRAAWAYRG ATTCCCAGGT ACASCMMRRT AGCCAGACCA TTAWATACAC  1000

MSRV pol             TAATTAGGGA AACTCAGAAA GCCAGTACCT ATTTAGTAAG ATGGACACCT  1050
cons ADN 41,42,43    GAATTAAGGA AACTCAAAAA GCCAATACCC ATTTAGTAAG ATGGACAACT   408
Consensus            KAATTARGGA AACTCARAAA GCCARTACCY ATTTAGTAAG ATGGACAMCT  1050

MSRV pol             --AGCAGAAG TGGCTTTCCA GGCCCTAAAG AAGGCCCTAA CCCAAGCCCC  1097
cons ADN 41,42,43    GAAGCAGAAG TGGCTTTCCA GGCCCTAAAG ---------- ----------   438
Consensus            GAAGCAGAAG TGGCTTTCCA GGCCCTAAAG AAGGCCCTAA CCCAAGCCCC  1100

MSRV pol             AGTGTTCAGC TTGCCAACAG GGCAAGATTT TTCTTTATAT GCCACAGAAA  1147
cons ADN 41,42,43    ---------- ---------- ---------- ---------- ----------   438
Consensus            AGTGTTCAGC TTGCCAACAG GGCAAGATTT TTCTTTATAT GCCACAGAAA  1150

MSRV pol             AAACAGGAAT AGCTCTAGGA GTCCTTACGC AGGTCTCAGG GATGAGCTTG  1197
cons ADN 41,42,43    ---------- ---------- ---------- ---------- ----------   438
Consensus            AAACAGGAAT AGCTCTAGGA GTCCTTACGC AGGTCTCAGG GATGAGCTTG  1200

MSRV pol             CAACCCGTGG TATACCTGAG TAAGGAAATT GATGTAGTGG CAAAGGGTTG  1247
cons ADN 41,42,43    ---------- ---------- ---------- ---------- ----------   438
Consensus            CAACCCGTGG TATACCTGAG TAAGGAAATT GATGTAGTGG CAAAGGGTTG  1250

MSRV pol             GCCTCATTGT TTATGGGTAA TGGCGGCAGT AGCAGTCTTA GTATCTGAAG  1297
cons ADN 41,42,43    ---------- ---------- ---------- ---------- ----------   438
Consensus            GCCTCATTGT TTATGGGTAA TGGCGGCAGT AGCAGTCTTA GTATCTGAAG  1300

MSRV pol             CAGTTAAAAT AATACAGGGA AGAGATCTTA CTGTGTGGAC ATCTCATGAT  1347
cons ADN 41,42,43    ---------- ---------- ---------- ---------- ----------   438
Consensus            CAGTTAAAAT AATACAGGGA AGAGATCTTA CTGTGTGGAC ATCTCATGAT  1350

MSRV pol             GTGAACGGCA TACTCACTGC TAAAGGAGAC TTGTGGTTGT CAGACAACCA  1397
cons ADN 41,42,43    ---------- ---------- ---------- ---------- ----------   438
Consensus            GTGAACGGCA TACTCACTGC TAAAGGAGAC TTGTGGTTGT CAGACAACCA  1400

MSRV pol             TTTACTTAAT TATCAGGCTC TATTACTTGA AGAGCCAGTG CTGAGACTGC  1447
cons ADN 41,42,43    ---------- ---------- ---------- ---------- ----------   438
Consensus            TTTACTTAAT TATCAGGCTC TATTACTTGA AGAGCCAGTG CTGAGACTGC  1450

MSRV pol             GCACTTGTGC AACTCTTAAA CCCGCCACAT TTCTTCCAGA CAATGAAGAA  1497
cons ADN 41,42,43    ---------- ---------- ---------- ---------- ----------   438
Consensus            GCACTTGTGC AACTCTTAAA CCCGCCACAT TTCTTCCAGA CAATGAAGAA  1500

MSRV pol             AAGATAGAAC ATAACTGTCA ACAAGTAATT GCTCAAACCT ATGCTGCTCG  1547
cons ADN 41,42,43    ---------- ---------- ---------- ---------- ----------   438
Consensus            AAGATAGAAC ATAACTGTCA ACAAGTAATT GCTCAAACCT ATGCTGCTCG  1550

MSRV pol             AGGGGACCTT CTAGAGGTTC CCTTGACTGA TCCCGACCTC AACTTGTATA  1597
cons ADN 41,42,43    ---------- ---------- ---------- ---------- ----------   438
Consensus            AGGGGACCTT CTAGAGGTTC CCTTGACTGA TCCCGACCTC AACTTGTATA  1600
```

FIG 52C

```
Trans of MSRV pol     IMPESPTPLL GRDILAKAGA IIHLNIGKGI PICCPLLEEG INPEVWAIEG    50
cons prot 41,42,43    ---------- ---------- ---------- ---------- ----------
Consensus             .......... .......... .......... .......... ..........    50

Trans of MSRV pol     QYGQAKNARP VQVKLKDSAS FPYQRKYPLR PEALQGXQKI VKDLKAQGLV   100
cons prot 41,42,43    ---------- ---------- ---------- ---------- ----------
Consensus             .......... .......... .......... .......... ..........   100

Trans of MSRV pol     KPCSSPCNTP ILGVRKPNGQ WRLVQDLRII NEAVFPLYPA VSSPYTLLSL   150
cons prot 41,42,43    ---------- ---------- ---------- ---------- ----------
Consensus             .......... .......... .......... .......... ..........   150

Trans of MSRV pol     IPEEAEWFTV LDLKDAFFCI PVRPDSQFLF AFEDPLNPTS QLTWTVLPQG   200
cons prot 41,42,43    ---------- ---------- ---------- ---------- ----------
Consensus             .......... .......... .......... .......... ..........   200

Trans of MSRV pol     FRDSPHLFGQ ALAQDLSQHS YLDTLVLQYV DDLLIVARSE TLCHQATQEL   250
cons prot 41,42,43    ---------- ----DLSQSS YLDTLVLRYM DDLLIATHSE TLCHQATQAL    36
Consensus             .......... ....DLSQ.S YLDTLVL.Y. DDLLI...SE TLCHQATQ.L   250

Trans of MSRV pol     LIFLITCGYK VSKPKAHLCS QEIRYLGLKL SKGTRALSEE RIQPILAYPH   300
cons prot 41,42,43    LNFLATCGYK VSKPKAQLCS QQVKYLGLKL SKGTRILSEE RIQPILGYPH    86
Consensus             L.FL.TCGYK VSKPKA.LCS Q...YLGLKL SKGTR.LSEE RIQPIL.YPH   300

Trans of MSRV pol     PKTLKQLRGF LGITGFCRKQ IPRYTEIARP LMTLIRETQK ANTMLVRWTP   350
cons prot 41,42,43    PKTLKQLTAF LGITGFCQIW IPRYSKIARP LNTRIKETQK ANTHLVRWTP   136
Consensus             PKTLKQL..F LGITGFC... IPRY..IARP L.T.I.ETQK ANT.LVRWTP   350

Trans of MSRV pol     TEVAFQALKK ALTQAPVFSL PTGQDFSLYA TERTGIALGV LTQVSGMSLQ   400
cons prot 41,42,43    ---------- ---------- ---------- ---------- ----------   136
Consensus             .......... .......... .......... .......... ..........   400

Trans of MSRV pol     PVVYLSKEID VVAKGWPHCL WVMAAVAVLV SEAVKIIQGR DLTVWTSHDV   450
cons prot 41,42,43    -------EAE V--------- ---------- ---------- ----------   140
Consensus             .......E.. V......... .......... .......... ..........   450

Trans of MSRV pol     NGILTAKGDL WLSDNHLLNY QALLLEEPVL RLRTCATLKP ATFLPDNEEK   500
cons prot 41,42,43    ---------- --------AF QALK------ ---------- ----------   146
Consensus             .......... .......... QAL....... .......... ..........   500

Trans of MSRV pol     IEHNCQQVIA QTYAARGDLL EVPLTDPDLN LYTDGSSLAE KGLRKAGYAV   550
cons prot 41,42,43    ---------- ---------- ---------- ---------- ----------   146
Consensus             .......... .......... .......... .......... ..........   550

Trans of MSRV pol     ISDNGILESN RLTPGTSAHL AELIALTWAL ELGEGKRVNI YSDSKYAYLV   600
cons prot 41,42,43    ---------- ---------- ---------- ---------- ----------   146
Consensus             .......... .......... .......... .......... ..........   600

Trans of MSRV pol     LHAHAAIWRE REFLTSEGTP INHQEAIRRL LLAVQKPKEV AVLHCQGHQE   650
cons prot 41,42,43    ---------- ---------- ---------- ---------- ----------   146
Consensus             .......... .......... .......... .......... ..........   650

Trans of MSRV pol     EEEREIEGNR QADIEAKKAA RQDSPLEMLI EGP                     683
cons prot 41,42,43    ---------- ---------- ---------- ---                     146
Consensus             .......... .......... .......... ...                     683
```

FIG 53A

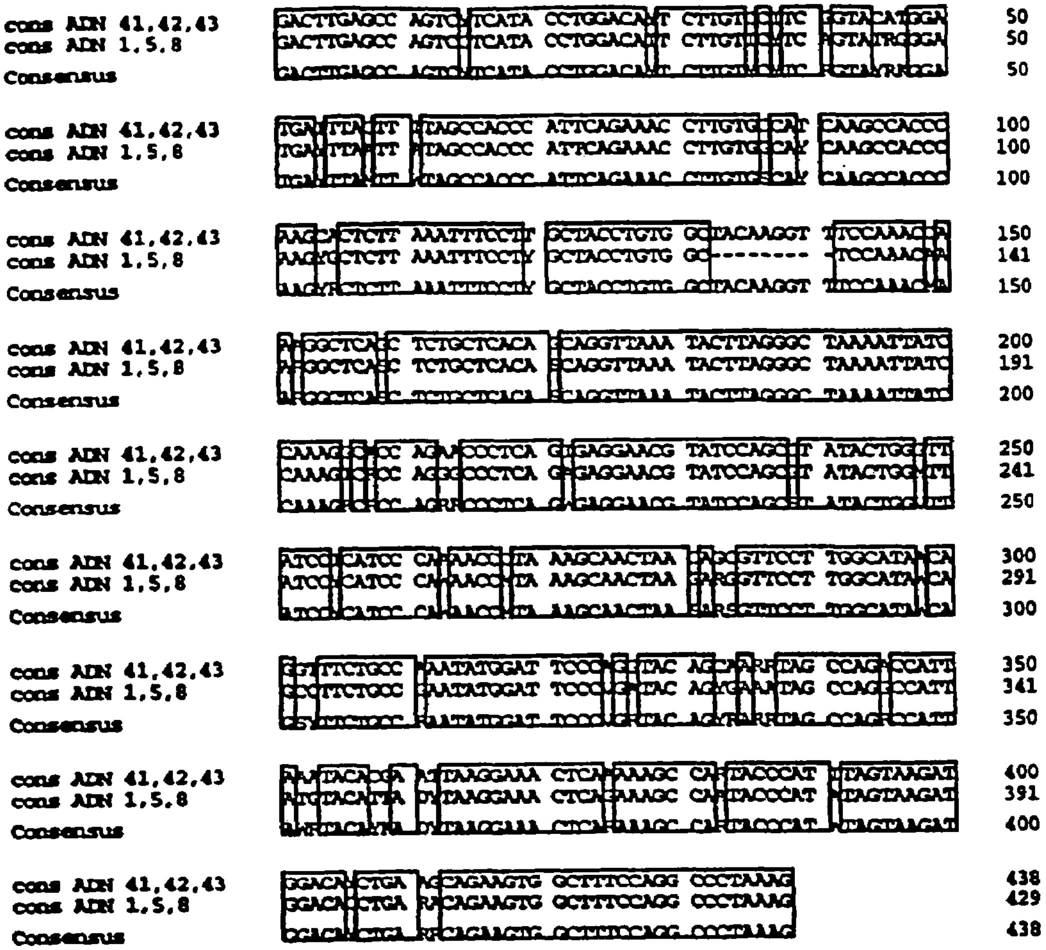

FIG 53B

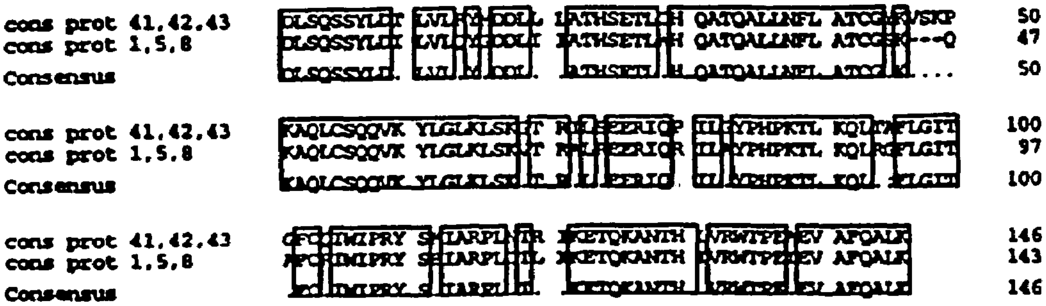

| | | |
|---|---|---|
| cons ADN 41,42,43 | GACTTGAGCC AGTC TCATA CCTGGACA T CTTGT C TC GTA CA GA | 50 |
| cons ADN 1,5,8 | GACTTGAGCC AGTC TCATA CCTGGACA T CTTGT C TC GTA TR GA | 50 |
| Consensus | GACTTGAGCC AGTC TCATA CCTGGACA T CTTGT C TC GTA R GA | 50 |
| cons ADN 41,42,43 | TGA TT TT TAGCCACC ATTCAGAAAC CTTGTG CAT CAAGCCACC | 100 |
| cons ADN 1,5,8 | TGA TT TT TAGCCACC ATTCAGAAAC CTTGTG CA CAAGCCACC | 100 |
| Consensus | TGA TT TT TAGCCACC ATTCAGAAAC CTTGTG CA CAAGCCACC | 100 |
| cons ADN 41,42,43 | AAG CTCTT AAATTCCT GCTACCTGTG GC ACAAGGT T CCAAA | 150 |
| cons ADN 1,5,8 | AAG CTCTT AAATTCCT GCTACCTGTG GC------- TCCAAA | 141 |
| Consensus | AAG CTCTT AAATTCCT GCTACCTGTG GC ACAAGGT T CCAAA | 150 |
| cons ADN 41,42,43 | GGCTCA C TCTGCTCACA CAGGTTAAA TACTTAGGGC TAAAATTATC | 200 |
| cons ADN 1,5,8 | GGCTCA TCTGCTCACA CAGGTTAAA TACTTAGGGC TAAAATTATC | 191 |
| Consensus | GGCTCA TCTGCTCACA CAGGTTAAA TACTTAGGGC TAAAATTATC | 200 |
| cons ADN 41,42,43 | CAAAG CC AG CCTCA G GAGGAACG TATCCAGC T ATACTGG T | 250 |
| cons ADN 1,5,8 | CAAAG CC AG CCTCA G GAGGAACG TATCCAGC T ATACTGG T | 241 |
| Consensus | CAAAG CC AG CCTCA G GAGGAACG TATCCAGC T ATACTGG T | 250 |
| cons ADN 41,42,43 | ATCC CATCC CA AAC TA AAGCAACTAA G GTTCCT TGGCATA CA | 300 |
| cons ADN 1,5,8 | ATCC CATCC CA AAC TA AAGCAACTAA G GTTCCT TGGCATA CA | 291 |
| Consensus | ATCC CATCC CA AAC TA AAGCAACTAA G GTTCCT TGGCATA CA | 300 |
| cons ADN 41,42,43 | G TTCTGCC AATATGGAT TCC TAC AG R TAG CCAG CATT | 350 |
| cons ADN 1,5,8 | G TTCTGCC AATATGGAT TCC TAC AG TAG CCAG CATT | 341 |
| Consensus | G TTCTGCC AATATGGAT TCC TAC AG TAG CCAG CATT | 350 |
| cons ADN 41,42,43 | A TACA A TAAGGAAA CTCA AAGC CA TACCCAT TAGTAAGAT | 400 |
| cons ADN 1,5,8 | A TACA A TAAGGAAA CTCA AAGC CA TACCCAT TAGTAAGAT | 391 |
| Consensus | A TACA A TAAGGAAA CTCA AAGC CA TACCCAT TAGTAAGAT | 400 |
| cons ADN 41,42,43 | GGACA TGA C AGAAGTG GCTTTCCAGG CCCTAAAG | 438 |
| cons ADN 1,5,8 | GGACA TGA C AGAAGTG GCTTTCCAGG CCCTAAAG | 429 |
| Consensus | GGACA TGA C AGAAGTG GCTTTCCAGG CCCTAAAG | 438 |

| | | |
|---|---|---|
| cons prot 41,42,43 | DLSQSSYL L LVL DDLL I THSETL H QATQALLNFL ATCG V SKP | 50 |
| cons prot 1,5,8 | DLSQSSYLI LVL DDLL I THSETL H QATQALLNFL ATCG K ---Q | 47 |
| Consensus | DLSQSSYL LVL DDL I THSETL H QATQALLNFL ATCG K ... | 50 |
| cons prot 41,42,43 | KAQLCSQQVK YLGLKLSK T R L EERIQ IL YPHPKTL KQL FLGIT | 100 |
| cons prot 1,5,8 | KAQLCSQQVK YLGLKLSK T R L EERIQ IL YPHPKTL KQL FLGIT | 97 |
| Consensus | KAQLCSQQVK YLGLKLSK T R L EERIQ IL YPHPKTL KQL FLGIT | 100 |
| cons prot 41,42,43 | C IMIPRY S IARPL R ETQKANTH VRWTP EV APQAL | 146 |
| cons prot 1,5,8 | C IMIPRY S IARPL R ETQKANTH VRWTP EV APQAL | 143 |
| Consensus | C IMIPRY S IARPL R ETQKANTH VRWTP EV APQAL | 146 |

VIRAL MATERIAL AND NUCLEOTIDE FRAGMENTS ASSOCIATED WITH MULTIPLE SCLEROSIS, FOR DIAGNOSTIC, PROPHYLACTIC AND THERAPEUTIC PURPOSES

This application is a divisional of U.S. patent application Ser. No. 10/114,104, filed Apr. 3, 2002 (now abandoned), which is a divisional of U.S. patent application Ser. No. 08/979,847, filed Nov. 26, 1997, U.S. Pat. No. 6,582,703, issued Jun. 24, 2003, which is a continuation-in-part of U.S. patent application Ser. No. 08/756,429, filed Nov. 26, 1996 (now abandoned).

Multiple sclerosis (MS) is a demyelinating disease of the central nervous system (CNS), the cause of which remains as yet unknown.

"Multiple sclerosis (MS) is the most common neurological disease of young adults with a prevalence in Europe and North America of between 20 and 200 per 100,000. It is characterized clinically by a relapsing/remitting or chronic progressive course, frequently leading to severe disability. Current knowledge suggests that MS is associated with autoimmunity, that genetic background has an important influence and that "infectious" agent(s) may be involved. Indeed, many viruses have been proposed as possible candidates but as yet, none of them has been shown to play an aetiological role.

Many studies have supported the hypothesis of a viral aetiology of the disease, but none of the known viruses tested has proved to be the causal agent sought: a review of the viruses sought for several years in MS has been compiled by E. Norrby (1) and R. T. Johnson (2).

The discovery of pathogenic retroviruses in man (HTLVs and HIVs) was followed by great interest in their ability to impair the immune system and to provoke central nervous system inflammation and/or degeneration. In the case of HTLV-1, its association with a chronic inflammatory demyelinating disease in man (48) led to extensive investigations to search for an HTLV1-like retrovirus in MS patients. However, despite initial claims, the presence of HTLV-1 or HTLV-like retroviruses was not confirmed.

Recently, a retrovirus different from the known human retroviruses has been isolated in patients suffering from MS (3, 4, and 5).

In 1989, the authors described the production of extracellular virions, associated with reverse transcriptase (RT) activity, by a culture of leptomeningeal cells (LM7) obtained from the cerebrospinal fluid of a patient with MS (3). This was followed by similar findings in monocyte cultures from a series of MS patients (5). Neither viral particles nor viral RT-activity were found in control individuals. Furthermore, the authors were able to transfer the LM7 virus to non-infected leptomeningeal cells in vitro (26). The molecular characterization of the "LM7" retrovirus was a prerequisite for further evaluation of its possible role in MS. Considerable difficulties arose from the absence of continuously productive retroviral cultures and from the low levels of expression in the few transient cultures. The strategy described here focused on RNA from extracellular virions, in order to avoid non-specific detection of cellular RNA and of endogenous elements from contaminating human DNA. A specific retroviral sequence associated with virions produced by cell cultures from several MS patients has been identified. The entire sequence of this novel retroviral genome is currently being obtained using RT-PCR on RNA from extracellular virions. The retrovirus previously called "LM7 virus" corresponds to an oncovirus and is now designated MSRV (Multiple Sclerosis-associated RetroVirus).

The authors were also able to show that this retrovirus could be transmitted in vitro, that patients suffering from MS produced antibodies capable of recognizing proteins associated with the infection of leptomeningeal cells by this retrovirus, and that the expression of the latter could be strongly stimulated by the immediate-early genes of some herpesviruses (6).

All these results point to the role in MS of at least one unknown retrovirus or of a virus having reverse transcriptase activity which is detectable according to the method published by H. Perron (3) and qualified as "LM7-like RT" activity. The content of the publication identified by (3) is incorporated in the present description by reference.

Recently, the Applicant's studies have enabled two continuous cell lines infected with natural isolates originating from two different patients suffering from MS to be obtained by a culture method as described in the document WO-A-93/20188, the content of which is incorporated in the present description by reference. These two lines, derived from human choroid plexus cells, designated LM7PC and PLI-2, were deposited with the ECACC on 22 Jul. 1992 and 8 Jan. 1993, respectively, under numbers 92072201 and 93010817, in accordance with the provisions of the Budapest Treaty. Moreover, the viral isolates possessing LM7-like RT activity were also deposited with the ECACC under the overall designation of "strains". The "strain" or isolate harboured by the PLI-2 line, designated POL-2, was deposited with the ECACC on 22 Jul. 1992 under No. V92072202. The "strain" or isolate harboured by the LM7PC line, designated MS7PG, was deposited with the ECACC on 8 Jan. 1993 under No. V93010816.

Starting from the cultures and isolates mentioned above, characterized by biological and morphological criteria, the next step was to endeavour to characterize the nucleic acid material associated with the viral particles produced in these cultures.

The portions of the genome which have already been characterized have been used to develop tests for molecular detection of the viral genome and immunoserological tests, using the amino acid sequences encoded by the nucleotide sequences of the viral genome, in order to detect the immune response directed against epitopes associated with the infection and/or viral expression.

These tools have already enabled an association to be confirmed between MS and the expression of the sequences identified in the patents cited later. However, the viral system discovered by the Applicant is related to a complex retroviral system. In effect, the sequences to be found encapsidated in the extracellular viral particles produced by the different cultures of cells of patients suffering from MS show clearly that there is coencapsidation of retroviral genomes which are related but different from the "wild-type" retroviral genome which produces the infective viral particles. This phenomenon has been observed between replicative retroviruses and endogenous retroviruses belonging to the same family, or even heterologous retroviruses. The notion of endogenous retroviruses is very important in the context of our discovery since, in the case of MSRV-1, it has been observed that endogenous retroviral sequences comprising sequences homologous to the MSRV-1 genome exist in normal human DNA. The existence of endogenous retroviral elements (ERV) related to MSRV-1 by all or part of their genome explains the fact that the expression of the MSRV-1 retrovirus in human cells is able to interact with closely related endogenous sequences. These interactions are to be found in the case of pathogenic and/or infectious endogenous retroviruses (for example some ecotropic strains of the murine leukaemia virus), and in the case of exogenous retroviruses whose nucleotide sequence may be found partially or wholly, in the form of ERVs, in the host animal's genome (e.g. mouse exogenous mammary tumor virus transmitted via the milk). These interactions consist mainly of (i) a trans-activation or coactivation of ERVs by the replicative retrovirus (ii) and "illegitimate" encapsidation of RNAs related to ERVS, or of ERVs—or even of cellular RNAs—simply possessing compatible encapsidation sequences, in the retroviral particles produced by the expression of the replicative strain, which are sometimes transmissible and sometimes with a pathogenicity of their own, and (iii) more or less substantial recombinations between the coencapsidated genomes, in particular in the phases of reverse transcription, which lead to the formation of hybrid genomes, which are sometimes transmissible and sometimes with a pathogenicity of their own.

Thus, (i) different sequences related to MSRV-1 have been found in the purified viral particles; (ii) molecular analysis of the different regions of the MSRV-1 retroviral genome should be carried out by systematically analyzing the coencapsidated, interfering and/or recombined sequences which are generated by the infection and/or expression of MSRV-1; furthermore, some clones may have defective sequence portions produced by the retroviral replication and template errors and/or errors of transcription of the reverse transcriptase; (iii) the families of sequences related to the same retroviral genomic region provide the means for an overall diagnostic detection which may be optimized by the identification of invariable regions among the clones expressed, and by the identification of reading frames responsible for the production of antigenic and/or pathogenic polypeptides which may be produced only by a portion, or even by just one, of the clones expressed, and, under these conditions, the systematic analysis of the clones expressed in the region of a given gene enables the frequency of variation and/or of recombination of the MSRV-1 genome in this region to be evaluated and the optimal sequences for the applications, in particular diagnostic applications, to be defined; (iv) the pathology caused by a retrovirus such as MSRV-1 may be a direct effect of its expression and of the proteins or peptides produced as a result thereof, but also an effect of the activation, the encapsidation or the recombination of related or heterologous genomes and of the proteins or peptides produced as a result thereof; thus, these genomes associated with the expression of and/or infection by MSRV-1 are an integral part of the potential pathogenicity of this virus, and hence constitute means of diagnostic detection and special therapeutic targets. Similarly, any agent associated with or cofactor of these interactions responsible for the pathogenesis in question, such as MSRV-2 or the gliotoxic factor which are described in the patent application published under No. FR-2,716,198, may participate in the development of an overall and very effective strategy for the diagnosis, prognosis, therapeutic monitoring and/or integrated therapy of MS in particular, but also of any other disease associated with the same agents.

In this context, a parallel discovery has been made in another autoimmune disease, rheumatoid arthritis (RA), which has been described in the French Patent Application filed under No. 95/02960. This discovery shows that, by applying methodological approaches similar to the ones which were used in the Applicant's work on MS, it was possible to identify a retrovirus expressed in RA which shares the sequences described for MSRV-1 in MS, and also the coexistence of an associated MSRV-2 sequence also described in MS. As regards MSRV-1, the sequences detected in common in MS and RA relate to the pol and gag genes. In the current state of knowledge, it is possible to associate the gag and pol sequences described with the MSRV-1 strains expressed in these two diseases.

The present patent application relates to various results which are additional to those already protected by the following French Patent Applications:

No. 92/04322 of 3 Apr. 1992, published under No. 2,689,519;

No. 92/13447 of 3 Nov. 1992, published under No. 2,689,521;

No. 92/13443 of 3 Nov. 1992, published under No. 2,689,520;

No. 94/01529 of 4 Feb. 1994, published under No. 2,715,936;

No. 94/01531 of 4 Feb. 1994, published under No. 2,715,939;

No. 94/01530 of 4 Feb. 1994, published under No. 2,715,936;

No. 94/01532 of 4 Feb. 1994, published under No. 2,715,937;

No. 94/14322 of 24 Nov. 1994, published under No. 2,727,428;

and No. 94/15810 of 23 Dec. 1994; published under No. 2,728,585.

SUMMARY OF THE INVENTION

The present invention relates, in the first place, to a viral material, in the isolated or purified state, which may be recognized or characterized in different ways:

its genome comprises a nucleotide sequence chosen from the group including the sequences SEQ ID NO:42, SEQ ID NO:47, SEQ ID NO:48, SEQ ID NO:49, SEQ ID NO:52, SEQ ID NO:54, SEQ ID NO:55, SEQ ID NO:56, SEQ ID NO:57, SEQ ID NO:83, their complementary sequences and their equivalent sequences, in particular nucleotide sequences displaying, for any succession of 100 contiguous monomers, at least 50% and preferably at least 70% homology with the said sequences SEQ ID NO:42, SEQ ID NO:47, SEQ ID NO:48, SEQ ID NO:49, SEQ ID NO:52, SEQ ID NO:54, SEQ ID NO:55, SEQ ID NO:56, SEQ ID NO:57, SEQ ID NO:83, respectively, and their complementary sequences;

the region of its genome comprising the env and pol genes and a portion of the gag gene, excluding the subregion having a sequence identical or equivalent to SEQ ID NO:1, codes for any polypeptide displaying, for any contiguous succession of at least 30 amino acids, at least 50% and preferably at least 70% homology with a peptide sequence encoded by any nucleotide sequence chosen from the group including SEQ ID NO:42, SEQ ID NO:47, SEQ ID NO:48, SEQ ID NO:49, SEQ ID NO:52, SEQ ID NO:54, SEQ ID NO:55, SEQ ID NO:56, SEQ ID NO:57, SEQ ID NO:83 and their complementary sequences;

the pol gene comprises a nucleotide sequence partially or totally identical or equivalent to SEQ ID NO:53 or SEQ ID NO:87, excluding SEQ ID NO:1.

the gag gene comprises a nucleotide sequence partially or totally identical or equivalent to SEQ ID NO:82.

As indicated above, according to the present invention, the viral material as defined above is associated with MS. And as defined by reference to the pol or gag gene of MSRV-1, and more especially to the sequences SEQ ID NOS 47, 52, 53, 55, 56, 57, 82, 83, 87, 128, 129, 130, 131, 135, 136, 137 and 138, this viral material is associated with RA.

The present invention also relates to a nucleic material, in the isolated or purified state, having at least one of the following definitions a nucleic material comprising a nucleotide sequence selected from the group including sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences and their equivalent sequences, in particular nucleotide sequences displaying, for any succession of 100 contiguous monomers, at least 50% and preferably at least 60% homology with said sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, and their complementary sequences, excluding HSERV-9 (or ERV-9); advantageously, the nucleotide sequence of said nucleic material is selected from the group including sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences and their equivalent sequences, in particular nucleotide sequences displaying, for any succession of 100 contiguous monomers, at least 70% and preferably at least 80% homology with said sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, and their complementary sequences a nucleic material, in the isolated or purified state, coding for any polypeptide displaying, for any contiguous succession of at least 30 amino acids, at least 50%, preferably at least 60%, and most preferably at least 70% homology with a peptide sequence encoded by any nucleotide sequence selected from the group including SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138 and their complementary sequences;

a nucleic material, in the isolated or purified state, of retroviral type, comprising a nucleotide sequence identical or similar to at least part of the pol gene of an isolated retrovirus associated with multiple sclerosis or rheumatoid arthritis; advantageously, said nucleotide sequence is 80% similar to said at least part of the gene pol;

a nucleic material comprising a nucleotide sequence identical or similar to at least part of the pol gen of an isolated virus encoding a reverse transcriptase having a enzymatic site comprised between the amino acid domains LPQG-YXDD, having a phylogenic distance with HSERV-9 of 0.063±0.1, and preferably 0.063±0.05; the phylogenic distances are calculated on the basis of a reference sequence according to UPGM tree option of the Geneworks™ Software (INTELLIGENETICS);

By enzymatic site, we understand the amino acids domain(s) conferring the specific activity of a given enzyme.

The present invention also relates to different nucleotide fragments each comprising a nucleotide sequence chosen from the group including:

(a) all the genomic sequences, partial and total, of the pol gene of the MSRV-1 virus, except for the total sequence of the nucleotide fragment defined by SEQ ID NO:1;

(b) all the genomic sequences, partial and total, of the env gene of MSRV-1;

(c) all the partial genomic sequences of the gag gene of MSRV-1;

(d) all the genomic sequences overlapping the pol gene and the env gene of the MSRV-1 virus, and overlapping the pol gene and the gag gene;

(e) all the sequences, partial and total, of a clone chosen from the group including the clones FBd3 (SEQ ID NO:42), t pol (SEQ ID NO:47), JLBc1 (SEQ ID NO:48), JLBc2 (SEQ ID NO:49) and GM3 (SEQ ID NO:52), FBd13 (SEQ ID NO:54), LB19 (SEQ ID NO:55), LTRGAG12 (SEQ ID NO:56), FP6 (SEQ ID NO:57), G+E+A (SEQ ID NO:83), excluding any nucleotide sequence identical to or lying within the sequence defined by SEQ ID NO:1;

(f) sequences complementary to the said genomic sequences;

(g) sequences equivalent to the said sequences (a) to (e), in particular nucleotide sequences displaying, for any succession of 100 contiguous monomers, at least 50% and preferably at least 70% homology with the said sequences (a) to (d), provided that this nucleotide fragment does not comprise or consist of the sequence ERV-9 as described in LA MANTIA et al. (18).

The term genomic sequences, partial or total, includes all sequences associated by coencapsidation or by coexpression, or recombined sequences.

Preferably, such a fragment comprises:

either a nucleotide sequence identical to a partial or total genomic sequence of the pol gene of the MSRV-1 virus, except for the total sequence of the nucleotide fragment defined by SEQ ID NO:1, or identical to any sequence equivalent to the said partial or total genomic sequence, in particular one which is homologous to the latter;

or a nucleotide sequence identical to a partial or total genomic sequence of the env gene of the MSRV-1 virus, or identical to any sequence complementary to the said nucleotide sequence, or identical to any sequence equivalent to the said nucleotide sequence, in particular one which is homologous to the latter.

In particular, the invention relates to a nucleotide fragment comprising a coding nucleotide sequence which is partially or totally identical to a nucleotide sequence chosen from the group including:

the nucleotide sequence defined by SEQ ID NO:36, SEQ ID NO:58 or SEQ ID NO:83;

sequences complementary to SEQ ID NO:36, SEQ ID NO:58 or SEQ ID NO:83;

sequences equivalent, and in particular homologous to SEQ ID NO:36, SEQ ID NO:58 or SEQ ID NO:83;

sequences coding for all or part of the peptide sequence defined by SEQ ID NO:35, SEQ ID NO:59 or SEQ ID NO:84;

sequences coding for all or part of a peptide sequence equivalent, in particular homologous to SEQ ID NO:35, SEQ ID NO:59 or SEQ ID NO:84, which is capable of being recognized by sera of patients infected with the MSRV-1 virus, or in whom the MSRV-1 virus has been reactivated.

The invention also relates to a nucleotide fragment (called fragment I) having at least one of the following definitions:

a nucleotide fragment comprising a nucleotide sequence selected from the group including SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences, and their equivalent sequences, in particular nucleotide sequences displaying, for any succession of 100 contiguous monomers, at least 50% and preferably at least 60% homology with said sequences and their complementary sequences, said group excluding SEQ ID NO:1, said nucleotide fragment not comprising nor consisting of the sequence HSERV-9 (or ERV-9); preferably the nucleotide sequence of said fragment is selected from the group including SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences, and their equivalent sequences, in particular nucleotide sequences displaying, for any succession of 100 contiguous monomers, at least 70% and preferably at least 80% homology with said sequences and their complementary sequences;

a nucleotide fragment comprising a coding nucleotide sequence which is partially or totally identical to a nucleotide sequence selected from the group including SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138; their complementary sequences; their equivalent sequences, in particular homologous to SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138;

sequences encoding all or parts of the peptide sequence defined by SEQ ID NO:89, SEQ ID NO:132, SEQ ID NO:133, SEQ ID NO:134, SEQ ID NO:139, SEQ ID NO:140, SEQ ID NO:141;

sequences encoding all or parts of a peptide sequence equivalent, in particular homologous to SEQ ID NO:89, SEQ ID NO:132, SEQ ID NO:133, SEQ ID NO:134, SEQ ID NO:139, SEQ ID NO:140, SEQ ID NO:141, which is capable of being recognized by sera of patients infected with the MSRV-1 virus, or in whom the MSRV-1 virus has been reactivated.

The invention also relates to any nucleic acid probe for the detection of virus associated with MS and/or rheumatoid arthritis (RA), which is capable of hybridizing specifically with any fragment such as is defined above, belonging or lying within the genome of the said pathogenic agent. It relates, in addition, to any nucleic acid probe for detection of a pathogenic and/or infective agent associated with RA, which is capable of hybridizing specifically with any fragment as defined above by reference to the pol and gag genes, and especially with respect to the sequences SEQ ID NOS 36, 47, 52, 55, 56, 57, 58, 83 and SEQ ID NOS 35, 59 and 84.

The invention also relates to a primer for the amplification by polymerization of an RNA or a DNA of a viral material, associated with MS and/or RA, comprising a nucleotide sequence identical or equivalent to at least one portion of the nucleotide sequence of any fragment such as is defined above, in particular a nucleotide sequence displaying, for any succession of at least 10 contiguous monomers, preferably 15 contiguous monomers, more preferably 18 contiguous monomers and even most preferably 20 contiguous monomers, at least 70% homology with at least the said portion of the said fragment. Preferably, the nucleotide sequence of such a primer is identical to any one of the sequences selected from the group including SEQ ID NO:15 to SEQ ID NO:18, SEQ ID NO:43 to SEQ ID NO:46, SEQ ID NO:51, SEQ ID NO:60, SEQ ID NO:72, SEQ ID NO:76, SEQ ID NO:80, SEQ ID NO:93 to SEQ ID NO:99, SEQ ID NO:142, SEQ ID NO:143, SEQ ID NO:144, and SEQ ID NO:145.

Generally speaking the invention also encompasses any RNA or DNA, and in particular replication vector, comprising a genomic fragment of the viral material such as is defined above, or a nucleotide fragment such as is defined above.

The invention also relates to the different peptides encoded by any open reading frame belonging to a nucleotide fragment such as is defined above, in particular any polypeptide, for example any oligopeptide forming or comprising an antigenic determinant recognized by sera of patients infected with the MSRV-1 virus and/or in whom the MSRV-1 virus has been reactivated. Preferably, this polypeptide is antigenic, and is encoded by the open reading frame beginning, in the 5'-3' direction, at nucleotide 181 and ending at nucleotide 330 of SEQ ID NO:1.

The invention also encompasses the following polypeptides a)

a polypeptide encoded by any open reading frame belonging to a nucleotide fragment, fragment I, as defined above;

a polypeptide, characterized in that the open reading frame encoding it, is comprised, in the 5'-3' direction, between nucleotide 19 and nucleotide 2304 of SEQ ID NO:87;

a polypeptide, having a peptide sequence comprising a sequence partially or totally identical to SEQ ID NO:89;

b)

a polypeptide, recombinant or synthetic, having a peptide sequence which comprises a sequence identical or equivalent to SEQ ID NO:90; in particular said polypeptide exhibits an enzymatic activity consisting of proteolytic activity;

a polypeptide, recombinant or synthetic, characterized in that the open reading frame encoding it begins, in the 5'-3' direction, at nucleotide 19 and ends at nucleotide 342 of SEQ ID NO:87;

a polypeptide having an inhibitory activity on the proteolytic activity of a polypeptide as defined according to b);

c)

a polypeptide, recombinant or synthetic, having a peptide sequence which comprises a sequence identical or equivalent to SEQ ID NO:91; in particular said polypeptide exhibits a reverse transcriptase activity;

a polypeptide having a peptide sequence which comprises a sequence identical or equivalent to SEQ ID NO:92; in particular said polypeptide exhibits a ribonuclease activity;

a polypeptide, recombinant or synthetic, characterized in that the open reading frame encoding it begins, in the 5'-3' direction, at nucleotide 343 and ends at nucleotide 2304 of SEQ ID NO:87;

a polypeptide, recombinant or synthetic, characterized in that the open reading frame encoding it begins, in the 5'-3' direction, at nucleotide 1858 and ends at nucleotide 2304 of SEQ ID NO:87.

a polypeptide having an inhibitory activity on the reverse transcriptase activity of a polypeptide as defined according to c) or on the ribonuclease H activity of a polypeptide as defined according to c).

In particular, the invention relates to an antigenic polypeptide recognized by the sera of patients infected with the MSRV-1 virus, and/or in whom the MSRV-1 virus has been reactivated, whose peptide sequence is partially or totally identical or is equivalent to the sequence defined by SEQ ID NO:35, SEQ ID NO:59, SEQ ID NO:81, SEQ ID NO:89, SEQ ID NO:90, SEQ ID NO:91, SEQ ID NO:92, SEQ ID NO:132, SEQ ID NO:133, SEQ ID NO:134, SEQ ID NO:139, SEQ ID NO:140 and SEQ ID NO:141; such a sequence is identical, for example, to any sequence selected from the group including the sequences SEQ ID NO:37 to SEQ ID NO:40, SEQ ID NO:59 and SEQ ID NO:81.

The present invention also encompasses mono- or polyclonal antibodies directed against the MSRV-1 virus, which are obtained by the immunological reaction of a human or animal body or cells to an immunogenic agent consisting of an antigenic polypeptide such as is defined above.

The invention next relates to:

reagents for detection of the MSRV-virus, or of an exposure to the latter, comprising, at least one reactive substance selected from the group consisting of a probe of the present invention, a polypeptide, in particular an antigenic peptide, such as is defined above, or an anti-ligand, in particular an antibody to the said polypeptide;

all diagnostic, prophylactic or therapeutic compositions comprising one or more peptides, in particular antigenic peptides, such as are defined above, or one or more anti-ligands, in particular antibodies to the peptides, discussed above; such a composition is preferably, and by way of example, a vaccine composition.

The invention also relates to any diagnostic, prophylactic or therapeutic composition, in particular for inhibiting the expression of at least one virus associated with MS or RA, and/or the enzymatic activities of the proteins of said virus, comprising a nucleotide fragment such as is defined above or a polynucleotide, in particular oligonucleotide, whose sequence is partially identical to that of the said fragment, except for that of the fragment having the nucleotide sequence SEQ ID NO:1. Likewise, it relates to any diagnostic, prophylactic or therapeutic composition, in particular for inhibiting the expression of at least one pathogenic and/or infective agent associated with RA, comprising a nucleotide fragment such as is defined above by reference to the pol and gag genes, and especially with respect to the sequences SEQ ID NOS 36, 47, 52, 55, 56, 57, 58 and 83.

According to the invention, these same fragments or polynucleotides, in particular oligonucleotides, may participate in all suitable compositions for detecting, according to any suitable process or method, a pathological and/or infective agent associated with MS and with RA, respectively, in a biological sample. In such a process, an RNA and/or a DNA presumed to belong or originating from the said pathological and/or infective agent, and/or their complementary RNA and/or DNA, is/are brought into contact with such a composition.

The present invention also relates to any process for detecting the presence or exposure to such a pathological and/or infective agent, in a biological sample, by bringing this sample into contact with a peptide, in particular an antigenic peptide such as is defined above, or an anti-ligand, in particular an antibody to this peptide, such as is defined above.

In practice, and for example, a device for detection of the MSRV-1 virus comprises a reagent such as is defined above, supported by a solid support which is immunologically compatible with the reagent, and a means for bringing the biological sample, for example a sample of blood or of cerebrospinal fluid, likely to contain anti-MSRV-1 antibodies, into contact with this reagent under conditions permitting a possible immunological reaction, the foregoing items being accompanied by means for detecting the immune complex formed with this reagent.

Lastly, the invention also relates to the detection of anti-MSRV-1 antibodies in a biological sample, for example a sample of blood or of cerebrospinal fluid, according to which this sample is brought into contact with a reagent such as is defined above, consisting of an antibody, under conditions permitting their possible immunological reaction, and the presence of the immune complex thereby formed with the reagent is then detected.

DEFINITIONS

Before describing the invention in detail, different terms used in the description and the claims are now defined:

strain or isolate is understood to mean any infective and/or pathogenic biological fraction containing, for example, viruses and/or bacteria and/or parasites, generating pathogenic and/or antigenic power, harbored by a culture or a living host; as an example, a viral strain according to the above definition can contain a coinfective agent, for example a pathogenic protist, the term "MSRV" used in the present description denotes any pathogenic and/or infective agent associated with MS, in particular a viral species, the attenuated strains of the said viral species or the defective-interfering particles or particles containing coencapsidated genomes, or alternatively genomes recombined with a portion of the MSRV-1 genome, derived from this species. Viruses, and especially viruses containing RNA, are known to have a variability resulting, in particular, from relatively high rates of spontaneous mutation (7), which will be borne in mind below for defining the notion of equivalence, human virus is understood to mean a virus capable of infecting, or of being harbored by human beings, in view of all the natural or induced variations and/or recombination which may be encountered when implementing the present invention, the subjects of the latter, defined above and in the claims, have been expressed including the equivalents or derivatives of the different biological materials defined below, in particular of the homologous nucleotide or peptide sequences, the variant of a virus or of a pathogenic and/or infective agent according to the invention comprises at least one antigen recognized by at least one antibody directed against at least one corresponding antigen of the said virus and/or said pathogenic and/or infective agent, and/or a genome any part of which is detected by at least one hybridization probe and/or at least one nucleotide amplification primer specific for the said virus and/or pathogenic and/or infective agent, such as, for example, for the MSRV-1 virus, the primers and probes having a nucleotide sequence chosen from SEQ ID NO:15 to SEQ ID NO:21, SEQ ID NO:23, SEQ ID NO:27 to SEQ ID NO:29, SEQ ID NO:41, SEQ ID NO:43, SEQ ID NO:44, SEQ ID NO:45, SEQ ID NO:46, and their complementary sequences, under particular hybridization conditions well known to a person skilled in the art, according to the invention, a nucleotide fragment or an oligonucleotide or polynucleotide is an arrangement of monomers, or a biopolymer, characterized by the informational sequence of the natural nucleic acids, which is capable of hybridizing with any other nucleotide fragment under predetermined conditions, it being possible for the arrangement to contain monomers of different chemical structures and to be obtained from a molecule of natural nucleic acid and/or by genetic recombination and/or by chemical synthesis; a nucleotide fragment may be identical to a genomic fragment of the MSRV-1 virus discussed in the present invention, in particular a gene of this virus, for example pol or env in the case of the said virus, thus, a monomer can be a natural nucleotide of nucleic acid whose constituent elements are a sugar, a phosphate group and a nitrogenous base; in RNA the sugar is ribose, in DNA the sugar is 2-deoxyribose; depending on whether the nucleic acid is DNA or RNA, the nitrogenous base is chosen from adenine, guanine, uracil, cytosine and thymine; or the nucleotide can be modified in at least one of the three constituent elements; as an example, the modification can occur in the bases, generating modified bases such as inosine, 5-methyldeoxycytidine, deoxyuridine, 5-(dimethylamino)deoxyuridine, 2,6-diaminopurine, 5-bromodeoxyuridine and any other modified base promoting hybridization; in the sugar, the modification can consist of the replacement of at least one deoxyribose by a polyamide (8), and in the phosphate group, the modification can consist of its replacement by esters chosen, in particular, from diphosphate, alkyl- and arylphosphonate and phosphorothioate esters, "informational sequence" is understood to mean any ordered succession of monomers whose chemical nature and order in a reference direction constitute an item of functional information of the same quality as that of the natural nucleic acids, hybridization is understood to mean the process during which, under suitable working conditions, two nucleotide fragments having sufficiently complementary sequences pair to form a complex structure, in particular double or triple, preferably in the form of a helix, a probe comprises a nucleotide fragment synthesized chemically or obtained by digestion or enzymatic cleavage of a longer nucleotide fragment, comprising at least six monomers, advantageously from 10 to 1000 monomers, preferably 10 to 30 monomers and more preferably 18 to 30, and possessing a specificity of hybridization under particular conditions; preferably, a probe possessing fewer than 10 monomers, but preferably fewer than 15 monomers is not used alone, but is used in the presence of other probes of equally short size or otherwise; under certain special conditions, it may be useful to use probes of size greater than 100 monomers; a probe may be used, in particular, for diagnostic purposes, such molecules being, for example, capture and/or detection probes, the capture probe may be immobilized on a solid support by any suitable means, that is to say directly or indirectly, for example by covalent bonding or passive adsorption, the detection probe may be labelled by means of a label chosen, in particular, from radioactive isotopes, enzymes chosen, in particular, from peroxidase and alkaline phosphatase and those capable of hydrolyzing a chromogenic, fluorogenic or luminescent substrate, chromophoric chemical compounds, chromogenic, fluorogenic or luminescent compounds, nucleotide base analogues and biotin, the probes used for diagnostic purposes of the invention may be employed in all known hybridization techniques, and in particular the techniques termed "DOT-BLOT" (9), "SOUTHERN BLOT" (10), "NORTHERN BLOT", which is a technique identical to the "SOUTHERN BLOT" technique but which uses RNA as target, and the SANDWICH technique (11); advantageously, the SANDWICH technique is used in the present invention, comprising a specific capture probe and/or a specific detection probe, on the understanding that the capture probe and the detection probe must possess an at least partially different nucleotide sequence, any probe according to the present invention can hybridize in vivo or in vitro with RNA and/or with DNA in order to block the phenomena of replication, in particular translation and/or transcription, and/or to degrade the said DNA and/or RNA, a primer is a probe comprising at least six monomers, and advantageously from 10 to 30 monomers, and preferably from 18 to 25 monomers, possessing a specificity of hybridization under particular conditions for the initiation of an enzymatic polymerization, for example in an amplification technique such as PCR (polymerase chain reaction), in an elongation process such as sequencing, in a method of reverse transcription or the like, two nucleotide or peptide sequences are termed equivalent or derived with respect to one another, or with respect to a reference sequence, if functionally the corresponding biopolymers can perform substantially the same role, without being identical, as regards the application or use in question, or in the technique in which they participate; two sequences are, in particular, equivalent if they are obtained as a result of natural variability, in particular spontaneous mutation of the species from which they have been identified, or induced variability, as are two homologous sequences, homology being defined below, "variability" is understood to mean any spontaneous or induced modification of a sequence, in particular by substitution and/or insertion and/or deletion of nucleotides and/or of nucleotide fragments, and/or extension and/or shortening of the sequence at one or both ends; an unnatural variability can result from the genetic engineering techniques used, for example the choice of synthesis primers, degenerate or otherwise, selected for amplifying a nucleic acid; this variability can manifest itself in modifications of any starting sequence, considered as reference, and capable of being expressed by a degree of homology relative to the said reference sequence, homology characterizes the degree of identity of two nucleotide or peptide fragments compared; it is measured by the percentage identity which is determined, in particular, by direct comparison of nucleotide or peptide sequences, relative to reference nucleotide or peptide sequences, this percentage identity has been specifically determined for the nucleotide fragments, clones in particular, dealt with in the present invention, which are homologous to the fragments identified, for the MSRV-1 virus, by SEQ ID NO:1 to NO:9, SEQ ID NO:42, SEQ ID NO:47 to SEQ ID NO:49, SEQ ID NO:36, SEQ ID NO:52, SEQ ID NO:53 and SEQ ID NO:87, as well as for the probes and primers homologous to the probes and primers identified by SEQ ID NO:17 to SEQ ID NO:21, SEQ ID NO:23, SEQ ID NO:15, SEQ ID NO:16, SEQ ID NO:27 to SEQ ID NO:29, SEQ ID NO:41, SEQ ID NO:43, SEQ ID NO:44, SEQ ID NO:45, SEQ ID NO:46, SEQ ID NO:51, SEQ ID NO:36, SEQ ID NO:52, SEQ ID NO:53, SEQ ID NO:72, SEQ ID NO:76, and SEQ ID NO:93 to SEQ ID NO:99; as an example, the smallest percentage identity observed between the different general consensus sequences of nucleic acids obtained from fragments of MSRV-1 viral RNA, originating from the LM7PC and PLI-2 lines according to a protocol detailed later, is 67% in the region described in FIG. 1, any nucleotide fragment is termed equivalent or derived from a reference fragment if it possesses a nucleotide sequence equivalent to the sequence of the reference fragment; according to the above definition, the following in particular are equivalent to a reference nucleotide fragment:

a) any fragment capable of hybridizing at least partially with the complement of the reference fragment, b) any fragment whose alignment with the reference fragment results in the demonstration of a larger number of identical contiguous bases than with any other fragment originating from another taxonomic group, c) any fragment resulting, or capable of resulting, from the natural variability of the species from which it is obtained, d) any fragment capable of resulting from the genetic engineering techniques applied to the reference fragment, e) any fragment containing at least eight contiguous nucleotides encoding a peptide which is homologous or identical to the peptide encoded by the reference fragment, f) any fragment which is different from the reference fragment by insertion, deletion or substitution of at least one monomer, or extension or shortening at one or both of its ends; for example, any fragment corresponding to the reference fragment flanked at one or both of its ends by a nucleotide sequence not coding for a polypeptide, polypeptide is understood to mean, in particular, any peptide of at least two amino acids, in particular an oligopeptide, or protein, and for example an enzyme, extracted, separated or substantially isolated or synthesized through human intervention, in particular those obtained by chemical synthesis or by expression in a recombinant organism, polypeptide partially encoded by a nucleotide fragment is understood to mean a polypeptide possessing at least three amino acids encoded by at least nine contiguous monomers lying within the said nucleotide fragment, an amino acid is termed analogous to another amino acid when their respective physicochemical properties, such as polarity, hydrophobicity and/or basicity and/or acidity and/or neutrality are substantially the same; thus, a leucine is analogous to an isoleucine.

any polypeptide is termed equivalent or derived from a reference polypeptide if the polypeptides compared have substantially the same properties, and in particular the same antigenic, immunological, enzymological and/or molecular recognition properties; the following in particular are equivalent to a reference polypeptide:

a) any polypeptide possessing a sequence in which at least one amino acid has been replaced by an analogous amino acid, b) any polypeptide having an equivalent peptide sequence, obtained by natural or induced variation of the said reference polypeptide and/or of the nucleotide fragment coding for the said polypeptide, c) a mimotope of the said reference polypeptide, d) any polypeptide in whose sequence one or more amino acids of the L series are replaced by an amino acid of the D series, and vice versa, e) any polypeptide into whose sequence a modification of the side chains of the amino acids has been introduced, such as, for example, an acetylation of the amine functions, a carboxylation of the thiol functions, an esterification of the carboxyl functions, f) any polypeptide in whose sequence one or more peptide bonds have been modified, such as, for example, carba, retro, inverso, retro-inverso, reduced and methylenoxy bonds, (g) any polypeptide at least one antigen of which is recognized by an antibody directed against a reference polypeptide, the percentage identity characterizing the homology of two peptide fragments compared is, according to the present invention, at least 50% and preferably at least 70%.

In view of the fact that a virus possessing reverse transcriptase enzymatic activity may be genetically characterized equally well in RNA and in DNA form, both the viral DNA and RNA will be referred to for characterizing the sequences relating to a virus possessing such reverse transcriptase activity, termed MSRV-1 according to the present description.

The expressions of order used in the present description and the claims, such as "first nucleotide sequence", are not adopted so as to express a particular order, but so as to define the invention more clearly.

Detection of a substance or agent is understood below to mean both an identification and a quantification, or a separation or isolation, of the said substance or said agent.

BRIEF DESCRIPTION OF THE DRAWINGS

A better understanding of the invention will be gained on reading the detailed description which follows, prepared with reference to the attached figures, in which:

FIG. 1 shows general consensus sequences of nucleic acids of the MSRV-1B clones amplified by the PCR technique in the "pol" region defined by Shih (12), from viral DNA originating from the LM7PC and PLI-2 lines, and identified under the references SEQ ID NO:3, SEQ ID NO:4, SEQ ID NO:5 and SEQ ID NO:6, and the common consensus with amplification primers bearing the reference SEQ ID NO:7;

FIG. 2 gives the definition of a functional reading frame for each MSRV-1B/"PCR pol" type family, the said families A to D being defined, respectively, by the nucleotide sequences SEQ ID NO:3, SEQ ID NO:4, SEQ ID NO:5 and SEQ ID NO:6 described in FIG. 1;

FIG. 3 gives an example of consensus of the MSRV-2B sequences, identified by SEQ ID NO:11;

FIG. 6 shows the nucleotide sequence of the clone PSJ17 (SEQ ID NO:9);

FIG. 7 shows the nucleotide sequence SEQ ID NO:8 of the clone designated M003-P004;

FIG. 8 shows the nucleotide sequence SEQ ID NO:2 of the clone F11-1; the portion located between the two arrows in the region of the primer corresponds to a variability imposed by the choice of primer which was used for the cloning of F11-1; in this same Figure, the translation into amino acids is shown;

FIG. 9, split into FIGS. 9A and 9B, shows the nucleotide sequence SEQ ID NO: 1, and a possible functional reading frame of SEQ ID NO: 1 in terms of amino acids; on this sequence, the consensus sequences of the pol gene are underlined;

FIG. 13 shows the nucleotide sequence SEQ ID NO:42 of the clone FBd3;

FIG. 15 shows the nucleotide sequence SEQ ID NO:47 of the clone t pol;

FIGS. 16 and 17 show, respectively, the nucleotide sequences SEQ ID NO:48 and SEQ ID NO:49 of the clones JLBc1 and JLBc2, respectively;

FIG. 23 shows the nucleotide sequence SEQ ID NO:52 of the clone GM3;

FIG. 27, split into three successive FIGS. 27*a*-27*c*, shows a possible reading frame covering the whole of the pol gene;

FIG. 28 shows, according to SEQ ID NO:36, the nucleotide sequence coding for the peptide fragment POL2B, having the amino acid sequence identified by SEQ ID NO:35;

FIG. 34 shows the SEQ ID NO:37 and SEQ ID NO:38 of two polypeptides comprising immunodominant regions, while SEQ ID NO:39 and 40 represent immunoreactive polypeptides specific to MS;

FIG. 35 shows the nucleotide sequence SEQ ID NO:55 of the clone LB19 and three potential reading frames of SEQ ID NO:55 in terms of amino acids;

FIG. 36 shows the nucleotide sequence SEQ ID NO:82 (GAG*) and a potential reading frame of SEQ ID NO:82 in terms of amino acids;

FIG. 38, split into FIGS. 38A-38C, shows the nucleotide sequence SEQ ID NO: 57 of the clone FP6 and three potential reading frames of SEQ ID NO: 57 in terms of amino acids;

FIG. 39, split into FIGS. 39A-39D, shows the nucleotide sequence SEQ ID NO: 83 of the clone G+E+A and three potential reading frames of SEQ ID NO: 83 in terms of amino acids;

FIG. 40 shows a reading frame found in the region E and coding for an MSRV-1 retroviral protease identified by SEQ ID NO:84;

FIG. 44 shows the nucleotide and amino acid alignment of the conserved pol regions of viruses detected in the study (cf Example 18) by the "Pan-retrovirus" PCR. "Deletions" are represented by dashes and standard single-letter abbreviations are used to designate amino acids and nucleotides (i=inosine). The most highly conserved VLPQG and YXDD regions are shown as separate blocks in bold type at the end of each sequence. Amino acids which are present in all or in all but one of the sequences are underlined. PCR primers (modified from (12)) PAN-UO and PAN-UI are orientated 5' to 3' (sense) whereas primer PAN-DI is 3' to 5' (antisense). Degeneracies are shown above (PAN-UO & PAN-DI) or below (PAN-UI) the PCR primer sequences. "I̲" denotes the nine base 5' extension cttggatcc, "–I" denotes the nine base 5' extension ctcaagctt. The capture and detector probes DpV1 and CpV1b used in the ELOSA assay are shown below a representative MSRV-cpol sequence. At three positions below the translated MSRV-cpol sequence alternative amino acids (representing "non-silent" nucleic acid variations) are shown in italics—K and Y substitutions were only observed in PLI-1 derived clones whereas R and W were encoded by a significant proportion of the clones irrespective of derivation. Note that DpV1 is peroxidase labelled and that CpV1b may be biotinylated at the 5' end if streptavidin coated plates are used. The name of each sequence is indicated at the left of the figure.

HTLV1: Human Leukaemia Virus type 1; HIV1: Human Immunodeficiency Virus type 1; MoMLV: Moloney-Murine Leukaemia Virus; MPMV: Mason-Pfizer Monkey Virus. ERV9: Endogenous Retrovirus 9. MSRV-cpol: Multiple Sclerosis associated RetroVirus conserved pol region.

Figure 45:
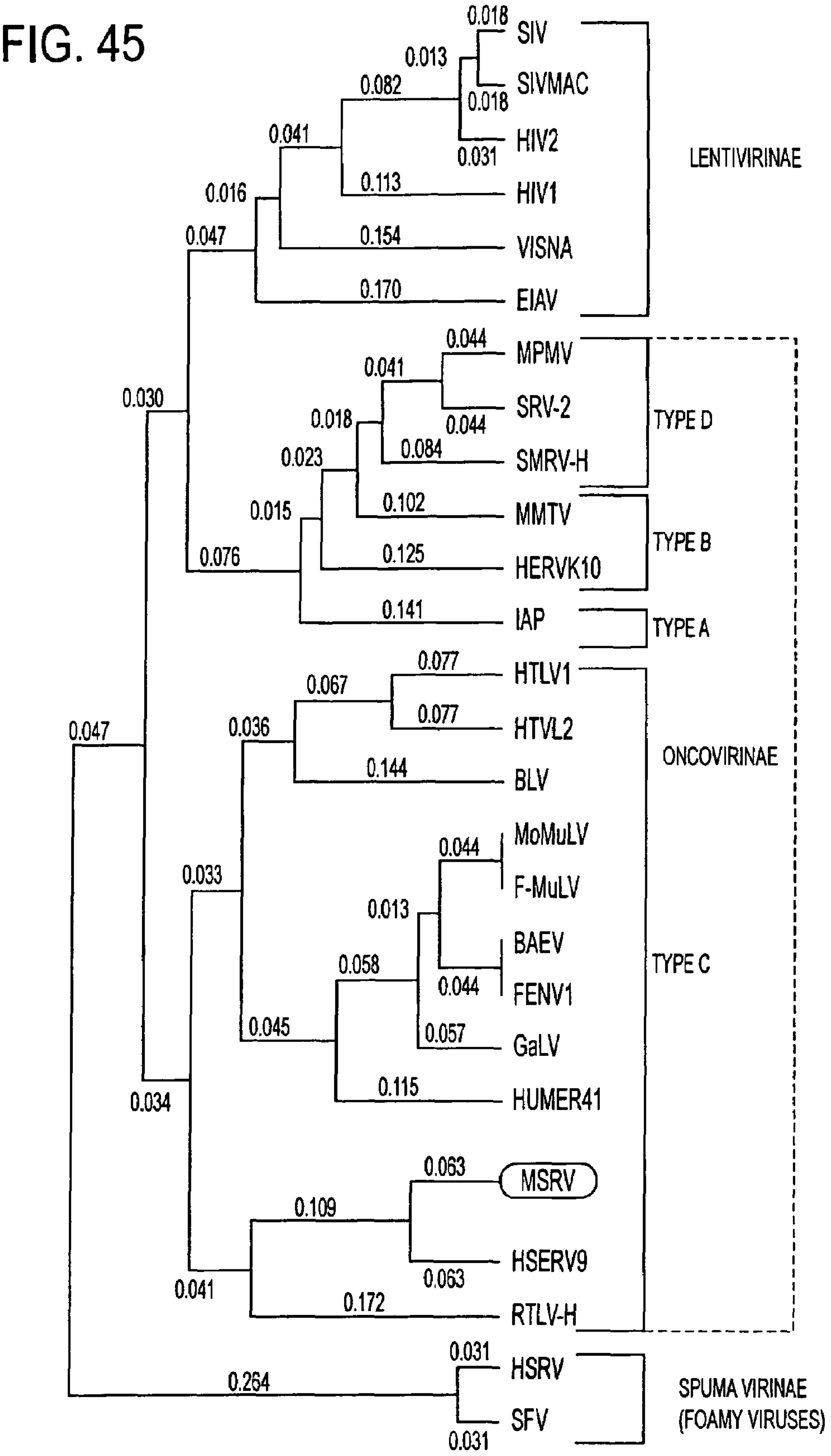

FIG. 45 shows a phylogenic tree which is based on the conserved amino acid region encoded by the pol gene of MSRV and of representative endogenous and exogenous retroviruses and DNA viruses with reverse transcriptase. It was generated by the U.P.G.M.A. tree program of Geneworks® software. HSRV: Human Spumaretrovirus. EIAV: Equine Infectious Aenemia Virus. BLV: Bovine Leukaemia Virus. HIV1, HIV2: Human Immunodeficiency Viruses type 1 and 2. HTLV1 and HTLV2: Human Leukaemia Viruses type 1 and 2. F-MuLV: Friend-Murine Leukaemia Virus. MoMLV: Moloney-Murine Leukaemia Virus. BAEV: Baboon Endogenous Virus. GaLV/Gibbon Ape Leukaemia Virus.

HUMER41: Human Endogenous Retroviral sequence, clone 41. IAP: Intracistemal A-type Particle. MPMV: Mason-Pfizer Monkey Virus. HERVK10: Human Endogenous Retrovirus K10. MMTV: Mouse Mammary tumour Virus. HSERV9 (ERV9 database sequence): Human sequence of Endogenous Retrovirus 9. MSRV: Multiple Sclerosis associated RetroVirus. SIV: Simian Immunodeficiency Virus; RTLV-H: Reverse Transcriptase-Like Viral sequence H; SFV: Simian Foamy Virus; VISNA: Visna retrovirus; SIV1: Simian Immunodeficiency Virus type 1; SRV-2: Simian Retrovirus type 2; SMRV-H: Squirrel Monkey Retrovirus H.

Figure 46:
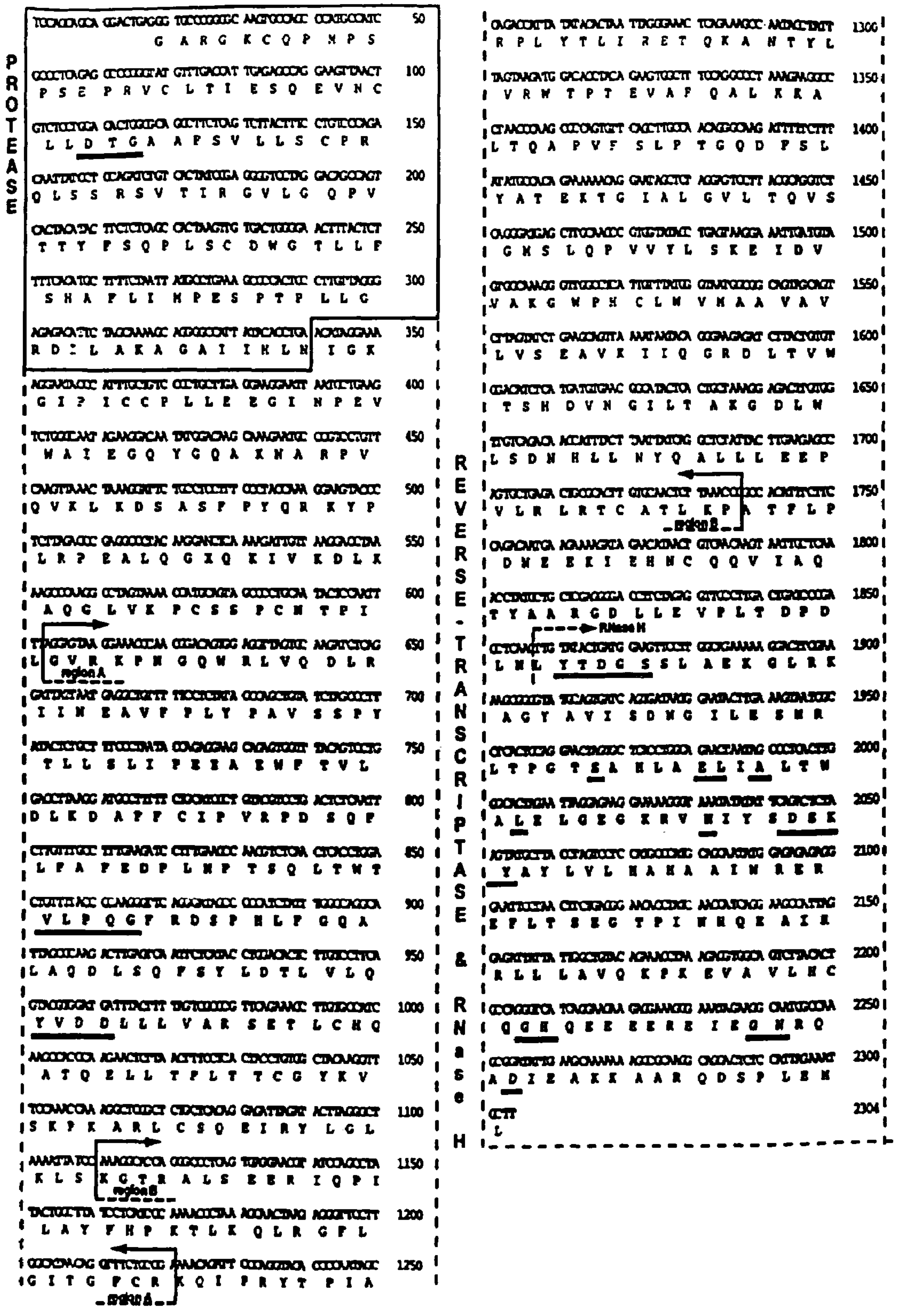

FIG. 46 shows the MSRV sequence (SEQ ID NO: 87) in the Protease and Reverse-Transcriptase regions of the pol gene. The amino acid translation is aligned under the corresponding nucleotide sequence. The region corresponding to the Protease (PRT) ORF cloned in a recombinant vector and expressed in *E. coli*, is boxed. The regions corresponding the A and B fragments amplified on plasma samples from MS patients are indicated by brackets. The Reverse-Transcriptase (RT) and RNaseH (RNH) region is boxed with a dotted line. The highly conserved amino acids and/or active sites of enzyme activities of both PRT and RT (including RNH) are shown underlined.

Figure 47A:
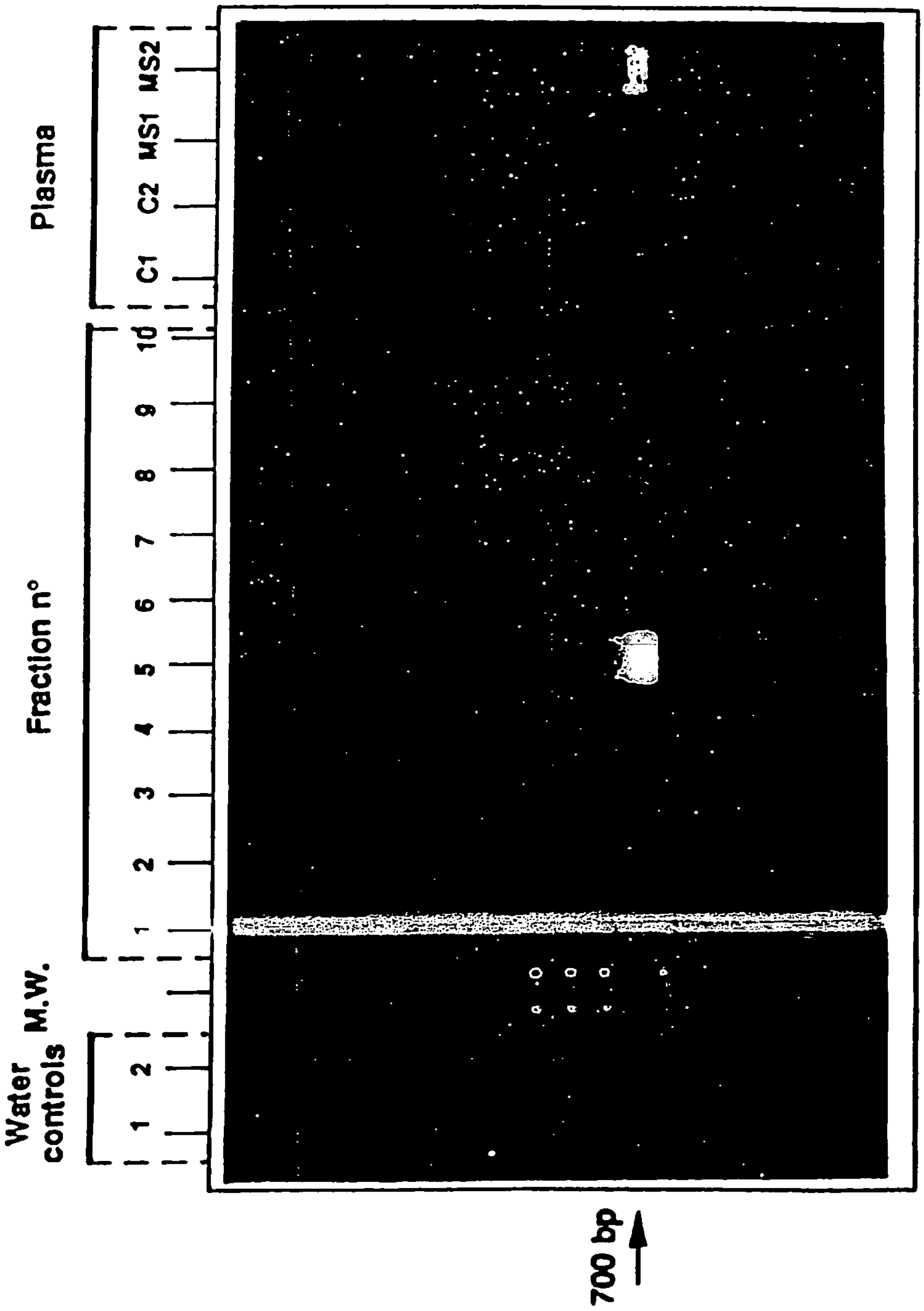
Figure 47B:
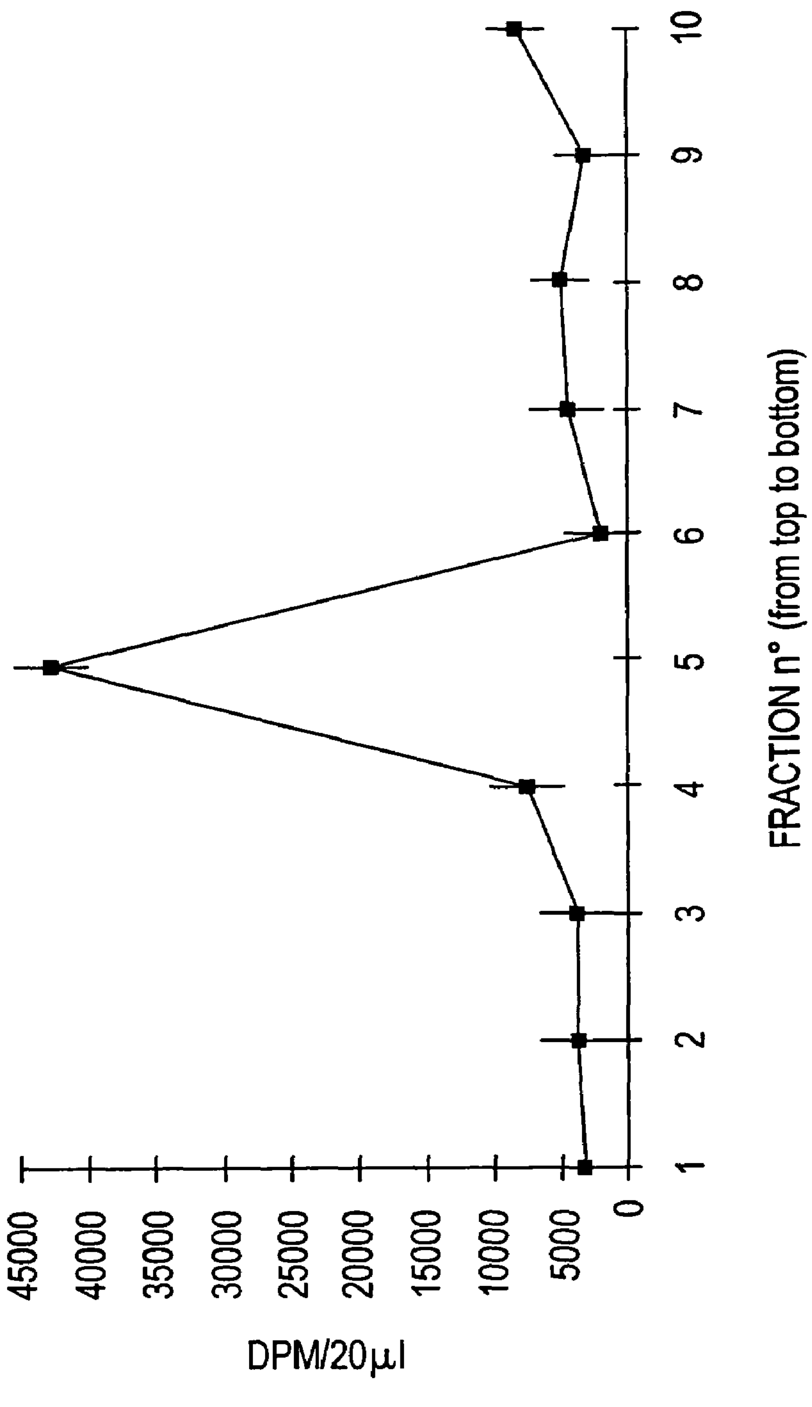

FIG. 47A illustrates the specific detection of MSRV-pol RNA sequence by RT-PCR in the sucrose density fraction associated with RT-activity and in MS plasma; FIG. 47B shows the RT-activity profile on a sucrose density gradient obtained with extracellular virion pelleted from an MS choroid-plexus culture. The photograph below shows an agarose gel loaded with PCR products amplified from round 1 (ST1.1) RT-PCR products with the ST1.2 primer set. From left to right: water control 1 from RT-PCR step with ST1.1 set; water control 2 amplified from water control 1 with ST1.2 nested primers; Molecular weight markers; Fraction n°1 to 10 corresponding to the RT-activity profile shown above; Plasma samples C1 and C2 from healthy blood donors. Plasma samples MS1 and MS2 from two MS patients.

Figure 25:
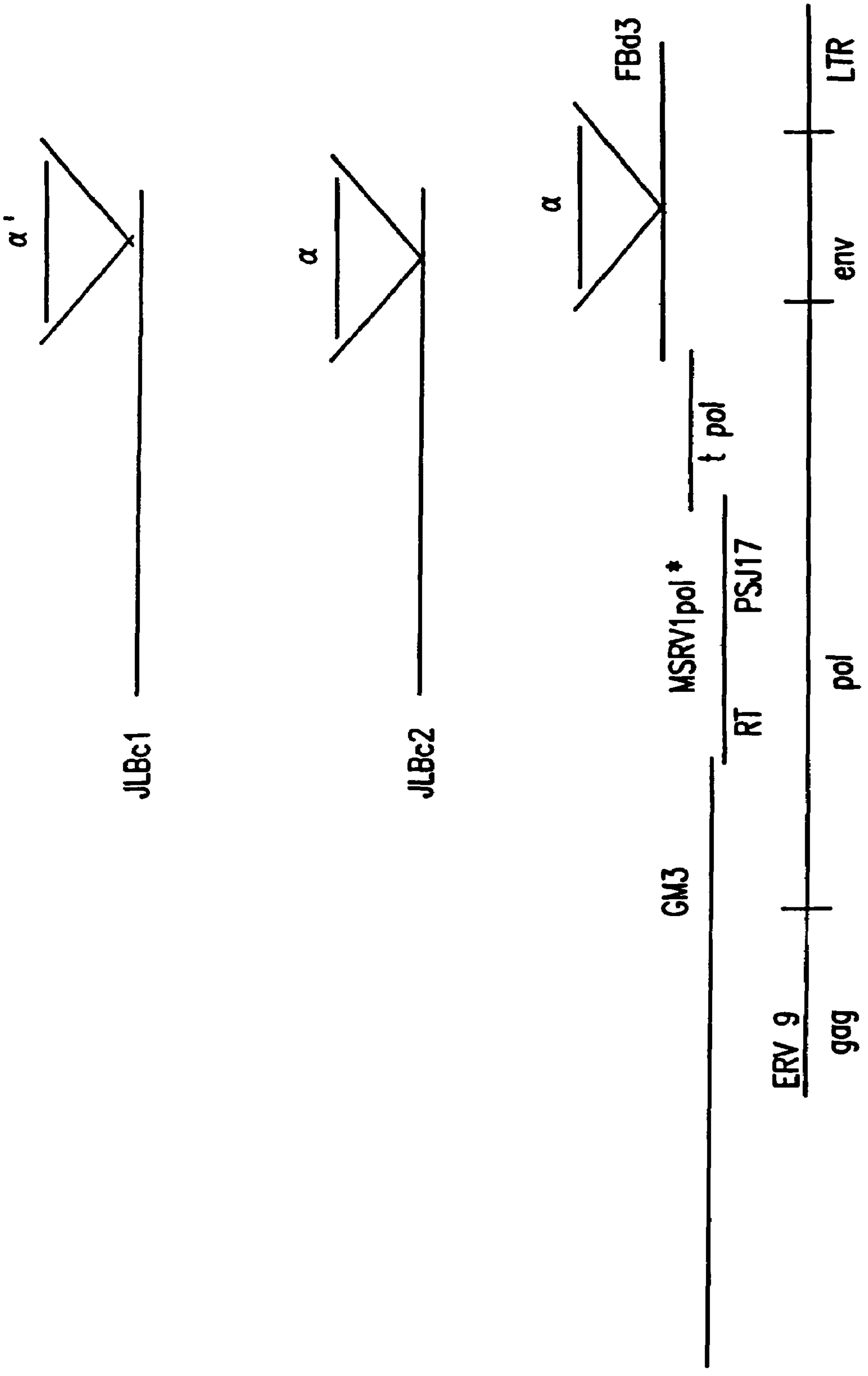
FIG. 25 shows the localization of the different clones studied, relative to the genome of the known retrovirus ERV9.

FIG. 48, split into FIGS. 48A-48E, shows an example of a variant and/or recombined sequence (SEQ ID NO: 88) in the region of the pol gene defined by homology with the overlapping regions described in FIG. 25, as GM3, MSRV-1 pol*, t pol and FBd3.

FIG. 49 shows the nucleotide (FIG. 49A) (SEQ ID NOS: 135-138) and amino acid (FIG. 49B) (SEQ ID NOS: 139-141) alignments of the pol region between clones 1, 5 and 8 of the same patient (Experiment 46-7).

FIG. 50 shows the nucleotide (FIG. 50A) (SEQ ID NOS: 128-131) and amino acid (FIG. 50B) (SEQ ID NOS: 132-134) alignments of the pol region between clones 41, 43 and 42 of the same patient (Experiment 68-1).

FIG. 51 shows the nucleotide (split into FIGS. 51A and 51B) and amino acid (FIG. 51C) alignments of the pol region between the consensus sequence (SEQ ID NO: 135) of clones 1, 5 and 8 of the same patient (Experiment 46-7) and SEQ ID NO: 1, a portion of which is contained within the depicted MSRV pol sequence (SEQ ID NO: 205), resulting in consensus sequence SEQ ID NO: 206, and between their corresponding peptide sequences, SEQ ID NOS: 198 and 199, resulting in consensus sequence SEQ ID NO: 200.

FIG. 52 shows the nucleotide (split into FIGS. 52A and 52B) and amino acid (FIG. 52C) alignments of the pol region between the consensus sequence (SEQ ID NO: 128) of clones 41, 43, 42 of the same patient (Experiment 68-1) and SEQ ID NO: 1, a portion of which is contained within the depicted MSRV pol sequence (SEQ ID NO: 205), resulting in consensus sequence SEQ ID NO: 207, and between their corresponding peptide sequences, SEQ ID NOS: 208 and 209, resulting in consensus sequence SEQ ID NO: 210.

FIG. 53 shows the nucleotide (FIG. 53A) and amino acid (FIG. 53B) alignments of the pol region between the consensus sequence (SEQ ID NO: 135) of clones 1, 5 and 8 of the same patient (Experiment 46-7) and the consensus sequence (SEQ ID NO: 128) of clones 41, 43, 42 of same patient (Experiment 68-1), resulting in consensus sequence SEQ ID NO: 201, and between their corresponding peptide sequence, SEQ ID NOS: 202, 203, resulting in consensus sequence SEQ ID NO: 204.

Table 5 (at the end of the description) shows the sequences obtained by RT-PCR with degenerate pol primers on sucrose density gradient fractions containing the peak of RT-activity or its negative control (cf Example 18); and Table 6 (at the end of the description) shows the clinical data and results of MSRV-cpol detection by "Pan-retro" PCR with specific ELOSA assay, on CSF from MS and control patients (cf Example 18).

DETAILED DESCRIPTION OF PREFERRED EMBODIMENTS

Example 1

Obtaining Clones Designated MSRV-1B and MSRV-2B, Defining, Respectively, a Retrovirus MSRV-1 and a Coinfective Agent MSRV2, by "Nested" PCR Amplification of the Conserved Pol Regions of Retroviruses on Virion Preparations Originating from the LM7PC and PLI-2 Lines A PCR technique derived from the technique published by Shih (12) was used. This technique enables all trace of contaminant DNA to be removed by treating all the components of the reaction medium with DNase. It concomitantly makes it possible, by the use of different but overlapping primers in two successive series of PCR amplification cycles, to increase the chances of amplifying a cDNA synthesized from an amount of RNA which is small at the outset and further reduced in the sample by the spurious action of the DNAse on the RNA. In effect, the DNase is used under conditions of activity in excess which enable all trace of contaminant DNA to be removed before inactivation of this enzyme remaining in the sample by heating to 85° C. for 10 minutes. This variant of the PCR technique described by Shih (12) was used on a cDNA synthesized from the nucleic acids of fractions of infective particles purified on a sucrose gradient according to the technique described by H. Perron (13) from the "POL-2" isolate (ECACC No. V92072202) produced by the PLI-2 line (ECACC No. 92072201) on the one hand, and from the MS7PG isolate (ECACC No. V93010816) produced by the LM7PC line (ECACC No. 93010817) on the other hand. These cultures were obtained according to the methods which formed the subject of the patent applications published under Nos WO 93/20188 and WO 93/20189.

After cloning the products amplified by this technique with the TA Cloning Kit™ and analysis of the sequence using an Applied Biosystems model 373A Automatic Sequencer, the sequences were analysed using the Geneworks® software on the latest available version of the GenBank™ data bank.

The sequences cloned and sequenced from these samples correspond, in particular, to two types of sequence: a first type of sequence, to be found in the majority of the clones (55% of the clones originating from the POL-2 isolates of the PLI-2 culture, and 67% of the clones originating from the MS7PG isolates of the LM7PC cultures), which corresponds to a family of "pol" sequences closely similar to, but different from, the endogenous human retrovirus designated ERV-9 or HSERV-9, and a second type of sequence which corresponds to sequences very strongly homologous to a sequence attributed to another infective and/or pathogenic agent designated MSRV-2.

The first type of sequence, representing the majority of the clones, consists of sequences whose variability enables four subfamilies of sequences to be defined. These subfamilies are sufficiently similar to one another for it to be possible to consider them to be quasi-species originating from the same retrovirus, as is well known for the HIV-1 retrovirus (14), or to be the outcome of interference with several endogenous proviruses coregulated in the producing cells. These more or less defective endogenous elements are sensitive to the same regulatory signals possibly generated by a replicative provirus, since they belong to the same family of endogenous retroviruses (15). This new family of endogenous retroviruses, or alternatively this new retroviral species from which the generation of quasi-species has been obtained in culture, and which contains a consensus of the sequences described below, is designated MSRV-1B.

FIG. 1 presents the general consensus sequences of the sequences of the different MSRV-1B clones sequenced in this experiment, these sequences being identified, respectively, by SEQ ID NO:3, SEQ ID NO:4, SEQ ID NO:5 and SEQ ID NO:6. These sequences display a homology with respect to nucleic acids ranging from 70% to 88% with the HSERV9 sequence referenced X57147 and M37638 in the GenBank® data base. Four "consensus" nucleic acid sequences representative of different quasi-species of a possibly exogenous retrovirus MSRV-1B, or of different subfamilies of an endogenous retrovirus MSRV-1B, have been defined. These representative consensus sequences are presented in FIG. 2, with the translation into amino acids. A functional reading frame exists for each subfamily of these MSRV-1B sequences, and it can be seen that the functional open reading frame corresponds in each instance to the amino acid sequence appearing on the second line under the nucleic acid sequence. The general consensus of the MSRV-1B sequence, identified by SEQ ID NO:7 and obtained by this PCR technique in the "pol" region, is presented in FIG. 1.

The second type of sequence representing the majority of the clones sequenced is represented by the sequence MSRV-2B presented in FIG. 3 and identified by SEQ ID NO:11. The differences observed in the sequences corresponding to the PCR primers are explained by the use of degenerate primers in mixture form used under different technical conditions.

The MSRV-2B sequence (SEQ ID NO:11) is sufficiently divergent from the retroviral sequences already described in the data banks for it to be suggested that the sequence region in question belongs to a new infective agent, designated MSRV-2. This infective agent would, in principle, on the basis of the analysis of the first sequences obtained, be related to a retrovirus but, in view of the technique used for obtaining this sequence, it could also be a DNA virus whose genome codes for an enzyme which incidentally possesses reverse transcriptase activity, as is the case, for example, with the hepatitis B virus, HBV (12). Furthermore, the random nature of the degenerate primers used for this PCR amplification technique may very well have permitted, as a result of unforeseen sequence homologies or of conserved sites in the gene for a related enzyme, the amplification of a nucleic acid originating from a prokaryotic or eukaryotic pathogenic and/or coinfective agent (protist).

Example 2

Figure 4:
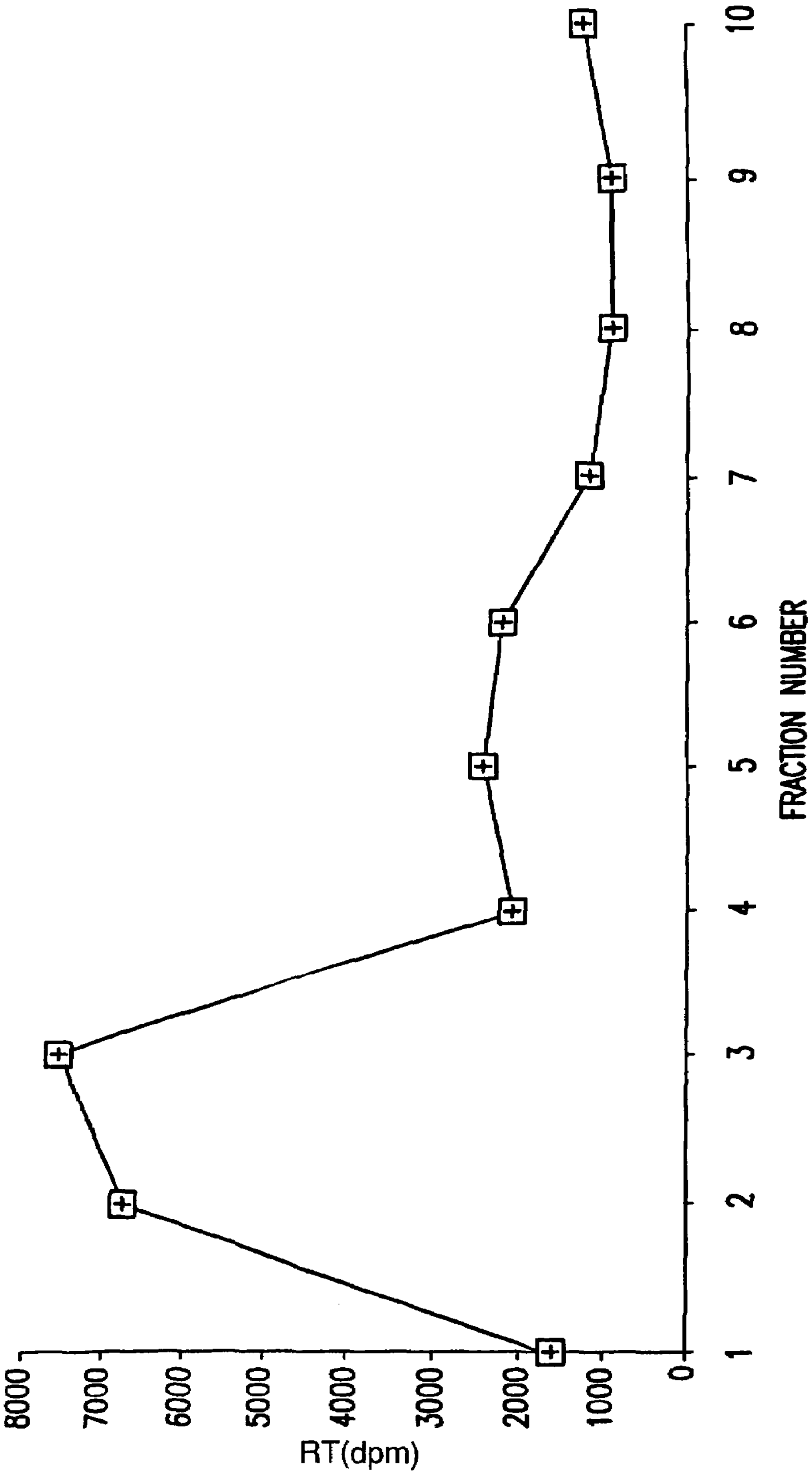
FIG. 4 is a representation of the reverse transcriptase (RT) activity in dpm (disintegrations per minute) in the sucrose fractions taken from a purification gradient of the virions produced by the B lymphocytes in culture from a patient suffering from MS.
Figure 5:
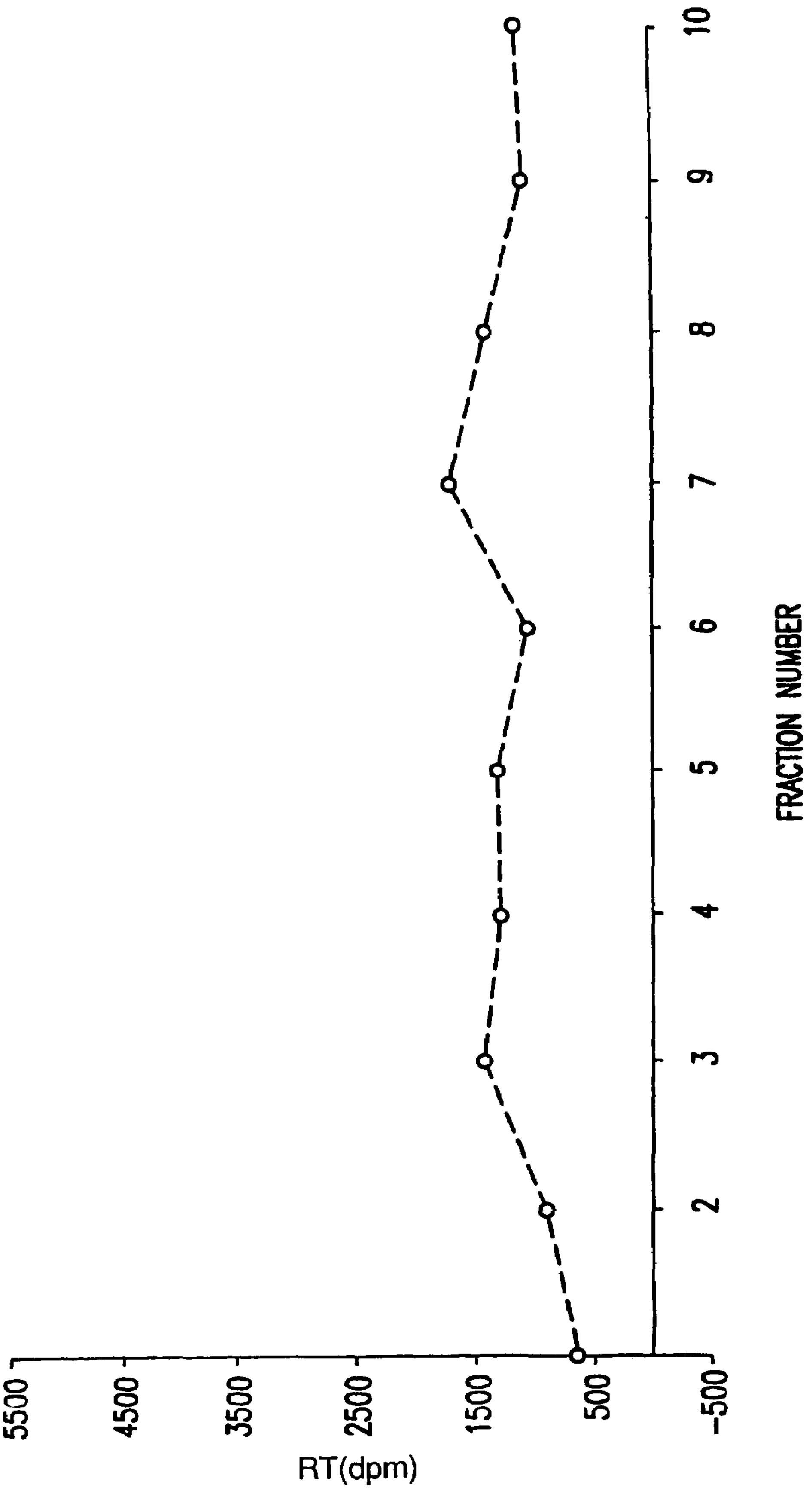
FIG. 5 gives, under the same experimental conditions as in FIG. 4, the assay of the reverse transcriptase activity in the culture of a B lymphocyte line obtained from a control free from MS.

Obtaining Clones Designated MSRV-1B and MSRV-2B, Defining a Family MSRV-1 and MSRV-2, by "Nested" PCR Amplification of the Conserved Pol Regions of Retroviruses on Preparations of B Lymphocytes from a New Case of MS The same PCR technique, modified according to the technique of Shih (12), was used to amplify and sequence the RNA nucleic acid material present in a purified fraction of virions at the peak of "LM7-like" reverse transcriptase activity on a sucrose gradient according to the technique described by H. Perron (13), and according to the protocols mentioned in Example 1, from a spontaneous lymphoblastoid line obtained by self-immortalization in culture of B lymphocytes from an MS patient who was seropositive for the Epstein-Barr virus (EBV), after setting up the blood lymphoid cells in culture in a suitable culture medium containing a suitable concentration of cyclosporin A. A representation of the reverse transcriptase activity in the sucrose fractions taken from a purification gradient of the virions produced by this line is presented in FIG. 4. Similarly, the culture supernatants of a B line obtained under the same conditions from a control free from MS were treated under the same conditions, and the assay of reverse transcriptase activity in the sucrose gradient fractions proved negative throughout (background), and is presented in FIG. 5. Fraction 3 of the gradient corresponding to the MS B line and the same fraction without reverse transcriptase activity of the non-MS control gradient were analysed by the same RT-PCR technique as before, derived from Shih (12), followed by the same steps of cloning and sequencing as described in Example 1.

It is particularly noteworthy that the MSRV-1 and MSRV-2 type sequences are to be found only in the material associated with a peak of "LM7-like" reverse transcriptase activity originating from the MS B lymphoblastoid line. These sequences were not to be found with the material from the control (non-MS) B lymphoblastoid line in 26 recombinant clones taken at random. Only Mo-MuLV type contaminant sequences, originating from the commercial reverse transcriptase used for the cDNA synthesis step, and sequences without any particular retroviral analogy were to be found in this control, as a result of the "consensus" amplification of homologous polymerase sequences which is produced by this PCR technique. Furthermore, the absence of a concentrated target which competes for the amplification reaction in the control sample permits the amplification of dilute contaminants. The difference in results is manifestly highly significant (chi-squared, $p<0.001$).

Example 3

Obtaining a Clone PSJ17, Defining a Retrovirus MSRV-1, by Reaction of Endogenous Reverse Transcriptase with a Virion Preparation Originating from the PLI-2 Line This approach is directed towards obtaining reverse-transcribed DNA sequences from the supposedly retroviral RNA in the isolate using the reverse transcriptase activity present in this same isolate. This reverse transcriptase activity can theoretically function only in the presence of a retroviral RNA linked to a primer tRNA or hybridized with short strands of DNA already reverse-transcribed in the retroviral particles (16). Thus, the obtaining of specific retroviral sequences in a material contaminated with cellular nucleic acids was optimized according to these authors by means of the specific enzymatic amplification of the portions of viral RNAs with a viral reverse transcriptase activity. To this end, the authors determined the particular physicochemical conditions under which this enzymatic activity of reverse transcription on RNAs contained in virions could be effective in vitro. These conditions correspond to the technical description of the protocols presented below (endogenous RT reaction, purification, cloning and sequencing).

The molecular approach consisted in using a preparation of concentrated but unpurified virion obtained from the culture supernatants of the PLI-2 line, prepared according to the following method: the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virion. This concentrated but unpurified viral sample was used to perform a so-called endogenous reverse transcription reaction, as described below.

A volume of 200 ml of virion purified according to the protocol described above, and containing a reverse transcriptase activity of approximately 1-5 million dpm, is thawed at 37° C. until a liquid phase appears, and then placed on ice. A 5-fold concentrated buffer was prepared with the following components: 500 mM Tris-HCl pH 8.2; 75 mM NaCl; 25 mM $MgCl_2$; 75 mM DTT and 0.10% NP 40; 100 ml of 5× buffer+25 ml of a 100 mM solution of dATP+25 ml of a 100 mM solution of dTTP+25 ml of a 100 mM solution of dGTP+25 ml of a 100 mM solution of dCTP+100 ml of sterile distilled water+200 ml of the virion suspension (RT activity of 5 million DPM) in PBS were mixed and incubated at 42° C. for 3 hours. After this incubation, the reaction mixture is added directly to a buffered phenol/chloroform/isoamyl alcohol mixture (Sigma ref. P 3803); the aqueous phase is collected and one volume of sterile distilled water is added to the organic phase to re-extract the residual nucleic acid material. The collected aqueous phases are combined, and the nucleic acids contained are precipitated by adding 3M sodium acetate pH 5.2 to 1/10 volume+2 volumes of ethanol+1 ml of glycogen (Boehringer-Mannheim ref. 901 393) and placing the sample at −20° C. for 4 h or overnight at +4° C. The precipitate obtained after centrifugation is then washed with 70% ethanol and resuspended in 60 ml of distilled water. The products of this reaction were then purified, cloned and sequenced according to the protocol which will now be described: blunt-ended DNAs with unpaired adenines at the ends were generated: a "filling-in" reaction was first performed: 25 ml of the previously purified DNA solution were mixed with 2 ml of a 2.5 mM solution containing, in equimolar amounts, dATP+dGTP+dTTP+dCTP/1 ml of T4 DNA polymerase (Boehringer-Mannheim ref. 1004 786)/5 ml of 10× "incubation buffer for restriction enzyme" (Boehringer-Mannheim ref. 1417 975)/1 ml of a 1% bovine serum albumin solution/16 ml of sterile distilled water. This mixture was incubated for 20 minutes at 11° C. 50 ml of TE buffer and 1 ml of glycogen (Boehringer-Mannheim ref. 901 393) were added thereto before extraction of the nucleic acids with phenol/chloroform/isoamyl alcohol (Sigma ref. P 3803) and precipitation with sodium acetate as described above. The DNA precipitated after centrifugation is resuspended in 10 ml of 10 mM Tris buffer pH 7.5. 5 ml of this suspension were then mixed with 20 ml of 5× Taq buffer, 20 ml of 5 mM dATP, 1 ml (5 U) of Taq DNA polymerase (Amplitaq™) and 54 ml of sterile distilled water. This mixture is incubated for 2 h at 75° C. with a film of oil on the surface of the solution. The DNA suspended in the aqueous solution drawn off under the film of oil after incubation is precipitated as described above and resuspended in 2 ml of sterile distilled water. The DNA obtained was inserted into a plasmid using the TA Cloning™ kit. The 2 ml of DNA solution were mixed with 5 ml of sterile distilled water, 1 ml of a 10-fold concentrated ligation buffer "10× LIGATION BUFFER", 2 ml of "pCR™ VECTOR" (25 ng/ml) and 1 ml of "TA DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning™ kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

Discriminating analysis on the computerized data banks of the sequences cloned from the DNA fragments present in the reaction mixture enabled a retroviral type sequence to be revealed. The corresponding clone PSJ17 was completely sequenced, and the sequence obtained, presented in FIG. 6 and identified by SEQ ID NO:9, was analysed using the "Geneworks®" software on the updated "GenBank™" data banks. An identical sequence already described could not be found by analysis of the data banks. Only a partial homology with some known retroviral elements was to be found. The most useful relative homology relates to an endogenous retrovirus designated ERV-9, or HSERV-9, according to the references (18).

Example 4

PCR Amplification of the Nucleic Acid Sequence Contained between the 5' Region Defined by the Clone "Pol MSRV-1B" and the 3' Region Defined by the Clone PSJ17

Five oligonucleotides, M001, M002-A, M003-BCD, P004 and P005, were defined in order to amplify the RNA originating from purified POL-2 virions. Control reactions were performed so as to check for the presence of contaminants (reaction with water). The amplification consists of an RT-PCR step according to the protocol described in Example 2, followed by a "nested" PCR according to the PCR protocol described in the document EP-A-0,569,272. In the first RT-PCR cycle, the primers M001 and P004 or P005 are used. In the second PCR cycle, the primers M002-A or M003-BCD and the primer P004 are used. The primers are positioned as follows:

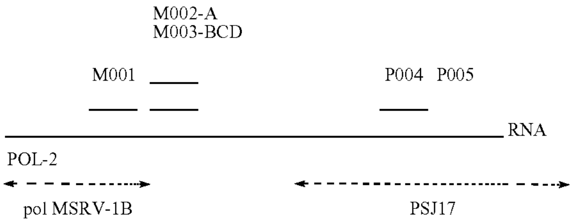

Their composition is:

```
primer M001:
GGTCITICCICAIGG              (SEQ ID NO:19)

primer M002-A:
TTAGGGATAGCCCTCATCTCT        (SEQ ID NO:20)

primer M003-BCD:
TCAGGGATAGCCCCCATCTAT        (SEQ ID NO:17)

primer P004:
AACCCTTTGCCACTACATCAATTT     (SEQ ID NO:18)

primer P005:
GCGTAAGGACTCCTAGAGCTATT      (SEQ ID NO:21)
```

The "nested" amplification product obtained, and designated M003-P004, is presented in FIG. 7, and corresponds to the sequence SEQ ID NO:8.

Example 5

Amplification and Cloning of a Portion of the MSRV-1 Retroviral Genome Using a Sequence Already Identified, in a Sample of Virus Purified at the Peak of Reverse Transcriptase Activity A PCR technique derived from the technique published by Frohman (19) was used. The technique derived makes it possible, using a specific primer at the 3' end of the genome to be amplified, to elongate the sequence towards the 5' region of the genome to be analyzed. This technical variant is described in the documentation of the firm "Clontech Laboratories Inc.", (Palo-Alto Calif., USA) supplied with its product "5'-AmpliFINDER™ RACE Kit", which was used on a fraction of virion purified as described above.

The specific 3' primers used in the kit protocol for the synthesis of the cDNA and the PCR amplification are, respectively, complementary to the following MSRV-1 sequences:

```
cDNA:          TCATCCATGTACCGAAGG    (SEQ ID NO:22)

amplification: ATGGGGTTCCCAAGTTCCCT  (SEQ ID NO:23)
```

The products originating from the PCR were obtained after purification on agarose gel according to conventional methods (17), and then resuspended in 10 μl of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 μl of DNA solution were mixed with 5 ml of sterile distilled water, 1 μl of a 10-fold concentrated ligation buffer "10× LIGATION BUFFER", 2 μl of "pCR™ VECTOR" (25 ng/ml) and 1 μl of "TA DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning™ Kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer model 373 A" apparatus according to the manufacturer's instructions.

This technique was applied first to two fractions of virion purified as described below on sucrose from the "POL-2" isolate produced by the PLI-2 line on the one hand, and from the MS7PG isolate produced by the LM7PC line on the other hand. The culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virions. The concentrated virus is then applied to a sucrose gradient in sterile PBS buffer (15 to 50% weight/weight) and ultracentrifuged at 35,000 rpm (100,000 g) for 12 h at +4° C. in a swing-out rotor. 10 fractions are collected, and 20 ml are withdrawn from each fraction after homogenization to assay the reverse transcriptase activity therein according to the technique described by H. Perron (3). The fractions containing the peak of "LM7-like" RT activity are then diluted in sterile PBS buffer and ultra-centrifuged for one hour at 35,000 rpm (100,000 g) to sediment the viral particles. The pellet of purified virion thereby obtained is then taken up in a small volume of a buffer which is appropriate for the extraction of RNA. The cDNA synthesis reaction mentioned above is carried out on this RNA extracted from purified extracellular virion. PCR amplification according to the technique mentioned above enabled the clone F1-11 to be obtained, whose sequence, identified by SEQ ID NO:2, is presented in FIG. 8.

Figure 12:
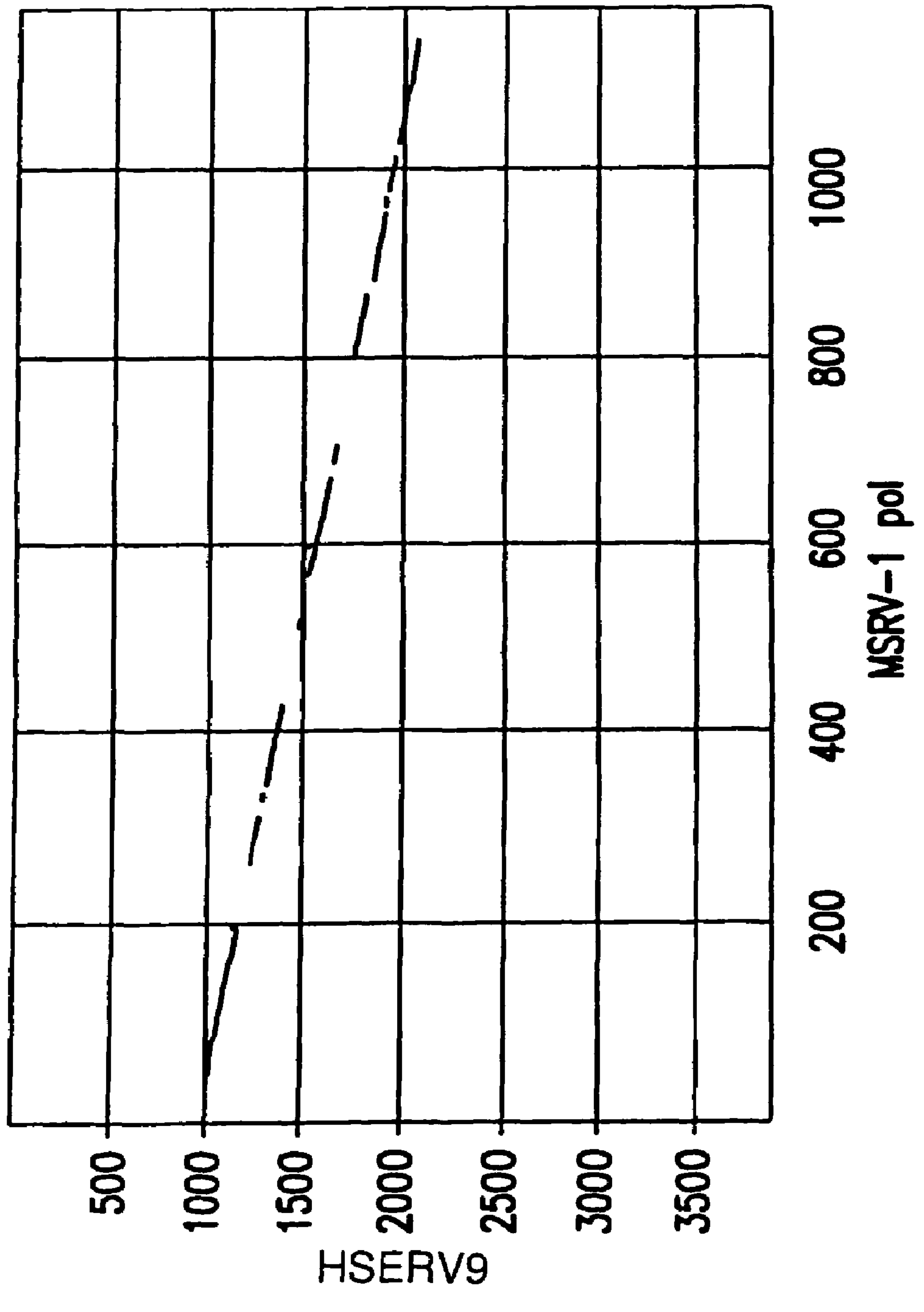
FIG. 12 gives a representation in matrix form of the homology between SEQ ID NO:1 of MSRV-1 and that of an endogenous retrovirus designated HSERV9; this homology of at least 65% is demonstrated by a continuous line, the absence of a line meaning a homology of less than 65%.

This clone makes it possible to define, with the different clones previously sequenced, a region of considerable length (1.2 kb) representative of the "pol" gene of the MSRV-1 retrovirus, as presented in FIG. 9. This sequence, designated SEQ ID NO:1, is reconstituted from different clones overlapping one another at their ends, correcting the artefacts associated with the primers and with the amplification or cloning techniques which would artificially interrupt the reading frame of the whole. This sequence will be identified below under the designation "MSRV-1 pol* region". Its degree of homology with the HSERV-9 sequence is shown in FIG. 12.

In FIG. 9, the potential reading frame with its translation into amino acids is presented below the nucleic acid sequence.

Example 6

Detection of Specific MSRV-1 and MSRV-2 Sequences in Different Samples of Plasma Originating from Patients Suffering from MS or from Controls A PCR technique was used to detect the MSRV-1 and MSRV-2 genomes in plasmas obtained after taking blood samples from patients suffering from MS and from non-MS controls onto EDTA.

Extraction of the RNAs from plasma was performed according to the technique described by P. Chomzynski (20), after adding one volume of buffer containing guanidinium thiocyanate to 1 ml of plasma stored frozen at −80° C. after collection.

For MSRV-2, the PCR was performed under the same conditions and with the following primers:

```
5' primer, identified by SEQ ID NO:14
5' GTAGTTCGATGTAGAAAGCG 3';
3' primer, identified by SEQ ID NO:13
5' GCATCCGGCAACTGCACG 3'.
```

However, similar results were also obtained with the following PCR primers in two successive amplifications by "nested" PCR on samples of nucleic acids not treated with DNase.

The primers used for this first step of 40 cycles with a hybridization temperature of 48° C. are the following:

5' primer, identified by SEQ ID NO:24

5' GCCGATATCACCCGCCATGG 3', corresponding to a 5' MSRV-2 PCR primer, for a first PCR on samples from patients, 3' primer, identified by SEQ ID NO:13

5' GCATCCGGCAACTGCACG 3', corresponding to a 3' MSRV-2 PCR primer, for a first PCR on samples from patients.

After this step, 10 ml of the amplification product are taken and used to carry out a second, so-called "nested" PCR amplification with primers located within the region already amplified. This second step takes place over 35 cycles, with a primer hybridization ("annealing") temperature of 50° C. The reaction volume is 100 ml.

The primers used for this second step are the following:

5' primer, identified by SEQ ID NO:25

5' CGCGATGCTGGTTGGAGAGC 3', corresponding to a 5' MSRV-2 PCR primer, for a nested PCR on samples from patients, 3' primer, identified by SEQ ID NO:26

5' TCTCCACTCCGAATATTCCG 3', corresponding to a 3' MSRV-2 PCR primer, for a nested PCR on samples from patients.

For MSRV-1, the amplification was performed in two steps. Furthermore, the nucleic acid sample is treated beforehand with DNase, and a control PCR without RT (AMV reverse transcriptase) is performed on the two amplification steps so as to verify that the RT-PCR amplification comes exclusively from the MSRV-1 RNA. In the event of a positive control without RT, the initial aliquot sample of RNA is again treated with DNase and amplified again.

The protocol for treatment with DNase lacking RNAse activity is as follows: the extracted RNA is aliquoted in the presence of "RNAse inhibitor" (Boehringer-Mannheim) in water treated with DEPC at a final concentration of 1 mg in 10 ml; to these 10 ml, 1 ml of "RNAse-free DNAse" (Boehringer-Mannheim) and 1.2 ml of pH 5 buffer containing 0.1 mM/l sodium acetate and 5 mM/l $MgSO_4$ is added; the mixture is incubated for 15 min at 20° C. and brought to 95° C. for 1.5 min in a "thermocycler".

The first MSRV-1 RT-PCR step is performed according to a variant of the RNA amplification method as described in Patent Application No. EP-A-0,569,272. In particular, the cDNA synthesis step is performed at 42° C. for one hour; the PCR amplification takes place over 40 cycles, with a primer hybridization ("annealing") temperature of 53° C. The reaction volume is 100 μl.

The primers used for this first step are the following:

```
5' primer, identified by SEQ ID NO:15
5' AGGAGTAAGGAAACCCAACGGAC 3';
3' primer, identified by SEQ ID NO:16
5' TAAGAGTTGCACAAGTGCG 3'.
```

After this step, 10 ml of the amplification product are taken and used to carry out a second, so-called "nested" PCR amplification with primers located within the region already amplified. This second step takes place over 35 cycles, with a primer hybridization ("annealing") temperature of 53° C. The reaction volume is 100 μl.

The primers used for this second step are the following:

```
5' primer, identified by SEQ ID NO:17
5' TCAGGGATAGCCCCCATCTAT 3';
3' primer, identified by SEQ ID NO:18
5' AACCCTTTGCCACTACATCAATTT 3'.
```

Figure 10:
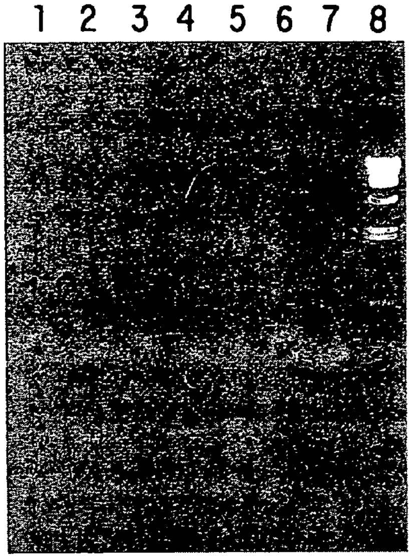
FIGS. 10 and 11 give the results of a PCR, in the form of a photograph under ultraviolet light of an ethidium bromide-impregnated agarose gel, of the amplification products obtained from the primers identified by SEQ ID NO:15, SEQ ID NO:16, SEQ ID NO:17 and SEQ ID NO:18.
Figure 11:
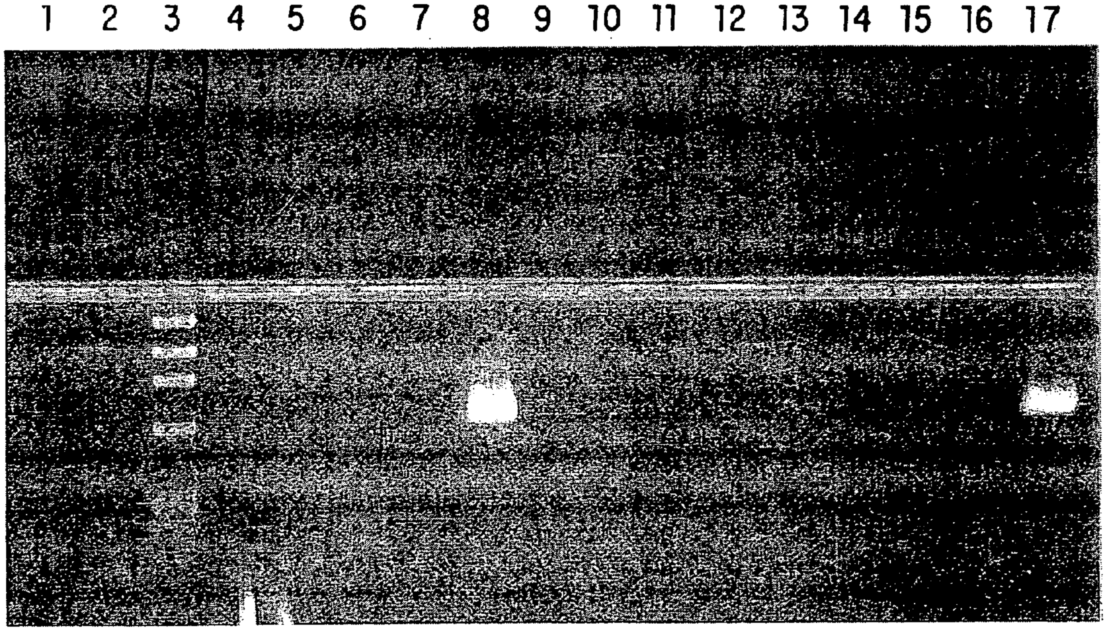

FIGS. 10 and 11 present the results of PCR in the form of photographs under ultraviolet light of ethidium bromide-impregnated agarose gels, in which an electrophoresis of the PCR amplification products applied separately to the different wells was performed.

The top photograph (FIG. 10) shows the result of specific MSRV-2 amplification.

Well number 8 contains a mixture of DNA molecular weight markers, and wells 1 to 7 represent, in order, the products amplified from the total RNAs of plasmas originating from 4 healthy controls free from MS (wells 1 to 4) and from 3 patients suffering from MS at different stages of the disease (wells 5 to 7).

In this series, MSRV-2 nucleic acid material is detected in the plasma of one case of MS out of the 3 tested, and in none of the 4 control plasmas. Other results obtained on more extensive series confirm these results.

The bottom photograph (FIG. 11) shows the result of specific amplification by MSRV-1 "nested" RT-PCR:

well No. 1 contains the PCR product produced with water alone, without the addition of AMV reverse transcriptase; well No. 2 contains the PCR product produced with water alone, with the addition of AMV reverse transcriptase; well number 3 contains a mixture of DNA molecular weight markers; wells 4 to 13 contain, in order, the products amplified from the total RNAs extracted from sucrose gradient fractions (collected in a downward direction), on which gradient a pellet of virion originating from a supernatant of a culture infected with MSRV-1 and MSRV-2 was centrifuged to equilibrium according to the protocol described by H. Perron (13); to well 14 nothing was applied; to wells 15 to 17, the amplified products of RNA extracted from plasmas originating from 3 different patients suffering from MS at different stages of the disease were applied.

The MSRV-1 retroviral genome is indeed to be found in the sucrose gradient fraction containing the peak of reverse transcriptase activity measured according to the technique described by H. Perron (3), with a very strong intensity (fraction 5 of the gradient, placed in well No. 8). A slight amplification has taken place in the first fraction (well No. 4), probably corresponding to RNA released by lysed particles which floated at the surface of the gradient; similarly, aggregated debris has sedimented in the last fraction (tube bottom), carrying with it a few copies of the MSRV-1 genome which have given rise to an amplification of low intensity.

Of the 3 MS plasmas tested in this series, MSRV-1 RNA turned up in one case, producing a very intense amplification (well No. 17).

In this series, the MSRV-1 retroviral RNA genome, probably corresponding to particles of extracellular virus present in the plasma in extremely small numbers, was detected by "nested" RT-PCR in one case of MS out of the 3 tested. Other results obtained on more extensive series confirm these results.

Furthermore, the specificity of the sequences amplified by these PCR techniques may be verified and evaluated by the "ELOSA" technique as described by F. Mallet (21) and in the document FR-A-2,663,040.

For MSRV-1, the products of the nested PCR described above may be tested in two ELOSA systems enabling a consensus A and a consensus B+C+D of MSRV-1 to be detected separately, corresponding to the subfamilies described in Example 1 and FIGS. 1 and 2. In effect, the sequences closely resembling the consensus B+C+D are to be found essentially in the RNA samples originating from MSRV-1 virions purified from cultures or amplified in extracellular biological fluids of MS patients, whereas the sequences closely resembling the consensus A are essentially to be found in normal human cellular DNA.

The ELOSA/MSRV-1 system for the capture and specific hybridization of the PCR products of the subfamily A uses a capture oligonucleotide cpV1A with an amine bond at the 5' end and a biotinylated detection oligonucleotide dpV1A having as their sequence, respectively:

cpV1A identified by SEQ ID NO:27

5' GATCTAGGCCACTTCTCAGGTCCAGS 3', corresponding to the ELOSA capture oligonucleotide for the products of MSRV-1 nested PCR performed with the primers identified by SEQ ID NO:15 and SEQ ID NO:16, optionally followed by amplification with the primers identified by SEQ ID NO:17 and SEQ ID NO:18 on samples from patients;

dpV1A identified by SEQ ID NO:28;

5' CATCTITTTGGICAGGCAITAGC 3', corresponding to the ELOSA capture oligonucleotide for the subfamily A of the products of MSRV-1 "nested" PC R performed with the primers identified by SEQ ID NO:15 and SEQ ID NO:16, optionally followed by amplification with the primers identified by SEQ ID NO:17 and SEQ ID NO:18 on samples from patients.

The ELOSA/MSRV-1 system for the capture and specific hybridization of the PCR products of the subfamily B+C+D uses the same biotinylated detection oligonucleotide dpV1A and a capture oligonucleotide cpV1B with an amine bond at the 5' end having as its sequence:

dpV1B identified by SEQ ID NO:29

5' CTTGAGCCAGTTCTCATACCTGGA 3', corresponding to the ELOSA capture oligonucleotide for the subfamily B+C+D of the products of MSRV-1 "nested" PCR performed with the primers identified by SEQ ID NO:15 and SEQ ID NO:16, optionally followed by amplification with the primers identified by SEQ ID NO:17 and SEQ ID NO:18 on samples from patients.

This ELOSA detection system enabled it to be verified that none of the PCR products thus amplified from DNase-treated plasmas of MS patients contained a sequence of the subfamily A, and that all were positive with the consensus of the subfamilies B, C and D.

For MSRV-2, a similar ELOSA technique was evaluated on isolates originating from infected cell cultures, using the following PCR amplification primers, 5' primer, identified by SEQ ID NO:30

5' AGTGYTRCCMCARGGCGCTGAA 3', corresponding to a 5' MSRV-2 PCR primer, for PCR on samples from cultures, 3' primer, identified by SEQ ID NO:31

5' GMGGCCAGCAGSAKGTCATCCA 3', corresponding to a 3'-MSRV-2 PCR primer, for PCR on samples from cultures, and the capture oligonucleotides with an amine bond at the 5' end cpV2 and the biotinylated detection oligonucleotide dpV2 having as their respective sequences:

cpV2 identified by SEQ ID NO:32

5 GGATGCCGCCTATAGCCTCTAC 3', corresponding to an ELOSA capture oligonucleotide for the products of MSRV-2 PCR performed with the primers SEQ ID NO:34 and SEQ ID NO:35, or optionally with the degenerate primers defined by Shih (12).

dpV2 identified by SEQ ID NO:33

5' AAGCCTATCGCGTGCAGTTGCC 3', corresponding to an ELOSA detection oligonucleotide for the products of MSRV-2 PCR performed with the primers SEQ ID NO:30 and SEQ ID NO:31, or optionally with the degenerate primers defined by Shih (12)

This PCR amplification system with a pair of primers different from those which were described previously for amplification on the samples from patients made it possible to confirm the infection with MSRV-2 of in vitro cultures and of samples of nucleic acids used for the molecular biology studies.

All things considered, the first results of PCR detection of the genome of pathogenic and/or infective agents show that it is possible that free "virus" may circulate in the blood stream of patients in an acute, virulent phase, outside the nervous system. This is compatible with the almost invariable presence of "gaps" in the blood-brain barrier of patients in an active phase of MS.

Example 7

Obtaining Sequences of the "env" Gene of the MSRV-1 Retroviral Genome

As has already been described in Example 5, a PCR technique derived from the technique published by Frohman (19) was used. The technique derived makes it possible, using a specific primer at the 3' end of the genome to be amplified, to elongate the sequence towards the 5' region of the genome to be analysed. This technical variant is described in the documentation of "Clontech Laboratories Inc., (Palo-Alto Calif., USA) supplied with its product "5'-AmpliFINDER™ RACE Kit", which was used on a fraction of virion purified as described above.

In order to carry out an amplification of the 3' region of the MSRV-1 retroviral genome encompassing the region of the "env" gene, a study was carried out to determine a consensus sequence in the LTR regions of the same type as those of the defective endogenous retrovirus HSERV-9 (18, 24), with which the MSRV-1 retrovirus displays partial homologies.

The same specific 3' primer was used in the kit protocol for the synthesis of the cDNA and the PCR amplification; its sequence is as follows:

```
GTGCTGATTGGTGTATTTACAATCC      (SEQ ID NO 41)
```

Synthesis of the complementary DNA (cDNA) and unidirectional PCR amplification with the above primer were carried out in one step according to the method described in Patent EP-A-0,569,272.

The products originating from the PCR were extracted after purification of agarose gel according to conventional methods (17), and then resuspended in 10 μl of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 μl of DNA solution were mixed with 5 μl of sterile distilled water, 1 μl of a 10-fold concentrated ligation buffer "10× LIGATION BUFFER", 2 μl of "pCR™ VECTOR" (25 ng/ml) and 1 μl of "TA DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning™ Kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "automatic sequencer, model 373 A" apparatus according to the manufacturer's instructions.

This technical approach was applied to a sample of virion concentrated as described below from a mixture of culture supernatants produced by B lymphoblastoid lines such as are described in Example 2, established from lymphocytes of patients suffering from MS and possessing reverse transcriptase activity which is detectable according to the technique described by Perron et al. (3): the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g for 2 h at 4° C. After removal of the supernatant, the sedimented pellet constitutes the sample of concentrated but unpurified virions. The pellet thereby obtained is then taken up in a small volume of an appropriate buffer for the extraction of RNA. The cDNA synthesis reaction mentioned above is carried out on this RNA extracted from concentrated extracellular virion.

RT-PCR amplification according to the technique mentioned above enabled the clone FBd3 to be obtained, whose sequence, identified by SEQ ID NO:42, is presented in FIG. 13.

Figure 14:
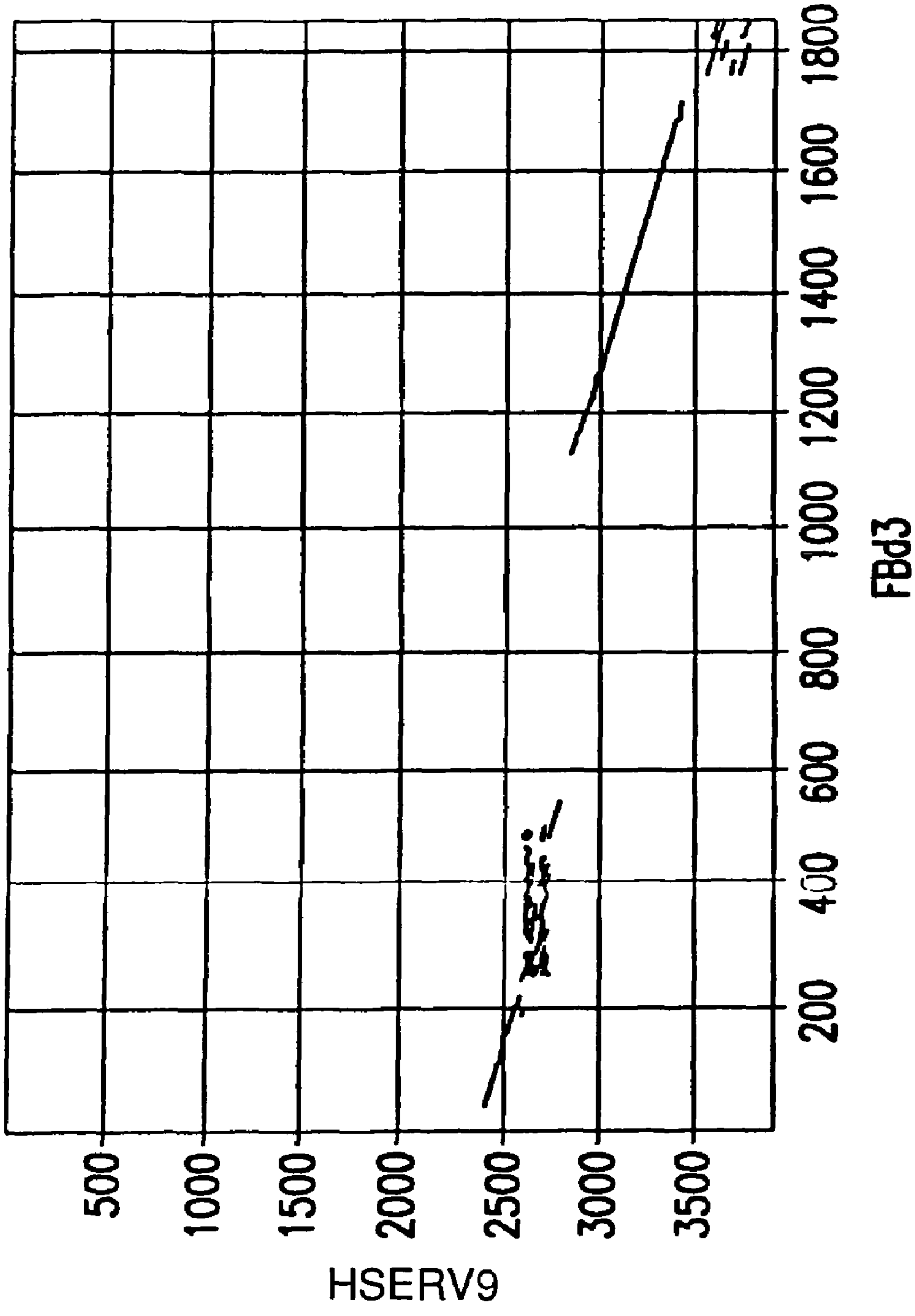
FIG. 14 shows the sequence homology between the clone FBd3 and the HSERV-9 retrovirus.

In FIG. 14, the sequence homology between the clone FBd3 and the HSERV-9 retrovirus is shown on the matrix chart by a continuous line for any partial homology greater than or equal to 65%. It can be seen that there are homologies in the flanking regions of the clone (with the pol gene at the 5' end and with the env gene and then the LTR at the 3' end), but that the internal region is totally divergent and does not display any homology, even weak, with the "env" gene of HSERV9. Furthermore, it is apparent that the clone FBd3 contains a longer "env" region than the one which is described for the defective endogenous HSERV-9; it may thus be seen that the internal divergent region constitutes an "insert" between the regions of partial homology with the HSERV-9 defective genes.

Example 8

Amplification, Cloning and Sequencing of the Region of the MSRV-1 Retroviral Genome Located between the Clones PSJ17 and FBd3

Four oligonucleotides, F1, B4, F6 and B1, were defined for amplifying RNA originating from concentrated virions of the strains POL2 and MS7PG. Control reactions were performed so as to check for the presence of contaminants (reaction with water). The amplification consists of a first step of RT-PCR according to the protocol described in Patent Application EP-A-0,569,272, followed by a second step of PCR performed on 10 μl of product of the first step with primers internal to the amplified first region ("nested" PCR). In the first RT-PCR cycle, the primers F1 and B4 are used. In the second PCR cycle, the primers F6 and the primer B1 are used. The primers are positioned as follows:

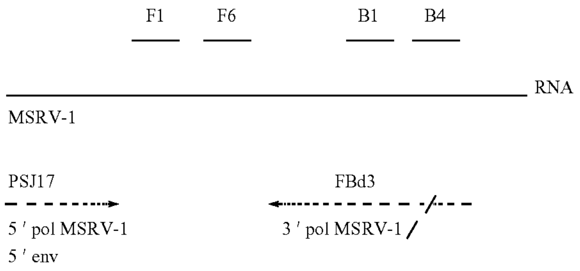

Their composition is:

```
primer F1:
TGATGTGAACGGCATACTCACTG         (SEQ ID NO:43)

primer B4:
CCCAGAGGTTAGGAACTCCCTTTC        (SEQ ID NO 44)

primer F6:
GCTAAAGGAGACTTGTGGTTGTCAG       (SEQ ID NO 45)

primer B1:
CAACATGGGCATTTCGGATTAG          (SEQ ID NO 46)
```

The product of "nested" amplification obtained and designated "t pol" is presented in FIG. 15, and corresponds to the sequence SEQ ID NO:47.

Example 9

Obtaining New Sequences, Expressed as RNA in Cells in Culture Producing MSRV-1, and Comprising an "env" Region of the MSRV-1 Retroviral Genome A library of cDNA was produced according to the procedure described by the manufacturer of the "cDNA synthesis module, cDNA rapid adaptator ligation module, cDNA rapid cloning module and lambda gt10 in vitro packaging module" kits (Amersham, ref RPN1256Y/Z, RPN1712, RPN1713, RPN1717, N334Z), from the messenger RNA extracted from cells of a B lymphoblastoid line such as is described in Example 2, established from the lymphocytes of a patient suffering from MS and possessing reverse transcriptase activity which is detectable according to the technique described by Perron et al. (3).

Oligonucleotides were defined for amplifying the cDNA cloned into the nucleic acid library between the 3' region of the clone PSJ17 (pol) and the 5'(LTR) region of the clone FBd3. Control reactions were performed so as to check for the presence of contaminants (reaction with water). PCR reactions performed on the nucleic acids cloned into the library with different pairs of primers enabled a series of clones linking pol sequences to the MSRV-1 type env or LTR sequences to be amplified.

Two clones are representative of the sequences obtained in the cellular cDNA library:

the clone JLBc1, whose sequence SEQ ID NO:48 is presented in FIG. 16;

the clone JLBc2, whose sequence SEQ ID NO:49 is presented in FIG. 17.

Figure 18:
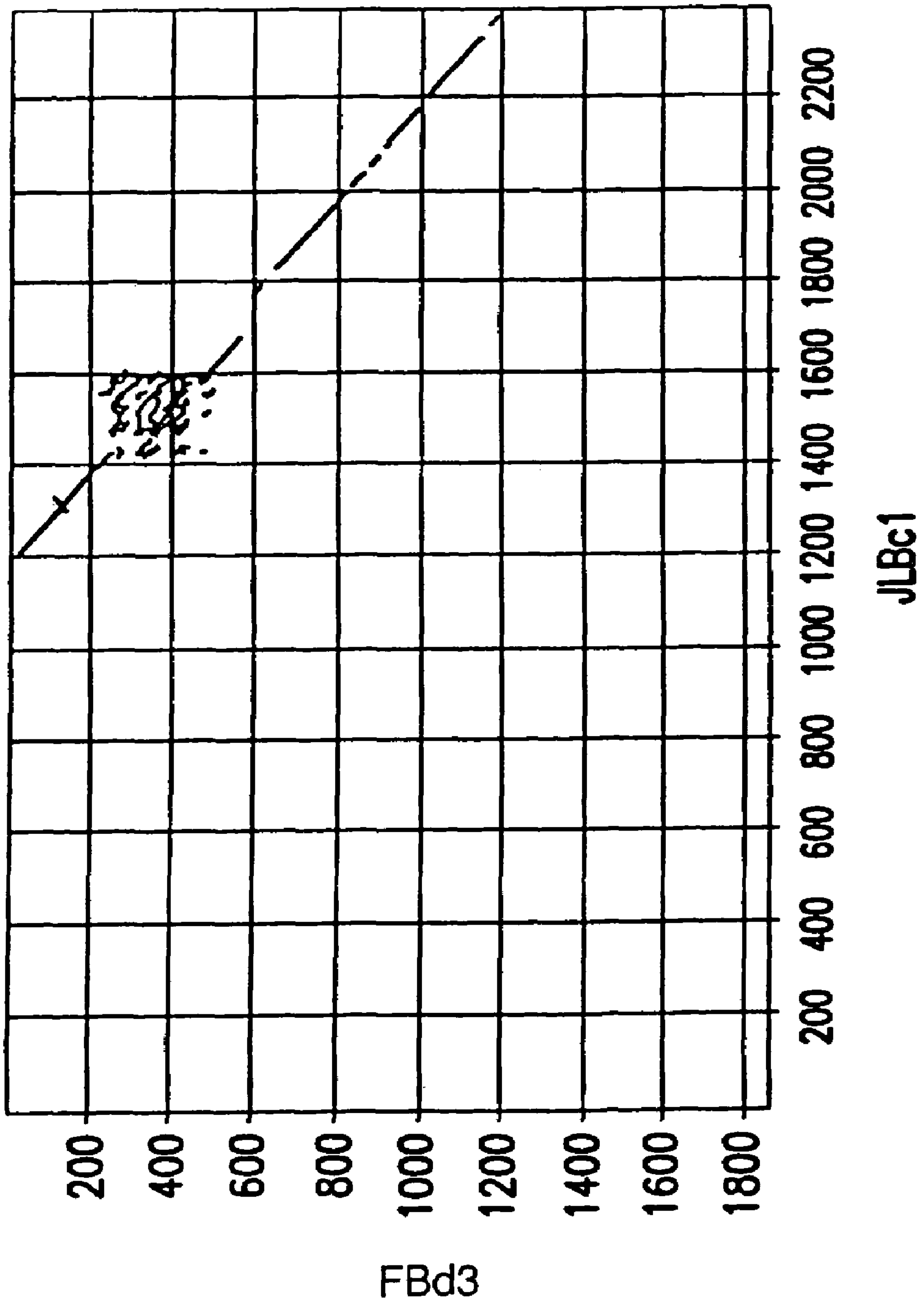
FIG. 18 shows the sequence homology between the clone JLBc1 and the clone FBd3.
Figure 19:
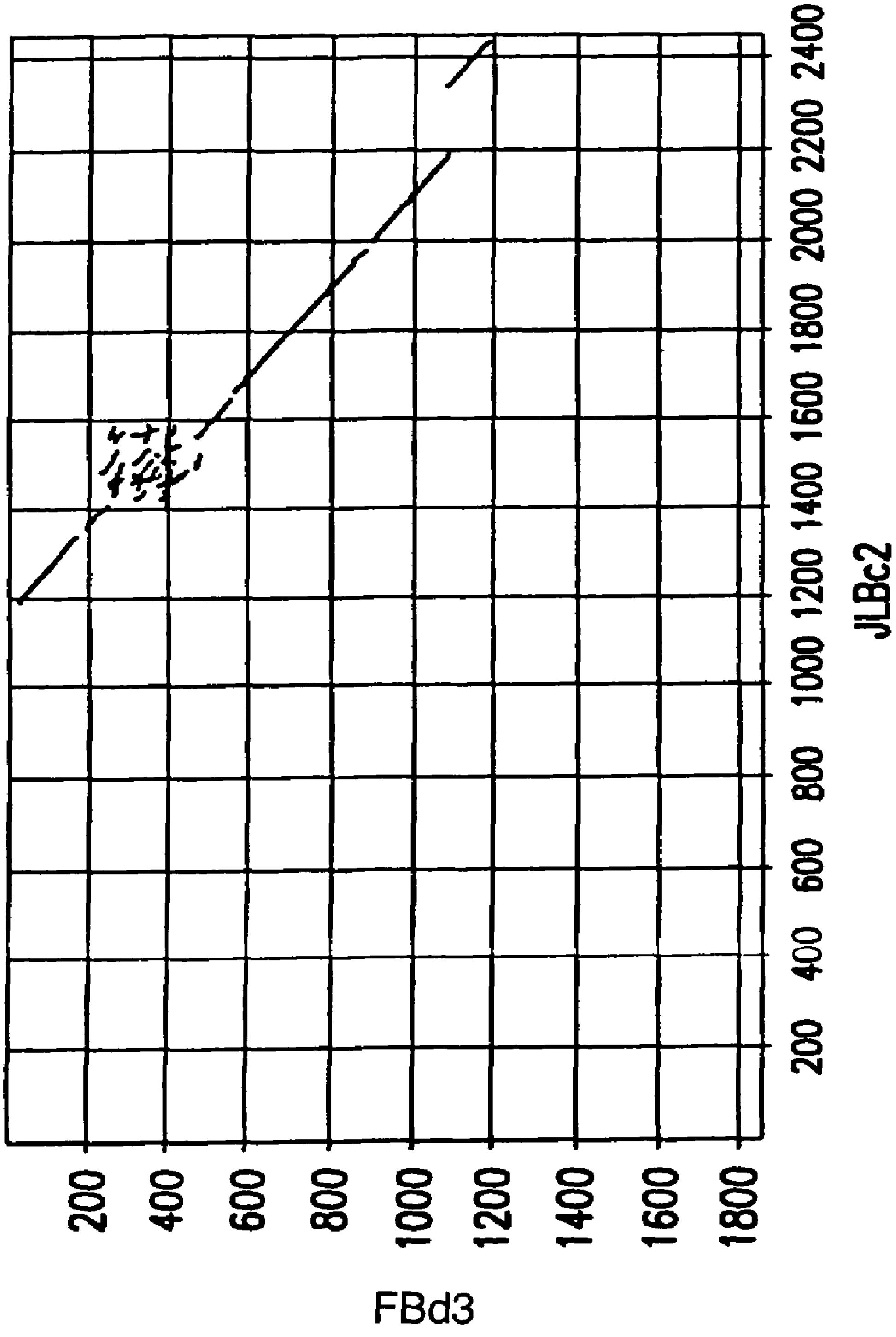
FIG. 19 shows the sequence homology between the clone JLBc2 and the clone FBd3.
Figure 20:
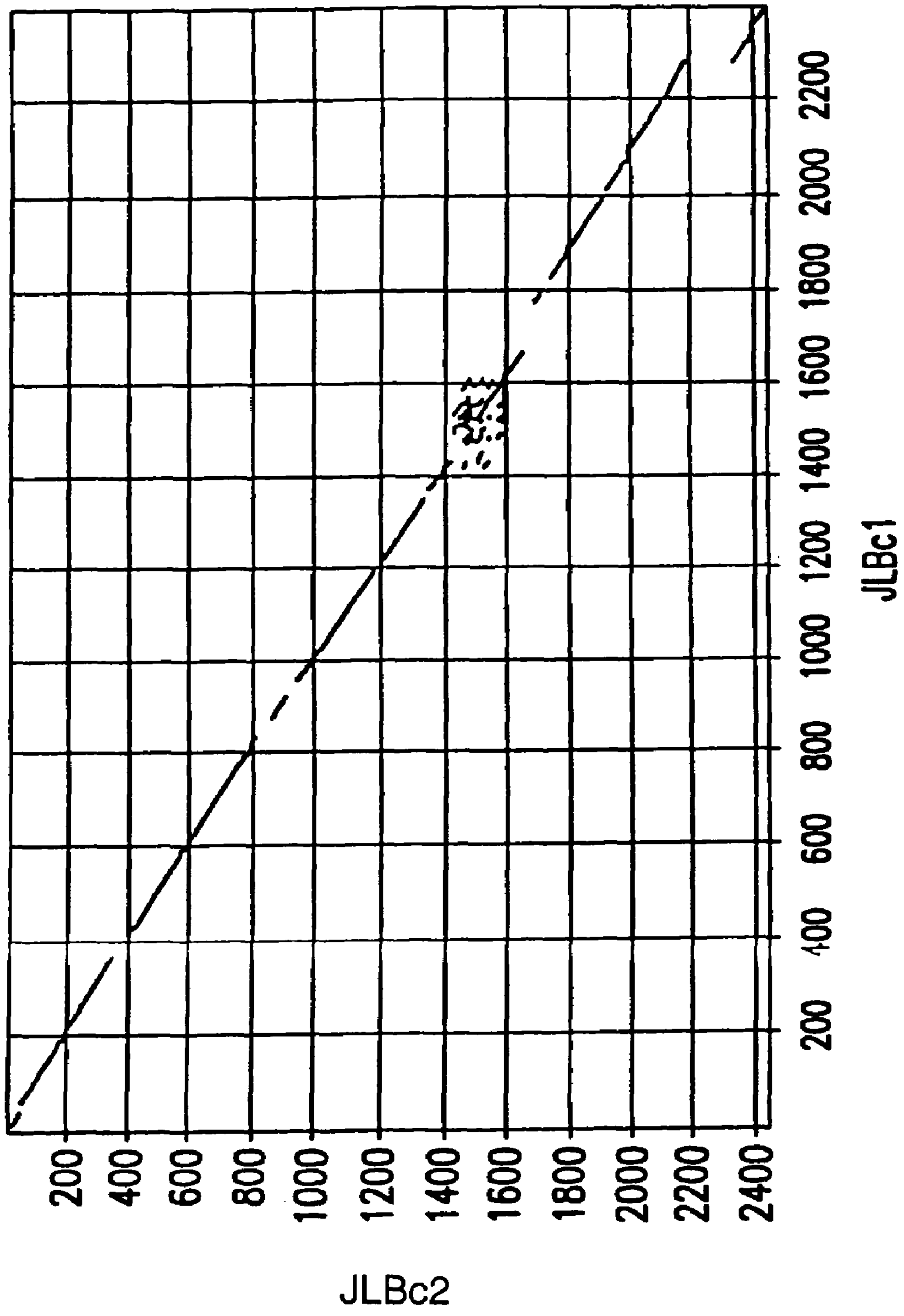
FIG. 20 shows the sequence homology between the clones JLBc1 and JLBc2.

The sequences of the clones JLBc1 and JLBc2 are homologous to that of the clone FBd3, as is apparent in FIGS. 18 and 19. The homology between the clone JLBc1 and the clone JLBc2 is shown in FIG. 20.

Figure 21:
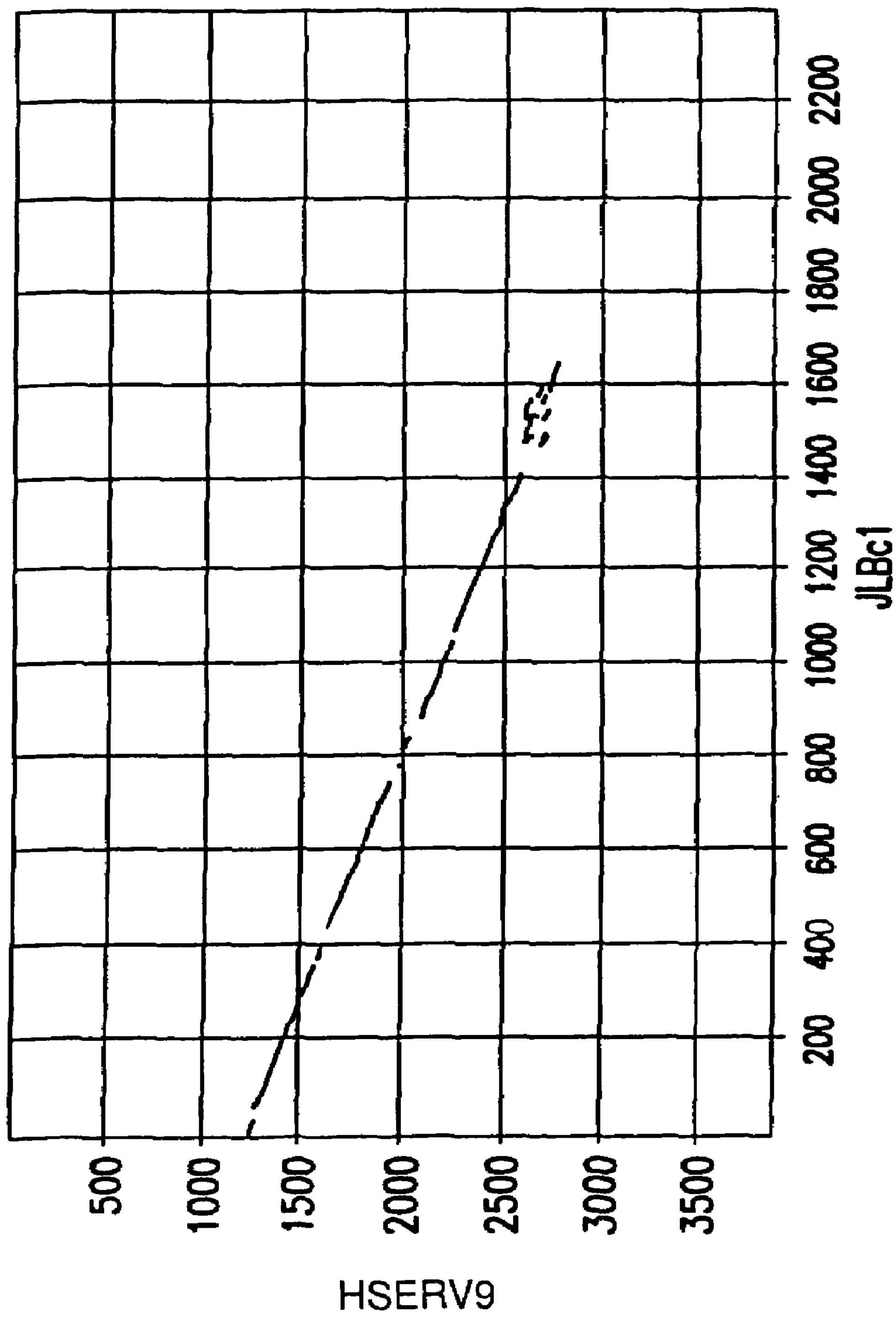
FIGS. 21 and 22 show the sequence homology between the HSERV-9 retrovirus and the clones JLBc1 and JLBc2, respectively.
Figure 22:
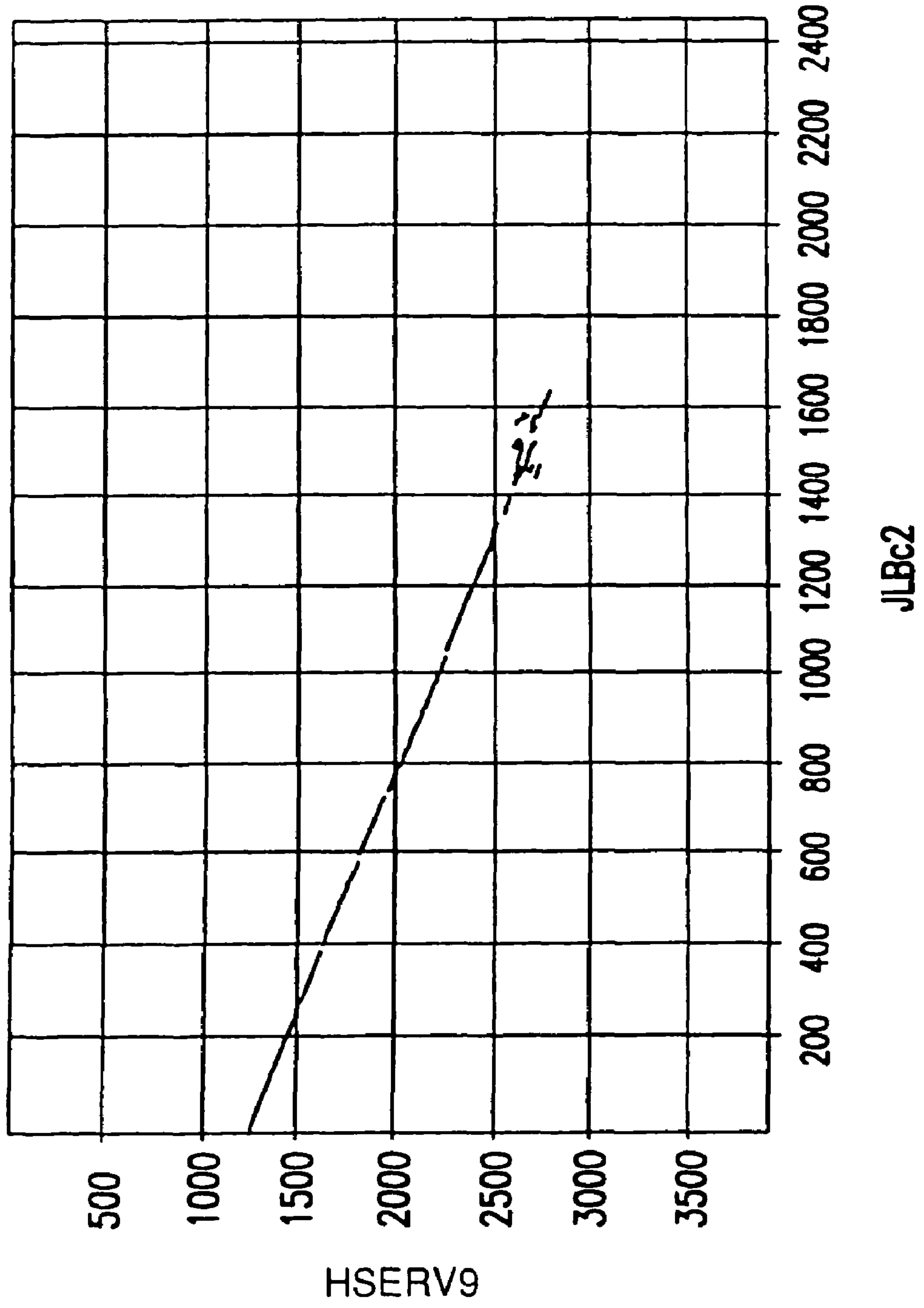

The homologies between the clones JLBc1 and JLBc2 on the one hand and the HSERV9 sequence on the other hand are presented, respectively, in FIGS. 21 and 22.

It will be noted that the region of homology between JLB1, JLB2 and FBd3 comprises, with a few sequence and size variations of the "insert", the additional sequence absent ("inserted") in the HSERV-9 env sequence, as described in Example 8.

It will also be noted that the cloned "pol" region is very homologous to HSERV-9, does not possess a reading frame (bearing in mind the sequence errors induced by the techniques used, including even the automatic sequencer) and diverges from the MSRV-1 sequences obtained from virions. In view of the fact that these sequences were cloned from the RNA of cells expressing MSRV-1 particles, it is probable that they originate from endogenous retroviral elements related to the ERV9 family; this is all the more likely for the fact that the pol and env genes are present on the same RNA which is clearly not the MSRV-1 genomic RNA. Some of these ERV9 elements possess functional LTRs which can be activated by replicative viruses coding for homologous or heterologous transactivators. Under these conditions, the relationship between MSRV-1 and HSERV-9 makes probable the transactivation of the defective (or otherwise) endogenous ERV9 elements by homologous, or even identical, MSRV-1 transactivating proteins.

Such a phenomenon may induce a viral interference between the expression of MSRV-1 and the related endogenous elements. Such an interference generally leads to a so-called "defective-interfering" expression, some features of which were to be found in the MSRV-1-infected cultures studied. Furthermore, such a phenomenon does not lack generation of the expression of polypeptides, or even of endogenous retroviral proteins which are not necessarily tolerated by the immune system. Such a scheme of aberrant expression of endogenous elements related to MSRV-1 and induced by the latter is liable to multiply the aberrant antigens, and hence to contribute to the induction of autoimmune processes such as are observed in MS.

It is, however, essential to note that the clones JLBc1 and JLBc2 differ from the ERV9 or HSERV9 sequence already described, in that they possess a longer env region comprising an additional region totally divergent from ERV9. Their kinship with the endogenous ERV9 family may hence be defined, but they clearly constitute novel elements never hitherto described. In effect, interrogation of the data banks of nucleic acid sequences available in version No. 15 (1995) of the "Entrez" software (NCBI, NIH, Bethesda, USA) did not enable a known homologous sequence in the env region of these clones to be identified.

Example 10

Obtaining Sequences Located in the 5' pol and 3' gag Region of the MSRV-1 Retroviral Genome As has already been described in Example 5, a PCR technique derived from the technique published by Frohman (19) was used. The technique derived makes it possible, using a specific primer at the 3' end of the genome to be amplified, to elongate the sequence towards the 5' region of the genome to be analyzed. This technical variant is described in the documentation of the firm Clontech Laboratories Inc., (Palo-Alto Calif., USA) supplied with its product "5'-AmpliFINDER™ RACE Kit", which was used on a fraction of virion purified as described above.

In order to carry out an amplification of the 5' region of the MSRV-1 retroviral genome starting from the pol sequence already sequenced (clone F11-1) and extending towards the gag gene, MSRV-1 specific primers were defined.

The specific 3' primers used in the kit protocol for the synthesis of the cDNA and the PCR amplification are, respectively, complementary to the following MSRV-1 sequences:

```
cDNA:
CCTGAGTTCTTGCACTAACCC        (SEQ ID NO:50)

amplification:
GTCCGTTGGGTTTCCTTACTCCT      (SEQ ID NO:51)
```

The products originating from the PCR were extracted after purification on agarose gel according to conventional methods (17), and then resuspended in 10 ml of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 ml of DNA solution were mixed with 5 ml of sterile distilled water, 1 ml of a 10-fold concentrated ligation buffer "10× LIGATION BUFFER", 2 ml of "pCR™ VECTOR" (25 ng/ml) and 1 ml of "TA DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning™ Kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "automatic sequencer model 373 A" apparatus according to the manufacturer's instructions.

This technical approach was applied to a sample of virion concentrated as described below from a mixture of culture supernatants produced by B lymphoblastoid lines such as are described in Example 2, established from lymphocytes of patients suffering from MS and possessing reverse transcriptase activity which is detectable according to the technique described by Perron et al. (3): the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g for 2 h at 4° C. After removal of the supernatant, the sedimented pellet constitutes the sample of concentrated but unpurified virions. The pellet thereby obtained is then taken up in a small volume of an appropriate buffer for the extraction of RNA. The cDNA synthesis reaction mentioned above is carried out on this RNA extracted from concentrated extracellular virion.

RT-PCR amplification according to the technique mentioned above enabled the clone GM3 to be obtained, whose sequence, identified by SEQ ID NO 52, is presented in FIG. 23.

Figure 24:
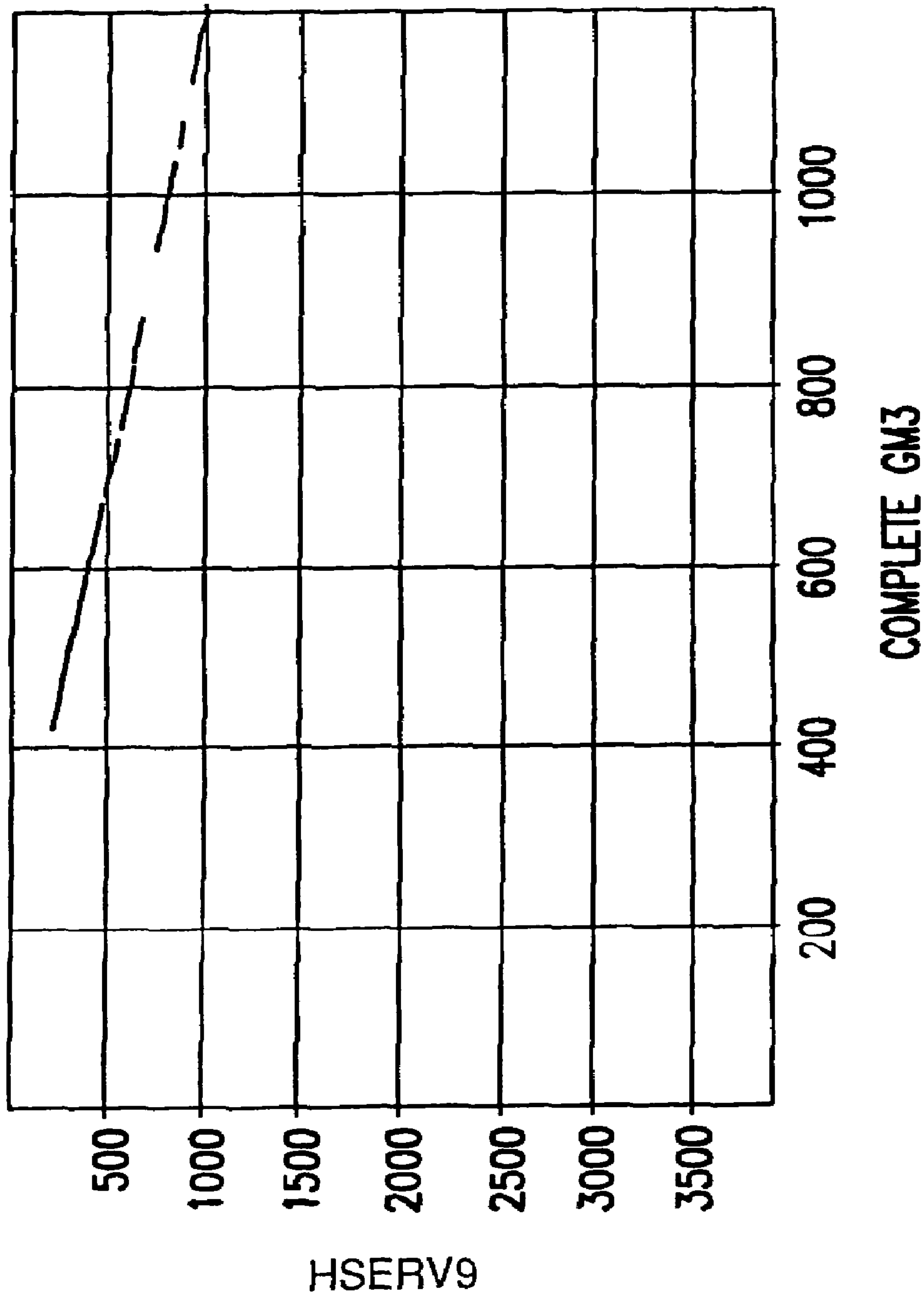
FIG. 24 shows the sequence homology between the HSERV-9 retrovirus and the clone GM3.

In FIG. 24, the sequence homology between the clone GMP3 and the HSERV-9 retrovirus is shown on the matrix chart by a continuous line, for any partial homology greater than or equal to 65%.

Figure 26:
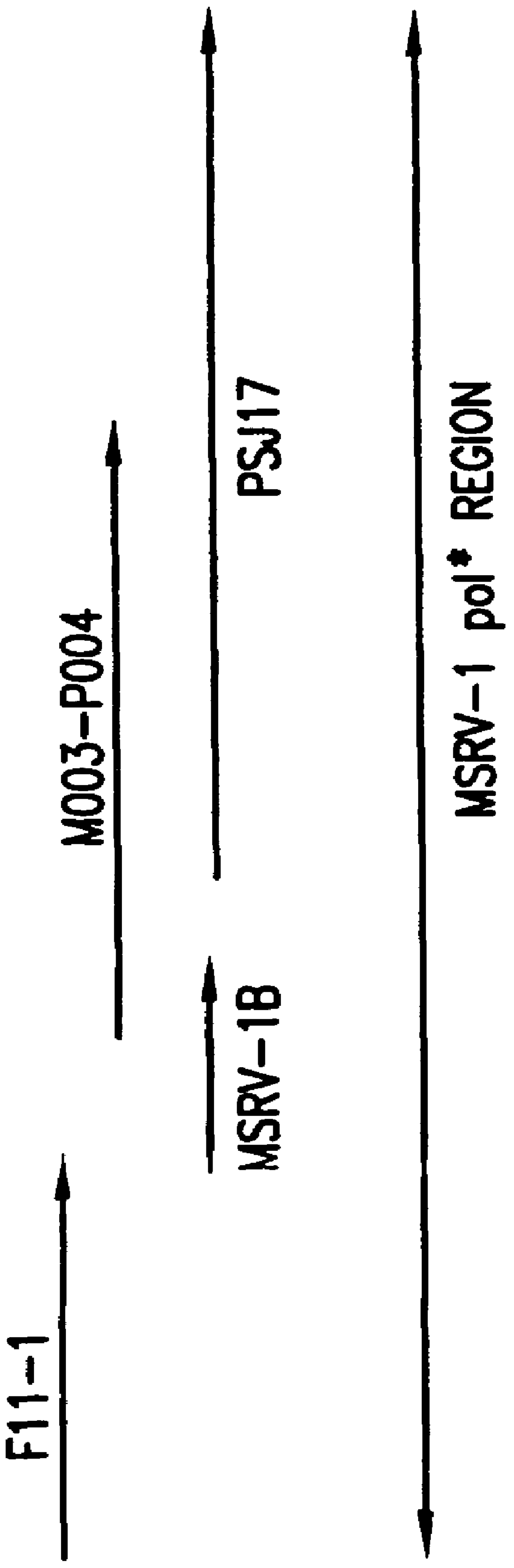
FIG. 26 shows the position of the clones F11-1, M003-P004, MSRV-1B and PSJ17 in the region hereinafter designated MSRV-1 pol*.

In summary, FIG. 25 shows the localization of the different clones studied above, relative to the known ERV9 genome. In FIG. 25, since the MSRV-1 env region is longer than the reference ERV9 env gene, the additional region is shown above the point of insertion according to a "V", on the understanding that the inserted material displays a sequence and size variability between the clones shown (JLBc1, JLBc2, FBd3). And FIG. 26 shows the position of different clones studied in the MSRV-1 pol* region.

By means of the clone GM3 described above, a possible reading frame could be defined, covering the whole of the pol gene, referenced according to SEQ ID NO:57, shown in the successive FIGS. 27*a* to 27*c*.

Example 11

Detection of Anti-MSRV-1 Specific Antibodies in Human Serum

Identification of the sequence of the pol gene of the MSRV-1 retrovirus and of an open reading frame of this gene enabled the amino acid sequence SEQ ID NO:35 of a region of the said gene, referenced SEQ ID NO:36, to be determined (see FIG. 28).

Different-synthetic peptides corresponding to fragments of the protein sequence of MSRV-1 reverse transcriptase encoded by the pol gene were tested for their antigenic specificity with respect to sera of patients suffering from MS and of healthy controls.

The peptides were synthesized chemically by solid-phase synthesis according to the Merrifield technique (Barany G, and Merrifielsd R. B, 1980, In the Peptides, 2, 1-284, Gross E and Meienhofer J, Eds., Academic Press, New York). The practical details are those described below.

a) Peptide Synthesis:

The peptides were synthesized on a phenylacetamidomethyl (PAM)/polystyrene/divinylbenzene resin (Applied Biosystems, Inc. Foster City, Calif.), using an "Applied Biosystems 430A" automatic synthesizer. The amino acids are coupled in the form of hydroxybenzotriazole (HOBT) esters. The amino acids used are obtained from Novabiochem (Läuflerlfingen, Switzerland) or Bachem (Bubendorf, Switzerland).

The chemical synthesis was performed using a double coupling protocol with N-methylpyrrolidone (NMP) as solvent. The peptides were cut from the resin, as well as the side-chain protective groups, simultaneously, using hydrofluoric acid (HF) in a suitable apparatus (type I cleavage apparatus, Peptide Institute, Osaka, Japan).

For 1 g of peptidyl resin, 10 ml of HF, 1 ml of anisole and 1 ml of dimethyl sulphide 5DMS are used. The mixture is stirred for 45 minutes at −2° C. The HF is then evaporated off under vacuum. After intensive washes with ether, the peptide is eluted from the resin with 10% acetic acid and then lyophilized.

The peptides are purified by preparative high performance liquid chromatography on a VYDAC C18 type column (250×21 mm) (The Separation Group, Hesperia, Calif., USA). Elution is carried out with an acetonitrile gradient at a flow rate of 22 ml/min. The fractions collected are monitored by an elution under isocratic conditions on a VYDACr C18 analytical column (250×4.6 mm) at a flow rate of 1 ml/min. Fractions having the same retention time are pooled and lyophilized. The preponderant fraction is then analysed by analytical high performance liquid chromatography with the system described above. The peptide which is considered to be of acceptable purity manifests itself in a single peak representing not less than 95% of the chromatogram.

The purified peptides are then analyzed with the object of monitoring their amino acid composition, using an Applied Biosystems 420H automatic amino acid analyzer. Measurement of the (average) chemical molecular mass of the peptides is obtained using LSIMS mass spectrometry in the positive ion mode on a VG. ZAB.ZSEQ double focusing instrument connected to a DEC-VAX 2000 acquisition system (VG analytical Ltd, Manchester, England).

The reactivity of the different peptides was tested against sera of patients suffering from MS and against sera of healthy controls. This enabled a peptide designated POL2B to be selected, whose sequence is shown in FIG. 28 in the identifier SEQ ID NO:35, below, encoded by the pol gene of MSRV-1 (nucleotides 181 to 330).

b) Antigenic Properties:

The antigenic properties of the POL2B peptide were demonstrated according to the ELISA protocol described below.

The lyophilized POL2B peptide was dissolved in sterile distilled water at a concentration of 1 mg/ml. This stock solution was aliquoted and kept at +4° C. for use over a fortnight, or frozen at −20° C. for use within 2 months. An aliquot is diluted in PBS (phosphate buffered saline) solution so as to obtain a final peptide concentration of 1 microgram/ml. 100 microlitres of this dilution are placed in each well of microtitration plates ("high-binding" plastic, COSTAR ref: 3590). The plates are covered with a "plate-sealer" type adhesive and kept overnight at +4° C. for the phase of adsorption of the peptide to the plastic. The adhesive is removed and the plates are washed three times with a volume of 300 microliters of a solution A (1× PBS, 0.05% Tween 20r), then inverted over an absorbent tissue. The plates thus drained are filled with 200 microliters per well of a solution B (solution A+10% of goat serum), then covered with an adhesive and incubated for 45 minutes to 1 hour at 37° C. The plates are then washed three times with the solution A as described above.

The test serum samples are diluted beforehand to 1/50 in the solution B, and 100 microliters of each dilute test serum are placed in the wells of each micro-titration plate. A negative control is placed in one well of each plate, in the form of 100 microliters of buffer B. The plates covered with an adhesive are then incubated for 1 to 3 hours at 37° C. The plates are then washed three times with the solution A as described above. In parallel, a peroxidase-labelled goat antibody directed against human IgG (Sigma Immunochemicals ref. A6029) or IgM (Cappel ref. 55228) is diluted in the solution B (dilution 1/5000 for the anti-IgG and 1/1000 for the anti-IgM). 100 microliters of the appropriate dilution of the labelled antibody are then placed in each well of the microtitration plates, and the plates covered with an adhesive are incubated for 1 to 2 hours at 37° C. A further washing of the plates is then performed as described above. In parallel, the peroxidase substrate is prepared according to the directions of the "Sigma fast OPD kit" (Sigma Immunochemicals, ref. P9187). 100 microliters of substrate solution are placed in each well, and the plates are placed protected from light for 20 to 30 minutes at room temperature.

When the color reaction has stabilized, the plates are placed immediately in an ELISA plate spectrophotometric reader, and the optical density (OD) of each well is read at a wavelength of 492 nm. Alternatively, 30 microliters of 1N HCl are placed in each well to stop the reaction, and the plates are read in the spectrophotometer within 24 hours.

The serological samples are introduced in duplicate or in triplicate, and the optical density (OD) corresponding to the serum tested is calculated by taking the mean of the OD values obtained for the same sample at the same dilution.

The net OD of each serum corresponds to the mean OD of the serum minus the mean OD of the negative control (solution B: PBS, 0.05% Tween 20r, 10% goat serum).

c) Detection of Anti-MSRV-1 IgG Antibodies by ELISA:

The technique described above was used with the POLB2 peptide to test for the presence of anti-MSRV-1 specific IgG antibodies in the serum of 29 patients for whom a definite or probable diagnosis of MS was established according to the criteria of Poser (23), and of 32 healthy controls (blood donors).

Figure 29:
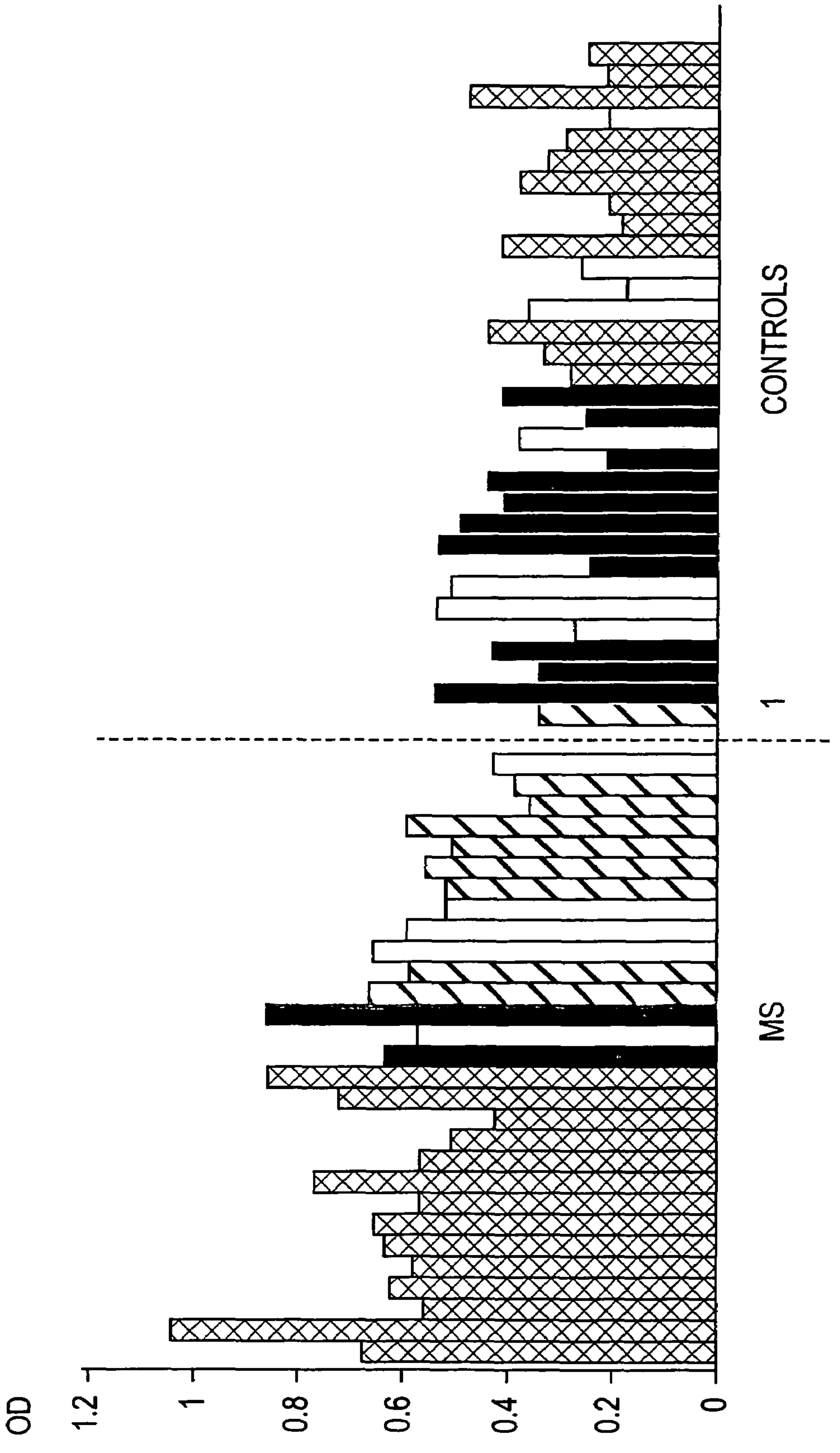
FIG. 29 shows the OD values (ELISA tests) at 492 nm obtained for 29 sera of MS patients and 32 sera of healthy controls tested with an anti-IgG antibody.

FIG. 29 shows the results for each serum tested with an anti-IgG antibody. Each vertical bar represents the net optical density (OD at 492 nm) of a serum tested. The ordinate axis gives the net OD at the top of the vertical bars. The first 29 vertical bars lying to the left of the vertical broken line represent the sera of 29 cases of MS tested, and the 32 vertical bars lying to the right of the vertical broken line represent the sera of 32 healthy controls (blood donors).

The mean of the net OD values for the MS sera tested is 0.62. The diagram enables 5 controls to be revealed whose net OD rises above the grouped values of the control population. These values may represent the presence of specific IgGs in symptomless seropositive patients. Two methods were hence evaluated in order to determine the statistical threshold of positivity of the test.

The mean of the net OD values for the controls, including the controls with high net OD values, is 0.36. Without the 5 controls whose net OD values are greater than or equal to 0.5, the mean of the "negative" controls is 0.33. The standard deviation of the negative controls is 0.10. A theoretical threshold of positivity may be calculated according to the formula:

threshold value(mean of the net OD values of the seronegative controls)+(2 or 3×standard deviation of the net OD values of the seronegative controls).

In the first case, there are considered to be symptomless seropositives, and the threshold value is equal to 0.33+(2×0.10)=0.53. The negative results represent a non-specific "background" of the presence of antibodies directed specifically against an epitope of the peptide.

In the second case, if the set of controls consisting of blood donors in apparent good health is taken as a reference basis, without excluding the sera which are, on the face of it, seropositive, the standard deviation of the "non-MS controls" is 0.116. The threshold value then becomes 0.36+(2×0.116)=0.59.

According to this analysis, the test is specific for MS. In this respect, it is seen that the test is specific for MS, since, as shown in Table 1, no control has a net OD above this threshold. In fact, this result reflects the fact that the antibody titers in patients suffering from MS are, for the most part, higher than in healthy controls who have been in contact with MSRV-1.

TABLE NO. 1

| | MS | CONTROLS |
|---|---|---|
| | 0.681 | 0.3515 |
| | 1.0425 | 0.56 |
| | 0.5675 | 0.3565 |
| | 0.63 | 0.449 |
| | 0.588 | 0.2825 |
| | 0.645 | 0.55 |
| | 0.6635 | 0.52 |
| | 0.576 | 0.2535 |
| | 0.7765 | 0.55 |
| | 0.5745 | 0.51 |
| | 0.513 | 0.426 |
| | 0.4325 | 0.451 |
| | 0.7255 | 0.227 |
| | 0.859 | 0.3905 |
| | 0.6435 | 0.265 |
| | 0.5795 | 0.4295 |
| | 0.8655 | 0.291 |
| | 0.671 | 0.347 |
| | 0.596 | 0.4495 |
| | 0.662 | 0.3725 |
| | 0.602 | 0.181 |
| | 0.525 | 0.2725 |
| | 0.53 | 0.426 |
| | 0.565 | 0.1915 |
| | 0.517 | 0.222 |
| | 0.607 | 0.395 |
| | 0.3705 | 0.34 |
| | 0.397 | 0.307 |
| | 0.4395 | 0.219 |
| | | 0.491 |
| | | 0.2265 |
| | | 0.2605 |
| MEAN | 0.62 | 0.33 |
| STD DEV | 0.14 | 0.10 |
| THRESHOLD VALUE | | 0.53 |

In accordance with the first method of calculation, and as shown in FIG. 29 and in the corresponding Table 1, 26 of the 29 MS sera give a positive result (net OD greater than or equal to 0.50), indicating the presence of IgGs specifically directed against the POL2B peptide, hence against a portion of the reverse transcriptase enzyme of the MSRV-1 retrovirus encoded by its pol gene, and consequently against the MSRV-1 retrovirus. Thus, approximately 90% of the MS patients tested have reacted against an epitope carried by the POL2B peptide and possess circulating IgGs directed against the latter.

Five out of 32 blood donors in apparent good health show a positive result. Thus, it is apparent that approximately 15% of the symptomless population may have been in contact with an epitope carried by the POL2B peptide under conditions which have led to an active immunization which manifests itself in the persistence of specific serum IgGs. These conditions are compatible with an immunization against the MSRV-1 retrovirus reverse transcriptase during an infection with (and/or reactivation of) the MSRV-1 retrovirus. The absence of apparent neurological pathology recalling MS in these seropositive controls may indicate that they are healthy carriers and have eliminated an infectious virus after immunizing themselves, or that they constitute an at-risk population of chronic carriers. In effect, epidemiological data showing that a pathogenic agent present in the environment of regions of high prevalence of MS may be the cause of this disease imply that a fraction of the population free from MS has necessarily been in contact with such a pathogenic agent. It has been shown that the MSRV-1 retrovirus constitutes all or part of this "pathogenic agent" at the source of MS, and it is hence normal for controls taken from a healthy population to possess IgG type antibodies against components of the MSRV-1 retrovirus. Thus, the difference in seroprevalence between the MS and control populations is extremely significant: "chi-squared" test, $p<0.001$. These results hence point to an aetiopathogenic role of MSRV-1 in MS.

d) Detection of Anti-MSRV-1 IgM Antibodies by ELISA:

The ELISA technique with the POL2B peptide was used to test for the presence of anti-MSRV-1 IgM specific antibodies in the serum of 36 patients for whom a definite or probable diagnosis of MS was established according to the criteria of Poser (23), and of 42 healthy controls (blood donors).

Figure 30:
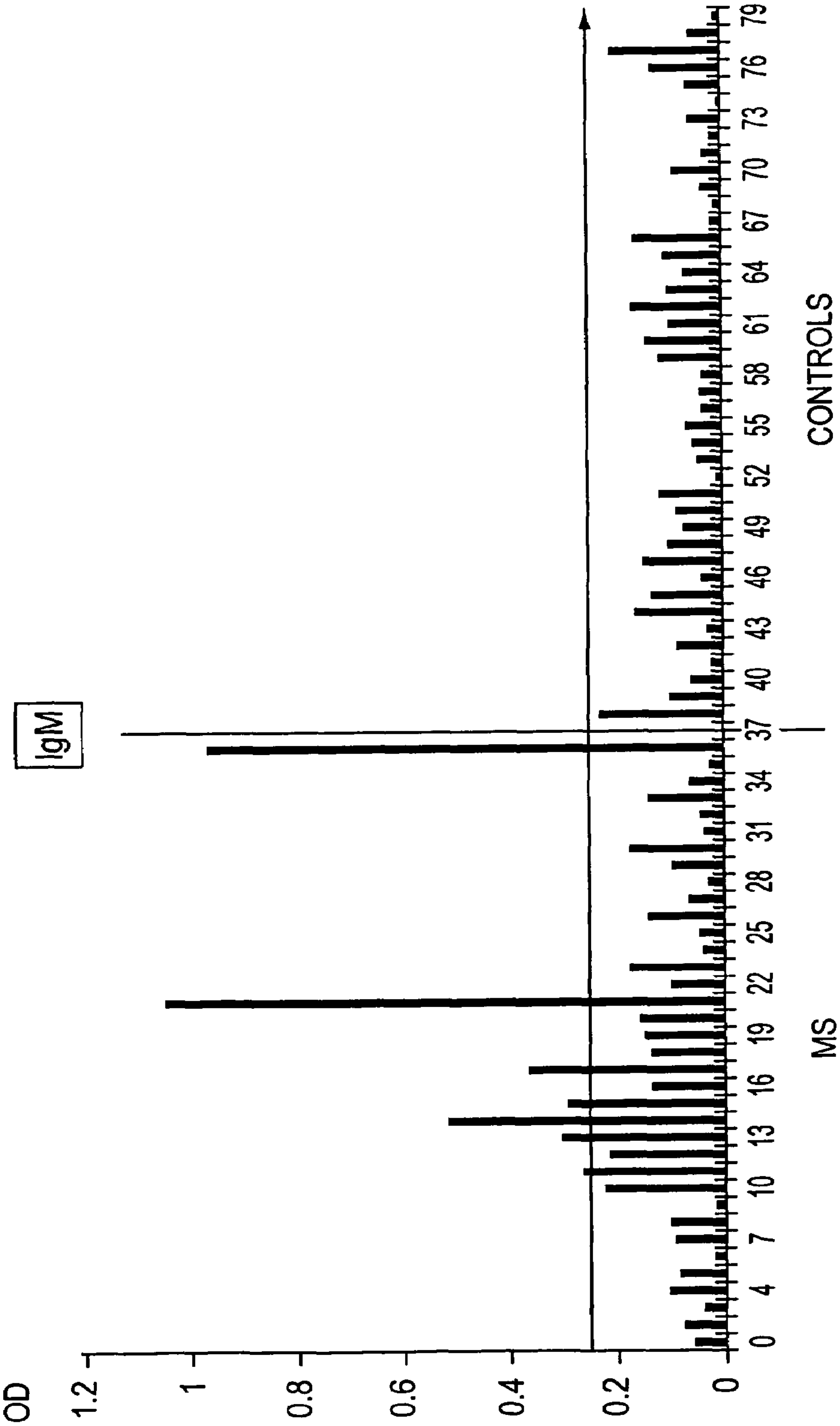
FIG. 30 shows the OD values (ELISA tests) at 492 nm obtained for 36 sera of MS patients and 42 sera of healthy controls tested with an anti-IgM antibody.

FIG. 30 shows the results for each serum tested with an anti-IgM antibody. Each vertical bar represents the net optical density (OD at 492 nm) of a serum tested. The ordinate axis gives the net OD at the top of the vertical bars. The first 36 vertical bars lying to the left of the vertical line cutting the abscissa axis represent the sera of 36 cases of MS tested, and the vertical bars lying to the right of the vertical broken line represent the sera of 42 healthy controls (blood donors). The horizontal line drawn in the middle of the diagram represents a theoretical threshold defining the boundary of the positive results (in which the top of the bar lies above) and the negative results (in which the top of the bar lies below).

The mean of the net OD values for the MS cases tested is 0.19.

The mean of the net OD values for the controls is 0.09.

The standard deviation of the negative controls is 0.05.

In view of the small difference between the mean and the standard deviation of the controls, the threshold of theoretical positivity may be calculated according to the formula:

threshold value=(mean of the net OD values of the seronegative controls)+(3×standard deviation of the net OD values of the seronegative controls).

The threshold value is hence equal to $0.09+(3\times0.05)=0.26$; or, in practice, 0.25.

The negative results represent a non-specific "background" of the presence of antibodies directed specifically against an epitope of the peptide.

According to this analysis, and as shown in FIG. 30 and in the corresponding Table 2, the IgM test is specific for MS, since no control has a net OD above the threshold. Seven of the 36 MS sera produce a positive IgM result; now, a study of the clinical data reveals that these positive sera were taken during a first attack of MS or an acute attack in untreated patients. It is known that IgMs directed against pathogenic agents are produced during primary infections or during reactivations following a latency phase of the said pathogenic agent.

The difference in seroprevalence between the MS and control populations is extremely significant: "chi-squared" test, $p<0.001$.

These results point to an aetiopathogenic role of MSRV-1 in MS.

The detection of IgM and IgG antibodies against the POL2B peptide enables the course of an MSRV-1 infection and/or of the viral reactivation of MSRV-1 to be evaluated.

TABLE NO. 2

| | MS | CONTROLS |
|---|---|---|
| | 0.064 | 0.243 |
| | 0.087 | 0.11 |
| | 0.044 | 0.098 |
| | 0.115 | 0.028 |
| | 0.089 | 0.094 |
| | 0.025 | 0.038 |
| | 0.097 | 0.176 |
| | 0.108 | 0.146 |
| | 0.018 | 0.049 |
| | 0.234 | 0.161 |
| | 0.274 | 0.113 |
| | 0.225 | 0.079 |
| | 0.314 | 0.093 |
| | 0.522 | 0.127 |
| | 0.306 | 0.02 |
| | 0.143 | 0.052 |
| | 0.375 | 0.062 |
| | 0.142 | 0.074 |
| | 0.157 | 0.043 |
| | 0.168 | 0.046 |
| | 1.051 | 0.041 |
| | 0.104 | 0.13 |
| | 0.187 | 0.153 |
| | 0.044 | 0.107 |
| | 0.053 | 0.178 |
| | 0.153 | 0.114 |
| | 0.07 | 0.078 |
| | 0.033 | 0.118 |
| | 0.104 | 0.177 |
| | 0.187 | 0.026 |
| | 0.044 | 0.024 |
| | 0.053 | 0.046 |
| | 0.153 | 0.116 |
| | 0.07 | 0.04 |
| | 0.033 | 0.028 |
| | 0.973 | 0.073 |
| | | 0.008 |
| | | 0.074 |
| | | 0.141 |
| | | 0.219 |
| | | 0.047 |
| | | 0.017 |
| MEAN | 0.19 | 0.09 |
| STD. DEV. | 0.23 | 0.05 |
| THRESHOLD VALUE | | 0.26 |

e) Search for Immunodominant Epitopes in the POL2B Peptide:

In order to reduce the non-specific background and to optimize the detection of the responses of the anti-MSRV-1 antibodies, the synthesis of octapeptides, advancing in successive one amino acid steps, covering the whole of the sequence determined by POL2B, was carried out according to the protocol described below.

The chemical synthesis of overlapping octapeptides covering the amino acid sequence 61-110 shown in the identifier SEQ ID NO:35 was carried out on an activated cellulose membrane according to the technique of BERG et al. (1989. J. Ann. Chem. Soc., 111, 8024-8026) marketed by Cambridge Research Biochemicals under the trade name Spotscan. This technique permits the simultaneous synthesis of a large number of peptides and their analysis.

The synthesis is carried out with esterified amino acids in which the a-amino group is protected with an FMOC group (Nova Biochem) and the side-chain groups with protective groups such as trityl, t-butyl ester or t-butyl ether. The esterified amino acids are solubilized in N-methylpyrrolidone (NMP) at a concentration of 300 nM, and 0.9 ml are applied to spots of deposit of bromophenol blue. After incubation for 15 minutes, a further application of amino acids is carried out according to another 15-minute incubation. If the coupling between two amino acids has taken place correctly, a coloration modification (change from blue to yellow-green) is observed. After three washes in DMF, an acetylation step is performed with acetic anhydride. Next, the terminal amino groups of the peptides in the process of synthesis are deprotected with 20% pyridine in DMF. The spots of deposit are restained with a 1% solution of bromophenol blue in DMF, washed three times with methanol and dried. This set of operations constitutes one cycle of addition of an amino acid, and this cycle is repeated until the synthesis is complete. When all the amino acids have been added, the $NH_2$-terminal group of the last amino acid is deprotected with 20% piperidine in DMF and acetylated with acetic anhydride. The groups protecting the side chain are removed with a dichloromethane/trifluoroacetic acid/triisobutylsilane (5 ml/5 ml/250 ml) mixture. The immunoreactivity of the peptides is then tested by ELISA.

Figure 31:
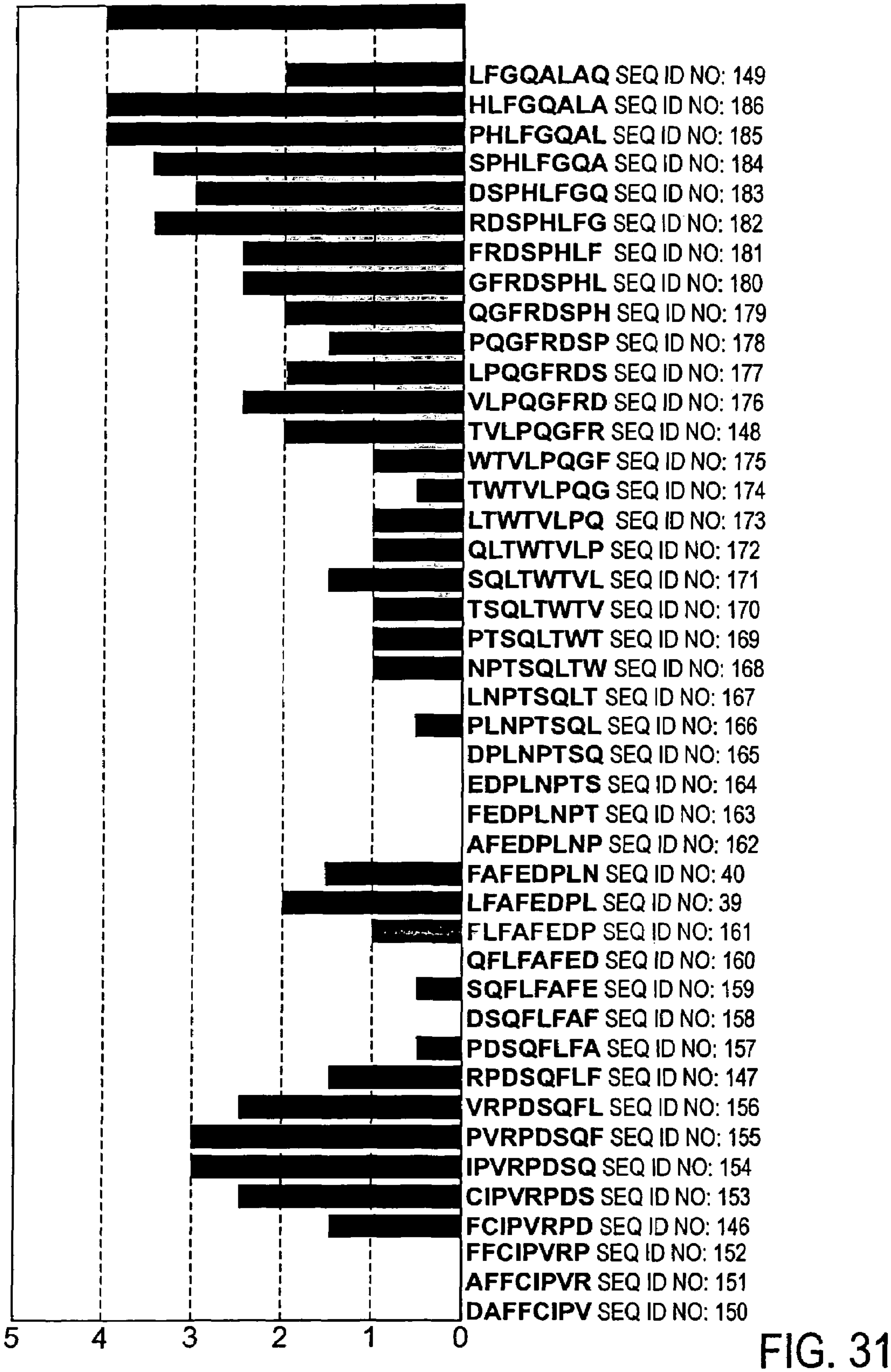
FIGS. 31 to 33 show the results obtained (relative intensity of the spots) for 43 overlapping octapeptides covering the amino acid sequence 61-110, according to the Spotscan technique, respectively with a pool of MS sera, with a pool of control sera and with the pool of MS sera after deduction of a background corresponding to the maximum signal detected on at least one octapeptide with the control serum (intensity=1), on the understanding that these sera were diluted to 1/50. The bar at the far right-hand end represents a graphic scale standard unrelated to the serological test.
Figure 32:
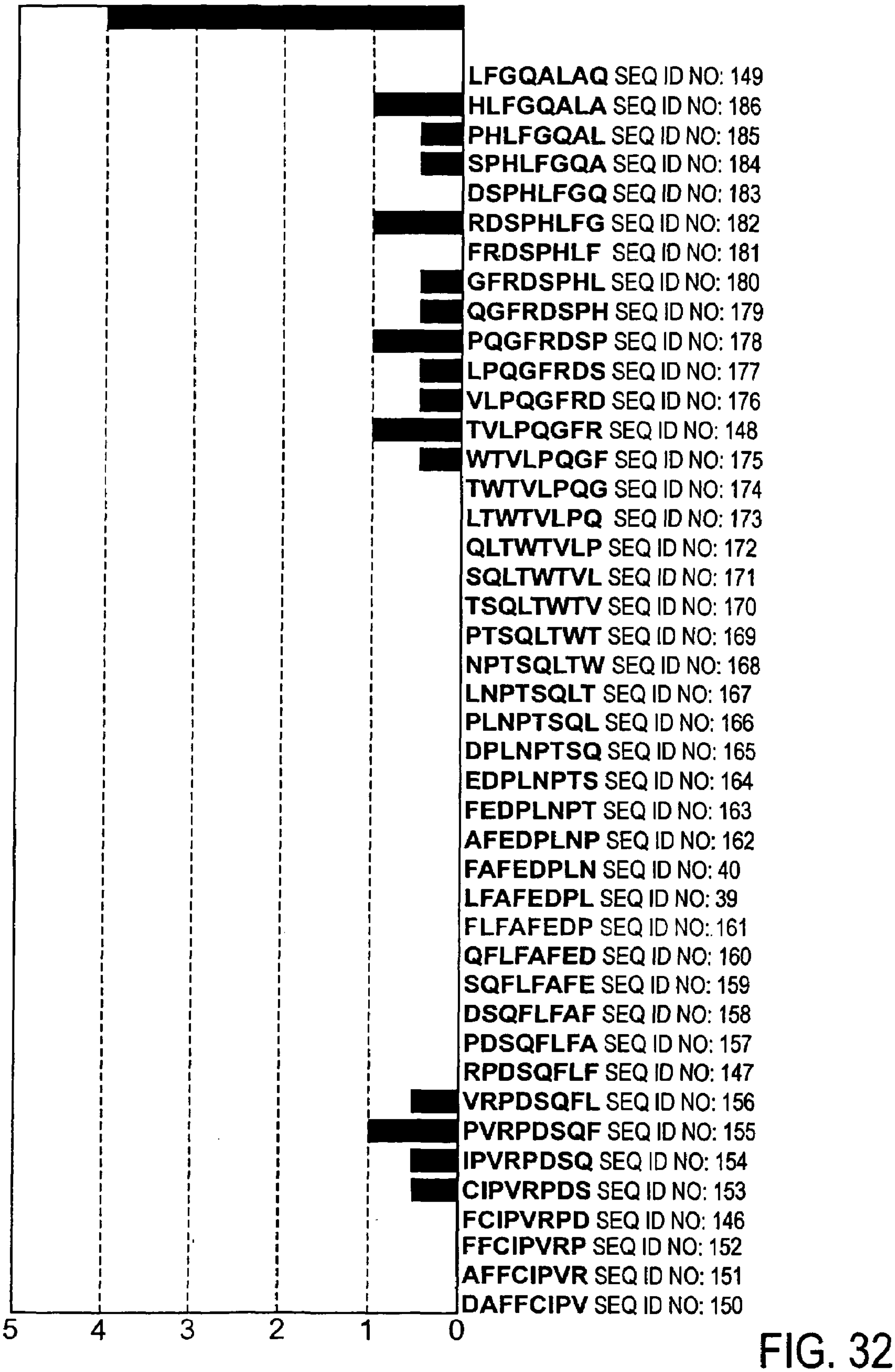
Figure 33:
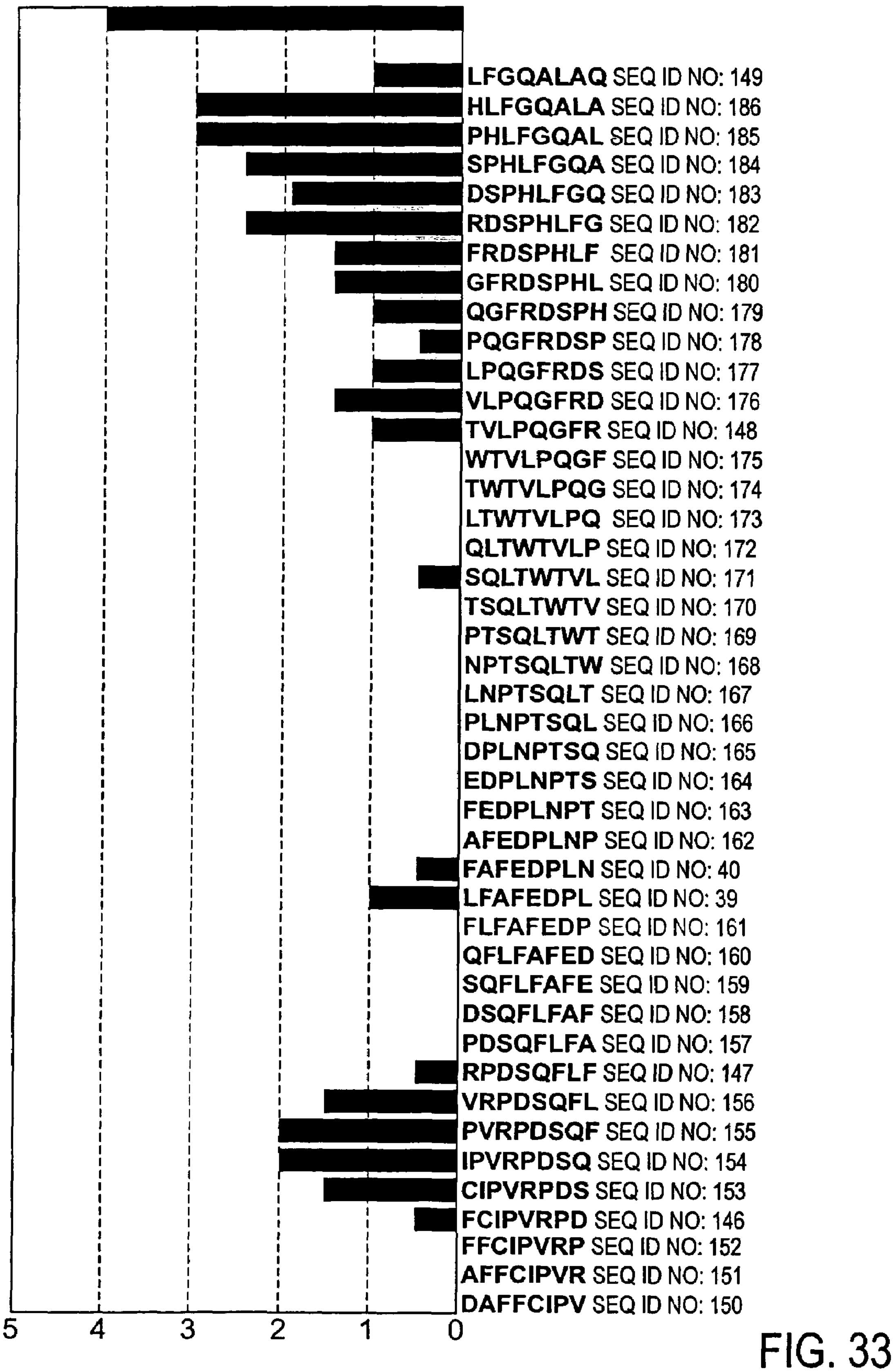

After synthesis of the different octapeptides in duplicate on two different membranes, the latter are rinsed with methanol and washed in TBS (0.1M Tris pH 7.2), then incubated overnight at room temperature in a saturation buffer. After several washes in TBS-T (0.1M Tris pH 7.2-0.05% Tween 20), one membrane is incubated with a 1/50 dilution of a reference serum originating from a patient suffering from MS, and the other membrane with a 1/50 dilution of a pool of sera of healthy controls. The membranes are incubated for 4 hours at room temperature. After washes with TBS-T, a β-galactosidase-labelled anti-human immunoglobulin conjugate (marketed by Cambridge Research Biochemicals) is added at a dilution of 1/200, and the mixture is incubated for two hours at room temperature. After washes of the membranes with 0.05% TBS-T and PBS, the immunoreactivity in the different spots is visualized by adding 5-bromo-4-chloro-3-indolyl b-D-galactopyranoside in potassium. The intensity of coloration of the spots is estimated qualitatively with a relative value from 0 to 5 as shown in the attached FIGS. 31 to 33.

In this way, it is possible to determine two immunodominant regions at each end of the POL2B peptide, corresponding, respectively, to the amino acid sequences 65-75 (SEQ ID NO:37) and 92-109 (SEQ ID NO:38), according to FIG. 34, and lying, respectively, between the octapeptides Phe-Cys-Ile-Pro-Val-Arg-Pro-Asp (FCIPVRPD) (SEQ ID NO:146) and Arg-Pro-Asp-Ser-Gln-Phe-Leu-Phe (RPDSQFLF) (SEQ ID NO:147), and Thr-Val-Leu-Pro-Gln-Gly-Phe-Arg (TVLPQGFR) (SEQ ID NO:148) and Leu-Phe-Gly-Gln-Ala-Leu-Ala-Gln (LFGQALAQ) (SEQ ID NO:149), and a region which is less reactive but apparently more specific, since it does not produce any background with the control serum, represented by the octapeptides Leu-Phe-Ala-Phe-Glu-Asp-Pro-Leu (LFAFEDPL) (SEQ ID NO:39) and Phe-Ala-Phe-Glu-Asp-Pro-Leu-Asn (FAFEDPLN) (SEQ ID NO:40).

These regions make it possible to define new peptides which are more specific and more immunoreactive according to the usual techniques.

It is thus possible, as a result of the discoveries made and the methods developed by the inventors, to carry out a diagnosis of MSRV-1 infection and/or reactivation and to evaluate a therapy in MS on the basis of its efficacy in "negativing" the detection of these agents in the patients' biological fluids. Furthermore, early detection in individuals not yet displaying neurological signs of MS could make it possible to institute a treatment which would be all the more effective with respect to the subsequent clinical course for the fact that it would precede the lesion stage which corresponds to the onset of neurological disorders. Now, at the present time, a diagnosis of MS cannot be established before a symptomatology of neurological lesions has set in, and hence no treatment is instituted before the emergence of a clinical picture suggestive of lesions of the central nervous system which are already significant. The diagnosis of an MSRV-1 and/or MSRV-2 infection and/or reactivation in man is hence of decisive importance, and the present invention provides the means of doing this.

It is thus possible, apart from carrying out a diagnosis of MSRV-1 infection and/or reactivation, to evaluate a therapy in MS on the basis of its efficacy in "negativing" the detection of these agents in the patients' biological fluids.

Example 12

Obtaining a Clone LB19 Containing a Portion of the gag Gene of the MSRV-1 Retrovirus A PCR technique derived from the technique published by Gonzalez-Quintial R et al. (19) and PLAZA et al. (25) was used. From the total RNAs extracted from a fraction of virion purified as described above, the cDNA was synthesized using a specific primer (SEQ ID No.60) at the 3' end of the genome to be amplified, using EXPAND™ REVERSE TRANSCRIPTASE (BOEHRINGER MANNHEIM).

```
cDNA:
AAGGGGCATG GACGAGGTGG TG (SEQ ID NO:61) (antisense)
GCTTATTT
```

After purification, a poly(G) tail was added at the 5' end of the cDNA using the "Terminal transferases kit" marketed by the company Boehringer Mannheim, according to the manufacturer's protocol.

An anchoring PCR was carried out using the following 5' and 3' primers:

```
AGATCTGCAG AATTCGATAT   (SEQ ID No. 85)  (sense),
CACCCCCCCC CCCCCC
and
AAATGTCTGC GGCACCAATC   (SEQ ID No. 60)  (antisense)
TCCATGTT
```

Next, a semi-nested anchoring PCR was carried out with the following 5' and 3' primers:

```
AGATCTGCAG AATTCGATAT   (SEQ ID No. 86)  (sense),
CA
and

AAATGTCTGC GGCACCAATC   (SEQ ID No. 60)  (antisense)
TCCATGTT
```

The products originating from the PCR were purified after purification on agarose gel according to conventional methods (17), and then resuspended in 10 microliters of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 μl of DNA solution were mixed with 5 μl of sterile distilled water, 1 μl of 10-fold concentrated ligation buffer "10× LIGATION BUFFER", 2 μl of "pCR™ VECTOR" (25 ng/μl) and 1 μl of "T4 DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning Kit™. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

PCR amplification according to the technique mentioned above was used on a cDNA synthesized from the nucleic acids of fractions of infective particles purified on a sucrose gradient, according to the technique described by H. Perron (13), from culture supernatants of B lymphocytes of a patient suffering from MS, immortalized with Epstein-Barr virus (EBV) strain B95 and expressing retroviral particles associated with reverse transcriptase activity as described by Perron et al. (3) and in French Patent Applications MS 10, 11 and 12. the clone LB19, whose sequence, identified by SEQ ID NO:55, is presented in FIG. 35.

The clone makes it possible to define, with the clone GM3 previously sequenced and the clone G+E+A (see Example 15), a region of 690 base pairs representative of a significant portion of the gag gene of the MSRV-1 retrovirus, as presented in FIG. 36. This sequence designated SEQ ID NO:82 is reconstituted from different clones overlapping at their ends. This sequence is identified under the name MSRV-1 "gag*" region. In FIG. 36, a potential reading frame with the translation into amino acids is presented below the nucleic acid sequence.

Example 13

Obtaining A Clone FBd13 Containing a pol Gene Region Related to the MSRV-1 Retrovirus and an Apparently Incomplete ENV Region Containing a Potential Reading Frame (ORF) for a Glycoprotein Extraction of viral RNAs: The RNAs were extracted according to the method briefly described below.

A pool of culture supernatant of B lymphocytes of patients suffering from MS (650 ml) is centrifuged for 30 minutes at 10,000 g. The viral pellet obtained is resuspended in 300 microliters of PBS/10 mM $MgCl_2$. The material is treated with a DNAse (100 mg/ml)/RNAse (50 mg/ml) mixture for 30 minutes at 37° C. and then with proteinase K (50 mg/ml) for 30 minutes at 46° C.

The nucleic acids are extracted with one volume of a phenol/0.1% SDS (VN) mixture heated to 60° C., and then re-extracted with one volume of phenol/chloroform (1:1; V/V).

Precipitation of the material is performed with 2.5 V of ethanol in the presence of 0.1 V of sodium acetate pH 5.2. The pellet obtained after centrifugation is resuspended in 50 microliters of sterile DEPC water.

The sample is treated again with 50 mg/ml of "RNAse free" DNAse for 30 minutes at room temperature, extracted with one volume of phenol/chloroform and precipitated in the presence of sodium acetate and ethanol.

The RNA obtained is quantified by an OD reading at 260 nm. The presence of MSRV-1 and the absence of DNA contaminant is monitored by a PCR and an MSRV-1-specific RTPCR associated with a specific ELOSA for the MSRV-1 genome.

Synthesis of cDNA:

5 μg of RNA are used to synthesize a cDNA primed with a poly(DT) oligonucleotide according to the instructions of the "cDNA Synthesis Module" kit (ref RPN 1256, Amersham) with a few modifications: The reverse transcription is performed at 45° C. instead of the recommended 42° C.

The synthesis product is purified by a double extraction and a double purification according to the manufacturer's instructions.

The presence of MSRV-1 is verified by an MSRV-1 PCR associated with a specific ELOSA for the MSRV-1 genome.

"Long Distance PCR": (LD-PCR)

500 ng of cDNA are used for the LD-PCR step (Expand Long Template System; Boehringer (ref. 1681 842)).

Several pairs of oligonucleotides were used. Among these, the pair defined by the following primers:

```
5' primer:
GGAGAAGAGC AGCATAAGTG G        (SEQ ID NO:62)

3' primer:
GTGCTGATTG GTGTATTTAC AATCC.   (SEQ ID NO:63)
```

The amplification conditions are as follows:

94° C. 10 seconds

56° C. 30 seconds

68° C. 5 minutes;

10 cycles, then 20 cycles with an increment of 20 seconds in each cycle on the elongation time. At the end of this first amplification, 2 microliters of the amplification product are subjected to a second amplification under the same conditions as before.

The LD-PCR reactions are conducted in a Perkin model 9600 PCR apparatus in thin-walled microtubes (Boehringer).

The amplification products are monitored by electrophoresis of ⅕th of the amplification volume (10 microliters) in 1% agarose gel. For the pair of primers described above, a band of approximately 1.7 kb is obtained.

Cloning of the Amplified Fragment:

The PCR product was purified by passage through a preparative agarose gel and then through a Costar column (Spin; D. Dutcher) according to the supplier's instructions.

2 microliters of the purified solution are joined up with 50 ng of vector PCRII according to the supplier's instructions (TA Cloning Kit; British Biotechnology)).

The recombinant vector obtained is isolated by transformation of competent DH5aF' bacteria. The bacteria are selected using their resistance to ampicillin and the loss of metabolism for Xgal (=white colonies). The molecular structure of the recombinant vector is confirmed by plasmid minipreparation and hydrolysis with the enzyme EcoR1.

FBd13, a positive clone for all these criteria, was selected. A large-scale preparation of the recombinant plasmid was performed using the Midiprep Quiagen kit (ref 12243) according to the supplier's instructions.

Sequencing of the clone FBd13 is performed by means of the Perkin Prism Ready Amplitaq FS dye terminator kit (ref. 402119) according to the manufacturer's instructions. The sequence reactions are introduced into a Perkin type 377 or 373A automatic sequencer. The sequencing strategy consists in gene walking carried out on both strands of the clone Fbd13.

The sequence of the clone FBd13 is identified by SEQ ID NO:54.

Figure 37:
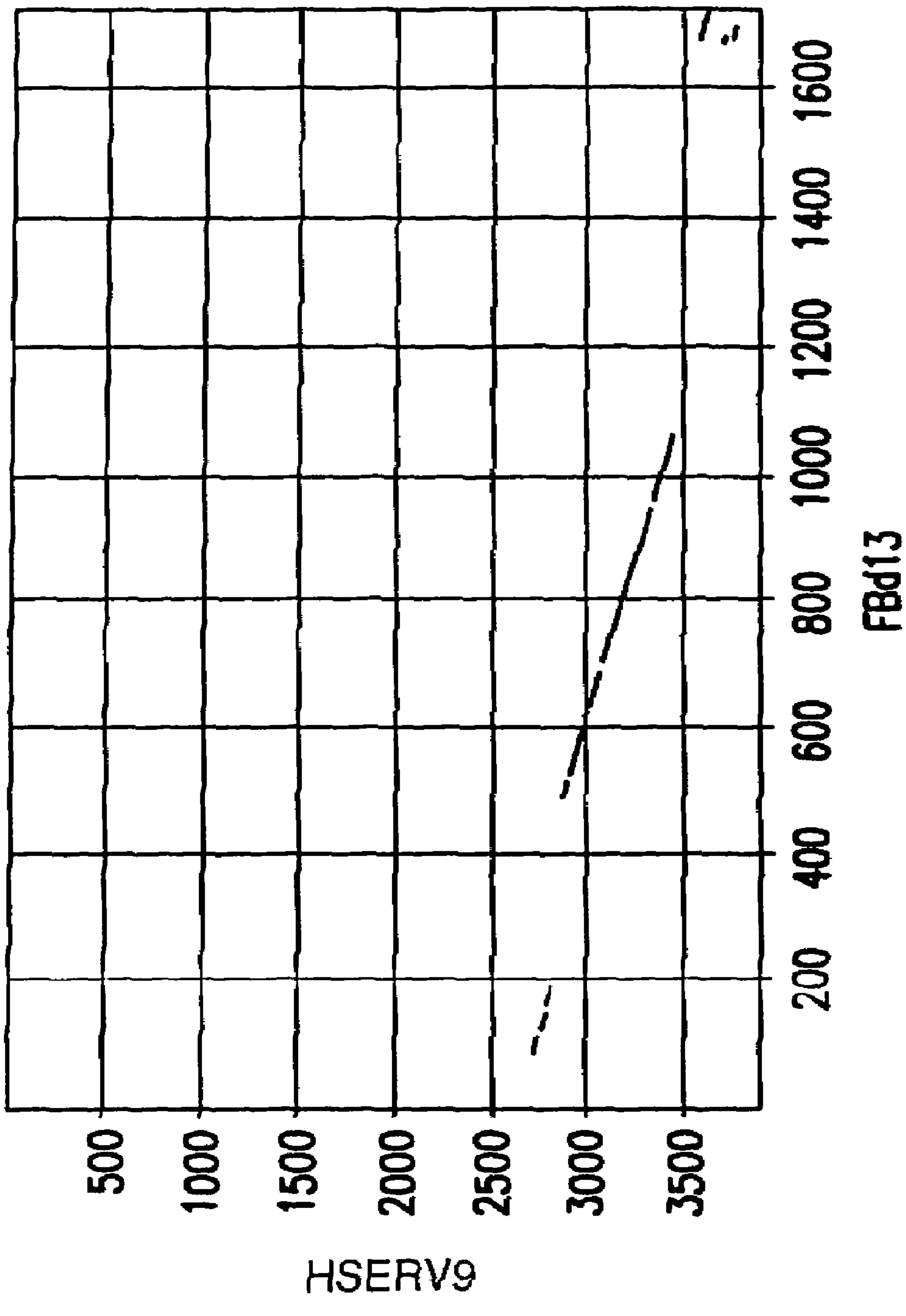
FIG. 37 shows the sequence homology between the clone FBd13 and the HSERV-9 retrovirus; according to this representation, the continuous line means a percentage homology greater than or equal to 70% and the absence of a line means a smaller percentage homology.

In FIG. 37, the sequence homology between the clone FBd13 and the HSERV-9 retrovirus is shown on the matrix chart by a continuous line for any partial homology greater than or equal to 70%. It can be seen that there are homologies in the flanking regions of the clone (with the pol gene at the 5' end and with the env gene and then the LTR at the 3' end), but that the internal region is totally divergent and does not display any homology, even weak, with the env gene of HSERV-9. Furthermore, it is apparent that the clone FBd13 contains a longer "env" region than the one which is described for the defective endogenous HSERV-9; it may thus be seen that the internal divergent region constitutes an "insert" between the regions of partial homology with the HSERV-9 defective genes.

This additional sequence determines a potential orf, designated ORF B13, which is represented by its amino acid sequence SEQ ID NO:81.

The molecular structure of the clone FBd13 was analyzed using the GenWorks® software and GenBank™ and SwissProt data banks.

5 glycosylation sites were found.

The protein does not have significant homology with already known sequences.

It is probable that this clone originates from a recombination of an endogenous retroviral element (ERV), linked to the replication of MSRV-1.

Such a phenomenon does not lack generation of the expression of polypeptides, or even of endogenous retroviral proteins which are not necessarily tolerated by the immune system. Such a scheme of aberrant expression of endogenous elements related to MSRV-1 and/or induced by the latter is liable to multiply the aberrant antigens, and hence tends to contribute to the induction of autoimmune processes such as are observed in MS. It clearly constitutes a novel element never hitherto described. In effect, interrogation of the data banks of nucleic acid sequences available in version No. 19 (1996) of the "Entrez" software (NCBI, NIH, Bethesda, USA) did not enable a known homologous sequence comprising the whole of the env region of this clone to be identified.

Example 14

Obtaining a Clone FP6 Containing a Portion of the pol Gene, with a Region Coding for the Reverse Transcriptase Enzyme Homologous to the Clone Pol* MSRV-1, and a 3'pol Region Divergent from the Equivalent Sequences Described in the Clones Pol*, tpol, FBd3, JLBc1 and JLBc2

A 3'RACE was performed on total RNA extracted from plasma of a patient suffering from MS. A healthy control plasma treated under the same conditions was used as negative control. The synthesis of cDNA was carried out with the following modified oligo(dT) primer:

5' GACTCGCTGC AGATCGATTT TTTTTTTTTT  (SEQ ID NO:64)
TTTT 3' and Boehringer "Expand RT" reverse transcriptase according to the conditions recommended by the company. A PCR was performed with the enzyme Klentaq (Clontech) under the following conditions: 94° C. 5 min then 93° C. 1 min, 58° C. 1 min, 68° C. 3 min for 40 cycles and 68° C. for 8 min, and with a final reaction volume of 50 µl.

Primers Used for the PCR:

- 5' primer, identified by SEQ ID NO:65

5' GCCATCAAGC CACCCAAGAA CTCTTAACTT 3';

3' primer, identified by SEQ ID NO:64 (=the same as for the cDNA)

A second, so-called "semi-nested" PCR was carried out with a 5' primer located within the region already amplified. This second PCR was performed under the same experimental conditions as those used in the first PCR, using 10 ml of the amplification product originating from the first PCR.

Primers Used for the Semi-Nested PCR:

- 5' primer, identified by SEQ ID NO:66

5' CCAATAGCCA GACCATTATA TACACTAATT 3';

3' primer, identified by SEQ ID NO:64 (=the same as for the cDNa)

Primers SEQ ID NO:65 and SEQ ID NO:66 are specific for the pol* region: position No. 403 to No. 422 and No. 641 to No. 670, respectively.

An amplification product was thus obtained from the extracellular RNA extracted from the plasma of a patient suffering from MS. The corresponding fragment was not observed for the plasma of the healthy control. This amplification product was cloned in the following manner.

The amplified DNA was inserted into a plasmid using the TA Cloning™ kit. The 2 µl of DNA solution were mixed with 5 µl of sterile distilled water, 1 µl of a 10-fold concentrated ligation buffer "10× LIGATION BUFFER", 2 µl of "pCR™

VECTOR" (25 ng/μl) and 1 μl of "TA DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide was selected for sequencing of the insert, after hybridization with a primer complementary to the Sp6 promoter present on the cloning plasmid of the TA Cloning Kit™. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

The clone obtained, designated FP6, enables a region of 467 bp which is 89% homologous to the pol* region of the MSRV-1 retrovirus and a region of 1167 bp which is 64% homologous to the pol region of ERV-9 (No. 1634 to 2856) to be defined.

The clone FP6 is represented in FIG. 38 by its nucleotide sequence identified by SEQ ID NO:57. The three potential reading frames of this clone are indicated by their amino acid sequence under the nucleotide sequence.

Example 15

Obtaining a Region Designated G+E+A Containing and ORF for a Retroviral Protease, by PCR Amplification of the Nucleic Acid Sequence Contained between the 5' Region Defined by the Clone "GM3" and the 3' Region Defined by the Clone Pol*, from the RNA Extracted form a Pool of Plasmas of Patients Suffering from MS Oligonucleotides specific for the MSRV-1 sequences already identified by the Applicant were defined in order to amplify the retroviral RNA originating from virions present in the plasma of patients suffering from MS. Control reactions were performed so as to monitor the presence of contaminants (reaction with water). The amplification consists of a step of RT-PCR followed by a "nested" PCR. Pairs of primers were defined for amplifying three overlapping regions (designated G, E and A) on the regions defined by the sequences of the clones GM3 and pol* described above.

Semi-Nested RT-PCR for Amplification of the Region G:

- in the first RT-PCR cycle, the following primers are used:
  - primer 1: SEQ ID NO:67 (sense)
  - primer 2: SEQ ID NO:68 (antisense)
- in the second PCR cycle, the following primers are used:
  - primer 1: SEQ ID NO:69 (sense)
  - primer 4: SEQ ID NO:70 (antisense)

Nested RT-PCR for Amplification of the Region E:

- in the first RT-PCR cycle, the following primers are used:
  - primer 5: SEQ ID NO:71 (sense)
  - primer 6: SEQ ID NO:72 (antisense)
- in the second PCR cycle, the following primers are used:
  - primer 7: SEQ ID NO:73 (sense)
  - primer 8: SEQ ID NO:72 (antisense)

Semi-Nested RT-PCR for Amplification of the Region A:

- in the first RT-PCR cycle, the following primers are used:
  - primer 9: SEQ ID NO:74 (sense)
  - primer 10: SEQ ID NO:75 (antisense)
- in the second PCR cycle, the following primers are used:
  - primer 9: SEQ ID NO:74 (sense)
  - primer 11: SEQ ID NO:76 (antisense)

The primers and the regions G, E and A which they define are positioned as follows:

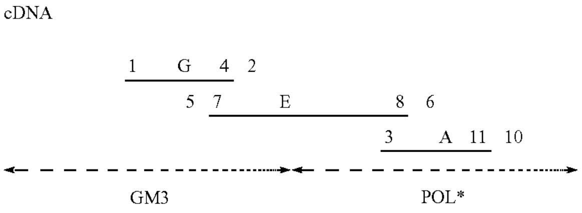

The sequence of the region defined by the different clones G, E and A was determined after cloning and sequencing of the "nested" amplification products.

The clones G, E and A were assembled together by PCR with the primers 1 at the 5' end of the fragment G and 11 at the 3' end of the fragment A, the primers being described above. An approximately 1580-bp fragment G+E+A was amplified and inserted into a plasmid using the TA Cloning™ kit. The sequence of the amplification product corresponding to G+E+A was determined and analysis of the G+E and E+A overlaps was carried out. The sequence is shown in FIG. 39, and corresponds to the sequence SEQ ID NO:83.

A reading frame coding for an MSRV-1 retroviral protease was found in the region E. The amino acid sequence of the protease, identified by SEQ ID NO:84, is presented in FIG. 40.

Example 16

Obtaining a Clone LTRGAG12, Related to an Endogenous Retroviral Element (ERV) Close to MSRV-1, in the DNA of an MS Lymphoblastoid Line Producing Virions and Expressing the MSRV-1 Retrovirus A nested PCR was performed on the DNA extracted from a lymphoblastoid line (B lymphocytes immortalized with the EBV virus strain B95, as described above and as is well known to a person skilled in the art) expressing the MSRV-1 retrovirus and originating from peripheral blood lymphocytes of a patient suffering from MS.

In the first PCR step, the following primers are used:

```
primer 4327:
CTCGATTTCT TGCTGGGCCT TA      (SEQ ID NO:77)

primer 3512:
GTTGATTCCC TCCTCAAGCA         (SEQ ID NO:78)
```

This step comprises 35 amplification cycles with the following conditions: 1 min at 94° C., 1 min at 54° C. and 4 min at 72° C.

In the second PCR step, the following primers are used:

```
primer 4294: CTCTACCAAT CAGCATGTGG   (SEQ ID NO:79)

primer 3591: TGTTCCTCTT GGTCCCTAT    (SEQ ID NO:80)
```

This step comprises 35 amplification cycles with the following conditions: 1 min at 94° C., 1 min at 54° C. and 4 min at 72° C.

The products originating from the PCR were purified after purification on agarose gel according to conventional methods (17), and then resuspended in 10 μl of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 ml of DNA solution were mixed with 5 μl of sterile distilled water, 1 μl of a 10-fold concentrated ligation buffer "10× LIGATION BUFFER", 2 μl of "pCR™ VECTOR" (25 ng/μl) and 1 μl of "TA DNA LIGASE". This mixture was incubated overnight at 12° C. The following steps were carried out according to the instructions of the TA Cloning™ kit (British Biotechnology). At the end of the procedure, the white colonies of recombinant bacteria were picked out in order to be cultured and to permit extraction of the plasmids incorporated according to the so-called "miniprep" procedure (17). The plasmid preparation from each recombinant colony was cut with a suitable restriction enzyme and analyzed on agarose gel. The plasmids possessing an insert detected under UV light after staining the gel with ethidium bromide were selected for sequencing of the insert, after hybridization with a primer complementary to the Sp6 promoter present on the cloning plasmid of the TA Cloning Kit™. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

Thus, a clone designated LTRGAG12 could be obtained, and is represented by its internal sequence identified by SEQ ID NO:56.

This clone is probably representative of endogenous elements close to ERV-9, present in human DNA, in particular in the DNA of patients suffering from MS, and capable of interfering with the expression of the MSRV-1 retrovirus, hence capable of having a role in the pathogenesis associated with the MSRV-1 retrovirus and capable of serving as marker for a specific expression in the pathology in question.

Example 17

Detection of Anti-MSRV-1 Specific Antibodies in Human Serum

Identification of the sequence of the pol gene of the MSRV-1 retrovirus and of an open reading frame of this gene enabled the amino acid sequence SEQ ID NO:63 of a region of the said gene, referenced SEQ ID NO:58, to be determined.

Different synthetic peptides corresponding to fragments of the protein sequence of MSRV-1 reverse transcriptase encoded by the pol gene were tested for their antigenic specificity with respect to sera of patients suffering from MS and of healthy controls.

The peptides were synthesized chemically by solid-phase synthesis according to the Merrifield technique (22). The practical details are those described below.

a) Peptide Synthesis:

The peptides were synthesized on a phenylacetamidomethyl (PAM)/polystyrene/divinylbenzene resin (Applied Biosystems, Inc. Foster City, Calif.), using an "Applied Biosystems 430A" automatic synthesizer. The amino acids are coupled in the form of hydroxybenzotriazole (HOBT) esters. The amino acids used are obtained from Novabiochem (Läuflerlfingen, Switzerland) or Bachem (Bubendorf, Switzerland).

The chemical synthesis was performed using a double coupling protocol with N-methylpyrrolidone (NMP) as solvent. The peptides were cut from the resin, as well as the side-chain protective groups, simultaneously, using hydrofluoric acid (HF) in a suitable apparatus (type I cleavage apparatus, Peptide Instiute, Osaka, Japan).

For 1 g of peptidyl resin, 10 ml of HF, 1 ml of anisole and 1 ml of dimethyl sulphide 5DMS are used. The mixture is stirred for 45 minutes at −2° C. The HF is then evaporated off under vacuum. After intensive washes with ether, the peptide is eluted from the resin with 10% acetic acid and then lyophilized.

The peptides are purified by preparative high performance liquid chromatography on a VYDAC C18 type column (250×21 mm) (The Separation Group, Hesperia, Calif., USA). Elution is carried out with an acetonitrile gradient at a flow rate of 22 ml/min. The fractions collected are monitored by an elution under isocratic conditions on a VYDAC™ C18 analytical column (250×4.6 mm) at a flow rate of 1 ml/min. Fractions having the same retention time are pooled and lyophilized. The preponderant fraction is then analyzed by analytical high performance liquid chromatography with the system described above. The peptide which is considered to be of acceptable purity manifests itself in a single peak representing not less than 95% of the chromatogram.

The purified peptides are then analyzed with the object of monitoring their amino acid composition, using an Applied Biosystems 420H automatic amino acid analyzer. Measurement of the (average) chemical molecular mass of the peptides is obtained using LSIMS mass spectrometry in the positive ion mode on a VG. ZAB.ZSEQ double focusing instrument connected to a DEC-VAX 2000 acquisition system (VG analytical Ltd, Manchester, England).

The reactivity of the different peptides was tested against sera of patients suffering from MS and against sera of healthy controls. This enabled a peptide designated S24Q to be selected, whose sequence is identified by SEQ ID NO:59, encoded by a nucleotide sequence of the pol gene of MSRV-1 (SEQ ID NO:58).

b) Antigenic Properties:

The antigenic properties of the S24Q peptide were demonstrated according to the ELISA protocol described below.

The lyophilized S24Q peptide was dissolved in 10% acetic acid at a concentration of 1 mg/ml. This stock solution was aliquoted and kept at +4° C. for use over a fortnight, or frozen at −20° C. for use within 2 months. An aliquot is diluted in PBS (phosphate buffered saline) solution so as to obtain a final peptide concentration of 5 micrograms/ml. 100 microliters of this dilution are placed in each well of Nunc Maxisorb (trade name) microtitration plates. The plates are covered with a "plate-sealer" type adhesive and kept for 2 hours at +37° C. for the phase of adsorption of the peptide to the plastic. The adhesive is removed and the plates are washed three times with a volume of 300 microliters of a solution A (1×' PBS, 0.05% Tween 20r), then inverted over an absorbent tissue. The plates thus drained are filled with 250 microliters per well of a solution B (solution A+10% of goat serum), then covered with an adhesive and incubated for 1 hour at 37° C. The plates are then washed three times with the solution A as described above.

The test serum samples are diluted beforehand to 1/100 in the solution B, and 100 microliters of each dilute test serum are placed in the wells of each micro-titration plate. A negative control is placed in one well of each plate, in the form of 100 microliters of buffer B. The plates covered with an adhesive are then incubated for 1 hour 30 min at 37° C. The plates are then washed three times with the solution A as described above. For the IgG response, a peroxidase-labelled goat antibody directed against human IgG (marketed by Jackson Immuno Research Inc.) is diluted in the solution B (dilution 1/10,000). 100 microliters of the appropriate dilution of the labelled antibody are then placed in each well of the microtitration plates, and the plates covered with an adhesive are incubated for 1 hour at 37° C. A further washing of the plates is then performed as described above. In parallel, the peroxidase substrate is prepared according to the directions of the bioMérieux kits. 100 microliters of substrate solution are placed in each well, and the plates are placed protected from light for 20 to 30 minutes at room temperature.

When the color reaction has stabilized, 50 microliters of Color 2 (bioMérieux trade name) are placed in each well in order to stop the reaction. The plates are placed immediately in an ELISA plate spectrophotometric reader, and the optical density (OD) of each well is read at a wavelength of 492 nm.

The serological samples are introduced in duplicate or in triplicate, and the optical density (OD) corresponding to the serum tested is calculated by taking the mean of the OD values obtained for the same sample at the same dilution.

The net OD of each serum corresponds to the mean OD of the serum minus the mean OD of the negative control (solution B: PBS, 0.05% Tween 20×, 10% goat serum).

c) Detection of anti-MSRV-1 IgG Antibodies (S24Q) by ELISA:

The technique described above was used with the S24Q peptide to test for the presence of anti-MSRV-1 specific IgG antibodies in the serum of 15 patients for whom a definite diagnosis of MS was established according to the criteria of Poser (23), and of 15 healthy controls (blood donors).

Figure 41:
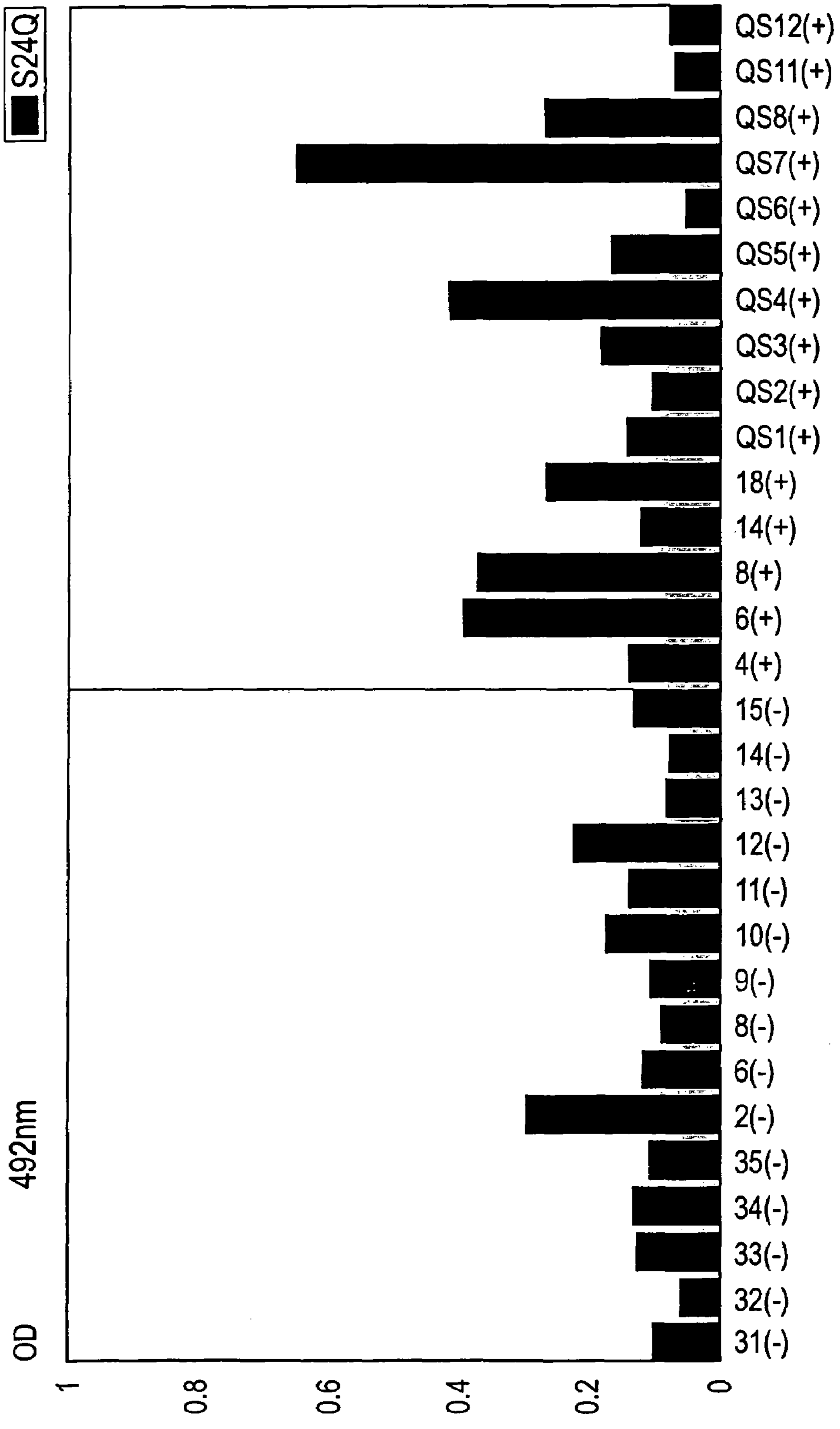
FIG. 41 shows the response of each serum of patients suffering from MS, indicated by the symbol (+), and of healthy patients, symbolised by (–), tested with an anti-IgG antibody, expressed as net optical density at 492 nm.

FIG. 41 shows the results for each serum tested with an anti-IgG antibody. Each vertical bar represents the net optical density (OD at 492 nm) of a serum tested. The ordinate axis gives the net OD at the top of the vertical bars. The first 15 vertical bars lying to the left of the vertical broken line represent the sera of 15 healthy controls (blood donors), and the 15 vertical bars lying to the right of the vertical broken line represent the sera of 15 cases of MS tested. The diagram enables 2 controls to be revealed whose OD rises above the grouped values of the control population. These values may represent the presence of specific IgGs in symptomless seropositive patients. Two methods were hence evaluated in order to determine the statistical threshold of positivity of the test.

The mean of the net OD values for the controls, including the controls with high net OD values, is 0.129 and the standard deviation is 0.06. Without the 2 controls whose OD values are greater than 0.2, the mean of the "negative" controls is 0.107 and the standard deviation is 0.03. A theoretical threshold of positivity may be calculated according to the formula:

threshold value(mean of the net OD values of the negative controls)+(2 or 3' standard deviation of the net OD values of the negative controls).

In the first case, there are considered to be symptomless seropositives, and the threshold value is equal to 0.11+(3×0.03)=0.20. The negative results represent a non-specific "background" of the presence of antibodies directed specifically against an epitope of the peptide.

In the second case, if the set of controls consisting of blood donors in apparent good health is taken as a reference basis, without excluding the sera which are, on the face of it, seropositive, the standard deviation of the "non-MS controls" is 0.116. The threshold value then becomes 0.13+(3×0.06)=0.31.

According to this latter analysis, the test is specific for MS. In this respect, it is seen that the test is specific for MS, since, as shown in Table 1, no control has a net OD above this threshold. In fact, this result reflects the fact that the antibody titres in patients suffering from MS are, for the most part, higher than in healthy controls who have been in contact with MSRV-1.

In accordance with the first method of calculation, and as shown in FIG. 41 and in Table 3, 6 of the 15 MS sera give a positive result (OD greater than or equal to 0.2), indicating the presence of IgGs specifically directed against the S24Q peptide, hence against a portion of the reverse transcriptase enzyme of the MSRV-1 retrovirus encoded by its pol gene, and consequently against the MSRV-1 retrovirus.

Thus, approximately 40% of the MS patients tested have reacted against an epitope carried by the S24Q peptide and possess circulating IgGs directed against the latter.

Two out of 15 blood donors in apparent good health show a positive result. Thus, it is apparent that approximately 13% of the symptomless population may have been in contact with an epitope carried by the S24Q peptide under conditions which have led to an active immunization which manifests itself in the persistence of specific serum IgGs. These conditions are compatible with an immunization against the MSRV-1 retrovirus reverse transcriptase during an infection with (and/or reactivation of) the MSRV-1 retrovirus. The absence of apparent neurological pathology recalling MS in these seropositive controls may indicate that they are healthy carriers and have eliminated an infectious virus after immunizing themselves, or that they constitute an at-risk population of chronic carriers. In effect, epidemiological data showing that a pathogenic agent present in the environment of regions of high prevalence of MS may be the cause of this disease imply that a fraction of the population free from MS has necessarily been in contact with such a pathogenic agent. It has been shown that the MSRV-1 retrovirus constitutes all or part of this "pathogenic agent" at the source of MS, and it is hence normal for controls taken from a healthy population to possess IgG type antibodies against components of the MSRV-1 retrovirus.

Lastly, the detection of anti-S24Q antibodies in only one out of two MS cases tested here may reflect the fact that this peptide does not represent an immunodominant MSRV-1 epitope, that inter-individual strain variations may induce an immunization against a divergent peptide motif in the same region, or that the course of the disease and the treatments followed may modulate over time the antibody response against the S24Q peptide.

TABLE NO. 3

| | CONTROLS | MS |
|---|---|---|
| | 0.101 | 0.136 |
| | 0.058 | 0.391 |
| | 0.126 | 0.37 |
| | 0.131 | 0.119 |
| | 0.105 | 0.267 |
| | 0.294 | 0.141 |
| | 0.116 | 0.102 |
| | 0.088 | 0.18 |
| | 0.105 | 0.411 |
| | 0.172 | 0.164 |
| | 0.137 | 0.049 |
| | 0.223 | 0.644 |
| | 0.08 | 0.268 |
| | 0.073 | 0.065 |
| | 0.132 | 0.074 |
| Mean | 0.129 | |
| Std. Dev. | 0.06 | |
| Threshold | 0.31 | |

d) Detection of Anti-MSRV-1 IgM Antibodies by ELISA:

The ELISA technique with the S24Q peptide was used to test for the presence of anti-MSRV-1 IgM specific antibodies in the same sera as above.

Figure 42:
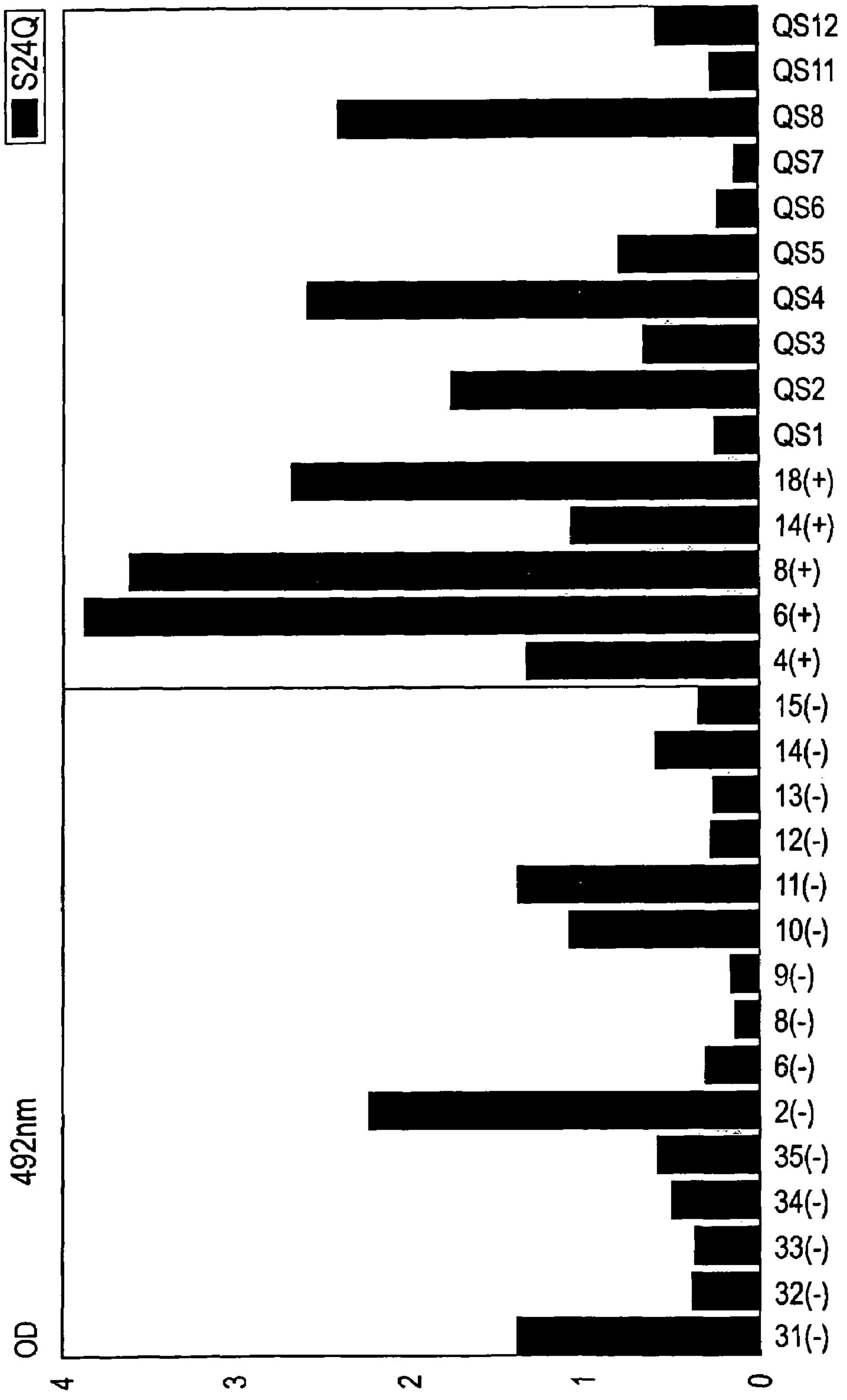
FIG. 42 shows the response of each serum of patients suffering from MS, indicated by the symbols (+) and (QS), and of healthy patients (–), tested with an anti-IgM antibody, expressed as net optical density at 492 nm.

FIG. 42 shows the results for each serum tested with an anti-IgM antibody. Each vertical bar represents the net optical density (OD at 492 nm) of a serum tested. The ordinate axis gives the net OD at the top of the vertical bars. The first 15 vertical bars lying to the left of the vertical line cutting the abscissa axis represent the sera of 15 healthy controls (blood donors), and the vertical bars lying to the right of the vertical broken line represent the sera of 15 cases of MS tested.

The mean of the OD values for the MS cases tested is 1.6.

The mean of the net OD values for the controls is 0.7.

The standard deviation of the negative controls is 0.6.

The threshold of theoretical positivity may be calculated according to the formula:

threshold value=(mean of the OD values of the negative controls)+(3×standard deviation of the OD values of the negative controls)

The threshold value is hence equal to 0.7+(3×0.6)=2.5;

The negative results represent a non-specific "background" of the presence of antibodies directed specifically against an epitope of the peptide.

According to this analysis, and as shown in FIG. 42 and in the corresponding Table 4, the IgM test is specific for MS, since no control has a net OD above the threshold. Six of the 15 MS sera produce a positive IgM result.

The difference in seroprevalence between the MS and control populations is extremely significant: "chi-squared" test, $p<0.002$.

These results point to an aetiopathogenic role of MSRV-1 in MS.

Thus, the detection of IgM and IgG antibodies against the S24Q peptide makes it possible to evaluate, alone or in combination with other MSRV-1 peptides, the course of an MSRV-1 infection and/or of the viral reactivation of MSRV-1.

TABLE NO. 4

| | CONTROLS | MS |
|---|---|---|
| | 1.449 | 0.974 |
| | 0.371 | 6.117 |
| | 0.448 | 2.883 |
| | 0.456 | 1.945 |
| | 0.885 | 1.787 |
| | 2.235 | 0.273 |
| | 0.301 | 1.766 |
| | 0.138 | 0.668 |
| | 0.16 | 2.603 |
| | 1.073 | 0.802 |
| | 1.366 | 0.245 |
| | 0.283 | 0.147 |
| | 0.262 | 2.441 |
| | 0.585 | 0.287 |
| | 0.356 | 0.589 |
| Mean | 0.7 | |
| Std. Dev. | 0.6 | |
| Threshold Value | 2.5 | |

It is possible, as a result of the new discoveries made and the new methods developed by the inventors, to permit the improved implementation of diagnostic tests for MSRV-1 infection and/or reactivation and to evaluate a therapy in MS and/or RA on the basis of its efficacy in "negativing" the detection of these agents in the patient's biological fluids. Furthermore, early detection in individuals not yet displaying neurological signs of MS or rheumatological signs of RA could make it possible to institute a treatment which would be all the more effective with respect to the subsequent clinical course for the fact that it would precede the lesion stage which corresponds to the onset of the clinical disorders. Now, at the present time, a diagnosis of MS or RA cannot be established before a symptomatology of lesions has set in, and hence no treatment is instituted before the emergence of a clinical picture suggestive of lesions which are already significant. The diagnosis of an MSRV-1 and/or MSRV-2 infection and/or reactivation in man is hence of decisive importance, and the present invention provides the means of doing this.

It is thus possible, apart from carrying out a diagnosis of MSRV-1 infection and/or reactivation, to evaluate a therapy in MS on the basis of its efficacy in "negativing" the detection of these agents in the patients' biological fluids.

Example 18

1) Materials and Methods

Patients and Clinical Samples

Choroid plexus cells from MS patients and controls were obtained from the brain-cell library, Laboratoire R. Escourolles, Hôpital de la Salpêtriére, Paris, France. Non-tumoral leptomeningeal cells from controls were obtained as previously described (26). Peripheral blood from MS and control patients used for obtaining B-cell lines and plasma, were obtained from the Neurological Departments, CHU de Grenoble, and from INSERM U 134, Hôpital de la Salpêtriére, France. Clinical details and origin of the 10 MS patients and of the 10 patients with other neurological diseases who provided CSF samples are given in Table 6.

Cell Cultures, Virus Isolation and Purification

All cell-types were cultured as previously described (3, 5, 26). All cultures were regularly screened for mycoplasma contamination with an ELISA mycoplasma-detection kit (Boehringer). No cell-extract nor supernatant used contained detectable mycoplasma.

Extracellular virion purification and sucrose density gradients were performed as previously described (3, 5, 26). From each sucrose gradient 0.5-1 ml fractions were collected from the top of the tubes, with a 1000 μl Pipetman and a different sterile tip for each fraction. 60 μl were used for RT activity assay and the rest was mixed with 1 volume of buffer containing 4M guanidinium thiocyanate, 0.5% N-Lauroyl sarcosin, 25 mM EDTA, 0.2% β-mercaptoethanol adjusted at pH 5.5 with acetic acid. These mixtures were frozen at −80° C. for further RNA extraction or directly processed according to Chomzynski (20), with an overnight precipitation step at −20° C., in the presence of RNase-free glycogen (Boehringer). RNA was dissolved in 20 to 50 μl of DEPC-treated water in the presence of 1-2 μl of recombinant RNase-inhibitor (PROMEGA) and 0.1 mM DTT. 10 μl aliquots were used for each RT-PCR.

Reverse Transcriptase Activity

RT-activity was tested with 20 mM Mg and poly-Cm or polyC templates, in virion pellets or fractions from sucrose gradients as previously described (3, 5, 26).

cDNA Synthesis and 'Pan-Retro' RT-PCR with Degenerate Primers

A total RT-activity between $10^6$-$10^7$ dpm was required in the fraction containing the peak of purified virions. The "Pan-retro" RT-PCR technique (27) was performed on virion RNA extracted by the method of Chomczynski (20) and dissolved in 20 μl RNase-free water. 5 μl RNA solution was incubated for 30 min at 37° C. with 0.3 units (3 units for CSF series) of RNase-free DNase-1 (Boehringer) in a 20 ml reaction containing 7.5 mM random hexamers, 5 mM Hepes-HCl pH 6.9, 75 mM KCl, 3 mM $MgCl_2$, 10 mM DTT, 50 mM Tris-HCl pH 7.5, 0.5 mM each dNTP, and 20 units recombinant RNase inhibitor (Promega). The DNase was then heat inactivated at 80° C. for 10 min. 20 units MoMLV RT (Pharmacia) and a further 20 units of RNase inhibitor were added to each tube in a Genesphere™ enclosure (Safetech, Ireland) and cDNA was synthesised for 90 min at 37° C. Following reverse transcription, the cDNA was boiled for 5 min then cooled rapidly on ice. The Round 1 PCR mix (final volume 25 μl per reaction; 20 mM Tris-HCl pH 8.4, 60 mM KCl, 2.5 mM $MgCl_2$, 200 ng each of primers PAN-UO and PAN-DI [see FIG. 44], 0.2 mM each dNTP) was treated with 0.3 units DNase-1 and then heat inactivated as above. 2.5 μl cDNA was added in the Genesphere™ enclosure and the tubes heated to 80° C. before adding 0.5 units Taq polymerase (Perkin Elmer) individually to each tube ("hot start"). Round 1 PCR parameters were 35 cycles of 95° C. for 1 min, 34° C. for 30 sec, 72° C. for 1 min, with a final 7 min extension at 72° C. 0.5 ml of Round 1 PCR product was transferred to the Round 2 DNase-treated PCR mix (composition as for Round 1 but containing primers PAN-UI and PAN-DI) using the "hot start" procedure. Round 2 PCR parameters were as for Round 1 but using 30 cycles only and annealing at 45° C. for 1 min.

Cloning of PCR Products

PCR products were cloned using the TA-Cloning™ kit (British Biotechnology) according to the manufacturer's recommendations.

Sequencing

Sequencing reactions were performed using the "Prism ready reaction kit dye deoxyterminator cycle sequencing kit" (Applied Biosystems). Automatic sequence analysis was performed on an automatic sequencer (Applied Biosystems, 373 A).

RT-PCR with ST1 Primer Sets

The first PCR round was performed directly from the cDNA reaction mixture according to the one-step RT-PCR technique described by Mallet et al. (28). This one-step RT-PCR procedure reduced the probability of airborne contamination when opening the tubes and transferring PCR reagents after an independent cDNA synthesis. RNA was extracted as previously from 2 ml of plasma (snap-frozen in liquid nitrogen and stored at −80° C.) or from a 500 ml sucrose fraction with a total RT-activity above $10^6$ dpm, and resuspended in 50 μl of RNase-free water. For each RT-PCR reaction 10 μl of RNA solution was incubated in a Perkin-Elmer 480 thermocycler, 15 min at 20° C. with 1 U of RNase-free DNASE 1 and 1.2 μl of 10× DNASE buffer (50 mM Tris, 10 mM $MgCl_2$ and 0.1 mM DTT) containing 1 U/ml of RNase-inhibitor (PROMEGA), and heated at 70° C. for 10 min for DNase inactivation. The solution was placed on ice and mixed (in conditions preventing airborne dust/DNA contamination) with 88 μl of PCR mix containing: 1× taq buffer, 25 nM/tube dNTPs, 40 pM/tube of each first round primer (ST1.1 upstream primer: 5' AGGAGTAAGGAAACCCAACGGAC 3' (SEQ ID NO:15); ST1.1 downstream primer: 5'TAAGAGTTGCACAAGTGCG 3' (SEQ ID NO:16)), 2.5 U/tube of taq (Appligene) and 10 U/tube of AMV-RT (Boehringer). Each tube was further incubated in a Perkin-Elmer 480 thermocycler for 10 min at 65° C., followed by 2 h at 42° C. for cDNA synthesis and 5 min at 95° C. for inactivation of AMV-RT and DNA denaturation. First round parameters were 40 cycles of 95° C. for 1 min, 53° C. for 2.5 min, 72° C. for 1 min, with a final extension of 10 min at 72° C. 10 μl of the first round were transferred to the second round PCR mix previously treated at 20° C. for 15 min with RNase-free DNase 1 (0.02 U/ml) followed by DNase inactivation at 70° C. for 10 min. This mix contained 1× taq buffer, 25 nM/tube dNTPs, 40 pM/tube of each second round primers [ST1.2 upstream primer: 5'TCAGGGATAGCCCCCATCTAT3' (SEQ ID NO:17); ST1.2 downstream primer: 5'AACCCTTTGCCACTACATCAATTT3' (SEQ ID NO:18)] and 2.5 U/tube of taq (Appligene). Second round parameters were 30 cycles of 95° C. for 1 min, 53° C. for 1.5 min, 72° C. for 1 min, with a final extension of 8 min at 72° C. 20 ml of this nested RT-PCR product were deposited on a 0.7% agarose gel containing ethidium bromide and exposed to UV light for the visualization of amplified products.

Hybridisation Analysis of PCR Products: MSRV-Pol Detection by ELOSA

The protocol was essentially as previously described (21) but with the following modifications: Nunc Maxisorb microtiter plates were coated with 100 ng per well capture probe CpV1b (see FIG. 44) either by passive adsorption (21) or alternatively by using streptavidin coated plates and biotinylated CpV1b. Peroxidase-labelled detector probe DpV1 (see FIG. 44) was used and the assay cut-off was defined as the mean of 4 negative controls plus 0.2 $OD_{492}$ units.

RNA Extraction, cDNA Synthesis and PCR Amplification from MS Plasma Samples:

Total RNA was extracted from human MS plasma by a guanidium method as described elsewhere (29). Total RNA extracted from 100 ul of plasma, were treated with RNase-free DNase I (0.1 U/ml; Boehringer Manheim, France) and reverse transcribed under the conditions recommended by the manufacturer, using Superscript reverse transcriptase (Gibco-BRL, FRANCE). The resulting cDNAs were amplified by semi-nested PCR through 35 cycles (94° C. 1 min, 55° C. 1 mn, 72° C. 1 min 30 sec) and 72° C. 8 min for a final extension.

Three different fragments in the RT region were amplified by the following specific primers:

in the protease (PRT) region, for the 1st and 2nd round of PCR, respectively, sense primer

[5' TCC AGC AGC AGG ACT GAG GGT 3' (SEQ ID NO: 93)] and antisense primers [5' CTG TCC GTT GGG TTT CCT TAC TGG T 3'/(SEQ ID NO: 72)/5' GAC AGC AAA TGG GTA TTC CTT TGG 3' (SEQ ID NO: 94)]

- in the fragment A of the RT region (Cf. FIG. 46), for the 1st and 2nd round of PCR, respectively, sense primer [5' AGG AGT AAG GAA ACC CAA CGG ACA G 3' (SEQ ID NO:95)] and antisense primers [5' TGT ATA TAA TGG TCT GGC TAT TGG G 3' (SEQ ID NO:96)/5' TTC GGC AGA AAC CTG TTA TGC CAA GG 3' (SEQ ID NO:76)]
- in the fragment B of the RT region (Cf. FIG. 46), for the 1st and 2nd round of PCR, respectively, sense primers [5' GGC TCT GCT CAC AGG AGA TTA GAT AC 3' (SEQ ID NO:97)/5' AAA GGC ACC AGG GCC CTC AGT GAG GA 3' (SEQ ID NO:98)] and antisense primer 3'[5' GGT TTA AGA GTT GCA CAA GTG CGC AGT C 3' (SEQ ID NO:99)].

The amplified fragments were analyzed on ethidium bromide-stained agarose gels, cloned in the TA cloning vector (Invitrogen) and sequenced.

2) Results

Specific Retroviral RNA is Found in Extracellular Virions from MS Patient-Derived Cell Cultures and in MS Patients' CSF.

Choroid plexus cells (4) (obtained post-mortem) and EBV-immortalized peripheral blood B-lymphocytes (30, 31) from MS patients gave rise to cultures expressing 100-120 nm viral particles associated with RT-activity similar to that of the original LM7 isolate (3). Similar cell-types from non-MS donors produced neither this RT-activity nor virions. All the 'infected' cultures were poorly and/or transiently productive and/or had a limited lifespan. Therefore, in order to analyze the genomic RNA present in the very limited quantity of extracellular virions, we used an RT-PCR approach to amplify, with degenerate primers, a conserved region of the pol gene present in all known retroviruses (12); the techniques based on this approach will be called "Pan-retro" RT-PCR. Extensive DNase treatment of samples and reagents was essential, because human DNA contains many endogenous retroviral elements amplifiable by this technique.

Figure 43:
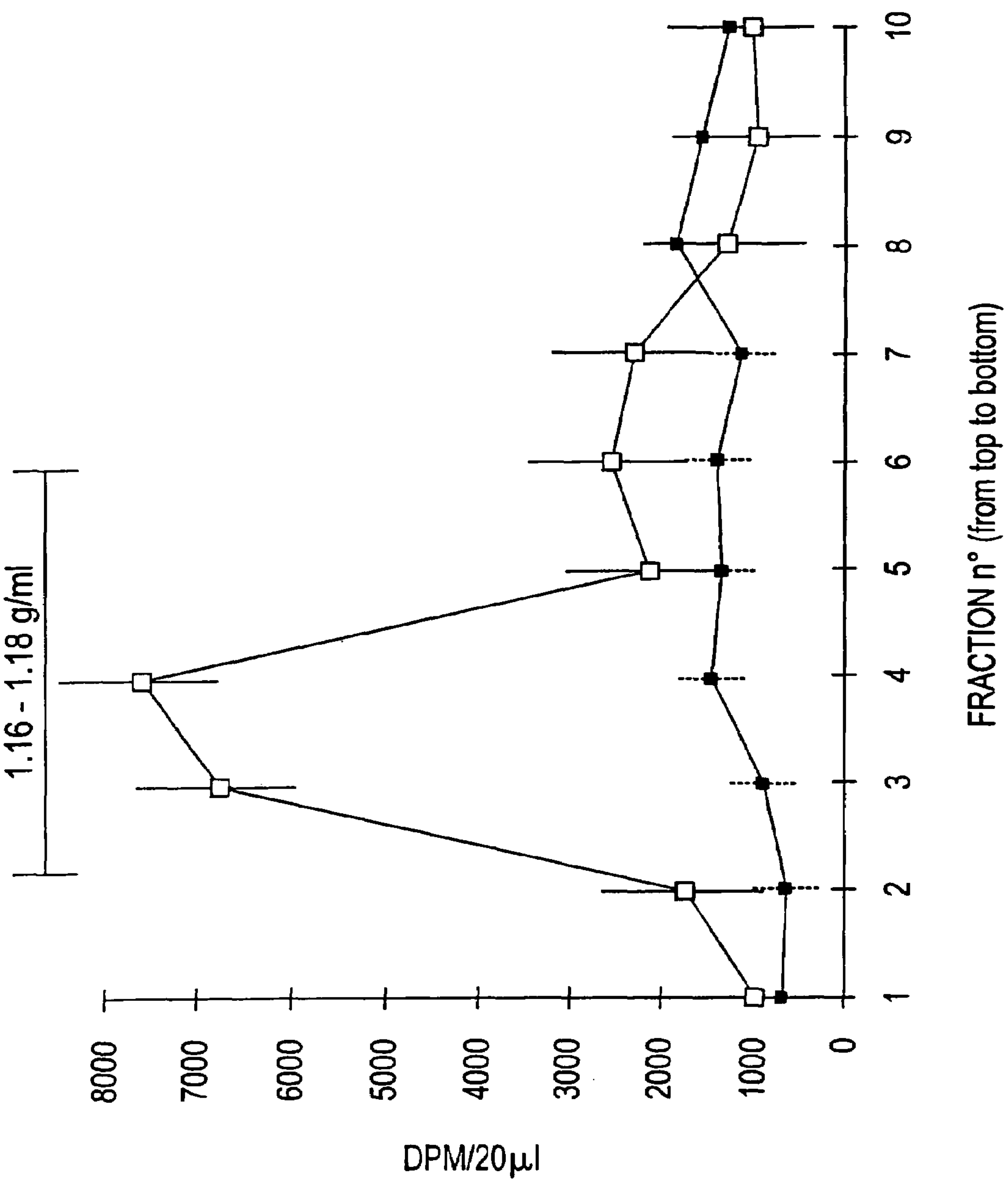
FIG. 43 shows the RT-activity profile in sucrose density gradients of pellets from B-cell line supernatants; Control B-cell line n was obtained from the relative of a patient with mitochondriopathy. MS B-Cell line o was obtained from a patient with definite MS.

"Pan-retro" RT-PCR experiments were performed on sucrose-density gradient purified virions from supernatants of different types of cell cultures and their non-infected controls: (i) choroid plexus cells sampled post-mortem from MS brain (PLI-1), (ii) choroid plexus cells from non-MS brain autopsy, infected by co-culture with irradiated LM7 cells (LM7P), and (iii) identical non-infected choroid-plexus cells. "Early" B-cell lines obtained by spontaneous in vitro transformation of two EBV-seropositive individuals, (iv) one MS patient and (v) one non-MS control, were also analysed. FIG. 43 illustrates the RT-activity in sucrose-gradient fractions obtained from the B-cell cultures. The technique described by Shih et al. (12) was modified in a semi-nested RT-PCR protocol (27) using degenerate primers (FIG. 2) and extensive DNase treatment. PCR amplifications were performed in London (Dpt of Virology, U.C.L.M.S.) on coded aliquots of the density gradient fractions. Blind and systematic cloning and sequencing of the PCR products were undertaken in an independent laboratory (bioMerieux, Lyon). After complete sequencing of 20 to 30 clones per sucrose gradient fractions the codes were broken and results analysed in parallel with the RT-activity data.

TABLE 5

SEQUENCES GENERATED BY 'PAN-RETROVIRUS' PCR OF DENSITY GRADIENT FRACTIONS
(containing the peak of RT-activity or the corresponding control fraction)

| CULTURE | MSRV c-pol | ERVg[(V)] | PCR artefacts[(VI)] | Total clones |
|---|---|---|---|---|
| LM7P (I) | 16 | 4 | 6 | 26 |
| PLI-I (II) | 9 | 1 | 13 | 23 |
| MS B-CELL LINE (III) | 9 | 2 | 8 | 19 |
| CONTROL B-CELL LINE (IV) | 0 | 0 | 26 | 26 |

(I) LM7-Infected choroid plexus cell culture.
(II) MS patient-derived choroid plexus cell culture (PLI-2).
(III) MS patient-derived spontaneous B-cell line (Immortalized by endogenous EBV strain).
(IV) Non-MS control B-cell line.
[(V)]Clones with >90% homology with the GenBank sequence HSERVg are designated ERVg in this study.
[(VI)]PCR artefacts included primer multimers, concatemore, single primer ampllifications, etc.

Table 5 presents the distribution of sequences obtained from sucrose gradient fractions containing the peak of viral RT-activity in MS-derived cultures and also the sequences amplified from the corresponding RT-activity negative fractions of uninfected cultures. The predominant sequence detected in bands of the expected size (≃140 bp) amplified in all the RT-activity positive fractions (but not in the RT-activity negative fractions) was different from known retroviruses and was designated MSRV-cpol. MSRV-cpol sequences exhibited partial homology (70-75%) with ERV9, a previously described endogenous retroviral sequence (18). A few ERV9 sequences (>90% homology with ERV9) were also present but clearly represented a minority of clones. In addition to typical pol sequences, numerous PCR artefacts (primer multimers, concatemers or single-primer amplifications) related to the use of degenerate primers and low-temperature annealing, were found in all samples (Table 5).

FIG. 44 shows an alignment of a consensus sequence of MSRV-cpol with the corresponding VLPQG/YMDD region of diverse retroviruses. FIG. 45 displays a phylogenic tree based on the evolutionarily conserved amino acid sequences of both exogenous and endogenous retroviruses in this region. From this tree it can be seen that the pol gene of MSRV is phylogenically related to the C-type group of oncovirinae.

A small scale study was performed to determine the prevalence of MSRV c-pol sequences in the CSF of patients with MS. Identification of MSRV-cpol in PCR products by cloning and sequencing is both laborious and time consuming. We therefore devised an enzyme-linked oligosorbent assay (ELOSA), using a capture probe (CpV1B) and a peroxidase-labelled detector probe (DpV1), for the rapid identification of MSRV-cpol sequences in 'Pan-retrovirus' PCR products (FIG. 44). The specificity of this sandwich hybridization-based assay for HMSRV-cpol was tested with both distantly related (HIV and MoMLV) and closely related (ERV9) pol sequences. No significant cross reactivity with such targets was observed despite the ability of the ELOSA to detect as little as 0.01 ng of MSRV-cpol DNA.

TABLE 6

DETECTION OF HMSRV IN THE CSF OF PATIENTS WITH MULTIPLE SCLEROSIS AND OTHER NEUROLOGICAL DISEASES

| Patient[1] | Age/Sex | Diagnosis | MS Type | MS Activity | MS Duration | MS Treatment at sampling | MSRV ELOSA |
|---|---|---|---|---|---|---|---|
| ITMS1 | 27 yrs/M | multiple sclerosis | 2° progressive | slow progression | 5 yrs | corticosteroids | negative |
| ITMS2 | 55 yrs/M | multiple sclerosis | 1° progressive | slow progression | 9 yrs | none | POSITIVE |
| ITMS3 | 51 yrs/F | multiple sclerosis | 1° progressive | slow progression | 2 yrs | none | negative |
| ITMS4 | 22 yrs/F | multiple sclerosis | relapsing/ remitting | In remission | 8 yrs | none | POSITIVE |
| ITMS5 | 27 yrs/F | multiple sclerosis | 1° progressive | slow progression | 8 yrs | cyclophosphamide | negative |
| ITMS6 | 33 yrs/M | multiple sclerosis | 2° progressive | slow progression | 16 yrs | none (previously cycloph. + corticost.) | negative |
| ITMS7 | 33 yrs/F | multiple sclerosis | 2° progressive | slow progression | 9 yrs | none | POSITIVE |
| ITMS8 | 25 yrs/F | multiple sclerosis | relapsing/ remitting | stable | 3 yrs | none | POSITIVE |
| ITMS9 | 36 yrs/F | multiple sclerosis | 2° progressive | slow progression | 3 yrs | none | POSITIVE |
| ITMS10 | 36 yrs/M | multiple sclerosis | 2° progressive | slow progression | 7 yrs | corticosteroids | negative |
| OND1 | 37 yrs/F | cerebellar atrophy | NA[2] | NA | NA | NA | negative |
| OND2 | 26 yrs/F | viral myelltis | NA | NA | NA | NA | negative |
| OND3 | 38 yrs/F | viral encephalitis | NA | NA | NA | NA | negative |
| OND4 | 28 yrs/F | viral encephalitis | NA | NA | NA | NA | negative |
| OND5 | 64 yrs/M | viral encephalitis | NA | NA | NA | NA | negative |
| OND6 | 32 yrs/M | Guillain - Barré | NA | NA | NA | NA | negative |
| OND7 | 54 yrs/F | cerebrovascular | NA | NA | NA | NA | negative |
| OND8 i | 52 yrs/F | hydrocephalus | NA | NA | NA | NA | negative |
| OND9 i | 25 yrs/F | 1° cerebral tumour | NA | NA | NA | NA | negative |
| OND10 | 21 yrs/M | epilapsy | NA | NA | NA | NA | negative |

[1]CSF samples from patients ITMS1–OND2 were made available by Prof. P. Ferrante. University Centre for Multiple Sclerosis. Milan, Italy. CSF samples from patients OND3–OND10 were made available by Profs. J. Pallat and J. Perrel, Dept. of Neurology, University Hospital, Grenoble, France.
[2]NA = Not Applicable Cerebrospinal fluid (CSF) samples were available from 10 patients with MS and from 10 patients with other neurological disorders. Total RNA was extracted from CSF pellets, reverse transcribed and amplified as above. ELOSA analysis (Table 6) of the PCR products revealed MSRV-cpol sequences in 5 of the 10 MS patient samples but in none of the 10 samples from patients with other neurological diseases ($P<0.05$). The presence of MSRV-cpol did not appear to be correlated with age, sex or type of MS, but was seen in untreated patients only (5/6). No patient with immunosuppressive therapy was found positive (0/4). No correlation between MSRV-cpol detection and CSF cell count was observed.

Cloning and Sequencing a Larger Region of the pol Gene

An independent identification of the MSRV genomic sequence was obtained by a non-PCR approach using RNA extracted from concentrated virions derived from 2.5 liters of LM7-infected sub-cultures of choroid plexus cells. A limited number of clones was obtained by direct cloning of the cDNA, one of which (PSJ17) showed partial homology with ERV9 pol. Specific primers based on the MSRV-cpol region and on the PSJ17 clone, amplified a 740 bp fragment linking the two independent sequences in RNA extracted from purified virions. PSJ17 was localized on the 3' side of MSRV-cpol. Further sequence extension on the 5' side of MSRV-cpol and on the 3' side of PSJ17, was obtained using RT-PCR approaches on RNA from purified LM7-like virions produced in MS choroid plexus cultures (4).

In FIG. 46, the nucleotide sequence corresponding to overlapping clones obtained by sequence extension in the pol gene is represented with the amino acid translation corresponding to the putative open reading frames (ORFs) of the protease and of the reverse-transcriptase. The active site motifs of the protease (PRT) and of the reverse-transcriptase (RT) are underlined. In the C-terminal region of the RT sequence, the dispersed amino acid residues regularly present in retroviral RNase H domains, are also underlined.

Non-Degenerate Primers Detect MSRV-Specific RNA in Virions Associated with the Peak of RT-Activity and in MS Patients' Plasma.

PCR primers (ST1.1 primer set; positions 603-625/1732-1714, on FIG. 4) based on overlapping clones in the pol gene, amplified a 1.15 kb segment of the RT region from several different isolates obtained from different MS patients. Nested primers (ST1.2; positions 869-889/1513-1490, on FIG. 46) generated a 700 bp fragment (FIG. 47) which was more easily visualized by ethidium bromide staining than the first round product generated by ST1.1. The specificity of PCR products was confirmed by stringent hybridization with a peroxidase-labeled MSRV-cpol probe (FIG. 44), using the ELOSA technique (21).

The ST1.1 and 2 primer set was used to detect extracellular MSRV RNA in human plasma, although non-optimal for this application. FIG. 47 illustrates the results of PCR amplification of cDNA derived from 2 MS patient and 2 control plasma samples tested in parallel with cDNA from the sucrose density gradient fractions of an MS choroid plexus isolate. Taq-sequencing of the 700 bp bands confirmed the presence of MSRV sequence. A very faint 700 bp band is also visible in fraction 10 which corresponds to the bottom of the tube where aggregated particles usually sediment. Control RT-PCR for cellular aldolase transcripts on plasma-derived RNA was negative, indicating that the results were not due to cellular RNA released by cell lysis during plasma separation. It should be noted that this PCR technique was not designed for epidemiological studies since its sensitivity is impaired by the length of the cDNA required (1.15 kb).

Non-degenerate primers amplifying three fragments of the pol gene (the whole protease region, regions A and B of the reverse transcriptase; Cf. FIG. 46) were also used to confirm the presence of MSRV sequences in DNase-treated RNA from MS plasma. These fragments were amplified from the plasma of a further 4 MS patients with active disease. Sequence analysis confirmed that the PRT and RT regions were homologous (>95% and >90% respectively) to MSRV sequences previously obtained on culture virion. No such sequence were detected in plasma from healthy controls (n=4), tested in parallel with MS plasma.

3) Discussion

Phylogeny of MSRV

From the results of this study, it can be concluded that the virus previously referred to as “LM7” (3, 5, 26) posseses an RNA genome containing the MSRV pol sequences described here. The conserved RT motif of both MSRV and ERV9 is two amino acids shorter than that of other retroviruses, apart from human foamy viruses which nonetheless have a functional RT. The potential ORF encompassing the entire PRT-RT region is consistent with the virion-associated RT-activity detected in sucrose density gradients with infected culture supernatants. Moreover, since we have recently succeeded in expressing a recombinant protein from the sequence of MSRV protease cloned from MS plasma, we can confirm the reality of the potential PRT ORF. Similar cloning and expression of other sequences containing potential ORFs for MSRV proteins, is being undertaken to confirm their ability to encode enzymes and structural proteins of MSRV virions. The phylogenic tree in FIG. 45, based on the most conserved amino acid sequence in retroviruses (VLPQG . . . YXDD), shows that the MSRV pol gene is related to the C-type oncoviruses. Apart from ERV9, the closest known retroviral element is RTLV-H, a human endogenous sequence known to have a subtype with a functional pol gene (32). In the pol region, this phylogenic affiliation to C-type oncoviruses apparently contradicts our previous assumptions based on the general morphology of the particles observed by electron microscopy (EM), which were compatible with a B or D-type oncovirus (3, 5, 26). However, preliminary data on env sequences detected in MSRV virions, would suggest a greater phylogenic proximity to D-type. Such difference in phylogenies of the pol and env genes have been described in MPMV and suggest a recombinatorial origin in D-type retroviruses (33). D to C type morphological conversion is also possible since it has been reported that a single amino acid substitution in the gag protein can convert retrovirus morphology to that of a different type (34).

Is MSRV an Exogenous Retrovirus Sharing Extensive Homology with a Related Endogenous Retrovirus Family or an Endogenous Retrovirus Producing Extracellular Virions?

Southern blot analysis with an MSRV pol probe under stringent conditions, showed hybridisation with a multicopy endogenous family (data not presented), indicating the existence of endogenous elements more closely related to MSRV than ERV9 itself. Consequently, we were unable to look for a virion-specific provirus in MSRV-producing cells. In agreement with southern blot findings, PCR studies on genomic DNA showed multiple band amplification of MSRV-related endogenous sequences. Since pol is the most conserved retroviral gene, the sequence described here is the least suitable region to discriminate between exogenous and endogenous sequences. It is hoped that sequence information from other parts of the genome may permit such a discrimination, would it be on a tiny portion as has recently been demonstrated for the Jaagsiekte retrovirus (JSRV) of sheep (35). With such sequence data, it would then become possible to identify the MSRV-specific provirus in the genome of virion-producing cell cultures.

MSRV could represent a virion-producing exogenous member of an ERV9-like endogenous family, just as exogenous strains exist in the well-studied mouse mammary tumour virus (MMTV) and murine leukaemia virus (MuLV) retroviral families of mice, and also, in the JSRV retroviral family of sheep (36). Alternatively, it is also conceivable that the extracellular MSRV virions may be produced by a replication-competent endogenous provirus. Whether MSRV is exogenous or endogenous, conceptual similarities exist with the category of retroviruses represented by MuLV, MMTV and JSRV. Unlike defective endogenous elements, this category of agents are known to produce infectious and pathogenic virions, to cause neurological disease (37), solid tumours/leukaemias (36, 38) and to express “endogenous superantigens” (39, 40). Furthermore, in MuLV infections, the genetic endogenous retroviral background of the mouse strain can determine susceptibility or resistance to disease (39, 41). Indeed, such interactions between an infectious retrovirus and its endogenous counterpart may be relevant in the pathogenesis of MS, since endogenous retroviral genotypes are not identical in all individuals. A genetic control due to related endogenous retroviral genotypes could therefore contribute to the known hereditary susceptibility to MS (43), if MSRV does indeed play an active role in this disease. Elsewhere, the data in Table 5 suggest that ERV9 elements may be co-expressed, possibly via trans-activation in infected cells, and give rise to heterologous RNA packaging in MSRV virions. Such heterologous packaging is known to occur in other retroviral systems (42).

A Role for the Numerous Common Viruses Previously Evoked in MS?

Among the numerous reports of viruses putatively involved in the aetiopathogenesis of MS, a significant proportion focus on two viral families, the paramyxoviridae and the herpesviridae. Regarding the paramyxoviridae, the key observation is of a frequently increased antibody titer to measles virus in MS patients essentially directed, in CSF, against measles fusion protein (44). The existence of aminoacid similarities between conserved domains of the fusion proteins of paramyxoviridae and the transmembrane protein of retroviruses (45), may explain this observation if antigenic cross-reactivity between these two proteins occured.

With regard to the herpesvirus family, the involvement of Epstein-Barr Virus (EBV), Herpes Simplex Virus type 1 (HSV-1) and, most recently, Human Herpes Virus 6 (HHV-6) has been proposed (31, 46, 47). From our previous studies and from those of other groups, it appears that herpesviruses may play an important role in MSRV expression: we have shown that HSV-1 immediate-early ICP0 and ICP4 proteins can transactivate MSRV/LM7 in vitro (6) and Haahr et al. have proposed an important epidemiological role for EBV, as a co-factor in MS, triggering retrovirus reactivation (31). The recent description by Challoner et al. (47) showing significant expression of HHV6 proteins in MS plaques may also suggest a similar role for HHV6 in the brain.

Example 19

MSRV Genome Detection Technique

Following 0.4 mm filtration to remove cellular debris and RNase digestion to remove residual non-encapsidated RNA, serum was processed to extract viral RNA by means of adsorption to a silica matrix. Viral RNA was subjected to DNase digestion, then a combined reverse transcription-PCR (RT-PCR) reaction was performed using primers PTpol-A (sense: 5'xxxx3', SEQ ID NO:142) and PTpol-F (antisense: 5'xxxx3', SEQ ID NO:143). A second round of amplification with nested primers PTpol-B (sense: 5'xxxx3', SEQ ID NO:144) and PTpol-E (antisense: 5'xxxx3', SEQ ID NO:145) generated a 435 bp PCR product which was identified by gel electrophoresis. The specificity of each product was confirmed by dideoxy sequencing. Control reactions without reverse transcriptase were performed to ensure that the products were derived from viral RNA. In addition, to exclude the possibility that the extracted viral RNA might be contaminated with host cell derived nucleic acids, aliquots were tested by nested PCR for the presence of pyruvate dehydrogenase (PDH) DNA and RNA. Samples which generated a signal in either the PDH or the "no-RT" PCR assays were excluded from the analysis.

Sera from patients with clinically active MS and controls were amplified by RT-PCR and sequenced. Virion associated MSRV-RNA was detected in the serum of 10 of 19 (53%) patients with MS but in only 3 of 44 controls without MS (P=0.0001). The control group consisted of 8 patients (all MSRV-RNA negative) with rheumatological disorders and 36 healthy adults. MSRV-RNA titres in both MS patients and controls were apparently low because even moderate dilution of sera (<10 fold) caused loss of signal.

In MS patients, detection of MSRV-RNA was not associated with age, sex, disease duration, or MS type, however a significant negative correlation with treatment was observed. 26 serum samples were obtained from the 19 patients; 100% of the sera from untreated patients contained detectable MSRV-RNA whereas it was detectable in only 4 of 19 samples (21%) obtained during treatment with corticosteroids and/or azathioprine (P=0.001).

The reason for the apparent loss of virion associated MSRV-RNA during immunosupressive treatment is unknown but the finding is in agreement with the previous observations on the detection of MSRV in cerebrospinal fluid.

TABLE 7

DETECTION OF VIRION ASSOCIATED MSRV-RNA IN MS UNTREATED PATIENTS & CONTROLS

| | Positive | Negative | Total | % Positive |
|---|---|---|---|---|
| Controls without MS[a] | 3[b] | 41 | 44 | 7% |
| MS sera untreated at time of sampling | 7 | 0 | 7 | 100% |

[a]The control group consisted of 8 patients with miscellaneous non-MS disorders and 36 healthy adults.
[b]The detection of MSRV RNA in plasma of a few controls in conditions which select virion-packaged RNA, is consistent with the knowledge that a virus associated with MS should be present in a minor proportion of apparently healthy population. Indeed, such individuals can be either healthy carriers or be in the pre-clinical (or sub-clinical) phase of the disease which can last for years.

Method:

Modified SNAP RNA Extraction with Filtration and RNase Digestion (All Centrifugation are at Room Temperature)

Up to 500 microliters of serum is filtered using 0.45 micron spin filters (Nanosep MF from Flowgen Catalogue No. U3-0126 Ref. ODM45). The serum is spun for 5 min at 130,000 g (or for further 10 min if necessary).

150 microliters of filtered serum is incubated with 10 units RNase One (Promega Catalogue No. M4261) for 30 min at 37° C.

The 150 microliters was then extracted using the SNAP RNA extraction kit (Invitrogen) as below:

10 micrograms of poly A RNA was added to the 450 microliters of Binding Buffer to act as a carrier; this was then added to the serum and mixed by inversion 6 times; 300 microliters of propan-2-ol was then added and mixed by inversion 10 times; 500 microliters was transferred to the SNAP column and spun at 1300 g for 1 min and the flow-through discarded; the remainder was then added to the SNAP column and spun at 1300 g for 1 min and the flow-through discarded the column was then washed with 600 microliters of Super wash and the flow-through discarded; the column was then washed with 600 microliters of 1× RNA wash and the flow-through discarded; this wash was repeated with a 2 min 1300 g spin and the flow-through discarded; the bound nucleic acid was then eluted by incubating with 135 microliters of RNase free water for 5 min and spun at 1300 g for 1 min.

15 microliters of 10× DNAse buffer and 3 microliters (30 units) of DNase I, RNase free (Boehringer Mannheim Cat. No. 776 785) was added and incubated for 30 min at 37° C.; 450 microliters of Binding Buffer was added and mixed by inversion 6 times; 300 microliters of propan-2-ol was then added and mixed by inversion 10 times; 500 microliters was transferred to the SNAP column and spun at 1300 g for 1 min and the flow-through discarded; the remainder was then added to the SNAP column and spun at 1300 g for 1 min and the flow-through discarded; the column was then washed with 600 microliters 1× RNA wash and the flow-through discarded; this wash was repeated with a 2 min 1300 g spin and the flow-through discarded; the bound nucleic acid was then eluted by incubating with 105 microliters of RNase free water for 5 min and spun at 1300 g for 1 min.

Titan RT-PCR

RT-PCR was performed using the Titan one tube RT-PCR system (Boehringer Mannheim Cat. No. 1 855 476) 25 microliters of RNA was used in the combined RT-PCR reaction.

The total reaction volume was 50 microliters. Promega rRNAsin (10 units) was the RNase inhibitor used. 170 ng of primers SEQ ID NO:142 and SEQ ID NO:143, respectively, were used. A single master mix was prepared and the sample RNA added last. This was performed at room temperature, not on ice.

The RT step consisted of two sequential 30 min incubations at 50° C. and then 60° C. This was immediately followed by the PCR which had the following steps:

Initial denaturation of template at 94° C. for 2 min, 40 cycles of 94° C. for 30 seconds; 60° C. for 30 seconds; 68° C. for 45 seconds, 1 cycle of 68° C. for 7 min.

The second round PCR was performed using the Expand long template PCR system (Boehringer Mannheim Cat. No. 1681 842). 0.5 microliters of the RT-PCR mix was added to 25 microliters of the round 2 PCR mix. Buffer No. 3 and 50 ng of primers B and E were used. The PCR had the following steps:

5 cycles of 94° C. for 30 seconds, 60° C. for 30 seconds, 68° C. for 45 seconds 1 cycle of 68° C. for 7 min.

The PCR products were then run on a 2% agarose gel.

The no RT controls were performed using "Expand" PCR system for both rounds. The first round was 40 cycles and the second round 20 cycles.

As a positive control a DNA dilution series was used in both the TR-PCR and the "no RT" PCR. For a result to be valid the RT-PCR and "no-RT" PCRs had to have detected DNA equivalent to between 1 and 0.1 cells.

The analysis of PCR products of an approximately 435 bp fragment in the pol region is shown in Table 8.

TABLE 8

ANALYSIS OF PCR PRODUCTS WITH ORF*

| Exp | Disease | Clone | ORF | Fragment (bp) | AA-RT Motif Site |
|---|---|---|---|---|---|
| 46-7 | MS | 1 | + | 429 | YGDD |
| | | 5 | + | 429 | YGDD |
| | | 8 | + | 429 | YGDD |
| 68-1 | MS | 41 | + | 438 | YMDD |
| | | 42 | + | 438 | YMDD |
| | | 43 | + | 438 | YMDD |

*Defective RNA can also be present in circulating virions, since the fidelity of the MSRV reverse transcriptase appears to be low and since recombination events with related endogenous elements can occur. It is then obvious that the intra- and inter- patients variability can be greater than that illustrated in this example, because of these encapsidated defective MSRV RNA copies.

Table 9, which data have been determined from the alignments of FIGS. 49 to 53, shows a variability:

between the clones obtained from the same patient plasma sample in the same PCR amplification experiment; this means that the patient possesses a virion population which comprises different MSRV variants for a given time, between the sequenced variant populations from different patients; this means that the variants differ from a patient to another one patient.

TABLE 9

Degree of identity (percentage) between nucleotide sequences and between peptide sequences, by direct comparison of said sequences (see FIGS. 49-53)

| Patient | 68-1 | 46-7 |
|---|---|---|
| Nucleotide sequences | between SEQ ID NO: 128 and MSRV-pol (SEQ ID NO: 1)<br>90.4%[b]<br>93.3%[a]<br>SEQ ID NOs: 129, 130, 131 between them<br>98.6%[b]<br>98.7%[a] | between SEQ ID NO: 135 and MSRV-pol (SEQ ID NO: 1)<br>82.5%[a]<br>84%[b]<br>SEQ ID NOs: 136, 137, 138 between them<br>94.5%[a]<br>95.1%[b] |
| Peptide sequences | between SEQ ID NOs: 132, 133, 134 and trans of MSRV-1 81%<br>SEQ ID NOs: 132, 133, 134 between them<br>97% | between SEQ ID NOs: 139, 140, 141 and trans of MSRV-1 73.5%<br>SEQ ID NOs: 139, 140, 141 between them<br>89% |

[a]this percentage is determined on the basis of sequences excluding the primers

[b]this percentage is determined on the basis of sequences including the primers.

From FIGS. 53A and 53B, the variability between tested patients sequences can be determined:

between SEQ ID NO:128 and SEQ ID NO:135: 16.5%[a] and 14.8%[b]

between the peptide sequences obtained from SEQ ID NO:128 and

SEQ ID NO:135: 20%.

BIBLIOGRAPHY (1) Norrby E., Prog. Med. Virol., 1978; 24, 1-39.

(2) Johnson R. T., "Handbook of clinical neurology, 47 Demyelinating diseases", Vinken P. and Bruyn G. W., eds. Amsterdam, Elsevier Science Publishing, 1985, 319-336.

(3) Perron H. et al., Res. Virol. 1989, 140, 551-561.

(4) Perron H. et al., "Current concepts in multiple sclerosis" Wiethölter et al., eds. Amsterdam, Elsevier, 1991, 111-116.

(5) Perron H. et al., The Lancet 1991, 337, 862-863.

(6) Perron H. et al., J. Gen. Virol. 1993, 74, 65-72.

(7) Fields and Knipe, Fondamental Virology 1986, Rev Press N.Y.

(8) Nielsen P. E. et al., Science 1991; 254, 1497-1500.

(9) Maniatis et al., Molecular Cloning, Cold Spring Harbour, 1982.

(10) Southern. E. M., J. Mol. Biol. 1975, 98, 503.

(11) Dunn A. R. and Hassel J. A., Cell 1977, 12, 23,

(12) Shih et al., J. Virol. 1989, 63, 64-75.

(13) Perron H. et al., Res. Vir. 1992, 143, 337-350.

(14) Meyerhans et al., Cell 1989, 58, 901-910.

(15) Linial M. L. and Miller A. D., "Current topics in microbiology and immunobiology. Retroviruses, strategies of replication" vol. 157, 125-152; Swanstrom R. and Vogt P. K., editors, Springer-Verlag, Heidelberg 1990.

(16) Lori F. et al., J. Virol. 1992, 66, 5067-5074.

(17) Sambrook J., Fritsch E. F. and Maniatis T., Molecular cloning, a laboratory manual. Cold Spring Harbour Laboratory Press, 1989.

(18) La Mantia et al., Nucleic Acids Research 1991, 19, 1513-1520.

(19) Gonzales-Quintial R, Baccala R, Pope R M and Theofilopoulos N, J. Clin. Invest, Vol. 97, Number 5, pp 1335-1343, 1996.

(20) Chomzynski P. and N. Sacchi, Analytical Biochemistry 1987, 162, 156-159.
(21) F. Mallet et al., Journal of Clinical Microbiology 1993; 31, 1444-1449.
(22) G. Barany and R. B. Merrifielsd, 1980, In the Peptides, 2, 1-284, Gross E and Meienhofer J, Eds., Academic Press, New York.
(23) Poser et al., Gbers G. C. eds. The diagnosis of multiple sclerosis Thieme Stratton Inc, New York 1984: 225-229.
(24) La Mantia et al., Nucleic Acid Research 1989, 17, 5913-22.
(25) PLAZA, A; KONO, D. H.; THEOFILOPOULOS, A. N. NEW HUMAN Vb GENES AND POLYMORPHIC VARIANTS. J. Imm; 147(12): 4360-4365, 1991.
(26) H. Perron, In vitro transmission and antigenicity of a retrovirus isolated from multiple sclerosis, Res. Virol. 143, 337-350 (1992).
(27) J. Garson et al., Development of a “Pan-retrovirus” detection system for multiple sclerosis studies. Acta Neurol. Scand. (in Press).
(28) F. Mallet, G. Oriol, C. Mary, B. Verrier and B. Mandrand. Continuous RT-PCR and taq DNA polymerase: Characterization and comparison to uncoupled procedures. Biotechniques 18, 678-687 (1995).
(29) R. Baccala, D. H. Kono, S. Walker, R. S. Balderas and Theophilopoulos. Genomically imposed and somatically modified human thymocyte vb gene repertoires. Proc. Natl. Acad. Sci. USA (1991) 88, 2908.
(30) Haahr S., Koch-Henriksen N., Moller-Larsen, A. Eriksen L. S. & Andersen H. M. K. Increased risk of multiple sclerosis after late Epstein-Barr virus infection: a historical prospective study. Multiple Sclerosis 1, 73-77 (1995).
(31) Haahr S et al. A putative new retrovirus associated with multiple sclerosis and the possible involvement of Epstein-Barr virus in this disease. Ann. NY Acad. Science. 724, 148-156 (1994).
(32) Wilkinson D. A., Goodchild N. L., Saxton T. M., Wood S. & Mager D. L. Evidence for a functional subclass of the RTLV-H family of human endogenous retrovirus-like sequences. J. Virol. 67, 2981-2989 (1993).
(33) Sonigo P., Barker C., Hunter E. and Wain-Hobson S. Nucleotide sequence of Mason-Pfizer monkey virus: an immunosuppressive D-type retrovirus. Cell 45, 375-85 (1986).
(34) Rhee S. S., and Hunter E. A single amino acid substitution within the matrix protein of a D-type retrovirus converts its morphogenesis to that of a C-type retrovirus. Cell 63, 77-86 (1990).
(35) Bai J., Zhu R. Y., Stedman K., Cousens C., Carlson J., Sharp J. M. and DeMartini J. C. Unique long terminal repeat U3 sequences distinguish exogenous Jaagsiekte sheep retroviruses associated with ovine pulmonary carcinoma from endogenous loci in the sheep genome. J. Virol. 70, 3159-3168 (1996).
(36) Palmarini M., Cousens C., Dalziel R. G., Bai J., Stedman K., DeMartini J. C. and Sharp J. M. The exogenous form of Jaagsiekte retrovirus is specifically associated with a contagious lung cancer of sheep. J. Virol. 70, 1618-1623 (1996).
(37) Portis J. L. Wild mouse retrovirus: pathogenesis. in “Retrovirus infections of the nervous system”. Oldstone M. B. A. and Koprowsky H. Eds. Current topics in microbiology and immunology, n°160, p. 11-27. (Springer-Verlag, Berlin 1990).
(38) Gardner M. B., Chivi A., Dougherty M. F., Casagrande J & Estes J. D. Congenital transmission of murine leukaemia virus from wild mice prone to development of lymphoma and paralysis. J. Natl. Cancer Inst. 62, 63-69 (1979).
(39) Marrack P., Kushnir E. & Kappler J. A maternally inherited superantigen encoded by a mammary tumor virus. Nature 349, 524-526 (1991).
(40) Hügin A. W., Vacchio M. S. & Morse H. C. A virus-encoded superantigen in a retrovirus-induced immunodeficiency syndrome of mice. Science 252, 424-427 (1991).
(41) Gardner M. B. Genetic resistance to a retroviral neurologic disease in wild mice, in “Retrovirus infections of the nervous system” Oldstone M. B. A. and Koprowsky H. Eds. Current topics in microbiology and immunology, n° 160, p. 3-10. (Springer-Verlag, Berlin 1990).
(42) Linial M. L. & Miller A. D. Retroviral RNA packaging: sequence requirements and implications, in “Retroviruses-strategies of replication” Swanstrom R. & Vogt P. K. Eds. Current topics in microbiology and immunology, n° 157, p. 125-152. (Springer-Verlag, Berlin 1990).
(43) Bell J. I. and Lathrop G. M. Multiple loci for multiple sclerosis. Nature Genetics 13, 377-78 (1996).
(44) Dhib-Jalbut S., Lewis K., Bradburn E., McFarlin D. E. and McFarland H. F. Measles virus polypeptide-specific antibody profile in multiple sclerosis. Neurology, 1990; 40: 430-435.
(45) Gonzalez-Scarano F., Waxham M. N., Ross A. M. and Hoxie J. A. Sequence similarities between human immunodeficiency virus gp41 and Paramyxovirus fusion proteins. AIDS Res. Hum. Retrov. 1987; 3: 245-252.
(46) Bergstrom, T., Andersen, O. & Vahlne A. (1989). Isolation of herpes virus type 1 during first attack of multiple sclerosis. Annales Neurology 26, 283-285.
(47) Challoner P. B. et al. Plaque-associated expression of human herpesvirus 6 in multiple sclerosis. Proc. Natl. Acad. Sci. USA 92, 7440-7444 (1995).
(48) A. Gessain et al; Antibodies to Human T-Lymphotrophic Virus type-I in patients with tropical spastic paraparesis. Lancet 2, 407-410 (1985).
(49) H. Perron, J. A. Garson, F. Bedin et al., Molecular identification of a novel retrovirus repeatedly isolated from patients with multiple sclerosis. Proc. Nat. Acad. Sci. USA 94:7583-7588 (1997).

What is claimed is:

1. An isolated nucleic acid molecule comprising a sequence that is at least 70% of homologous with a sequence set forth in SEQ ID NO: 87, wherein said sequence that is at least 70% homologous encodes a peptide having at least 30 contiguous successive amino acid residues of an amino acid sequence selected from the group consisting of the full-length amino acid sequence set forth in SEQ ID NOs:89-92, or its complementary sequence.

2. The nucleic acid according to claim 1, wherein said amino acid sequence is the full-length amino acid sequence set forth in SEQ ID NO:91.

3. The nucleic acid according to claim 1, wherein said amino acid sequence is the full-length amino acid sequence set forth in SEQ ID NO:92.

4. The nucleic acid according to claim 1, wherein said amino acid sequence is the full-length amino acid sequence set forth in SEQ ID NO:89.

5. The nucleic acid according to claim 1, wherein said amino acid sequence is the full-length amino acid sequence set forth in SEQ ID NO:90.

* * * * *

SEQUENCE LISTING (1) GENERAL INFORMATION:

(iii) NUMBER OF SEQUENCES: 212

(2) INFORMATION FOR SEQ ID NO: 1:

-continued (i) SEQUENCE CHARACTERISTICS:
(A) LENGTH: 1158 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 1:

```
CCCTTTGCCA CTACATCAAT TTTAGGAGTA AGGAAACCCA ACGGACAGTG GAGGTTAGTG     60

CAAGAACTCA GGATTATCAA TGAGGCTGTT GTTCCTCTAT ACCCAGCTGT ACCTAACCCT    120

TATACAGTGC TTTCCCAAAT ACCAGAGGAA GCAGAGTGGT TTACAGTCCT GGACCTTAAG    180

GATGCCTTTT TCTGCATCCC TGTACGTCCT GACTCTCAAT TCTTGTTTGC CTTTGAAGAT    240

CCTTTGAACC CAACGTCTCA ACTCACCTGG ACTGTTTTAC CCCAAGGGTT CAGGGATAGC    300

CCCCATCTAT TTGGCCAGGC ATTAGCCCAA GACTTGAGTC AATTCTCATA CCTGGACACT    360

CTTGTCCTTC AGTACATGGA TGATTTACTT TTAGTCGCCC GTTCAGAAAC CTTGTGCCAT    420

CAAGCCACCC AAGAACTCTT AACTTTCCTC ACTACCTGTG GCTACAAGGT TTCCAAACCA    480

AAGGCTCGGC TCTGCTCACA GGAGATTAGA TACTNAGGGC TAAAATTATC CAAAGGCACC    540

AGGGCCCTCA GTGAGGAACG TATCCAGCCT ATACTGGCTT ATCCTCATCC CAAAACCCTA    600

AAGCAACTAA GAGGGTTCCT TGGCATAACA GGTTTCTGCC GAAAACAGAT TCCCAGGTAC    660

ASCCCAATAG CCAGACCATT ATATACACTA ATTANGGAAA CTCAGAAAGC CAATACCTAT    720

TTAGTAAGAT GGACACCTAC AGAAGTGGCT TTCCAGGCCC TAAAGAAGGC CCTAACCCAA    780

GCCCCAGTGT TCAGCTTGCC AACAGGGCAA GATTTTTCTT TATATGCCAC AGAAAAAACA    840

GGAATAGCTC TAGGAGTCCT TACGCAGGTC TCAGGGATGA GCTTGCAACC CGTGGTATAC    900

CTGAGTAAGG AAATTGATGT AGTGGCAAAG GGTTGGCCTC ATNGTTTATG GGTAATGGNG    960

GCAGTAGCAG TCTNAGTATC TGAAGCAGTT AAAATAATAC AGGGAAGAGA TCTTNCTGTG   1020

TGGACATCTC ATGATGTGAA CGGCATACTC ACTGCTAAAG GAGACTTGTG GTTGTCAGAC   1080

AACCATTTAC TTAANTATCA GGCTCTATTA CTTGAAGAGC CAGTGCTGNG ACTGCGCACT   1140

TGTGCAACTC TTAAACCC                                                 1158
```

(2) INFORMATION FOR SEQ ID NO: 2:

(i) SEQUENCE CHARACTERISTICS:
(A) LENGTH: 297 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 2:

```
CCCTTTGCCA CTACATCAAT TTTAGGAGTA AGGAAACCCA ACGGACAGTG GAGGTTAGTG     60

CAAGAACTCA GGATTATCAA TGAGGCTGTT GTTCCTCTAT ACCCAGCTGT ACCTAACCCT    120

TATACAGTGC TTTCCCAAAT ACCAGAGGAA GCAGAGTGGT TTACAGTCCT GGACCTTAAG    180

GATGCCTTTT TCTGCATCCC TGTACGTCCT GACTCTCAAT TCTTGTTTGC CTTTGAAGAT    240

CCTTTGAACC CAACGTCTCA ACTCACCTGG ACTGTTTTAC CCCAAGGGTT CAAGGGA       297
```

(2) INFORMATION FOR SEQ ID NO: 3:

(i) SEQUENCE CHARACTERISTICS:
(A) LENGTH: 85 base pairs
(B) TYPE: nucleotide

-continued (C) STRANDEDNESS: single
(D) TOPOLOGY: linear (ii) MOLECULE TYPE: cDNA (xi) SEQUENCE DESCRIPTION: SEQ ID NO: 3:

GTTTAGGGAT ANCCCTCATC TCTTTGGTCA GGTACTGGCC CAAGATCTAG GCCACTTCTC 60

AGGTCCAGSN ACTCTGTYCC TTCAG 85

(2) INFORMATION FOR SEQ ID NO: 4:

(i) SEQUENCE CHARACTERISTICS:
(A) LENGTH: 86 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 4:

GTTCAGGGAT AGCCCCCATC TATTTGGCCA GGCACTAGCT CAATACTTGA GCCAGTTCTC 60

ATACCTGGAC AYTCTYGTCC TTCGGT 86

(2) INFORMATION FOR SEQ ID NO: 5:

(i) SEQUENCE CHARACTERISTICS:
(A) LENGTH: 85 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 5:

GTTCARRGAT AGCCCCCATC TATTTGGCCW RGYATTAGCC CAAGACTTGA GYCAATTCTC 60

ATACCTGGAC ACTCTTGTCC TTYRG 85

(2) INFORMATION FOR SEQ ID NO: 6:

(i) SEQUENCE CHARACTERISTICS:
(A) LENGTH: 85 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 6:

GTTCAGGGAT AGCTCCCATC TATTTGGCCT GGCATTAACC CGAGACTTAA GCCAGTTCTY 60

ATACGTGGAC ACTCTTGTCC TTTGG 85

(2) INFORMATION FOR SEQ ID NO: 7:

(i) SEQUENCE CHARACTERISTICS:
(A) LENGTH: 111 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 7:

GTGTTGCCAC AGGGGTTTAR RGATANCYCY CATCTMTTTG GYCWRGYAYT RRCYCRAKAY 60

YTRRGYCAVT TCTYAKRYSY RGSNAYTCTB KYCCTTYRGT ACATGGATGA C 111

-continued (2) INFORMATION FOR SEQ ID NO: 8:

(i) SEQUENCE CHARACTERISTICS:
(A) LENGTH: 645 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 8:

TCAGGGATAG CCCCCATCTA TTTGGCCAGG CATTAGCCCA AGACTTGAGT CAATTCTCAT 60

ACCTGGACAC TCTTGTCCTT CAGTACATGG ATGATTTACT TTTAGTCGCC CGTTCAGAAA 120

CCTTGTGCCA TCAAGCCACC CAAGAACTCT TAACTTTCCT CACTACCTGT GGCTACAAGG 180

TTTCCAAACC AAAGGCTCGG CTCTGCTCAC AGGAGATTAG ATACTNAGGG CTAAAATTAT 240

CCAAAGGCAC CAGGGCCCTC AGTGAGGAAC GTATCCAGCC TATACTGGCT TATCCTCATC 300

CCAAAACCCT AAAGCAACTA AGAGGGTTCC TTGGCATAAC AGGTTTCTGC CGAAAACAGA 360

TTCCCAGGTA CASCCCAATA GCCAGACCAT TATATACACT AATTANGGAA ACTCAGAAAG 420

CCAATACCTA TTTAGTAAGA TGGACACCTA CAGAAGTGGC TTTCCAGGCC CTAAAGAAGG 480

CCCTAACCCA AGCCCCAGTG TTCAGCTTGC CAACAGGGCA AGATTTTTCT TTATATGCCA 540

CAGAAAAAAC AGGAATAGCT CTAGGAGTCC TTACGCAGGT CTCAGGGATG AGCTTGCAAC 600

CCGTGGTATA CCTGAGTAAG GAAATTGATG TAGTGGCAAA GGGTT 645

(2) INFORMATION FOR SEQ ID NO: 9:

(i) SEQUENCE CHARACTERISTICS:
(A) LENGTH: 741 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 9:

CAAGCCACCC AAGAACTCTT AAATTTCCTC ACTACCTGTG GCTACAAGGT TTCCAAACCA 60

AAGGCTCAGC TCTGCTCACA GGAGATTAGA TACTTAGGGT TAAAATTATC CAAAGGCACC 120

AGGGGCCTCA GTGAGGAACG TATCCAGCCT ATACTGGGTT ATCCTCATCC CAAAACCCTA 180

AAGCAACTAA GAGGGTTCCT TAGCATGATC AGGTTTCTGC CGAAAACAAG ATTCCCAGGT 240

ACAACCAAAA TAGCCAGACC ATTATATACA CTAATTAAGG AAACTCAGAA AGCCAATACC 300

TATTTAGTAA GATGGACACC TAAACAGAAG GCTTTCCAGG CCCTAAAGAA GGCCCTAACC 360

CAAGCCCCAG TGTTCAGCTT GCCAACAGGG CAAGATTTTT CTTTATATGG CACAGAAAAA 420

ACAGGAATCG CTCTAGGAGT CCTTACACAG GTCCGAGGGA TGAGCTTGCA ACCCGTGGCA 480

TACCTGAATA AGGAAATTGA TGTAGTGGCA AAGGGTTGGC CTCATNGTTT ATGGGTAATG 540

GNGGCAGTAG CAGTCTNAGT ATCTGAAGCA GTTAAAATAA TACAGGGAAG AGATCTTNCT 600

GTGTGGACAT CTCATGATGT GAACGGCATA CTCACTGCTA AAGGAGACTT GTGGTTGTCA 660

GACAACCATT TACTTAANTA TCAGGCTCTA TTACTTGAAG AGCCAGTGCT GNGACTGCGC 720

ACTTGTGCAA CTCTTAAACC C 741

(2) INFORMATION FOR SEQ ID NO: 10:

(i) SEQUENCE CHARACTERISTICS:
(A) LENGTH: 93 base pairs

```
            (B) TYPE: nucleotide
            (C) STRANDEDNESS: single
            (D) TOPOLOGY: linear

    (ii) MOLECULE TYPE: cDNA

    (xi) SEQUENCE DESCRIPTION: SEQ ID NO: 10:

TGGAAAGTGT TGCCACAGGG CGCTGAAGCC TATCGCGTGC AGTTGCCGGA TGCCGCCTAT      60

AGCCTCTACA TGGATGACAT CCTGCTGGCC TCC                                  93

(2) INFORMATION FOR SEQ ID NO: 11:

    (i) SEQUENCE CHARACTERISTICS:
        (A) LENGTH: 96 base pairs
        (B) TYPE: nucleotide
        (C) STRANDEDNESS: single
        (D) TOPOLOGY: linear

    (ii) MOLECULE TYPE: cDNA

    (xi) SEQUENCE DESCRIPTION: SEQ ID NO: 11:

TTGGATCCAG TGYTGCCACA GGGCGCTGAA GCCTATCGCG TGCAGTTGCC GGATGCCGCC      60

TATAGCCTCT ACGTGGATGA CCTSCTGAAG CTTGAG                               96

(2) INFORMATION FOR SEQ ID NO: 12:

    (i) SEQUENCE CHARACTERISTICS:
        (A) LENGTH: 748 base pairs
        (B) TYPE: nucleotide
        (C) STRANDEDNESS: single
        (D) TOPOLOGY: linear

    (ii) MOLECULE TYPE: cDNA

    (xi) SEQUENCE DESCRIPTION: SEQ ID NO: 12:

TGCAAGCTTC ACCGCTTGCT GGATGTAGGC CTCAGTACCG GNGTGCCCCG CGCGCTGTAG      60

TTCGATGTAG AAAGCGCCCG GAAACACGCG GGACCAATGC GTCGCCAGCT TGCGCGCCAG     120

CGCCTCGTTG CCATTGGCCA GCGCCACGCC GATATCACCC GCCATGGCGC CGGAGAGCGC     180

CAGCAGACCG GCGGCCAGCG GCGCATTCTC AACGCCGGGC TCGTCGAACC ATTCGGGGGC     240

GATTTCCGCA CGACCGCGAT GCTGGTTGGA GAGCCAGGCC CTGGCCAGCA ACTGGCACAG     300

GTTCAGGTAA CCCTGCTTGT CCCGCACCAA CAGCAGCAGG CGGGTCGGCT TGTCGCGCTC     360

GTCGTGATTG GTGATCCACA CGTCAGCCCC GACGATGGGC TTCACGCCCT TGCCACGCGC     420

TTCCTTGTAG ANGCGCACCA GCCCGAAGGC ATTGGCGAGA TCGGTCAGCG CCAAGGCGCC     480

CATGCCATCT TTGGCGGCAG CCTTGACGGC ATCGTCGAGA CGGACATTGC CATCGACGAC     540

GGAATATTCG GAGTGGAGAC GGAGGTGGAC GAAGCGCGGC GAATTCATCC GCGTATTGTA     600

ACGGGTGACA CCTTCCGCAA AGCATTCCGG ACGTGCCCGA TTGACCCGGA GCAACCCCGC     660

ACGGCTGCGC GGGCAGTTAT AATTTCGGCT TACGAATCAA CGGGTTACCC CAGGGCGCTG     720

AAGCCTATCG CGTGCAGTTG CCGGATGC                                       748

(2) INFORMATION FOR SEQ ID NO: 13:

    (i) SEQUENCE CHARACTERISTICS:
        (A) LENGTH: 18 base pairs
        (B) TYPE: nucleotide
        (C) STRANDEDNESS: single
        (D) TOPOLOGY: linear

    (ii) MOLECULE TYPE: cDNA
```

(xi) SEQUENCE DESCRIPTION: SEQ ID NO: 13:

GCATCCGGCA ACTGCACG 18

(2) INFORMATION FOR SEQ ID NO: 14:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 14:

GTAGTTCGAT GTAGAAAGCG 20

(2) INFORMATION FOR SEQ ID NO: 15:

(i) SEQUENCE CHARACTERISTICS:
(A) LENGTH: 23 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 15:

AGGAGTAAGG AAACCCAACG GAC 23

(2) INFORMATION FOR SEQ ID NO: 16:

(i) SEQUENCE CHARACTERISTICS:
(A) LENGTH: 19 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 16:

TAAGAGTTGC ACAAGTGCG 19

(2) INFORMATION FOR SEQ ID NO: 17:

(i) SEQUENCE CHARACTERISTICS:
(A) LENGTH: 21 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 17:

TCAGGGATAG CCCCCATCTA T 21

(2) INFORMATION FOR SEQ ID NO: 18:

(i) SEQUENCE CHARACTERISTICS:
(A) LENGTH: 24 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 18:

AACCCTTTGC CACTACATCA ATTT 24

-continued (2) INFORMATION FOR SEQ ID NO: 19:

(i) SEQUENCE CHARACTERISTICS:
(A) LENGTH: 15 base pairs
(B) TYPE: nucleotide
(C) STRANDEDNESS: single
(D) TOPOLOGY: linear (ii) MOLECULE TYPE: cDNA (ix) FEATURE:
(B) LOCATION: 5, 7, 10, 13
(D) OTHER INFORMATION: N represents inosine (i)

(xi) SEQUENCE DESCRIPTION: SEQ ID NO: 19:

GGTCNTNCCN CANGG 15

(2) INFORMATION FOR SEQ ID NO: 20:

(i) SEQUENCE CHARACTERISTICS:
(A) LENGTH: 21 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 20:

TTAGGGATAG CCCTCATCTC T 21

(2) INFORMATION FOR SEQ ID NO: 21:

(i) SEQUENCE CHARACTERISTICS:
(A) LENGTH: 23 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 21:

GCGTAAGGAC TCCTAGAGCT ATT 23

(2) INFORMATION FOR SEQ ID NO: 22:

(i) SEQUENCE CHARACTERISTICS:
(A) LENGTH: 18 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 22:

TCATCCATGT ACCGAAGG 18

(2) INFORMATION FOR SEQ ID NO: 23:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 23:

ATGGGGTTCC CAAGTTCCCT 20

(2) INFORMATION FOR SEQ ID NO: 24:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 24:

GCCGATATCA CCCGCCATGG 20

(2) INFORMATION FOR SEQ ID NO: 25:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 25:

CGCGATGCTG GTTGGAGAGC 20

(2) INFORMATION FOR SEQ ID NO: 26:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 26:

TCTCCACTCC GAATATTCCG 20

(2) INFORMATION FOR SEQ ID NO: 27:

(i) SEQUENCE CHARACTERISTICS:
(A) LENGTH: 26 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 27:

GATCTAGGCC ACTTCTCAGG TCCAGS 26

(2) INFORMATION FOR SEQ ID NO: 28:

(i) SEQUENCE CHARACTERISTICS:
(A) LENGTH: 23 base pairs
(B) TYPE: nucleotide
(C) STRANDEDNESS: single
(D) TOPOLOGY: linear (ii) MOLECULE TYPE: cDNA (ix) FEATURE:
(B) LOCATION: 6, 12, 19
(D) OTHER INFORMATION: N represents inosine (i)

(xi) SEQUENCE DESCRIPTION: SEQ ID NO: 28:

CATCTNTTTG GNCAGGCANT AGC 23

-continued (2) INFORMATION FOR SEQ ID NO: 29:

(i) SEQUENCE CHARACTERISTICS:
(A) LENGTH: 24 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 29:

CTTGAGCCAG TTCTCATACC TGGA 24

(2) INFORMATION FOR SEQ ID NO: 30:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 30:

AGTGYTRCCM CARGGCGCTG AA 22

(2) INFORMATION FOR SEQ ID NO: 31:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 31:

GMGGCCAGCA GSAKGTCATC CA 22

(2) INFORMATION FOR SEQ ID NO: 32:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 32:

GGATGCCGCC TATAGCCTCT AC 22

(2) INFORMATION FOR SEQ ID NO: 33:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 33:

AAGCCTATCG CGTGCAGTTG CC 22

(2) INFORMATION FOR SEQ ID NO: 34:

(i) SEQUENCE CHARACTERISTICS:

-continued

```
          (A) LENGTH: 40 base pairs
          (B) TYPE: nucleotide
          (C) STRANDEDNESS: single
          (D) TOPOLOGY: linear

    (ii) MOLECULE TYPE: cDNA

    (xi) SEQUENCE DESCRIPTION: SEQ ID NO: 34:

TAAAGATCTA GAATTCGGCT ATAGGCGGCA TCCGGCAAGT                          40


(2) INFORMATION FOR SEQ ID NO: 35:

     (i) SEQUENCE CHARACTERISTICS:
          (A) LENGTH: 50 amino acids
          (B) TYPE: amino acid
          (C) STRANDEDNESS: not relevant
          (D) TOPOLOGY: linear

    (ii) MOLECULE TYPE: peptide

    (xi) SEQUENCE DESCRIPTION: SEQ ID NO: 35:

Asp Ala Phe Phe Cys Ile Pro Val Arg Pro Asp Ser Gln Phe Leu Phe
1               5                   10                  15

Ala Phe Glu Asp Pro Leu Asn Pro Thr Ser Gln Leu Thr Trp Thr Val
            20                  25                  30

Leu Pro Gln Gly Phe Arg Asp Ser Pro His Leu Phe Gly Gln Ala Leu
        35                  40                  45

Ala Gln
    50


(2) INFORMATION FOR SEQ ID NO: 36:

     (i) SEQUENCE CHARACTERISTICS:
          (A) LENGTH: 150 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO: 36:

GATGCCTTTT TCTGCATCCC TGTACGTCCT GACTCTCAAT TCTTGTTTGC CTTTGAAGAT     60

CCTTTGAACC CAACGTCTCA ACTCACCTGG ACTGTTTTAC CCCAAGGGTT CAGGGATAGC    120

CCCCATCTAT TTGGCCAGGC ATTAGCCCAA                                     150


(2) INFORMATION FOR SEQ ID NO: 37:

     (i) SEQUENCE CHARACTERISTICS:
          (A) LENGTH: 11 amino acids
          (B) TYPE: amino acid
          (C) STRANDEDNESS: not relevant
          (D) TOPOLOGY: linear

    (ii) MOLECULE TYPE: peptide

    (xi) SEQUENCE DESCRIPTION: SEQ ID NO: 37:

Cys Ile Pro Val Arg Pro Asp Ser Gln Phe Leu
1               5                   10


(2) INFORMATION FOR SEQ ID NO: 38:

     (i) SEQUENCE CHARACTERISTICS:
          (A) LENGTH: 17 amino acids
          (B) TYPE: amino acid
          (C) STRANDEDNESS: not relevant
          (D) TOPOLOGY: linear
```

-continued (ii) MOLECULE TYPE: peptide (xi) SEQUENCE DESCRIPTION: SEQ ID NO: 38:

```
Val Leu Pro Gln Gly Phe Arg Asp Ser Pro His Leu Phe Gly Glu Ala
1               5                   10                  15

Leu
```

(2) INFORMATION FOR SEQ ID NO: 39:

(i) SEQUENCE CHARACTERISTICS:
(A) LENGTH: 8 amino acid
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 39:

```
Leu Phe Ala Phe Glu Asp Pro Leu
1               5
```

(2) INFORMATION FOR SEQ ID NO: 40:

(i) SEQUENCE CHARACTERISTICS:
(A) LENGTH: 8 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 40:

```
Phe Ala Phe Glu Asp Pro Leu Asn
1               5
```

(2) INFORMATION FOR SEQ ID NO: 41:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 41:

```
GTGCTGATTG GTGTATTTAC AATCC                                        25
```

(2) INFORMATION FOR SEQ ID NO: 42:

(i) SEQUENCE CHARACTERISTICS:
(A) LENGTH: 1859 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 42:

```
GTGCTGATTG GTGTATTTAC AATCCTTTAT CTAATCCGAA ATGCCCATGT TGCAATATGG     60

AAAGAAAGGG AGTTCCTAAC CTCTGGGGGA ACCCCCATTA AATACCACAA GTAAATCATG    120

GAGTTATTGC ACACAGTGCA AAAACTCAAG GAGGTGGAAG TCTTACACTG CCAAAGCCAT    180

CAGAAAAGGG AAGAGGGGAG AAGAGCAGCA TAAGTGGCTA CAGAGGCAAG GAAAGACTAG    240

CAGAAAGGAA AGAGAGAAAG AGACAGAAAG TCAGAGAGAG AGAGAGGAAG AGACAGAGCA    300
```

-continued

CAAAGAGGGA GTCAGAGAGA GAGAGAGACA GAGAGTCAGA GAGAAGGAAA GAGAGAGAGG 360

AAGAGACAAA GAATGAATCA AACAGAGAGA CAGAAAGTCA GAGAGAGAGA GAGAGAGGAA 420

GAGACAGAGA AAAAGAGGGA GTCAGAAAAA GAGAGACCAA AGAAGAAGTC CAAAGAGAAA 480

GAAAGAGAGA TGGAAGTAGT AAAGGAAAAA CAGTGTACCC TATTCCTTTA AAAGCCGGGG 540

TAAATTTAAA ACCTATAATT GATAACTGAA GGTCTTCTCT GTAACCCTGT AACACTCCAA 600

TACCACCTTG TTGTCAAGTG TAAACAAGGG CGTAGCCCAA AAGCACTGAG GCCACTAACA 660

ACCCATAGCC TTCCTATCAA AATTCCTTAA CCCAGCAGGT TTCCTAACAG GGGATCTAAA 720

TCTTAATTAA TTACCATACA ATGGTCCAAC CAGACTTAGG AGGAATTCCC TTCAGGACGG 780

GAAGATAGAT GCTTCCTCCC AGGCGATTAA GGGAGAAAGA CACAATGGGT ATTCAGTAAG 840

TGCCAAGGGG AACACTTGTA GAAGCAAAGT TAGGAAAATT GCCAAATAAT TGGTTTGCTC 900

AAGAGTTGTT TGCACTCAGC CAAACCTTGA AGTACTTGCA GAATCAGAAA GGAGCCATCT 960

ATACCAATTC TAAGTTAATA TGGACTGAAG GAGGTTTTAT TAATACCAAA GAGAAATTAA 1020

AATCCCAAAC TTATAAGGTT TTCAACCAAA GTAAAGTTTG CTAAAAGTTA ACAGCGTAAC 1080

ATGTATTATC CTACTACCAC ACACTCTCAA AGGATTTCTC AGACAGTTTG CAAGAAATAA 1140

TGATATCTAT CCTTACTCTA CAATCCCAAA TAGACTCTTT GGCAGCAGTG ACTCTCCAAA 1200

ACCGTCAAGG CCTAGACCTC CTCACTGCTG AGAAAGGAGG ACTCTGCACC TTCTTAAGGG 1260

AAGAGTGTTG TCTTTACACT AACCAGTCAG GGATAGTATG AGATGCTGCC CGGCATTTAC 1320

AGAAAAAGGC TTCTGAAATC AGACAACGCC TTTCAAATTC CTATACCAAC CTCTGGAGTT 1380

GGGCAACATG GTTTCTTCCC TTTCTATGTC CCATGGCTGC CATCTTGCTA TTACTCGCCT 1440

TTGGGCCCTG TATTTTTAAC CTCCTTGTCA AATTTGTTTC TTCTAGGATC GAGGCCATCA 1500

AGCTACAGAT GGTCTTACAA ATGGAACCCC AAATGAGCTC AACTATCAAC TTCTACTGAG 1560

GACCCCTAGA CCAACCCCCT GGCCCTTTCA CTGGCCTAAA GAGTTCCCCT CTGGAGGACA 1620

CTACCACTGC AGGGCCCCAT CTTTGCCCCT ATCCAGAAGG AAGTAGCTAG AGCAGTCATT 1680

GCCCAATTCC CAAGAGCAGC TGGGGTGTCC CGTTTAGAGT GGGGATTGAG AGGTGAAGCC 1740

AGCTGGACTT CTGGGTCGGG TGGGGACTTG GAGAACTTTT GTGTCTAGCT AAAGGATTGT 1800

AAATGCAACA ATCAGTGCTC TGTGTCTAGC TAAAGGATTG TAAATACACC AATCAGCAC 1859

(2) INFORMATION FOR SEQ ID NO: 43:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 43:

TGATGTGAAC GGCATACTCA CTG 23

(2) INFORMATION FOR SEQ ID NO: 44:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA -continued (xi) SEQUENCE DESCRIPTION: SEQ ID NO: 44:

CCCAGAGGTT AGGAACTCCC TTTC 24

(2) INFORMATION FOR SEQ ID NO: 45:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 45:

GCTAAAGGAG ACTTGTGGTT GTCAG 25

(2) INFORMATION FOR SEQ ID NO: 46:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 46:

CAACATGGGC ATTTCGGATT AG 22

(2) INFORMATION FOR SEQ ID NO: 47:

(i) SEQUENCE CHARACTERISTICS:
(A) LENGTH: 400 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 47:

GGCTGCTAAA GGAGACTTGT GGTTGTCAGA CAATCGCCTA CTTAGGTACC AGGCCTTATT 60

ACTTGAGGGA CTGGTGCTTC AGATGCGCAC TTGTGCAGCT CTTAACCCAA ACTTATGCTG 120

CCCAGAAGGA TCTTTTAGAG GTCCCCTTAG CCAACCCTGA CCTCAACCTA TATATATACT 180

GATGGAAGTT CGTTTGTAGA AAAGGGATTA CAAAGGGNAG GATATNCCAT AGGTTAGTGA 240

TAAAGCAGTA CTTGAAAGTA AGCCTCTTCC CCCCAGGGAC CAGCGCCCCC GTTAGCAGAA 300

CTAGTGGCAC TGACCCCGAG CCTTAGAACT TGGAAAGGGA GGAGGATAAA TGTGTATACA 360

GATAGCAAGT ATGCTTATCT AATCCGAAAT GCCCATGTTG 400

(2) INFORMATION FOR SEQ ID NO: 48:

(i) SEQUENCE CHARACTERISTICS:
(A) LENGTH: 2389 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 48:

TCAGGGATAG CCCCCATCTA TTTGGTCAGG CACTGGCCCA AGATCTAGGG ACATGCCACT 60

TTTAAGAGCC ATTTCTCAAG TCCAGGTACT CTGGTCCTTC GGTATGTGGA TGATTTACTT 120

TTGGCTACCA GTTCAGTAGC CTCATGCCAG CAGGCTACTC TAGATCTCTT GAACTTTCTA 180

-continued

```
GCTAATCAAG GGTACAAGGC ATCTAGGTTG AAGGCCCAGC TTTGCCTACA GCAGGTCAAA    240
TATCTAGGCC TAATCTTAGC CAGAGGGACC AGGGCACTCA GCAAGGAACA AATACAGCCT    300
ATACTGGCTT ATCCTCACCC TAAGACATTA AAACAGTTGC GGGGGTTCCT TGGAATCACT    360
GGCTTTTTGG TGACTATGGA TTCCCAGATA CAGCAAGATT GGCAGGCCCC TCTATACTGT    420
AATCAAGGAG ACTCACGAGG GCAAGTACTC ATCTAGTAGA ATGGGAACTA GGGACAGAAA    480
CAGCCTTCAA AACCTTAAAG CAGGCCCTAG TACAATCTCC AGCTTTAAGC CTTCCCACAG    540
GACAAAACTT CTCTTTATAC ATCACAGAGA GGGCAGAGAT AGCTCTTGGT GTCCTTATTC    600
AGACTCATGG GACTACCCCA CAACCAGTGG CACACCTAAG TAAGGAAATT GATGTAGTAG    660
CAAAAGGCTG GCCTCACTGT TTATGGGTAG CTGTGGTGGT GGCTGTCTTA GTGTCAGAAG    720
CTATCAAAAT AATACAAGGA AAGGATCTCA CTGTCTGGAC TACTCATGAT GTAATGGCAT    780
ACTAGGTGCC AAAAGAAGTT TATGGGTATC AGACAACCAC CTGCTTAGAT ACCAGGGACT    840
ACTCCTGGAG GATTGGGCTT CAAGTGCGTT TTTTGTGGCC TCAACCCTGC CACTTTTCCT    900
CCAGAGGATG GAGAGCCGCT TGAGCATGCT TGCCAACAGG TTGTAGGCCA GAATTATTCC    960
ACCCGAGATG ATCTCTTAGA GTACCCTTAG CTAATCCTGA CCTTAACCTA TATACCAATG   1020
GAAGTTCATT TGTGGAAAAC GGGATATGAA GGGCAGGTTA TGTCATAGTT AGTGATGTAA   1080
TCATACTTGC AAGTAAGCCT CTTACCCCAG GGGCCAGCAC TCAGTTAGCA GAACTAGTCA   1140
CACTTACCTT AACCTTAGAA CTGGGAAAGG GAAAAAGAAT AAATATGTAT ACAGATAGTA   1200
AGTATGCTTA TCTAATCCTA CATGCCCATG CTGCAATATG GAAGGAAAGG GAGTTCCTAA   1260
CCCCTGGGGG AACCCCCATT AAATACCACA AGGYAAATCA TGGAGTTATT GCACGCAGTG   1320
CAAAAACTCA AGGAGGTGGC AGTCTTACAC TGCCGAAGCY ATCAAAAAGG GGAAGGAGAG   1380
GGGAGAACAG CAGCATAAGT GGTTGGCAGA GGCAGTGAAA GACCAGCAGA GAGAAGGAGA   1440
GAGACAACGT CAACGACAGA AGGAAAGAAG AGGAGGAGAC AGAGAGGAAG AGACAGAGAG   1500
ACAGTTAGTC CAAGAGAGAG ACAGAGAGAG GAAGAGACAG ACAGAAAGTC CAAGAGAGAA   1560
GGAAAGAGAG GAAGAGACCA AGGAGTCCNA GAGAGAGAAA GAGATAGAAG TAGTAAAGAA   1620
AAAACATTGT ACCCTATTCC TTTAAAAGCC GGGGTATATT TAAAACCTAT AATTGATAAT   1680
TGAGTTCTTG CACCCTCCTC CAGGGGATYG CTGGGAGGAA ACCCTCAACC GATATGTGAA   1740
AATTGTGGGT CGTCCCTATG TCTCAATTAC CAGCCAATAC CCCCTTGTTT TTAGTGTGAA   1800
CGAGGGTGTA GAGCGCAGAC AGGGAGACCT CTGACAATCC ATACCCTTCC TATCCAAAAT   1860
CCTTAACCCA GCAGGTTTTC TAAAAGGGGA TCTAAATCTT AATTAATTAC CATACAAAGG   1920
TCAAACCAGA TCTAGGAGGA ACTTCCTTCA GGACAGGATG ATAGATGGTT CCTCCCAGGC   1980
GATTAAAGAA AATAAAAAGA CACATGGGCA GCCAGTAAGT GATAAGGGAA CACTAGTAGA   2040
AGCAGTTAGG AGAAGTTGCC TAATAATTGG TCTACTCCAA ATGTGTGAGT TGTTCGCACT   2100
CAGCCCAAAT CTTAAAGTAC TTACAGAATT AGGGGAGGAGC CATTTACACC AATTCTAAGT  2160
TAATATGGAC TGGATGAGGT TTTATTAATA GCGAAGGAGA ATTAAATCCT AAACTNACAA   2220
GGTTTTCAAC TAAAGTAAAT TTTACTAAAA GCTAACAGTG TAACATGCAT TATCCTACTA   2280
CAACACACTC TCANAGGATT CCTCAGACAG TTTACAAGAA ATAACAAAAT CTATCTGGTA   2340
AGGATAGTAA CTACAATCCC AAATACATTC TTTGGCAGCA GTGACTCTC               2389
```

(2) INFORMATION FOR SEQ ID NO: 49:

(i) SEQUENCE CHARACTERISTICS:

-continued (A) LENGTH: 2448 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 49:

TCAGGGATAG CCCCCATCTA TTTGATCAGG CACTAGCCCA AGATCTAGGC CACTTCTGAA 60

GTCCAGGCAT TCTAGTCCTT CAGTATGTGG ATGATTTACT TTTGGCTACC AGTTTGGAAG 120

CCTCATGCCA GCAGGCTACT TGAGATCTCT TGAACTTTCT AGCTAATCAA GGGTGTATGG 180

CATCTAAATT GAAAGTCCAG CTCTGCCTAC AACAAGTCAA ATATCTAGGC CTAATCTTAG 240

ATAGAAGAAC CAGGGCCCTC AGCAAGGAAT GAATAAAGCC TATGCTGGCT TATCGGCACC 300

CTAAGACATT AAAACAATTG TGGGGGTTCC TTGGAATCAC TGGCTTTTGC CGACTATGGA 360

TCCCTGGATA GAGTGAGATA GCCAGGCCCC CTCTATTACT CTTATCAAGG AGACCCAGAG 420

GGCAAATACT TATCTAGTAT TATGGGNACC AGAGGCAGAA AAAGCCTTCC AAACCTTAAA 480

GGAGACCCTA GTACAAGCTC CAGCTTTAAG CCTTCCCACA GGACAAANCT TCTCTTTATA 540

TGTCACAGAG AGAGCAGGAA TAGCTCCTGG AGTCCTTACT CAGACTTTTG GACGACCCCA 600

CGGCCAGTGG CRTACCTAAG TAAGGAAATT GATGTAGTAG CAAAAGGCTG GCCTCACTGT 660

TTATGGGTAG TTGCGGCTGT GGCAGTCTTA CTGTCAAAGG CTATCAAAAT AATACAAGGA 720

AAGGATTTCA CTATCTGGAC TACTCATGAG GAAAATGGCA TATTAGGTGC CAAAGGAAGT 780

TTTTGGCTAT CAGACAACCA CCTGCTCAGA TTCCAGGCAC TACTGATTGA GAGACCAGTG 840

CTTTAAATAT GTATGTGTGT GTGTGGCCCT CAACCCTGCC ACTGTTCTCC CAGAAGATGG 900

AGAACCAATG AAGCATTACT GTCAACAAAT TAGAGTCCAG AGTTATGCTG CCTGAGAGGA 960

TCTCTTAGAA GTCCCCTTAG CTAATCCTGA CCTTAACCTA TATGCTGATG GAAGTTCACT 1020

TGTGGAGAAT GGGATACGAA AAGCACATTA TGCCATAGTT AGTGAGGTAA CAGTACTTGA 1080

AAGTAAGCCT ATTCCCCCAT GGACCAGAGC CCAGTTAGCA GAACTAGTGG CACTTACCCA 1140

AGCCTTAGAA CTAGGAAAGG GAAAAATAAT AAATGTGTAT ACAGATAGCA AGTATGCTTA 1200

TCTAATCCTA CATGCCCATG CTGCAGTATG GAAAGAAAGG GAGTTCCTAA CCTCTGGGGG 1260

AACCCCCATT AAATACCACA AGGCAAATCA TGGAGTTATT GCATGTAGTG CAAAACCTCA 1320

AGTAGGTGGC AGTTTTACAC TGCCTGAAGC TATGGGGAAG GAGAGAGGAG AACAGCAGCA 1380

TAAGTGGCTA GCAGAGGCAG CGAAAGACTA GCAGAGAGGA GAGGTAGGGG AAAGACAGAA 1440

AGTCAAAGAA AAGAAGTCAA AGACAGACAG AGAAAGAGAC AGAGGGAGCC AGAGAGAAAG 1500

AAAAGAGAGA ACGAAAGAGA CAGAATGTCA AAGAACAGAA GAGAGAGGCA GCGCCAGAAG 1560

AGTTAAGAAA GTGAGAAAGA GAGATGGAAA TAGTAAAGAA AAAACAGTGT ACCCTATTCC 1620

TTTAAAAGCC AGGGTAAATT TAAAACGTAT AATTTTATAA TTGGAAGGTC TTCTCCATAA 1680

CCCTATAACA TTAAAATACC ACCTTGTTGT CAGTGTAAAC AAGAGCATAG CCCAAAAGCA 1740

CTGAGGCCAC TGACAACCCA TAGCCTTCCT ATCAAAAATC CTTAACTCTG CAGGTTTCCT 1800

AACAGGGGAT CTAAATCTCA ACTAATCACC ATACAATGGT CCGACCAGAC CTAGGAGCGA 1860

CTCCCCTCAG GACAGAAGGA TGGATGGTTC CTCCCAGGCC ATTAAGGGAA AGAGACACAA 1920

TGGGTATTCA GTAAGTGATA AGGGAACTCT TGTAGAAGCA GTTAGGAAGA TTGCCTAATA 1980

TTTGGTCTGC TCAAATGTGC CAGCTGTTTG CACTCAGCTA AACCTTAAAT TACTTACAGA 2040

ATTAGGAAGG AGCCATCTAT ACCAATTCTG AGTTAATATG AGCTGAACAA GTTCTTATTA 2100

-continued

```
ATAGCAAAGA ATCATTGAAA TCTCAAACTT GCAAAGTTTT CAACAAAAGT AAAGTTTGCT   2160

GAAAGTTAGC AGTGTAACAT GTATTATCCT AACTTCTAAT CTTGTGGAAA TCAGACCCTA   2220

TCAGTGCCCC TCAAAGCTGA AGTCCATCAG CATATGGCCA TACAACTAAT ACCCCTATTT   2280

ATAGGGTTAG GAATGGCCAC TGCTACAGGA ATGGGAGTAA CAGGTTTATC TACTTCATTA   2340

TCCTATTACC ACACACTCTT AAAGGATTTC TCAGACAGTT TACAAGAAAT AACAAAATCT   2400

ATCCTTACTC TNTARTCCCA AATAGRTTCT TTGGCAGCAG TGACTCTC                2448
```

(2) INFORMATION FOR SEQ ID NO: 50:

(i) SEQUENCE CHARACTERISTICS:
(A) LENGTH: 21 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 50:

```
CCTGAGTTCT TGCACTAACC C                                               21
```

(2) INFORMATION FOR SEQ ID NO: 51:

(i) SEQUENCE CHARACTERISTICS:
(A) LENGTH: 23 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 51:

```
GTCCGTTGGG TTTCCTTACT CCT                                             23
```

(2) INFORMATION FOR SEQ ID NO: 52:

(i) SEQUENCE CHARACTERISTICS:
(A) LENGTH: 1196 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 52:

```
TTCCTGAGTT CTTGCACTAA CCTCAAATGA GAGAAGTGCC GCCATAACTG CAACCCAAGA     60

GTTTGGCGAT CCCTGGTATC TCAGTCAGGT CAATGACAGG ATGACAACAG AGGAAAGATA    120

ATGATTCCCC ACAGGCCAGC AGGCAGTTCC CAGTGTAGAC CCTCATTAGG ACACAGAATC    180

AGAACATGGA GATTGGTGCC GCAGACATTT GCTAACTTGC GTGCTAGAAG GACTAAGGAA    240

AACTAGGAAG ATATGAATTA TTCAATGATG TCCACTATAA CACAGGGGAA AGGAAGAAAA    300

TCCTACTGCC TTTCTGGAGA GACTAAGGGA GGCATTGAGG AAGCATACCA GGCAAGTGGA    360

CATTGGAGGC TCTGGAAAAG GGAAAAGTTG GGAAAAGTAT ATGTCTAATA GGGCTTGCTT    420

CCAGTGTGGT CTACAAGGAC ACTTTAAAAA AGATTGTCCA ATAGAAATAA GCCACCACCT    480

CGTCCATGCC CCTTATGTCA AGGGAATCAC TGGAAGGCCC ACTGCCCCAG GGGATGAAGG    540

TCCTCTGAGT CAGAAGCCAC TAACCAGATG ATCCAGCAGC AGGACTGAGG GTGCCCGGGG    600

CAAGCGCCAG CCCATGCCAT CACCCTCACA GAGCCCCAGG TATGCTTGAC CATTGAGGGT    660

CAGAAGGGTA CTGTCTCCTG GACACTGGCG GGCCTTCTCA GTCTTACTTT CCTGTCCTGG    720
```

-continued

ACAACTGTCC TCCAGATCTG TCACTGTCCG AGGGGTCCTA GGACAGCCAG TCACTAGATA 780

CTTCTCCCAG CCACTAAGTT GTGACTGGGG AACTTTACTC TTCCACATGC TTTTCTAATT 840

ATGCCTGAAA GCCCCACTCT CTTGTTAGGG GAGAGACATT CTAGCAAAAG CAGGGGCCAT 900

TATACATGTG AATATAGGAG AAGGAACAAC TGTTTGTTGT CCCCTGCTTG AGGAAGGAAT 960

TAATCCTGAA GTCCGGGCAA CAGAAGGACA ATATGGACAA GCAAAGAATG CCCGTCCTGT 1020

TCAAGTTAAA CTAAAGGATT CCACCTCCTT TCCCTACCAA AGGCAGTACC CCCTCAGACC 1080

CGAGACCCAA CAAGAACTCC AAAAGATTGT AAAGGACCTA AAAGCCCAAG GCCTAGTAAA 1140

ACCAAGCAAT AGCCCTTGCA AGACTCCAAT TTTAGGAGTA AGGAAACCCA ACGGAC 1196

(2) INFORMATION FOR SEQ ID NO: 53:

(i) SEQUENCE CHARACTERISTICS:
(A) LENGTH: 2391 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 53:

ATGATCCAGC AGCAGGACNG AGGGTGCCCG GGGCAAGCGC CAGCCCATGC CATCACCCTC 60

ACAGAGCCCC AGGTATGCTT GACCATTGAG GGTCAGAAGG GTNACTGTCT CCTGGACACT 120

GGCGGNGCCT TCTCAGTCTT ACTTTCCTGT CCTGGACAAC TGTCCTCCAG ATCTGTCACT 180

GTCCGAGGGG TCCTAGGACA GCCAGTCACT AGATACTTCT CCCAGCCACT AAGTTGTGAC 240

TGGGGAACTT TACTCTTCCC ACATGCTTTT CTAATTATGC CTGAAAGCCC CACTCTCTTG 300

TTGGGGAGAG ACATTCTAGC AAAAGCAGGG GCCATTATAC ATGTGAATAT AGGAGAAGGA 360

ACAACTGTTT GTTGTCCCCT GCTTGAGGAA GGAATTAATC CTGAAGTCCG GGCAACAGAA 420

GGACAATATG GACAAGCAAA GAATGCCCGT CCTGTTCAAG TTAAACTAAA GGATTCCACC 480

TCCTTTCCCT ACCAAAGGCA GTACCCCCTC AGACCCGAGA CCCAACAAGA ACTCCAAAAG 540

ATTGTAAAGG ACCTAAAAGC CCAAGGCCTA GTAAAACCAA GCAATAGCCC TTGCAAGACT 600

CCAATTTTAG GAGTAAGGAA ACCCAACGGA CAGTGGAGGT TAGTGCAAGA ACTCAGGATT 660

ATCAATGAGG CTGTTGTTCC TCTATACCCA GCTGTACCTA ACCCTTATAC AGTGCTTTCC 720

CAAATACCAG AGGAAGCAGA GTGGTTTACA GTCCTGGACC TTAAGGATGC CTTTTTCTGC 780

ATCCCTGTAC GTCCTGACTC TCAATTCTTG TTTGCCTTTG AAGATCCTTT GAACCCAACG 840

TCTCAACTCA CCTGGACTGT TTTACCCCAA GGGTTCAGGG ATAGCCCCCA TCTATTTGGC 900

CAGGCATTAG CCCAAGACTT GAGTCAATTC TCATACCTGG ACACTCTTGT CCTTCAGTAC 960

ATGGATGATT TACTTTTAGT CGCCCGTTCA GAAACCTTGT GCCATCAAGC CACCCAAGAA 1020

CTCTTAACTT TCCTCACTAC CTGTGGCTAC AAGGTTTCCA AACCAAAGGC TCGGCTCTGC 1080

TCACAGGAGA TTAGATACTN AGGGCTAAAA TTATCCAAAG GCACCAGGGC CCTCAGTGAG 1140

GAACGTATCC AGCCTATACT GGCTTATCCT CATCCCAAAA CCCTAAAGCA ACTAAGAGGG 1200

TTCCTTGGCA TAACAGGTTT CTGCCGAAAA CAGATTCCCA GGTACASCCC AATAGCCAGA 1260

CCATTATATA CACTAATTAN GGAAACTCAG AAAGCCAATA CCTATTTAGT AAGATGGACA 1320

CCTACAGAAG TGGCTTTCCA GGCCCTAAAG AAGGCCCTAA CCCAAGCCCC AGTGTTCAGC 1380

TTGCCAACAG GGCAAGATTT TTCTTTATAT GCCACAGAAA AAACAGGAAT AGCTCTAGGA 1440

GTCCTTACGC AGGTCTCAGG GATGAGCTTG CAACCCGTGG TATACCTGAG TAAGGAAATT 1500

-continued

```
GATGTAGTGG CAAAGGGTTG GCCTCATNGT TTATGGGTAA TGGNGGCAGT AGCAGTCTNA   1560
GTATCTGAAG CAGTTAAAAT AATACAGGGA AGAGATCTTN CTGTGTGGAC ATCTCATGAT   1620
GTGAACGGCA TACTCACTGC TAAAGGAGAC TTGTGGTTGT CAGACAACCA TTTACTTAAN   1680
TATCAGGCTC TATTACTTGA AGAGCCAGTG CTGNGACTGC GCACTTGTGC AACTCTTAAA   1740
CCCAAACTTA TGCTGCCCAG AAGGATCTTT NTAGAGGTCC CCTTAGCCAA CCCTGACCTC   1800
AACTATATAT ATACTGATGG AAGTTCGTTT GTAGAAAAGG GATTACAAAG GGNAGGATAT   1860
NCCATAGGTG TTAGTGATAA AGCAGTACTT GAAAGTAAGC CTCTTCCCCC CCAGGGACCA   1920
GCGCCCCCGT TAGCAGAACT AGTGGCACTG ACCCCGCGAG CCTTAGAACT TTGGAAAGGG   1980
AGGAGGATAA ATGTGTATAC AGATAGCAAG TATGCTTATC TAATCCGAAA TGCCCATGTT   2040
GTTTATCTAA TCCGAAATGC CCATGTTGCA ATATGGAAAG AAAGGGAGTT CCTAACCTCT   2100
GGGGGAACCC CCATTAAATA CCACAAGTTA ATCATGGAGT TATTGCACAC AGTGCAAAAA   2160
CTCAAGGAGG TGGAAGTCTT ACACTGCCAA AGCCATCAGA AAAGGGAAAG GGGAGAAGAG   2220
CAGCATAAGT GGCTACAGAG GCAAGGAAAG ACTAGCAGAA AGGAAAGAGA GAAAGAGACA   2280
GAAAGTCAGA GAGAGAGAGA GGAAGAGACA GAGCACAAAG AGGGAGTCAG AGAGAGAGAG   2340
AGACAGAGAG TCAGAGAGAA GGAAAGAGAG AGAGGAAGAG ACAAAGAATG A            2391
```

(2) INFORMATION FOR SEQ ID NO: 54:

(i) SEQUENCE CHARACTERISTICS:
(A) LENGTH: 1722 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 54:

```
TGGAGAATAG CAGCATAAGT TGGCTGGCAG AAGTAGGGAA AGACAGCAAG AAGTAAAGAA     60
AAAAARGAGA AAGTCAGAGA AAGAAAAAAA GAGAGGAAGA AACAAAGAAG AACTTGAAGA    120
GAGAAAGAAG TAGTAAAGAA AAAACAGTAT ACCCTATTCC TTTAAAAGCC AGGGTAAATT    180
TCTGTCTACC TAGCCAAGGC ATATTCTTCT TATGTGGAAC ATCAACCTAT ATCTGCCTCC    240
CCACTAACTG GACAGGCACC TGAACCTTAG TCTTTCTAAG TCCCAACATT AACATTGCCC    300
CAGGAAATCA GACCCTATTG GTACCTGTCA AAGCTAAAGT CCCGTCAGTG CAGAGCCATA    360
CAACTAATAT CCCTATTTAT AGGGTTAGGA ATGGCTACTG CTACAGGAAC TGGAATAGCC    420
GGTTTATCTA CTTCATTATC CTACTACCAT ACACTCTCAA AGAATTTCTC AGACAGTTTG    480
CAAGAAATAA TGAAATCTAT TCTTACTTTA CAATCCCAAT TAGACTCTTT GGCAGCAATG    540
ACTCTCCAAA ACCGCCGAGG CCCACACCTC CTCACTGCTG AGAAAGGAGG ACTCTGCACC    600
TTCTTAGGGG AAGAGTGTTG TTTTTACACT AACCAGTCAG GGATAGTACG AGATGCCACC    660
TGGCATTTAC AGGAAAGGGC TTCTGATATC AGACAATGCC TTTCAAACTC TTATACCAAC    720
CTCTGGAGTT GGGCAACATG GCTTCTTCCA TTTCTAGGTC CCATGGCAGC CATCTTGCTG    780
TTACTCACCT TTGGGCCCTG TATTTTTAAG CTTCTTGTCA AATTTGTTTC CTCTAGGATC    840
GAAGCCATCA AGCTACAGAT GGTCTTACAA ATGGAACCCC AAATGAGTTC AACTAACAAC    900
TTCTACCAAG GACCCCTGGA ACGATCCACT GGCACTTCCA CTAGCCTAGA GATTCCCCTC    960
TGGAAGACAC TACAACTGCA GGGCCCCTTC TTTGCCCCTA TCCAGCAGGA AGTAGCTAGA   1020
GCGGTCATCG GCCAAATTCC CAACAGCAGT TGGGGTGTCC TGTTTAGAGG GGGGATTGAA   1080
```

-continued

GAGGTGACAG CCTGCTGGCA GCCTCACAGC CCTCGTTGGY TCTCAGTGCC TCCTCAGCCT 1140

TGGTGCCCAC TCTGGCCGTG CTTGAGGAGC CCTTCAGCCT GCCACTGCAC TGTGGGAGCC 1200

TCTTTCTGGG CTGGACAAGG CCGGAGCCAG CTCCCTCAGC TTGCAGGGAG GTATGGAGGG 1260

AGAGATGCAG GCGGGAACCA GGGCTGCGCA TGGCGCTTGC GGGCCAGCAT GAGTTCCAGG 1320

TGGGCGTGGG CTCGGCGGGC CCCACACTCG GGCAGTGAGG GGCTTAGCAC CTGGGCCAGA 1380

CAGATGCTGT GCTCAACTTC TTCGCTGGGC CTTAGCTGCC TTCCCCGTGG GGCAGGGCTY 1440

CGGGAACMTG CAGCCTGCCC ATGCTTGAGC CCCCCACCCC GCCGTGGGTT CYTGCACAGC 1500

CCAAGCTTCC CGGACAAGCA CCACCCCTTA TCCACGGTGC CCAGTCCCAT CAACCACCCA 1560

AGGGTTGAGG AGTGCGGGCA CACAGCGCGG GATTGGCAGG CAGTTCCACT TGCGGCCTTG 1620

GTGCGGGATC CACTGCGTGA AGCCAGCTGG GCTCCTGAGT CTGGTGGGGA CTTGGAGAAT 1680

CTTTATGTCT AGCTAAGGGA TTGTAAATAC ACCAATCAGC AC 1722

(2) INFORMATION FOR SEQ ID NO: 55:

(i) SEQUENCE CHARACTERISTICS:
(A) LENGTH: 495 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 55:

CTTCCCCAAC TAATAAGGAC CCCCCTTTCA ACCCAAACAG TCCAAAAGGA CATAGACAAA 60

GGAGTAAACA ATGAACCAAA GAGTGCCAAT ATTCCCTGGT TATGCACCCT CCAAGCGGTG 120

GGAGAAGAAT TCGGCCCAGC CAGAGTGCAT GTACCTTTTT CTCTCTCACA CTTGAAGCAA 180

ATTAAAATAG ACNTAGGTNA ATTNTCAGAT AGCCCTGATG GYTATATTGA TGTTTTACAA 240

GGATTAGGAC AATCCTTTGA TCTGACATGG AGAGATATAA TATTACTGCT AAATCAGACG 300

CTAACCTCAA ATGAGAGAAG TGCTGCCATA ACTGGAGCCC GAGAGTTTGG CAATCTCTGG 360

TATCTCAGTC AGGTCAATGA TAGGATGACA ACGGAGGAAA GAGAACGATT CCCCACAGGG 420

CAGCAGGCAG TTCCCAGTGT AGCTCCTCAT TGGGACACAG AATCAGAACA TGGAGATTGG 480

TGCCGCAGAC ATTTA 495

(2) INFORMATION FOR SEQ ID NO: 56:

(i) SEQUENCE CHARACTERISTICS:
(A) LENGTH: 2503 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 56:

CCAAGAACCC ACCAATTCCG GANCACATTT TGGCGACCAC GAAGGGACTT TCGCATATCG 60

CCAAGCGGTG AGACAATAGC CGAGCGGTGA GACCTTTCCC AATCGCCAAG CAGTGAGTAC 120

CATCAGACCC CTTTCACTTG CTATTCTGTC CTATCTTTCT TTAGAATTCG GGGGCTAAAT 180

ACCGGGCATC TGTCAGCCAT TTAAAAGTGA CTAGCGGGCC GCCGGACTAA AGACACGGGT 240

GTCAAGCTTT CTGGGAAAGG GCTCTCTAAC AACCCCCAAC TCTTTGGAGT TGGGACCGTT 300

GGTTTGCCTA GAACCAGCTT CCGCTTTTCC TGTACTTCTG GGCTGAGCCG TGGGTTGACA 360

GTGAAGGAAA GCCATGCATC TCCGGGGTCT CGMCAACATG TTGGTTGACC CTGCGGCCAT 420

-continued

```
GAGTGGAACT CTCAAAAGCA TGTCGCCCAA GCGACACTCG CCTATCTATC CTATCTATCC    480
TGACCCTTGC CCTCTGGGTC CTAATGCCTG CCAGACAAAC TTCCTCTCGC CTCTCTTCTC    540
TGAAGCTAGA ACCGCTTCTA AAAATTGCTA CCTGGTCTCT GGTGCTTTTC CTARTTTCTC    600
CTATAAAGAA TGAWTTCTAG TATTAAACTC CAGGACTCTG TTACCTTCTT TAGGCACCCG    660
GGCTCACCAA TCAGAAAGAC ACAGTTTTTG CCCAAGGCCC CATCGTAGTG GGGACTACCT    720
GGAATTTTAG GATCCCTCCT CAGACTAACA GGCCTAACAA AAGTTATTCC TGAAGCTAGG    780
ATATGGGGAG CCTCAGAAAT TGTATCCCTC CTATTCATAT AAGTGAGAAC AAAAGGTGTC    840
ACTCTTCCAA CCCTGAAGAT CCCCTCCCTC CCTCAGGGTA TGGCCCTCCA TTTCATTTTT    900
GTGGCATAAC ATCTTTATAG GATGGGGTAA AGTCCCAATA CTAACAGGAG AATGCTTAGG    960
ACTCTAACAG GTTTTTGAGA ATGCGTCAGT AAGGGCCACT AAATCTGATT TTTCTCAGTC   1020
GGTCCTCCTT GTGGTCTAGG AGGACAGGCA AGGTTGTGCA GGTTTTCGAG AATGCGTCAG   1080
TAAGGACCAC TAAATCCGAC CTTCCTCGGT CCTCCATGTG GTCTGGGAGG AAAACTAGTG   1140
TTTCTGCTGC TGCGTCGGTG AGCGCAACTA TTCAAGTCAG CAGGGTCCAG GGACCGTTGC   1200
AGGTTCTTGG GCAGGGGTTG TTTCTGCTGC TGCATTGGTG AATGCAACTA TTCTGATCAG   1260
CAGGGTCCCA GGACCATTGC AGGTCCTTGG GCAGGGAGAG AAACAAAACA AACCAAAACT   1320
GTGGGCGGTT TTGTCTTTCA TATGGGAAAC ACTCAGGCAT CAACAGGTTC ACCCTTGAAA   1380
TGCATCCTAA GCCATTGGGA CCAATTTGAC CCACAAACCC TGAAAAAGAG GAGGCTCATT   1440
TTTTCCTGCA CTACGGCTTG GCCCCAATAT TCTCTTTYTG ATGGGGAAAA ATGGCCACCT   1500
GAGGGAAGCA CAAATTACAA TAYTATCCTA CAGCYTGATC TTTTCTGTAA GAGGGAAGGC   1560
AAATGGAGTG AATACCTTAT GTCCAAGCTT TCTTTTCATT GAGGGAGAAT ACACAACTAT   1620
GCAAAGCTTG CAATTTACAT CCCACAGGAG GACCCTTCAG CTTACCCCCA TATCCTAGCC   1680
TCCCTATAGC TTCCCTTCCT ATTGATGATA CTCCTCCTCT AATCTCCCCT GCCCAGAAGG   1740
AAATAAGCAA AGAAATCTCC AAAGGTCCAC AAAAACCCCC GGGCTATCGG TTATGTCCCT   1800
TCAAGYTGTA GGGGGAGGGG AATTTGGCCC AACCCGGGTG CATGTCCCTT CTCCCTCTCT   1860
GATTTAAAGC AGATCAAGGC AGACCTGGGG AAGTTTTCAG ATGATCCTGA TAGGTACATA   1920
GATGTCCTAC AGGGTCTAGG GCAAACCTTT GACCTCACTT GGAGAGACGT CATGCTACTG   1980
TTAGATCAAA CCCTGGCCTT TAATGAAAAG AATGCGGCTT TAGCTGCAGC CTGAGAGTTT   2040
GGAGATACCT GGTATCCTAG TCAAGTAAAT GAAAGAATGA CAGCCGAAGA AAGGGACAAC   2100
TTCCTTACTG GTCAGCAACC CATCCCCAGT ATGGATCCCC ACTGGGACTT TGACTCAGAT   2160
CATGGGGACT GGAGTCGTAA ACATCTGTTG ATCTGTGTTC TGGAAGGACT AAGGAGAATT   2220
GGGAAAAAGC CCATGAATTA TTCAATGATA TCCACCATAA CCCAGGGAAA GGAAGAAAAT   2280
CCTTCTGCCT TCCTCGAGCG GCTACAAGAG GCCTTAAGAA AATATACTCC CCTGTCACCC   2340
GAATCACTCG AGGGTCAATT GATTCTAAAA GATAAGTTTA TTACCCAATC AGCCACAGAT   2400
ATCAGGAGAA AGCTCCAAAA GCAAGCCCTG AGCCTGAACA AAATCTAGAG ACATTATTAA   2460
ACCTGGCAAC CTTGGTGTTC TATAATAGGG ACCAAGAGGA ACA                     2503
```

(2) INFORMATION FOR SEQ ID NO: 57:

(i) SEQUENCE CHARACTERISTICS:
(A) LENGTH: 1167 base pairs
(B) TYPE: nucleotide
(C) STRANDEDNESS: single
(D) TOPOLOGY: linear -continued (ii) MOLECULE TYPE: cDNA (xi) SEQUENCE DESCRIPTION: SEQ ID NO: 57:

AAGGAAACTC AGAAAGCCAA TACCCATTTA GTAAGATGGA CACCAGAAGC AGAAGCAGCT 60

TTCCAGGCCC TAAAGAAATC CCTAACCCAA GCCCCAGTGT TAAGCTTGCC AACGGGGCAA 120

GACTTTTCTT TATATGTCAC AGAAAAACAG GAATAGCTCT AGGAGTCCTT ACACAGGTCC 180

AAGGGACAAG CTTGCAACCT GTGGCATACC TGAGTAAGGA AACTGATGTA NTGGCAAAGG 240

GTTGGCCTCA TTGTTTACAG GTAGGGCAGC AGTAGCAGTC TTAGTTTCTG AAACAGTTAA 300

AATAATACAG GGAAGAGATC TTACTGTGTG GACATCTCAT GATGTGAACG GCATACTCAC 360

TGCTAAAGAG GACTTGTGGC TGTCAGACAA CCATTTACTT AAATAGCAGG TTCTATTACT 420

TGAAGTGCCA GTGCTGCGAC TGCACATTTG TGCAACTCTT AACCCAGCCA CATTTCTTCC 480

AGACAATGAA GAAAAGATAG AACATAACTG TCAACAAGTA ATTGCTCAAA CCTATGCTGC 540

TCGAGGGGAC CTTCTAGAGG TTCCCTTGAC TGATCCCGAC CTCAACTTGT ATACTGATGG 600

AAGTTCCTTG GCAGAAAAAG GACTTTGAAA AGCGGGGTAT GCAGTGATCA GTGATAATGG 660

AATACTTGAA AGTAATCGCC TCACTCCAGG AACTAGTGCT CACCTGGCAG AACTAATAGC 720

CCTCACTTGG GCACTAGAAT TAGGAGAAGG AAAAAGGGTA AATATATATT CAGACTCTAA 780

GTATGCTTAC CTAGTCCTCC ATGCCCATGC AGCAATATGG AGAGAGAGGG AATTCCTAAC 840

TTCTGAGGGA ACACCTATCA ACCATCAGGG AAGCCATTAG GAGATTATTA TTGGCTGTAC 900

AGAAACCTAA AGAGGTGGCA GTCTTACACT GCCAGGGTCA TCAGGAAGAA GAGGAAAGGG 960

AAATAGAAGG CAATCGCCAA GCGGATATTG AAGCAAAAAA AGCCGCAAGG CAGGACTCTC 1020

CATTAGAAAT GCTTATAGAA GGACCCCTAG TATGGGGTAA TCCCCTCTGG GAAACCAAGC 1080

CCCAGTACTC AGCAGGAAAA ATAGAATAGG AAACCTCACA AGGACATACT TTCCTCCCCT 1140

CCAGATGGCT AGCCACTGAG GAAGGAA 1167

(2) INFORMATION FOR SEQ ID NO: 58:

(i) SEQUENCE CHARACTERISTICS:
(A) LENGTH: 78 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 58:

TCCAAAGGCA CCAGGGCCCT CAGTGAGGAA CGTATCCAGC CTATACTGGC TTATCCTCAT 60

CCCAAAACCC TAAAGCAA 78

(2) INFORMATION FOR SEQ ID NO: 59:

(i) SEQUENCE CHARACTERISTICS:
(A) LENGTH: 26 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 59:

Ser Lys Gly Thr Arg Ala Leu Ser Glu Glu Arg Ile Gln Pro Ile Leu
1 5 10 15

Ala Tyr Pro His Pro Lys Thr Leu Lys Gln

-continued 20 25

(2) INFORMATION FOR SEQ ID NO: 60:

(i) SEQUENCE CHARACTERISTICS:
(A) LENGTH: 28 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 60:

AAATGTCTGC GGCACCAATC TCCATGTT 28

(2) INFORMATION FOR SEQ ID NO: 61:

(i) SEQUENCE CHARACTERISTICS:
(A) LENGTH: 30 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 61:

AAGGGGCATG GACGAGGTGG TGGCTTATTT 30

(2) INFORMATION FOR SEQ ID NO: 62:

(i) SEQUENCE CHARACTERISTICS:
(A) LENGTH: 21 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 62:

GGAGAAGAGC AGCATAAGTG G 21

(2) INFORMATION FOR SEQ ID NO: 63:

(i) SEQUENCE CHARACTERISTICS:
(A) LENGTH: 25 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 63:

GTGCTGATTG GTGTATTTAC AATCC 25

(2) INFORMATION FOR SEQ ID NO: 64:

(i) SEQUENCE CHARACTERISTICS:
(A) LENGTH: 34 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 64:

GACTCGCTGC AGATCGATTT TTTTTTTTTT TTTT 34

(2) INFORMATION FOR SEQ ID NO: 65:

-continued (i) SEQUENCE CHARACTERISTICS:
(A) LENGTH: 30 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 65:

GCCATCAAGC CACCCAAGAA CTCTTAACTT 30

(2) INFORMATION FOR SEQ ID NO: 66:

(i) SEQUENCE CHARACTERISTICS:
(A) LENGTH: 30 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 66:

CCAATAGCCA GACCATTATA TACACTAATT 30

(2) INFORMATION FOR SEQ ID NO: 67:

(i) SEQUENCE CHARACTERISTICS:
(A) LENGTH: 23 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 67:

GCCATAACTG CAACCCAAGA GTT 23

(2) INFORMATION FOR SEQ ID NO: 68:

(i) SEQUENCE CHARACTERISTICS:
(A) LENGTH: 23 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 68:

GGACGAGGTG GTGGCTTATT TCT 23

(2) INFORMATION FOR SEQ ID NO: 69:

(i) SEQUENCE CHARACTERISTICS:
(A) LENGTH: 25 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 69:

AACTTGCGTG CTAGAAGGAC TAAGG 25

(2) INFORMATION FOR SEQ ID NO: 70:

(i) SEQUENCE CHARACTERISTICS:
(A) LENGTH: 24 base pairs
(B) TYPE: nucleotide

-continued (C) STRANDEDNESS: single
(D) TOPOLOGY: linear (ii) MOLECULE TYPE: cDNA (xi) SEQUENCE DESCRIPTION: SEQ ID NO: 70:

AACTTTTCCC TTTTCCAGAT CCTC 24

(2) INFORMATION FOR SEQ ID NO: 71:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 71:

GCATACCAGG CAAGTGGACA TT 22

(2) INFORMATION FOR SEQ ID NO: 72:

(i) SEQUENCE CHARACTERISTICS:
(A) LENGTH: 25 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 72:

CTGTCCGTTG GGTTTCCTTA CTCCT 25

(2) INFORMATION FOR SEQ ID NO: 73:

(i) SEQUENCE CHARACTERISTICS:
(A) LENGTH: 24 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 73:

GAGGCTCTGG AAAAGGGAAA AGTT 24

(2) INFORMATION FOR SEQ ID NO: 74:

(i) SEQUENCE CHARACTERISTICS:
(A) LENGTH: 25 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 74:

AGGAGTAAGG AAACCCAACG GACAG 25

(2) INFORMATION FOR SEQ ID NO: 75:

(i) SEQUENCE CHARACTERISTICS:
(A) LENGTH: 25 base pairs
(B) TYPE: nucleotide
(C) STRANDEDNESS: single
(D) TOPOLOGY: linear (ii) MOLECULE TYPE: cDNA -continued (xi) SEQUENCE DESCRIPTION: SEQ ID NO: 75:

TGTATATAAT GGTCTGGCTA TTGGG 25

(2) INFORMATION FOR SEQ ID NO: 76:

(i) SEQUENCE CHARACTERISTICS:
(A) LENGTH: 26 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 76:

TTCGGCAGAA ACCTGTTATG CCAAGG 26

(2) INFORMATION FOR SEQ ID NO: 77:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 77:

CTCGATTTCT TGCTGGGCCT TA 22

(2) INFORMATION FOR SEQ ID NO: 78:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 78:

GTTGATTCCC TCCTCAAGCA 20

(2) INFORMATION FOR SEQ ID NO: 79:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 79:

CTCTACCAAT CAGCATGTGG 20

(2) INFORMATION FOR SEQ ID NO: 80:

(i) SEQUENCE CHARACTERISTICS:
(A) LENGTH: 19 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 80:

TGTTCCTCTT GGTCCCTAT 19

-continued (2) INFORMATION FOR SEQ ID NO: 81:

(i) SEQUENCE CHARACTERISTICS:
(A) LENGTH: 433 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 81:

```
Met Ala Thr Ala Thr Gly Thr Gly Ile Ala Gly Leu Ser Thr Ser Leu
1               5                   10                  15

Ser Tyr Tyr His Thr Leu Ser Lys Asn Phe Ser Asp Ser Leu Gln Glu
            20                  25                  30

Ile Met Lys Ser Ile Leu Thr Leu Gln Ser Gln Leu Asp Ser Leu Ala
        35                  40                  45

Ala Met Thr Leu Gln Asn Arg Arg Gly Pro His Leu Leu Thr Ala Glu
    50                  55                  60

Lys Gly Gly Leu Cys Thr Phe Leu Gly Glu Glu Cys Cys Phe Tyr Thr
65                  70                  75                  80

Asn Gln Ser Gly Ile Val Arg Asp Ala Thr Trp His Leu  Gln Glu Arg
                85                  90                  95

Ala Ser Asp Ile Arg Gln Cys Leu Ser Asn Ser Tyr Thr Asn Leu Trp
            100                 105                 110

Ser Trp Ala Thr Trp Leu Leu Pro Phe Leu Gly Pro Met Ala Ala Ile
        115                 120                 125

Leu Leu Leu Leu Thr Phe Gly Pro Cys Ile Phe Lys Leu Leu Val Lys
    130                 135                 140

Phe Val Ser Ser Arg Ile Glu Ala Ile Lys Leu Gln Met Val Leu Gln
145                 150                 155                 160

Met Glu Pro Gln Met Ser Ser Thr Asn Asn Phe Tyr Gln Gly Pro Leu
                165                 170                 175

Glu Arg Ser Thr Gly Thr Ser Thr Ser Leu Glu Ile Pro Leu Trp Lys
            180                 185                 190

Thr Leu Gln Leu Gln Gly Pro Phe Phe Ala Pro Ile Gln Gln Glu Val
        195                 200                 205

Ala Arg Ala Val Ile Gly Gln Ile Pro Asn Ser Ser Trp Gly Val Leu
    210                 215                 220

Phe Arg Gly Gly Ile Glu Glu Val Thr Ala Cys Trp Gln Pro His Ser
225                 230                 235                 240

Pro Arg Trp Xaa Ser Val Pro Pro Gln Pro Trp Cys Pro Leu Trp Pro
                245                 250                 255

Cys Leu Arg Ser Pro Ser Ala Cys His Cys Thr Val Gly Ala Ser Phe
            260                 265                 270

Trp Ala Gly Gln Gly Arg Ser Gln Leu Pro Gln Leu Ala Gly Arg Tyr
        275                 280                 285

Gly Gly Arg Asp Ala Gly Gly Asn Gln Gly Cys Ala Trp Arg Leu Arg
    290                 295                 300

Ala Ser Met Ser Ser Arg Trp Ala Trp Ala Arg Arg Ala  Pro His Ser
305                 310                 315                 320

Gly Ser Glu Gly Leu Ser Thr Trp Ala Arg Gln Met Leu Cys Ser Thr
                325                 330                 335

Ser Ser Leu Gly Leu Ser Cys Leu Pro Arg Gly Ala Gly Leu Arg Glu
            340                 345                 350
```

-continued

```
Xaa Ala Ala Cys Pro Cys Leu Ser Pro Pro Pro Arg Arg Gly Phe Leu
        355                 360                 365

His Ser Pro Ser Phe Pro Asp Lys His His Pro Leu Ser Thr Val Pro
    370                 375                 380

Ser Pro Ile Asn His Pro Arg Val Glu Glu Cys Gly His Thr Ala Arg
385                 390                 395                 400

Asp Trp Gln Ala Val Pro Leu Ala Ala Leu Val Arg Asp Pro Leu Arg
                405                 410                 415

Glu Ala Ser Trp Ala Pro Glu Ser Gly Gly Asp Leu Glu Asn Leu Tyr
            420                 425                 430

Val
```

(2) INFORMATION FOR SEQ ID NO: 82:

(i) SEQUENCE CHARACTERISTICS:
(A) LENGTH: 693 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 82:

```
CTTCCCCAAC TAATAAGGAC CCCCCTTTCA ACCCAAACAG TCCAAAAGGA CATAGACAAA     60

GGAGTAAACA ATGAACCAAA GAGTGCCAAT ATTCCCTGGT TATGCACCCT CCAAGCGGTG    120

GGAGAAGAAT TCGGCCCAGC CAGAGTGCAT GTACCTTTTT CTCTCTCACA CTTGAAGCAA    180

ATTAAAATAG ACNTAGGTNA ATTNTCAGAT AGCCCTGATG GYTATATTGA TGTTTTACAA    240

GGATTAGGAC AATCCTTTGA TCTGACATGG AGAGATATAA TATTACTGCT AAATCAGACG    300

CTAACCTCAA ATGAGAGAAG TGCTGCCATA ACTGGAGCCC GAGAGTTTGG CAATCTCTGG    360

TATCTCAGTC AGGTCAATGA TAGGATGACA ACGGAGGAAA GAGAACGATT CCCCACAGGG    420

CAGCAGGCAG TTCCCAGTGT AGCTCCTCAT TGGGACACAG AATCAGAACA TGGAGATTGG    480

TGCCGCAGAC ATTTACTAAC TTGCGTGCTA GAAGGACTAA GGAAAACTAG GAAGACTATG    540

AATTATTCAA TGATGTCCAC TATAACACAG GGGAAAGGAA GAAAATCCTA CTGCCTTTCT    600

GGAGAGACTA AGGGAGGCAT TGAGGAAGCA TACCAGGCAA GTGGACATTG GAGGCTCTGG    660

AAAAGGGAAA AGTTGGGCAA ATTGAATGCC TAA                                 693
```

(2) INFORMATION FOR SEQ ID NO: 83:

(i) SEQUENCE CHARACTERISTICS:
(A) LENGTH: 1577 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 83:

```
AACTTGCGTG CTAGAAGGAC TAAGGAAAAC TAGGAAGACT ATGAATTATT CAATGATGTC     60

CACTATAACA CAGGGGAAAG GAAGAAAATC CTACTGCCTT TCTGGAGAGA CTAAGGGAGG    120

CATTGAGGAA GCATACCAGG CAAGTGGACA TTGGAGGCTC TGGAAAAGGG AAAAGTTGGG    180

CAAATTGAAT GCCTAATAGG GCTTGCTTCC AGTGCAGTCT ACAAGGACGC TTTAGAAAAG    240

ATTGTCCAAG TAGAAATAAG CCGCCCCTCG TCCATGCCCC TTATGTCAAG GGAATCACTG    300

GAAGGCCTAC TGCCCCAGGG GACGAAGGTC CTCTGAGTCA GAAGCCACTA ACCTGATGAT    360
```

-continued

```
CCAGCAGCAG GACTGAGGGT GCCCGGGGCA AGTGCCAGCC CATGCCATCA CCCTCAGAGC    420

CCCGGGTATG TTTGACCATT GAGAGCCAGG AAGTTAACTG TCTCCTGGAC ACTGGCGCAG    480

CCTTCTCAGT CTTACTTTCC TGTCCCAGAC AATTGTCCTC CAGATCTGTC ACTATCCGAG    540

GGGTCCTAAG ACAGCCAGTC ACTACATACT TCTCTCAGCC ACTAAGTTGT GACTGGGGAA    600

CTTTACTCTT TTCACATGCT TTTCTAATTA TGCCTGAAAG CCCCACTCCC TTGTTAGGGA    660

GAGACATTTT AGCAAAAGCA GGGGCCATTA TACACCTGAA CATAGGAAAA GGAATACCCA    720

TTTGCTGTCC CCTGCTTGAG GAAGGAATTA ATCCTGAAGT CTGGGCAATA GAAGGACAAT    780

ATGGACAAGC AAAGAATGCC CGTCCTGTTC AAGTTAAACT AAAGGATTCT GCCTCCTTTC    840

CCTACCAAAG GAAGTACCCT CTTAGACCCG AGGCCCTACA AGGACTCAAA AGATTGTTAA    900

GGACCTAAAA GCCCAAGGCC TAGTAAAACC ATGCAGTAGC CCCTGCAATA CTCCAATTTT    960

AGGAGTAAGG AAACCCAACG GACAGTGGAG GTTAGTGCAA GATCTCAGGA TTATTAATGA   1020

GGCTGTTTTT CCTCTATACC CAGCTGTATC TAGCCCTTAT ACTCTGCTTT CCCTAATACC   1080

AGAGGAAGCA GAGTAGTTTA CAGTCCTGGA CCTTAAGGAT GCCTCTTTCT GCATCCCTGT   1140

ACATCCTGAT TCTCAATTCT TGTTTGTCTT TGAAGATCCT TTGAACCCAA TGTCTCAATT   1200

CACCTGGACT GTTTTACCCC AGGGGTTCCG GGATAGCCCC CATCTATTTG GCCAGGCATT   1260

AGCCCAAGAC TTGAGCCAAT TCTCATACCT GGACATCTTG TCCTTCGGTA TGGGATGATT   1320

TAATTTTAGC CACCCGTTCA GAAACCTTGT GCCATCAAGC CACCCAAGCG TTCTTAAATT   1380

TCCTCACTCC GTGTGGCTAC AAGGTTTCCA AACCAAAGGC TCAGCTCTGC TCACAGCAGG   1440

TTAAATACTT AGGGTTAAAA TTATCCAAAG GCACCAGGGC CCTCTGTGAG GAATGTATCC   1500

AACCTGTACT GGCTTATCTT CATCCCAAAA CCCTAAAGCA ACTAAGAAGG TCCTTGGCAT   1560

AACAGGTTTC TGCCGAA                                                  1577
```

(2) INFORMATION FOR SEQ ID NO: 84:

(i) SEQUENCE CHARACTERISTICS:
(A) LENGTH: 182 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 84:

```
Ser Ser Ser Arg Thr Glu Gly Ala Arg Gly Lys Cys Gln Pro Met Pro
1               5                   10                  15

Ser Pro Ser Glu Pro Arg Val Cys Leu Thr Ile Glu Ser Gln Glu Val
            20                  25                  30

Asn Cys Leu Leu Asp Thr Gly Ala Ala Phe Ser Val Leu Leu Ser Cys
        35                  40                  45

Pro Arg Gln Leu Ser Ser Arg Ser Val Thr Ile Arg Gly Val Leu Arg
    50                  55                  60

Gln Pro Val Thr Thr Tyr Phe Ser Gln Pro Leu Ser Cys Asp Trp Gly
65                  70                  75                  80

Thr Leu Leu Phe Ser His Ala Phe Leu Ile Met Pro Glu Ser Pro Thr
                85                  90                  95

Pro Leu Leu Gly Arg Asp Ile Leu Ala Lys Ala Gly Ala Ile Ile His
            100                 105                 110

Leu Asn Ile Gly Lys Gly Ile Pro Ile Cys Cys Pro Leu Leu Glu Glu
        115                 120                 125
```

-continued

```
Gly Ile Asn Pro Glu Val Trp Ala Ile Glu Gly Gln Tyr Gly Gln Ala
    130                 135                 140

Lys Asn Ala Arg Pro Val Gln Val Lys Leu Lys Asp Ser Ala Ser Phe
145                 150                 155                 160

Pro Tyr Gln Arg Lys Tyr Pro Leu Arg Pro Glu Ala Leu Gln Gly Leu
                165                 170                 175

Lys Arg Leu Leu Arg Thr
            180
```

(2) INFORMATION FOR SEQ ID NO: 85:

(i) SEQUENCE CHARACTERISTICS:
(A) LENGTH: 36 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 85:

```
AGATCTGCAG AATTCGATAT CACCCCCCCC CCCCCC                              36
```

(2) INFORMATION FOR SEQ ID NO: 86:

(i) SEQUENCE CHARACTERISTICS:
(A) LENGTH: 22 base pairs
(B) TYPE: nucleotide
(C) STRANDEDNESS: single
(D) TOPOLOGY: linear (ii) MOLECULE TYPE: cDNA (xi) SEQUENCE DESCRIPTION: SEQ ID NO: 86:

```
AGATCTGCAG AATTCGATAT CA                                             22
```

(2) INFORMATION FOR SEQ ID NO: 87:

(i) SEQUENCE CHARACTERISTICS:
(A) LENGTH: 2304 base pairs
(B) TYPE: nucleotide
(C) STRANDEDNESS: single
(D) TOPOLOGY: linear (xi) SEQUENCE DESCRIPTION: SEQ ID NO: 87:

```
TCCAGCAGCA GGACTGAGGG TGCCCGGGGC AAGTGCCAGC CCATGCCATC ACCCTCAGAG     60

CCCCGGGTAT GTTTGACCAT TGAGAGCCAG GAAGTTAACT GTCTCCTGGA CACTGGCGCA    120

GCCTTCTCAG TCTTACTTTC CTGTCCCAGA CAATTGTCCT CCAGATCTGT CACTATCCGA    180

GGGGTCCTAG GACAGCCAGT CACTACATAC TTCTCTCAGC CACTAAGTTG TGACTGGGGA    240

ACTTTACTCT TTTCACATGC TTTTCTAATT ATGCCTGAAA GCCCCACTCC CTTGTTAGGG    300

AGAGACATTT TAGCAAAAGC AGGGGCCATT ATACACCTGA ACATAGGAAA AGGAATACCC    360

ATTTGCTGTC CCCTGCTTGA GGAAGGAATT AATCCTGAAG TCTGGGCAAT AGAAGGACAA    420

TATGGACAAG CAAAGAATGC CCGTCCTGTT CAAGTTAAAC TAAAGGATTC TGCCTCCTTT    480

CCCTACCAAA GGAAGTACCC TCTTAGACCC GAGGCCCTAC AAGGANCTCA AAAGATTGTT    540

AAGGACCTAA AAGCCCAAGG CCTAGTAAAA CCATGCAGTA GCCCCTGCAA TACTCCAATT    600

TTAGGAGTAA GGAAACCCAA CGGACAGTGG AGGTTAGTGC AAGATCTCAG GATTATTAAT    660

GAGGCTGTTT TTCCTCTATA CCCAGCTGTA TCTAGCCCTT ATACTCTGCT TTCCCTAATA    720

CCAGAGGAAG CAGAGTGGTT TACAGTCCTG GACCTTAAGG ATGCCTTTTT CTGCATCCCT    780
```

-continued

GTACGTCCTG ACTCTCAATT CTTGTTTGCC TTTGAAGATC CTTTGAACCC AACGTCTCAA 840

CTCACCTGGA CTGTTTTACC CCAAGGGTTC AGGGATAGCC CCCATCTATT TGGCCAGGCA 900

TTAGCCCAAG ACTTGAGTCA ATTCTCATAC CTGGACACTC TTGTCCTTCA GTACGTGGAT 960

GATTTACTTT TAGTCGCCCG TTCAGAAACC TTGTGCCATC AAGCCACCCA AGAACTCTTA 1020

ACTTTCCTCA CTACCTGTGG CTACAAGGTT TCCAAACCAA AGGCTCGGCT CTGCTCACAG 1080

GAGATTAGAT ACTTAGGGCT AAAATTATCC AAAGGCACCA GGGCCCTCAG TGAGGAACGT 1140

ATCCAGCCTA TACTGGCTTA TCCTCATCCC AAAACCCTAA AGCAACTAAG AGGGTTCCTT 1200

GGCATAACAG GTTTCTGCCG AAAACAGATT CCCAGGTACA CCCCAATAGC CAGACCATTA 1260

TATACACTAA TTAGGGAAAC TCAGAAAGCC AATACCTATT TAGTAAGATG GACACCTACA 1320

GAAGTGGCTT TCCAGGCCCT AAAGAAGGCC CTAACCCAAG CCCCAGTGTT CAGCTTGCCA 1380

ACAGGGCAAG ATTTTTCTTT ATATGCCACA GAAAAAACAG GAATAGCTCT AGGAGTCCTT 1440

ACGCAGGTCT CAGGGATGAG CTTGCAACCC GTGGTATACC TGAGTAAGGA AATTGATGTA 1500

GTGGCAAAGG GTTGGCCTCA TTGTTTATGG GTAATGGCGG CAGTAGCAGT CTTAGTATCT 1560

GAAGCAGTTA AAATAATACA GGGAAGAGAT CTTACTGTGT GGACATCTCA TGATGTGAAC 1620

GGCATACTCA CTGCTAAAGG AGACTTGTGG TTGTCAGACA ACCATTTACT TAATTATCAG 1680

GCTCTATTAC TTGAAGAGCC AGTGCTGAGA CTGCGCACTT GTGCAACTCT TAAACCCGCC 1740

ACATTTCTTC CAGACAATGA AGAAAAGATA GAACATAACT GTCAACAAGT AATTGCTCAA 1800

ACCTATGCTG CTCGAGGGGA CCTTCTAGAG GTTCCCTTGA CTGATCCCGA CCTCAACTTG 1860

TATACTGATG GAAGTTCCTT GGCAGAAAAA GGACTTCGAA AAGCGGGGTA TGCAGTGATC 1920

AGTGATAATG GAATACTTGA AAGTAATCGC CTCACTCCAG GAACTAGTGC TCACCTGGCA 1980

GAACTAATAG CCCTCACTTG GGCACTAGAA TTAGGAGAAG GAAAAAGGGT AAATATATAT 2040

TCAGACTCTA AGTATGCTTA CCTAGTCCTC CATGCCCATG CAGCAATATG GAGAGAGAGG 2100

GAATTCCTAA CTTCTGAGGG AACACCTATC AACCATCAGG AAGCCATTAG GAGATTATTA 2160

TTGGCTGTAC AGAAACCTAA AGAGGTGGCA GTCTTACACT GCCAGGGTCA TCAGGAAGAA 2220

GAGGAAAGGG AAATAGAAGG CAATCGCCAA GCGGATATTG AAGCAAAAAA AGCCGCAAGG 2280

CAGGACTCTC CATTAGAAAT GCTT 2304

(2) INFORMATION FOR SEQ ID NO: 88:

(i) SEQUENCE CHARACTERISTICS:
(A) LENGTH: 2364 base pairs
(B) TYPE: nucleotide
(C) STRANDEDNESS: single
(D) TOPOLOGY: linear (xi) SEQUENCE DESCRIPTION: SEQ ID NO: 88:

ATGATCCAGC AGCAGGACNG AGGGTGCCCG GGGCAAGCGC CAGCCCATGC CATCACCCTC 60

ACAGAGCCCC AGGTATGCTT GACCATTGAG GGTCAGAAGG GTNACTGTCT CCTGGACACT 120

GGCGGNGCCT TCTCAGTCTT ACTTTCCTGT CCTGGACAAC TGTCCTCCAG ATCTGTCACT 180

GTCCGAGGGG TCCTAGGACA GCCAGTCACT AGATACTTCT CCCAGCCACT AAGTTGTGAC 240

TGGGGAACTT TACTCTTCCC ACATGCTTTT CTAATTATGC CTGAAAGCCC CACTCTCTTG 300

TTGGGGAGAG ACATTCTAGC AAAAGCAGGG GCCATTATAC ATGTGAATAT AGGAGAAGGA 360

ACAACTGTTT GTTGTCCCCT GCTTGAGGAA GGAATTAATC CTGAAGTCCG GGCAACAGAA 420

GGACAATATG GACAAGCAAA GAATGCCCGT CCTGTTCAAG TTAAACTAAA GGATTCCACC 480

-continued

```
TCCTTTCCCT ACCAAAGGCA GTACCCCCTC AGACCCGAGA CCCAACAAGA ACTCCAAAAG    540

ATTGTAAAGG ACCTAAAAGC CCAAGGCCTA GTAAAACCAA GCAATAGCCC TTGCAAGACT    600

CCAATTTTAG GAGTAAGGAA ACCCAACGGA CAGTGGAGGT TAGTGCAAGA ACTCAGGATT    660

ATCAATGAGG CTGTTGTTCC TCTATACCCA GCTGTACCTA ACCCTTATAC AGTGCTTTCC    720

CAAATACCAG AGGAAGCAGA GTGGTTTACA GTCCTGGACC TTAAGGATGC CTTTTTCTGC    780

ATCCCTGTAC GTCCTGACTC TCAATTCTTG TTTGCCTTTG AAGATCCTTT GAACCCAACG    840

TCTCAACTCA CCTGGACTGT TTTACCCCAA GGGTTCAGGG ATAGCCCCCA TCTATTTGGC    900

CAGGCATTAG CCCAAGACTT GAGTCAATTC TCATACCTGG ACACTCTTGT CCTTCAGTAC    960

ATGGATGATT TACTTTTAGT CGCCCGTTCA GAAACCTTGT GCCATCAAGC CACCCAAGAA   1020

CTCTTAACTT TCCTCACTAC CTGTGGCTAC AAGGTTTCCA AACCAAAGGC TCGGCTCTGC   1080

TCACAGGAGA TTAGATACTN AGGGCTAAAA TTATCCAAAG GCACCAGGGC CCTCAGTGAG   1140

GAACGTATCC AGCCTATACT GGCTTATCCT CATCCCAAAA CCCTAAAGCA ACTAAGAGGG   1200

TTCCTTGGCA TAACAGGTTT CTGCCGAAAA CAGATTCCCA GGTACASCCC AATAGCCAGA   1260

CCATTATATA CACTAATTAN GGAAACTCAG AAAGCCAATA CCTATTTAGT AAGATGGACA   1320

CCTACAGAAG TGGCTTTCCA GGCCCTAAAG AAGGCCCTAA CCCAAGCCCC AGTGTTCAGC   1380

TTGCCAACAG GGCAAGATTT TTCTTTATAT GCCACAGAAA AAACAGGAAT AGCTCTAGGA   1440

GTCCTTACGC AGGTCTCAGG GATGAGCTTG CAACCCGTGG TATACCTGAG TAAGGAAATT   1500

GATGTAGTGG CAAAGGGTTG GCCTCATNGT TTATGGGTAA TGGNGGCAGT AGCAGTCTNA   1560

GTATCTGAAG CAGTTAAAAT AATACAGGGA AGAGATCTTN CTGTGTGGAC ATCTCATGAT   1620

GTGAACGGCA TACTSRCTGC TAAAGGAGAC TTGTGGTTGT CAGACAACCA TTTACTTAAN   1680

TAYCAGGCYY TATTACTTGA AGAGCCAGTG CTGNGACTGC GCACTTGTCC AACTCTTAAA   1740

CCCAAACTTA TGCTGCCCAG AAGGATCTTT NTAGAGGTCC CCTTAGCCAA CCCTGACCTC   1800

AACTATATAT ATACTGATGG AAGTTCGTTT GTAGAAAAGG GATTACAAAG GGNAGGATAT   1860

NCCATAGGTG TTAGTGATAA AGCAGTACTT GAAAGTAAGC CTCTTCCCCC CCAGGGACCA   1920

GCGCCCCCGT TAGCAGAACT AGTGGCACTG ACCCCGCGAG CCTTAGAACT TTGGAAAGGG   1980

AGGAGGATAA ATGTGTATAC AGATAGCAAG TATGCTTATC TAATCCGAAA TGCCCATGTT   2040

GCAATATGGA AAGAAAGGGA GTTCCTAACC TCTGGGGGAA CCCCCATTAA ATACCACAAG   2100

TTAATCATGG AGTTATTGCA CACAGTGCAA AAACTCAAGG AGGTGGAAGT CTTACACTGC   2160

CAAAGCCATC AGAAAAGGGA AAGAGGGGAA GAGCAGCATA AGTGGCTACA GAGGCAAGGA   2220

AAGACTAGCA GAAAGGAAAG AGAGAAAGAG ACAGAAAGTC AGAGAGAGAG AGAGGAAGAG   2280

ACAGAGCACA AAGAGGGAGT CAGAGAGAGA GAGAGACAGA GAGTCAGAGA GAAGGAAAGA   2340

GAGAGAGGAA GAGACAAAGA ATGA                                          2364
```

(2) INFORMATION FOR SEQ ID NO: 89:

(i) SEQUENCE CHARACTERISTICS:
(A) LENGTH: 768 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 89:

Ser Ser Ser Arg Thr Glu Gly Ala Arg Gly Lys Cys Gln Pro Met Pro

-continued

```
1               5                   10                  15

Ser Pro Ser Glu Pro Arg Val Cys Leu Thr Ile Glu Ser Gln Glu Val
            20                  25                  30

Asn Cys Leu Leu Asp Thr Gly Ala Ala Phe Ser Val Leu Leu Ser Cys
        35                  40                  45

Pro Arg Gln Leu Ser Ser Arg Ser Val Thr Ile Arg Gly Val Leu Gly
    50                  55                  60

Gln Pro Val Thr Thr Tyr Phe Ser Gln Pro Leu Ser Cys Asp Trp Gly
65                  70                  75                  80

Thr Leu Leu Phe Ser His Ala Phe Leu Ile Met Pro Glu Ser Pro Thr
                85                  90                  95

Pro Leu Leu Gly Arg Asp Ile Leu Ala Lys Ala Gly Ala Ile Ile His
            100                 105                 110

Leu Asn Ile Gly Lys Gly Ile Pro Ile Cys Cys Pro Leu Leu Glu Glu
        115                 120                 125

Gly Ile Asn Pro Glu Val Trp Ala Ile Glu Gly Gln Tyr Gly Gln Ala
    130                 135                 140

Lys Asn Ala Arg Pro Val Gln Val Lys Leu Lys Asp Ser Ala Ser Phe
145                 150                 155                 160

Pro Tyr Gln Arg Lys Tyr Pro Leu Arg Pro Glu Ala Leu Gln Gly Xaa
                165                 170                 175

Gln Lys Ile Val Lys Asp Leu Lys Ala Gln Gly Leu Val Lys Pro Cys
            180                 185                 190

Ser Ser Pro Cys Asn Thr Pro Ile Leu Gly Val Arg Lys Pro Asn Gly
        195                 200                 205

Gln Trp Arg Leu Val Gln Asp Leu Arg Ile Ile Asn Glu Ala Val Phe
    210                 215                 220

Pro Leu Tyr Pro Ala Val Ser Ser Pro Tyr Thr Leu Leu Ser Leu Ile
225                 230                 235                 240

Pro Glu Glu Ala Glu Trp Phe Thr Val Leu Asp Leu Lys Asp Ala Phe
                245                 250                 255

Phe Cys Ile Pro Val Arg Pro Asp Ser Gln Phe Leu Phe Ala Phe Glu
            260                 265                 270

Asp Pro Leu Asn Pro Thr Ser Gln Leu Thr Trp Thr Val Leu Pro Gln
        275                 280                 285

Gly Phe Arg Asp Ser Pro His Leu Phe Gly Gln Ala Leu Ala Gln Asp
    290                 295                 300

Leu Ser Gln Phe Ser Tyr Leu Asp Thr Leu Val Leu Gln Tyr Val Asp
305                 310                 315                 320

Asp Leu Leu Leu Val Ala Arg Ser Glu Thr Leu Cys His Gln Ala Thr
                325                 330                 335

Gln Glu Leu Leu Thr Phe Leu Thr Thr Cys Gly Tyr Lys Val Ser Lys
            340                 345                 350

Pro Lys Ala Arg Leu Cys Ser Gln Glu Ile Arg Tyr Leu Gly Leu Lys
        355                 360                 365

Leu Ser Lys Gly Thr Arg Ala Leu Ser Glu Glu Arg Ile Gln Pro Ile
    370                 375                 380

Leu Ala Tyr Pro His Pro Lys Thr Leu Lys Gln Leu Arg Gly Phe Leu
385                 390                 395                 400

Gly Ile Thr Gly Phe Cys Arg Lys Gln Ile Pro Arg Tyr Thr Pro Ile
                405                 410                 415

Ala Arg Pro Leu Tyr Thr Leu Ile Arg Glu Thr Gln Lys Ala Asn Thr
            420                 425                 430
```

-continued

```
Tyr Leu Val Arg Trp Thr Pro Thr Glu Val Ala Phe Gln Ala Leu Lys
        435                 440                 445

Lys Ala Leu Thr Gln Ala Pro Val Phe Ser Leu Pro Thr Gly Gln Asp
    450                 455                 460

Phe Ser Leu Tyr Ala Thr Glu Lys Thr Gly Ile Ala Leu Gly Val Leu
465                 470                 475                 480

Thr Gln Val Ser Gly Met Ser Leu Gln Pro Val Val Tyr Leu Ser Lys
                485                 490                 495

Glu Ile Asp Val Val Ala Lys Gly Trp Pro His Cys Leu Trp Val Met
            500                 505                 510

Ala Ala Val Ala Val Leu Val Ser Glu Ala Val Lys Ile Ile Gln Gly
        515                 520                 525

Arg Asp Leu Thr Val Trp Thr Ser His Asp Val Asn Gly Ile Leu Thr
    530                 535                 540

Ala Lys Gly Asp Leu Trp Leu Ser Asp Asn His Leu Leu Asn Tyr Gln
545                 550                 555                 560

Ala Leu Leu Leu Glu Glu Pro Val Leu Arg Leu Arg Thr Cys Ala Thr
                565                 570                 575

Leu Lys Pro Ala Thr Phe Leu Pro Asp Asn Glu Glu Lys Ile Glu His
            580                 585                 590

Asn Cys Gln Gln Val Ile Ala Gln Thr Tyr Ala Ala Arg Gly Asp Leu
        595                 600                 605

Leu Glu Val Pro Leu Thr Asp Pro Asp Leu Asn Leu Tyr Thr Asp Gly
    610                 615                 620

Ser Ser Leu Ala Glu Lys Gly Leu Arg Lys Ala Gly Tyr Ala Val Ile
625                 630                 635                 640

Ser Asp Asn Gly Ile Leu Glu Ser Asn Arg Leu Thr Pro Gly Thr Ser
                645                 650                 655

Ala His Leu Ala Glu Leu Ile Ala Leu Thr Trp Ala Leu Glu Leu Gly
            660                 665                 670

Glu Gly Lys Arg Val Asn Ile Tyr Ser Asp Ser Lys Tyr Ala Tyr Leu
        675                 680                 685

Val Leu His Ala His Ala Ala Ile Trp Arg Glu Arg Glu Phe Leu Thr
    690                 695                 700

Ser Glu Gly Thr Pro Ile Asn His Gln Glu Ala Ile Arg Arg Leu Leu
705                 710                 715                 720

Leu Ala Val Gln Lys Pro Lys Glu Val Ala Val Leu His Cys Gln Gly
                725                 730                 735

His Gln Glu Glu Glu Glu Arg Glu Ile Glu Gly Asn Arg Gln Ala Asp
            740                 745                 750

Ile Glu Ala Lys Lys Ala Ala Arg Gln Asp Ser Pro Leu Glu Met Leu
        755                 760                 765
```

(2) INFORMATION FOR SEQ ID NO: 90:

(i) SEQUENCE CHARACTERISTICS:
(A) LENGTH: 114 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 90:

```
Ser Ser Ser Arg Thr Glu Gly Ala Arg Gly Lys Cys Gln Pro Met Pro
1               5                   10                  15
```

-continued

```
Ser Pro Ser Glu Pro Arg Val Cys Leu Thr Ile Glu Ser Gln Glu Val
            20                  25                  30

Asn Cys Leu Leu Asp Thr Gly Ala Ala Phe Ser Val Leu Leu Ser Cys
        35                  40                  45

Pro Arg Gln Leu Ser Ser Arg Ser Val Thr Ile Arg Gly Val Leu Gly
    50                  55                  60

Gln Pro Val Thr Thr Tyr Phe Ser Gln Pro Leu Ser Cys Asp Trp Gly
65                  70                  75                  80

Thr Leu Leu Phe Ser His Ala Phe Leu Ile Met Pro Glu Ser Pro Thr
                85                  90                  95

Pro Leu Leu Gly Arg Asp Ile Leu Ala Lys Ala Gly Ala Ile Ile His
            100                 105                 110

Leu Asn
```

(2) INFORMATION FOR SEQ ID NO: 91:

(i) SEQUENCE CHARACTERISTICS:
(A) LENGTH: 654 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 91:

```
Ile Gly Lys Gly Ile Pro Ile Cys Cys Pro Leu Leu Glu Glu Gly Ile
1               5                   10                  15

Asn Pro Glu Val Trp Ala Ile Glu Gly Gln Tyr Gly Gln Ala Lys Asn
            20                  25                  30

Ala Arg Pro Val Gln Val Lys Leu Lys Asp Ser Ala Ser Phe Pro Tyr
        35                  40                  45

Gln Arg Lys Tyr Pro Leu Arg Pro Glu Ala Leu Gln Gly Xaa Gln Lys
    50                  55                  60

Ile Val Lys Asp Leu Lys Ala Gln Gly Leu Val Lys Pro Cys Ser Ser
65                  70                  75                  80

Pro Cys Asn Thr Pro Ile Leu Gly Val Arg Lys Pro Asn Gly Gln Trp
                85                  90                  95

Arg Leu Val Gln Asp Leu Arg Ile Ile Asn Glu Ala Val Phe Pro Leu
            100                 105                 110

Tyr Pro Ala Val Ser Ser Pro Tyr Thr Leu Leu Ser Leu Ile Pro Glu
        115                 120                 125

Glu Ala Glu Trp Phe Thr Val Leu Asp Leu Lys Asp Ala Phe Phe Cys
    130                 135                 140

Ile Pro Val Arg Pro Asp Ser Gln Phe Leu Phe Ala Phe Glu Asp Pro
145                 150                 155                 160

Leu Asn Pro Thr Ser Gln Leu Thr Trp Thr Val Leu Pro Gln Gly Phe
                165                 170                 175

Arg Asp Ser Pro His Leu Phe Gly Gln Ala Leu Ala Gln Asp Leu Ser
            180                 185                 190

Gln Phe Ser Tyr Leu Asp Thr Leu Val Leu Gln Tyr Val Asp Asp Leu
        195                 200                 205

Leu Leu Val Ala Arg Ser Glu Thr Leu Cys His Gln Ala Thr Gln Glu
    210                 215                 220

Leu Leu Thr Phe Leu Thr Thr Cys Gly Tyr Lys Val Ser Lys Pro Lys
225                 230                 235                 240
```

-continued

```
Ala Arg Leu Cys Ser Gln Glu Ile Arg Tyr Leu Gly Leu Lys Leu Ser
                245                 250                 255

Lys Gly Thr Arg Ala Leu Ser Glu Glu Arg Ile Gln Pro Ile Leu Ala
            260                 265                 270

Tyr Pro His Pro Lys Thr Leu Lys Gln Leu Arg Gly Phe Leu Gly Ile
        275                 280                 285

Thr Gly Phe Cys Arg Lys Gln Ile Pro Arg Tyr Thr Pro Ile Ala Arg
    290                 295                 300

Pro Leu Tyr Thr Leu Ile Arg Glu Thr Gln Lys Ala Asn Thr Tyr Leu
305                 310                 315                 320

Val Arg Trp Thr Pro Thr Glu Val Ala Phe Gln Ala Leu Lys Lys Ala
                325                 330                 335

Leu Thr Gln Ala Pro Val Phe Ser Leu Pro Thr Gly Gln Asp Phe Ser
            340                 345                 350

Leu Tyr Ala Thr Glu Lys Thr Gly Ile Ala Leu Gly Val Leu Thr Gln
        355                 360                 365

Val Ser Gly Met Ser Leu Gln Pro Val Val Tyr Leu Ser Lys Glu Ile
    370                 375                 380

Asp Val Val Ala Lys Gly Trp Pro His Cys Leu Trp Val Met Ala Ala
385                 390                 395                 400

Val Ala Val Leu Val Ser Glu Ala Val Lys Ile Ile Gln Gly Arg Asp
                405                 410                 415

Leu Thr Val Trp Thr Ser His Asp Val Asn Gly Ile Leu Thr Ala Lys
            420                 425                 430

Gly Asp Leu Trp Leu Ser Asp Asn His Leu Leu Asn Tyr Gln Ala Leu
        435                 440                 445

Leu Leu Glu Glu Pro Val Leu Arg Leu Arg Thr Cys Ala Thr Leu Lys
    450                 455                 460

Pro Ala Thr Phe Leu Pro Asp Asn Glu Glu Lys Ile Glu His Asn Cys
465                 470                 475                 480

Gln Gln Val Ile Ala Gln Thr Tyr Ala Ala Arg Gly Asp Leu Leu Glu
                485                 490                 495

Val Pro Leu Thr Asp Pro Asp Leu Asn Leu Tyr Thr Asp Gly Ser Ser
            500                 505                 510

Leu Ala Glu Lys Gly Leu Arg Lys Ala Gly Tyr Ala Val Ile Ser Asp
        515                 520                 525

Asn Gly Ile Leu Glu Ser Asn Arg Leu Thr Pro Gly Thr Ser Ala His
    530                 535                 540

Leu Ala Glu Leu Ile Ala Leu Thr Trp Ala Leu Glu Leu Gly Glu Gly
545                 550                 555                 560

Lys Arg Val Asn Ile Tyr Ser Asp Ser Lys Tyr Ala Tyr Leu Val Leu
                565                 570                 575

His Ala His Ala Ala Ile Trp Arg Glu Arg Glu Phe Leu Thr Ser Glu
            580                 585                 590

Gly Thr Pro Ile Asn His Gln Glu Ala Ile Arg Arg Leu Leu Leu Ala
        595                 600                 605

Val Gln Lys Pro Lys Glu Val Ala Val Leu His Cys Gln Gly His Gln
    610                 615                 620

Glu Glu Glu Glu Arg Glu Ile Glu Gly Asn Arg Gln Ala Asp Ile Glu
625                 630                 635                 640

Ala Lys Lys Ala Ala Arg Gln Asp Ser Pro Leu Glu Met Leu
                645                 650
```

-continued (2) INFORMATION FOR SEQ ID NO: 92:

(i) SEQUENCE CHARACTERISTICS:
(A) LENGTH: 149 amino acids
(B) TYPE: amino acid
(C) STRANDEDNESS: not relevant
(D) TOPOLOGY: linear (ii) MOLECULE TYPE: peptide (xi) SEQUENCE DESCRIPTION: SEQ ID NO: 92:

```
Leu Tyr Thr Asp Gly Ser Ser Leu Ala Glu Lys Gly Leu Arg Lys Ala
1               5                   10                  15

Gly Tyr Ala Val Ile Ser Asp Asn Gly Ile Leu Glu Ser Asn Arg Leu
            20                  25                  30

Thr Pro Gly Thr Ser Ala His Leu Ala Glu Leu Ile Ala Leu Thr Trp
        35                  40                  45

Ala Leu Glu Leu Gly Glu Gly Lys Arg Val Asn Ile Tyr Ser Asp Ser
    50                  55                  60

Lys Tyr Ala Tyr Leu Val Leu His Ala His Ala Ala Ile Trp Arg Glu
65                  70                  75                  80

Arg Glu Phe Leu Thr Ser Glu Gly Thr Pro Ile Asn His Gln Glu Ala
                85                  90                  95

Ile Arg Arg Leu Leu Leu Ala Val Gln Lys Pro Lys Glu Val Ala Val
            100                 105                 110

Leu His Cys Gln Gly His Gln Glu Glu Glu Glu Arg Glu Ile Glu Gly
        115                 120                 125

Asn Arg Gln Ala Asp Ile Glu Ala Lys Lys Ala Ala Arg Gln Asp Ser
    130                 135                 140

Pro Leu Glu Met Leu
145
```

(2) INFORMATION FOR SEQ ID NO: 93:

(i) SEQUENCE CHARACTERISTICS:
(A) LENGTH: 21 base pairs
(B) TYPE: nucleotide
(C) STRANDEDNESS: single
(D) TOPOLOGY: linear (xi) SEQUENCE DESCRIPTION: SEQ ID NO: 93:

TCCAGCAGCA GGACTGAGGG T 21

(2) INFORMATION FOR SEQ ID NO: 94:

(i) SEQUENCE CHARACTERISTICS:
(A) LENGTH: 24 base pairs
(B) TYPE: nucleotide
(C) STRANDEDNESS: single
(D) TOPOLOGY: linear (xi) SEQUENCE DESCRIPTION: SEQ ID NO: 94:

GACAGCAAAT GGGTATTCCT TTCC 24

(2) INFORMATION FOR SEQ ID NO: 95:

(i) SEQUENCE CHARACTERISTICS:
(A) LENGTH: 25 base pairs
(B) TYPE: nucleotide
(C) STRANDEDNESS: single
(D) TOPOLOGY: linear (xi) SEQUENCE DESCRIPTION: SEQ ID NO: 95:

-continued

AGGAGTAAGG AAACCCAACG GACAG 25

(2) INFORMATION FOR SEQ ID NO: 96:

(i) SEQUENCE CHARACTERISTICS:
(A) LENGTH: 25 base pairs
(B) TYPE: nucleotide
(C) STRANDEDNESS: single
(D) TOPOLOGY: linear (xi) SEQUENCE DESCRIPTION: SEQ ID NO: 96:

TGTATATAAT GGTCTGGCTA TTGGG 25

(2) INFORMATION FOR SEQ ID NO: 97:

(i) SEQUENCE CHARACTERISTICS:
(A) LENGTH: 26 base pairs
(B) TYPE: nucleotide
(C) STRANDEDNESS: single
(D) TOPOLOGY: linear (xi) SEQUENCE DESCRIPTION: SEQ ID NO: 97:

GGCTCTGCTC ACAGGAGATT AGATAC 26

(2) INFORMATION FOR SEQ ID NO: 98:

(i) SEQUENCE CHARACTERISTICS:
(A) LENGTH: 26 base pairs
(B) TYPE: nucleotide
(C) STRANDEDNESS: single
(D) TOPOLOGY: linear (xi) SEQUENCE DESCRIPTION: SEQ ID NO: 98:

AAAGGCACCA GGGCCCTCAG TGAGGA 26

(2) INFORMATION FOR SEQ ID NO: 99:

(i) SEQUENCE CHARACTERISTICS:
(A) LENGTH: 28 base pairs
(B) TYPE: nucleotide
(C) STRANDEDNESS: single
(D) TOPOLOGY: linear (xi) SEQUENCE DESCRIPTION: SEQ ID NO: 99:

GGTTTAAGAG TTGCACAAGT GCGCAGTC 28

(2) INFORMATION FOR SEQ ID NO: 100:

(i) SEQUENCE CHARACTERISTICS:
(A) LENGTH: 310 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 100:

GCTTATAGAA GGACCCCTAG TATGGGGTAA TCCCCTCTGG GAAACCAAGC CCCAGTACTC 60

AGCAGGAAAA ATAGAATAGG AAACCTCACA AGGACATACT TTCCTCCCCT CCAGATGGCT 120

AGCCACTGAG GAAGGAAAAA TACTTTCACC TGCAGCTAAC CAACAGAAAT TACTTAAAAC 180

CCTTCACCAA ACCTTCCACT TAGGCATTGA TAGCACCCAT CAGATGGCCA AATTATTATT 240

TACTGGACCA GGCCTTTTCA AAACTATCAA GAAGATAGTC AGGGGCTGTG AAGTGTGCCA 300

AAGAAATAAT 310

(2) INFORMATION FOR SEQ ID NO: 101:

(i) SEQUENCE CHARACTERISTICS:
(A) LENGTH: 103 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 101:

```
Leu Ile Glu Gly Pro Leu Val Trp Gly Asn Pro Leu Trp Glu Thr Lys
1               5                   10                  15

Pro Gln Tyr Ser Ala Gly Lys Ile Glu Xaa Glu Thr Ser Gln Gly His
            20                  25                  30

Thr Phe Leu Pro Ser Arg Trp Leu Ala Thr Glu Glu Gly Lys Ile Leu
        35                  40                  45

Ser Pro Ala Ala Asn Gln Gln Lys Leu Leu Lys Thr Leu His Gln Thr
    50                  55                  60

Phe His Leu Gly Ile Asp Ser Thr His Gln Met Ala Lys Leu Leu Phe
65                  70                  75                  80

Thr Gly Pro Gly Leu Phe Lys Thr Ile Lys Lys Ile Val Arg Gly Cys
                85                  90                  95

Glu Val Cys Gln Arg Asn Asn
            100
```

(2) INFORMATION FOR SEQ ID NO: 102:

(i) SEQUENCE CHARACTERISTICS:
(A) LENGTH: 635 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 102:

```
CCCTGTATCT TTAACCTCCT TGTTAAGTTT GTCTCTTCCA GAATCAAAAC TGTAAAACTA     60

CAAATTGTTC TTCAAATGGA GCACCAGATG GAGTCCATGA CTAAGATCCA CCGTGGACCC    120

CTGGACCGGC CTGCTAGCCC ATGCTCCGAT GTTAATGACA TTGAAGGCAC CCCTCCCGAG    180

GAAATCTCAA CTGCACAACC CCTACTATGC CCCAATTCAG CGGGAAGCAG TTAGAGCGGT    240

CATCAGCCAA CCTCCCCAAC AGCACTTGGG TTTTCCTGTT GAGAGGGGGG ACTGAGAGAC    300

AGGACTAGCT GGATTTCCTA GGCCAACGAA GAATCCCTAA GCCTAGCTGG GAAGGTGACT    360

GCATCCACCT CTAAACATGG GGCTTGCAAC TTAGCTCACA CCCGACCAAT CAGAGAGCTC    420

ACTAAAATGC TAATTAGGCA AAAATAGGAG GTAAAGAAAT AGCCAATCAT CTATTGCCTG    480

AGAGCACAGC GGGAGGGACA AGGATCGGGA TATAAACCCA GGCATTCGAG CCGGCAACGG    540

CAACCCCCTT TGGGTCCCCT CCCTTTGTAT GGGCGCTCTG TTTTCACTCT ATTTCACTCT    600

ATTAAATCTT GCAACTGAAA AAAAAAAAAA AAAAA                               635
```

(2) INFORMATION FOR SEQ ID NO: 103:

(i) SEQUENCE CHARACTERISTICS:
(A) LENGTH: 77 amino acids
(B) TYPE: amino acid
(C) STRANDEDNESS: single
(D) TOPOLOGY: linear (ii) MOLECULE TYPE: peptide -continued (xi) SEQUENCE DESCRIPTION: SEQ ID NO: 103:

```
Pro Cys Ile Phe Asn Leu Leu Val Lys Phe Val Ser Ser Arg Ile Lys
1               5                   10                  15

Thr Val Lys Leu Gln Ile Val Leu Gln Met Glu His Gln Met Glu Ser
            20                  25                  30

Met Thr Lys Ile His Arg Gly Pro Leu Asp Arg Pro Ala Ser Pro Cys
        35                  40                  45

Ser Asp Val Asn Asp Ile Glu Gly Thr Pro Pro Glu Glu Ile Ser Thr
    50                  55                  60

Ala Gln Pro Leu Leu Cys Pro Asn Ser Ala Gly Ser Ser
65                  70                  75
```

(2) INFORMATION FOR SEQ ID NO: 104:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 104:

```
TGGGGTTCCA TTTGTAAGAC CATCTGTAGC TT                                 32
```

(2) INFORMATION FOR SEQ ID NO: 105:

(i) SEQUENCE CHARACTERISTICS:
(A) LENGTH: 1481 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 105:

```
ATGGCCCTCC CTTATCATAC TTTTCTCTTT ACTGTTCTCT TACCCCCTTT CGCTCTCACT     60
GCACCCCCTC CATGCTGCTG TACAACCAGT AGCTCCCCTT ACCAAGAGTT TCTATGAAGA    120
ACGCGGCTTC CTGGAAATAT TGATGCCCCA TCATATAGGA GTTTATCTAA GGGAAACTCC    180
ACCTTCACTG CCCACACCCA TATGCCCCGC AACTGCTATA ACTCTGCCAC TCTTTGCATG    240
CATGCAAATA CTCATTATTG GACAGGGAAA ATGATTAATC CTAGTTGTCC TGGAGGACTT    300
GGAGCCACTG TCTGTTGGAC TTACTTCACC CATACCAGTA TGTCTGATGG GGGTGGAATT    360
CAAGGTCAGG CAAGAGAAAA ACAAGTAAAG GAAGCAATCT CCCAACTGAC CCGGGGACAT    420
AGCACCCCTA GCCCCTACAA AGGACTAGTT CTCTCAAAAC TACATGAAAC CCTCCGTACC    480
CATACTCGCC TGGTGAGCCT ATTTAATACC ACCCTCACTC GGCTCCATGA GGTCTCAGCC    540
CAAAACCCTA CTAACTGTTG GATGTGCCTC CCCCTGCACT TCAGGCCATA CATTTCAATC    600
CCTGTTCCTG AACAATGGAA CAACTTCAGC ACAGAAATAA ACACCACTTC CGTTTTAGTA    660
GGACCTCTTG TTTCCAATCT GGAAATAACC CATACCTCAA ACCTCACCTG TGTAAAATTT    720
AGCAATACTA TAGACACAAC CAGCTCCCAA TGCATCAGGT GGGTAACACC TCCCACACGA    780
ATAGTCTGCC TACCCTCAGG AATATTTTTT GTCTGTGGTA CCTCAGCCTA TCATTGTTTG    840
AATGGCTCTT CAGAATCTAT GTGCTTCCTC TCATTCTTAG TGCCCCCTAT GACCATCTAC    900
ACTGAACAAG ATTTATACAA TCATGTCGTA CCTAAGCCCC ACAACAAAAG AGTACCCATT    960
CTTCCTTTTG TTATCAGAGC AGGAGTGCTA GGCAGACTAG GTACTGGCAT TGGCAGTATC   1020
```

-continued

```
ACAACCTCTA CTCAGTTCTA CTACAAACTA TCTCAAGAAA TAAATGGTGA CATGGAACAG   1080

GTCACTGACT CCCTGGTCAC CTTGCAAGAT CAACTTAACT CCCTAGCAGC AGTAGTCCTT   1140

CAAAATCGAA GAGCTTTAGA CTTGCTAACC GCCAAAAGAG GGGGAACCTG TTTATTTTTA   1200

GGAGAAGAAC GCTGTTATTA TGTTAATCAA TCCAGAATTG TCACTGAGAA AGTTAAAGAA   1260

ATTCGAGATC GAATACAATG TAGAGCAGAG GAGCTTCAAA ACACCGAACG CTGGGGCCTC   1320

CTCAGCCAAT GGATGCCCTG GGTTCTCCCC TTCTTAGGAC CTCTAGCAGC TCTAATATTG   1380

TTACTCCTCT TTGGACCCTG TATCTTTAAC CTCCTTGTTA AGTTTGTCTC TTCCAGAATT   1440

GAAGCTGTAA AGCTACAGAT GGTCTTACAA ATGGAACCCC A                       1481
```

(2) INFORMATION FOR SEQ ID NO: 106:

(i) SEQUENCE CHARACTERISTICS:
(A) LENGTH: 493 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 106:

```
Met Ala Leu Pro Tyr His Thr Phe Leu Phe Thr Val Leu Leu Pro Pro
1               5                   10                  15

Phe Ala Leu Thr Ala Pro Pro Pro Cys Cys Cys Thr Thr Ser Ser Ser
            20                  25                  30

Pro Tyr Gln Glu Phe Leu Xaa Arg Thr Arg Leu Pro Gly Asn Ile Asp
        35                  40                  45

Ala Pro Ser Tyr Arg Ser Leu Ser Lys Gly Asn Ser Thr Phe Thr Ala
    50                  55                  60

His Thr His Met Pro Arg Asn Cys Tyr Asn Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Ala Thr Val Cys Trp Thr Tyr Phe Thr His Thr
            100                 105                 110

Ser Met Ser Asp Gly Gly Gly Ile Gln Gly Gln Ala Arg Glu Lys Gln
        115                 120                 125

Val Lys Glu Ala Ile Ser Gln Leu Thr Arg Gly His Ser Thr Pro Ser
    130                 135                 140

Pro Tyr Lys Gly Leu Val Leu Ser Lys Leu His Glu Thr Leu Arg Thr
145                 150                 155                 160

His Thr Arg Leu Val Ser Leu Phe Asn Thr Thr Leu Thr Arg Leu His
                165                 170                 175

Glu Val Ser Ala Gln Asn Pro Thr Asn Cys Trp Met Cys Leu Pro Leu
            180                 185                 190

His Phe Arg Pro Tyr Ile Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Ile Asp Thr Thr Ser Ser Gln Cys Ile Arg Trp Val Thr
                245                 250                 255

Pro Pro Thr Arg Ile Val Cys Leu Pro Ser Gly Ile Phe Phe Val Cys
```

-continued

```
            260                 265                 270

Gly Thr Ser Ala Tyr His Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Asn His Val Val Pro Lys Pro His Asn Lys Arg Val Pro Ile
305                 310                 315                 320

Leu Pro Phe Val Ile Arg Ala Gly Val Leu Gly Arg Leu Gly Thr Gly
                325                 330                 335

Ile Gly Ser Ile Thr Thr Ser Thr Gln Phe Tyr Tyr Lys Leu Ser Gln
            340                 345                 350

Glu Ile Asn Gly Asp Met Glu Gln Val Thr Asp Ser Leu Val Thr Leu
        355                 360                 365

Gln Asp Gln Leu Asn Ser Leu Ala Ala Val Val Leu Gln Asn Arg Arg
    370                 375                 380

Ala Leu Asp Leu Leu Thr Ala Lys Arg Gly Gly Thr Cys Leu Phe Leu
385                 390                 395                 400

Gly Glu Glu Arg Cys Tyr Tyr Val Asn Gln Ser Arg Ile Val Thr Glu
                405                 410                 415

Lys Val Lys Glu Ile Arg Asp Arg Ile Gln Cys Arg Ala Glu Glu Leu
            420                 425                 430

Gln Asn Thr Glu Arg Trp Gly Leu Leu Ser Gln Trp Met Pro Trp Val
        435                 440                 445

Leu Pro Phe Leu Gly Pro Leu Ala Ala Leu Ile Leu Leu Leu Leu Phe
    450                 455                 460

Gly Pro Cys Ile Phe Asn Leu Leu Val Lys Phe Val Ser Ser Arg Ile
465                 470                 475                 480

Glu Ala Val Lys Leu Gln Met Val Leu Gln Met Glu Pro
                485                 490
```

(2) INFORMATION FOR SEQ ID NO: 107:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 107:

```
TCAAAATCGA AGAGCTTTAG ACTTGCTAAC CG                                  32
```

(2) INFORMATION FOR SEQ ID NO: 108:

(i) SEQUENCE CHARACTERISTICS:
(A) LENGTH: 1329 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 108:

```
TCAAAATCGA AGAGCTTTAG ACTTGCTAAC CGCCAAAAGA GGGGGAACCT GTTTATTTTT     60

AGGGGAAGAA TGCTGTTAGT ATGTTAATCA ATCTGGAATC ATTACTGAGA AAGTTAAAGA    120

AATTTGAGAT CGAATATAAT GTAGAGCAGA GGACCTTCAA AACACTGCAC CCTGGGGCCT    180

CCTCAGCCAA TGGATGCCCT GGACTCTCCC CTTCTTAGGA CCTCTAGCAG CTATAATATT    240
```

-continued

```
TTTACTCCTC TTTGGACCCT GTATCTTCAA CTTCCTTGTT AAGTTTGTCT CTTCCAGAAT    300

TGAAGCTGTA AAGCTACAAA TAGTTCTTCA AATGGAACCC CAGATGCAGT CCATGACTAA    360

AATCTACCGT GGACCCCTGG ACCGGCCTGC TAGACTATGC TCTGATGTTA ATGACATTGA    420

AGTCACCCCT CCCGAGGAAA TCTCAACTGC ACAACCCCTA CTACACTCCA ATTCAGTAGG    480

AAGCAGTTAG AGCAGTTGTC AGCCAACCTC CCCAACAGTA CTTGGGTTTT CCTGTTGAGA    540

GGGTGGACTG AGAGACAGGA CTAGCTGGAT TTCCTAGGCT GACTAAGAAT CCCNAAGCCT    600

ANCTGGGAAG GTGACCGCAT CCATCTTTAA ACATGGGGCT TGCAACTTAG CTCACACCCG    660

ACCAATCAGA GAGCTCACTA AAATGCTAAT CAGGCAAAAA CAGGAGGTAA AGCAATAGCC    720

AATCATCTAT TGCCTGAGAG CACAGCGGGA AGGACAAGGA TTGGGATATA AACTCAGGCA    780

TTCAAGCCAG CAACAGCAAC CCCCTTTGGG TCCCCTCCCA TTGTATGGGA GCTCTGTTTT    840

CACTCTATTT CACTCTATTA AATCATGCAA CTGCACTCTT CTGGTCCGTG TTTTTTATGG    900

CTCAAGCTGA GCTTTTGTTC GCCATCCACC ACTGCTGTTT GCCACCGTCA CAGACCCGCT    960

GCTGACTTCC ATCCCTTTGG ATCCAGCAGA GTGTCCACTG TGCTCCTGAT CCAGCGAGGT   1020

ACCCATTGCC ACTCCCGATC AGGCTAAAGG CTTGCCATTG TTCCTGCATG GCTAAGTGCC   1080

TGGGTTTGTC CTAATAGAAC TGAACACTGG TCACTGGGTT CCATGGTTCT CTTCCATGAC   1140

CCACGGCTTC TAATAGAGCT ATAACACTCA CCGCATGGCC CAAGATTCCA TTCCTTGGTA   1200

TCTGTGAGGC CAAGAACCCC AGGTCAGAGA ANGTGAGGCT TGCCACCATT TGGGAAGTGG   1260

CCCACTGCCA TTTTGGTAGC GGCCCACCAC CATCTTGGGA GCTGTGGGAG CAAGGATCCC   1320

CCAGTAACA                                                           1329
```

(2) INFORMATION FOR SEQ ID NO: 109:

(i) SEQUENCE CHARACTERISTICS:
(A) LENGTH: 162 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 109:

```
Gln Asn Arg Arg Ala Leu Asp Leu Leu Thr Ala Lys Arg Gly Gly Thr
1               5                   10                  15

Cys Leu Phe Leu Gly Glu Glu Cys Cys Xaa Tyr Val Asn Gln Ser Gly
            20                  25                  30

Ile Ile Thr Glu Lys Val Lys Glu Ile Xaa Asp Arg Ile Xaa Cys Arg
        35                  40                  45

Ala Glu Asp Leu Gln Asn Thr Ala Pro Trp Gly Leu Leu Ser Gln Trp
    50                  55                  60

Met Pro Trp Thr Leu Pro Phe Leu Gly Pro Leu Ala Ala Ile Ile Phe
65                  70                  75                  80

Leu Leu Leu Phe Gly Pro Cys Ile Phe Asn Phe Leu Val Lys Phe Val
                85                  90                  95

Ser Ser Arg Ile Glu Ala Val Lys Leu Gln Ile Val Leu Gln Met Glu
            100                 105                 110

Pro Gln Met Gln Ser Met Thr Lys Ile Tyr Arg Gly Pro Leu Asp Arg
        115                 120                 125

Pro Ala Arg Leu Cys Ser Asp Val Asn Asp Ile Glu Val Thr Pro Pro
    130                 135                 140
```

-continued

```
Glu Glu Ile Ser Thr Ala Gln Pro Leu Leu His Ser Asn Ser Val Gly
145                 150                 155                 160

Ser Ser
```

(2) INFORMATION FOR SEQ ID NO: 110:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 110:

```
GGCATTGATA GCACCCATCA G                                              21
```

(2) INFORMATION FOR SEQ ID NO: 111:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 111:

```
CATGTCACCA GGGTGGAATA G                                              21
```

(2) INFORMATION FOR SEQ ID NO: 112:

(i) SEQUENCE CHARACTERISTICS:
(A) LENGTH: 758 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 112:

```
GGCATTGATA GCACCCATCA GATGGCCAAA TCATTATTTA CTGGACCAGG CCTTTTCAAA    60

ACTATCAAGC AGATAGGGCC CGTGAAGCAT GCCAAAGAAA TAATCCCCTG CCTTATCGCC   120

ATGTTCCTTC AGGAGAACAA AGAACAGGCC ATTACCCAGG GGAAGACTGG CAACTAGATT   180

TTACCCACAT GGCCAAATGT CAGGGATTTC AGCATCTACT AGTCTGGGCA GATACTTTCA   240

CTGGTTGGGT GGAGTCTTCT CCTTGTAGGA CAGAAAAGAC CCAAGAGGTA ATAAAGGCAC   300

TAATGAAATA ATTCCCAGAT TTGGACTTCC CCCAGGATTA CAGGGTGACA ATGGCCCCGC   360

TTTCAAGGCT GCAGTAACCC AGGGAGTATC CCAGGTGTTA GGCATACAAT ATCACTTACA   420

CTGTGCCTGG AGGCCACAAT CCTCCAGAAA AGTCAAGAAA ATGAATGAAA CACTCAAAGA   480

TCTAAAAAAG CTAACCCAAG AAACCCACAT TGCATGACCT GTTCTGTTGC CTATAACCTT   540

ACTAAGAATC CATAACTATC CCCCAAAAAG CAGGACTTAG CCCATACGAG ATGCTATATG   600

GATGGCCTTT CCTAACCAAT GACCTTGTGC TTGACTGAGA AATGGCCAAC TTAGTTGCAG   660

ACATCACCTC CTTAGCCAAA TATCAACAAG TTCTTAAAAC ATCACAGGGA ACCTGTCCCC   720

GAGAGGAGGG AAAGGAACTA TTCCACCCTG GTGACATG                            758
```

(2) INFORMATION FOR SEQ ID NO: 113:

(i) SEQUENCE CHARACTERISTICS:
(A) LENGTH: 25 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 113:

CGGACATCCA AAGTGATGGG AAACG 25

(2) INFORMATION FOR SEQ ID NO: 114:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 114:

GGACAGGAAA GTAAGACTGA GAAGGC 26

(2) INFORMATION FOR SEQ ID NO: 115:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 115:

CCTAGAACGT ATTCTGGAGA ATTGGG 26

(2) INFORMATION FOR SEQ ID NO: 116:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 116:

TGGCTCTCAA TGGTCAAACA TACCCG 26

(2) INFORMATION FOR SEQ ID NO: 117:

(i) SEQUENCE CHARACTERISTICS:
(A) LENGTH: 1511 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 117:

CCTAGAACGT ATTCTGGAGA ATTGGGACCA ATGTGACACT CAGACGCTAA GAAAGAAACG 60

ATTTATATTC TTCTGCAGTA CCGCCTGGCC ACAATATCCT CTTCAAGGGA GAGAAACCTG 120

GCTTCCTGAG GGAAGTATAA ATTATAACAT CATCTTACAG CTAGACCTCT TCTGTAGAAA 180

GGAGGGCAAA TGGAGTGAAG TGCCATATGT GCAAACTTTC TTTTCATTAA GAGACAACTC 240

ACAATTATGT AAAAAGTGTG GTTTATGCCC TACAGGAAGC CCTCAGAGTC CACCTCCCTA 300

CCCCAGCGTC CCCTCCCCGA CTCCTTCCTC AACTAATAAG GACCCCCCTT TAACCCAAAC 360

-continued

```
GGTCCAAAAG GAGATAGACA AAGGGGTAAA CAATGAACCA AAGAGTGCCA ATATTCCCCG    420

ATTATGCCCC CTCCAAGCAG TGAGAGGAGG AGAATTCGGC CCAGCCAGAG TGCCTGTACC    480

TTTTTCTCTC TCAGACTTAA AGCAAATTAA AATAGACCTA GGTAAATTCT CAGATAACCC    540

TGACGGCTAT ATTGATGTTT TACAAGGGTT AGGACAATCC TTTGATCTGA CATGGAGAGA    600

TATAATGTTA CTACTAAATC AGACACTAAC CCCAAATGAG AGAAGTGCCG CTGTAACTGC    660

AGCCCGAGAG TTTGGCGATC TTTGGTATCT CAGTCAGGCC AACAATAGGA TGACAACAGA    720

GGAAAGAACA ACTCCCACAG GCCAGCAGGC AGTTCCCAGT GTAGACCCTC ATTGGGACAC    780

AGAATCAGAA CATGGAGATT GGTGCCACAA ACATTTGCTA ACTTGCGTGC TAGAAGGACT    840

GAGGAAAACT AGGAAGAAGC CTATGAATTA CTCAATGATG TCCACTATAA CACAGGGAAA    900

GGAAGAAAAT CTTACTGCTT TTCTGGACAG ACTAAGGGAG GCATTGAGGA AGCATACCTC    960

CCTGTCACCT GACTCTATTG AAGGCCAACT AATCTTAAAG GATAAGTTTA TCACTCAGTC   1020

AGCTGCAGAC ATTAGAAAAA ACTTCAAAAG TCTGCCTTAG GCCCGGAGCA GAACTTAGAA   1080

ACCCTATTTA ACTTGGCATC CTCAGTTTTT TATAATAGAG ATCAGGAGGA GCAGGCGAAA   1140

CGGGACAAAC GGGATAAAAA AAAAAGGGGG GGTCCACTAC TTTAGTCATG GCCCTCAGGC   1200

AAGCAGACTT TGGAGGCTCT GCAAAAGGGA AAAGCTGGGC AAATCAAATG CCTAATAGGG   1260

CTGGCTTCCA GTGCGGTCTA CAAGGACACT TTAAAAAAGA TTATCCAAGT AGAAATAAGC   1320

CGCCCCCTTG TCCATGCCCC TTACGTCAAG GGAATCACTG GAAGGCCCAC TGCCCCAGGG   1380

GATGAAGATA CTCTGAGTCA GAAGCCATTA ACCAGATGAT CCAGCAGCAG GACTGAGGGT   1440

GCCCGGGGCG AGCGCCAGCC CATGCCATCA CCCTCACAGA GCCCCGGGTA TGTTTGACCA   1500

TTGAGAGCCA A                                                         1511
```

(2) INFORMATION FOR SEQ ID NO: 118:

(i) SEQUENCE CHARACTERISTICS:
(A) LENGTH: 352 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 118:

```
Leu Glu Arg Ile Leu Glu Asn Trp Asp Gln Cys Asp Thr Gln Thr Leu
1               5                   10                  15

Arg Lys Lys Arg Phe Ile Phe Phe Cys Ser Thr Ala Trp Pro Gln Tyr
            20                  25                  30

Pro Leu Gln Gly Arg Glu Thr Trp Leu Pro Glu Gly Ser Ile Asn Tyr
        35                  40                  45

Asn Ile Ile Leu Gln Leu Asp Leu Phe Cys Arg Lys Glu Gly Lys Trp
    50                  55                  60

Ser Glu Val Pro Tyr Val Gln Thr Phe Phe Ser Leu Arg Asp Asn Ser
65                  70                  75                  80

Gln Leu Cys Lys Lys Cys Gly Leu Cys Pro Thr Gly Ser Pro Gln Ser
                85                  90                  95

Pro Pro Pro Tyr Pro Ser Val Pro Ser Pro Thr Pro Ser Ser Thr Asn
            100                 105                 110

Lys Asp Pro Pro Leu Thr Gln Thr Val Gln Lys Glu Ile Asp Lys Gly
        115                 120                 125

Val Asn Asn Glu Pro Lys Ser Ala Asn Ile Pro Arg Leu Cys Pro Leu
```

-continued

```
    130                 135                 140

Gln Ala Val Arg Gly Gly Glu Phe Gly Pro Ala Arg Val Pro Val Pro
145                 150                 155                 160

Phe Ser Leu Ser Asp Leu Lys Gln Ile Lys Ile Asp Leu Gly Lys Phe
                165                 170                 175

Ser Asp Asn Pro Asp Gly Tyr Ile Asp Val Leu Gln Gly Leu Gly Gln
            180                 185                 190

Ser Phe Asp Leu Thr Trp Arg Asp Ile Met Leu Leu Leu Asn Gln Thr
        195                 200                 205

Leu Thr Pro Asn Glu Arg Ser Ala Ala Val Thr Ala Ala Arg Glu Phe
    210                 215                 220

Gly Asp Leu Trp Tyr Leu Ser Gln Ala Asn Asn Arg Met Thr Thr Glu
225                 230                 235                 240

Glu Arg Thr Thr Pro Thr Gly Gln Gln Ala Val Pro Ser Val Asp Pro
                245                 250                 255

His Trp Asp Thr Glu Ser Glu His Gly Asp Trp Cys His Lys His Leu
            260                 265                 270

Leu Thr Cys Val Leu Glu Gly Leu Arg Lys Thr Arg Lys Lys Pro Met
        275                 280                 285

Asn Tyr Ser Met Met Ser Thr Ile Thr Gln Gly Lys Glu Glu Asn Leu
    290                 295                 300

Thr Ala Phe Leu Asp Arg Leu Arg Glu Ala Leu Arg Lys His Thr Ser
305                 310                 315                 320

Leu Ser Pro Asp Ser Ile Glu Gly Gln Leu Ile Leu Lys Asp Lys Phe
                325                 330                 335

Ile Thr Gln Ser Ala Ala Asp Ile Arg Lys Asn Phe Lys Ser Leu Pro
            340                 345                 350
```

(2) INFORMATION FOR SEQ ID NO: 119:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 119:

TGCTGGAATT CGGGATCCTA GAACGTATTC 30

(2) INFORMATION FOR SEQ ID NO: 120:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 120:

AGTTCTGCTC CGAAGCTTAG GCAGACTTTT 30

(2) INFORMATION FOR SEQ ID NO: 121:

(i) SEQUENCE CHARACTERISTICS:
(A) LENGTH: 398 amino acids
(B) TYPE: amino acid
(C) STRANDEDNESS: single
(D) TOPOLOGY: linear -continued (ii) MOLECULE TYPE: peptide (xi) SEQUENCE DESCRIPTION: SEQ ID NO: 121:

```
Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Ile Leu Glu Arg Ile Leu Glu Asn Trp Asp Gln Cys Asp Thr Gln Thr
        35                  40                  45

Leu Arg Lys Lys Arg Phe Ile Phe Phe Cys Ser Thr Ala Trp Pro Gln
    50                  55                  60

Tyr Pro Leu Gln Gly Arg Glu Thr Trp Leu Pro Glu Gly Ser Ile Asn
65                  70                  75                  80

Tyr Asn Ile Ile Leu Gln Leu Asp Leu Phe Cys Arg Lys Glu Gly Lys
                85                  90                  95

Trp Ser Glu Val Pro Tyr Val Gln Thr Phe Phe Ser Leu Arg Asp Asn
            100                 105                 110

Ser Gln Leu Cys Lys Lys Cys Gly Leu Cys Pro Thr Gly Ser Pro Gln
        115                 120                 125

Ser Pro Pro Pro Tyr Pro Ser Val Pro Ser Pro Thr Pro Ser Ser Thr
    130                 135                 140

Asn Lys Asp Pro Pro Leu Thr Gln Thr Val Gln Lys Glu Ile Asp Lys
145                 150                 155                 160

Gly Val Asn Asn Glu Pro Lys Ser Ala Asn Ile Pro Arg Leu Cys Pro
                165                 170                 175

Leu Gln Ala Val Arg Gly Gly Glu Phe Gly Pro Ala Arg Val Pro Val
            180                 185                 190

Pro Phe Ser Leu Ser Asp Leu Lys Gln Ile Lys Ile Asp Leu Gly Lys
        195                 200                 205

Phe Ser Asp Asn Pro Asp Gly Tyr Ile Asp Val Leu Gln Gly Leu Gly
    210                 215                 220

Gln Ser Phe Asp Leu Thr Trp Arg Asp Ile Met Leu Leu Leu Asn Gln
225                 230                 235                 240

Thr Leu Thr Pro Asn Glu Arg Ser Ala Ala Val Thr Ala Ala Arg Glu
                245                 250                 255

Phe Gly Asp Leu Trp Tyr Leu Ser Gln Ala Asn Asn Arg Met Thr Thr
            260                 265                 270

Glu Glu Arg Thr Thr Pro Thr Gly Gln Gln Ala Val Pro Ser Val Asp
        275                 280                 285

Pro His Trp Asp Thr Glu Ser Glu His Gly Asp Trp Cys His Lys His
    290                 295                 300

Leu Leu Thr Cys Val Leu Glu Gly Leu Arg Lys Thr Arg Lys Lys Pro
305                 310                 315                 320

Met Asn Tyr Ser Met Met Ser Thr Ile Thr Gln Gly Lys Glu Glu Asn
                325                 330                 335

Leu Thr Ala Phe Leu Asp Arg Leu Arg Glu Ala Leu Arg Lys His Thr
            340                 345                 350

Ser Leu Ser Pro Asp Ser Ile Glu Gly Gln Leu Ile Leu Lys Asp Lys
        355                 360                 365

Phe Ile Thr Gln Ser Ala Ala Asp Ile Arg Lys Asn Phe Lys Ser Leu
    370                 375                 380

Pro Lys Leu Ala Ala Ala Leu Glu His His His His His His
385                 390                 395
```

-continued (2) INFORMATION FOR SEQ ID NO: 122:

(i) SEQUENCE CHARACTERISTICS:
(A) LENGTH: 378 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 122:

```
Met Ala Ser Met Thr Gly Gly Gln Gln Met Gly Arg Ile Leu Glu Arg
1               5                   10                  15

Ile Leu Glu Asn Trp Asp Gln Cys Asp Thr Gln Thr Leu Arg Lys Lys
            20                  25                  30

Arg Phe Ile Phe Phe Cys Ser Thr Ala Trp Pro Gln Tyr Pro Leu Gln
        35                  40                  45

Gly Arg Glu Thr Trp Leu Pro Glu Gly Ser Ile Asn Tyr Asn Ile Ile
    50                  55                  60

Leu Gln Leu Asp Leu Phe Cys Arg Lys Glu Gly Lys Trp Ser Glu Val
65                  70                  75                  80

Pro Tyr Val Gln Thr Phe Phe Ser Leu Arg Asp Asn Ser Gln Leu Cys
                85                  90                  95

Lys Lys Cys Gly Leu Cys Pro Thr Gly Ser Pro Gln Ser Pro Pro Pro
            100                 105                 110

Tyr Pro Ser Val Pro Ser Pro Thr Pro Ser Ser Thr Asn Lys Asp Pro
        115                 120                 125

Pro Leu Thr Gln Thr Val Gln Lys Glu Ile Asp Lys Gly Val Asn Asn
    130                 135                 140

Glu Pro Lys Ser Ala Asn Ile Pro Arg Leu Cys Pro Leu Gln Ala Val
145                 150                 155                 160

Arg Gly Gly Glu Phe Gly Pro Ala Arg Val Pro Val Pro Phe Ser Leu
                165                 170                 175

Ser Asp Leu Lys Gln Ile Lys Ile Asp Leu Gly Lys Phe Ser Asp Asn
            180                 185                 190

Pro Asp Gly Tyr Ile Asp Val Leu Gln Gly Leu Gly Gln Ser Phe Asp
        195                 200                 205

Leu Thr Trp Arg Asp Ile Met Leu Leu Leu Asn Gln Thr Leu Thr Pro
    210                 215                 220

Asn Glu Arg Ser Ala Ala Val Thr Ala Ala Arg Glu Phe Gly Asp Leu
225                 230                 235                 240

Trp Tyr Leu Ser Gln Ala Asn Asn Arg Met Thr Thr Glu Glu Arg Thr
                245                 250                 255

Thr Pro Thr Gly Gln Gln Ala Val Pro Ser Val Asp Pro His Trp Asp
            260                 265                 270

Thr Glu Ser Glu His Gly Asp Trp Cys His Lys His Leu Leu Thr Cys
        275                 280                 285

Val Leu Glu Gly Leu Arg Lys Thr Arg Lys Lys Pro Met Asn Tyr Ser
    290                 295                 300

Met Met Ser Thr Ile Thr Gln Gly Lys Glu Glu Asn Leu Thr Ala Phe
305                 310                 315                 320

Leu Asp Arg Leu Arg Glu Ala Leu Arg Lys His Thr Ser Leu Ser Pro
                325                 330                 335

Asp Ser Ile Glu Gly Gln Leu Ile Leu Lys Asp Lys Phe Ile Thr Gln
            340                 345                 350
```

-continued

Ser Ala Ala Asp Ile Arg Lys Asn Phe Lys Ser Leu Pro Lys Leu Ala
355 360 365

Ala Ala Leu Glu His His His His His His
370 375

(2) INFORMATION FOR SEQ ID NO: 123:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 123:

CTTGGAGGGT GCATAACCAG GGAAT 25

(2) INFORMATION FOR SEQ ID NO: 124:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 124:

TGTCCGCTGT GCTCCTGATC 20

(2) INFORMATION FOR SEQ ID NO: 125:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 125:

CTATGTCCTT TTGGACTGTT TGGGT 25

(2) INFORMATION FOR SEQ ID NO: 126:

(i) SEQUENCE CHARACTERISTICS:
(A) LENGTH: 764 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 126:

TGTCCGCTGT GCTCCTGATC CAGCACAGGC GCCCATTGCC TCTCCCAATT GGGCTAAAGG 60

CTTGCCATTG TTCCTGCACA GCTAAGTGCC TGGGTTCATC CTAATCGAGC TGAACACTAG 120

TCACTGGGTT CCACGGTTCT CTTCCATGAC CCATGGCTTC TAATAGAGCT ATAACACTCA 180

CTGCATGGTC CAAGATTCCA TTCCTTGGAA TCCGTGAGAC CAAGAACCCC AGGTCAGAGA 240

ACACAAGGCT TGCCACCATG TTGGAAGCAG CCCACCACCA TTTTGGAAGC AGCCCGCCAC 300

TATCTTGGGA GCTCTGGGAG CAAGGACCCC AGGTAACAAT TTGGTGACCA CGAAGGGACC 360

TGAATCCGCA ACCATGAAGG GATCTCCAAA GCAATTGGAA ATGTTCCTCC CAAGGCAAAA 420

-continued

```
ATGCCCCTAA GATGTATTCT GGAGAATTGG GACCAATTTG ACCCTCAGAC AGTAAGAAAA    480

AAATGACTTA TATTCTTCTG CAGTACCGCC CTGGCCACGA TATCCTCTTC AAGGGGGAGA    540

AACCTGGCCT CCTGAGGGAA GTATAAATTA TAACACCATC TTACAGCTAG ACCTGTTTTG    600

TAGAAAAGGA GGCAAATGGA GTGAAGTGCC ATATTTACAA ACTTTCTTTT CATTAAAAGA    660

CAACTCGCAA TTATGTTAAC AGTGTGATTT GTGTTCCTAC ACGGAAGCCC TCAGATTCTA    720

CTCCCCACCC CCGGCATCTC CCCTGAATCC CTCCCCAACT TATT                     764
```

(2) INFORMATION FOR SEQ ID NO: 127:

(i) SEQUENCE CHARACTERISTICS:
(A) LENGTH: 800 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 127:

```
TGTCCGCTGT GCTCCTGATC CAGCACAGGC GCCCATTGCC TCTCCCAATT GGGCTAAAGG     60

CTTGCCATTG TTCCTGCACA GCTAAGTGCC TGGGTTCATC CTAATCGAGC TGAACACTAG    120

TCACTGGGTT CCACGGTTCT CTTCCATGAC CCATGGCTTC TAATAGAGCT ATAACACTCA    180

CTGCATGGTC CAAGATTCCA TTCCTTGGAA TCCGTGAGAC CAAGAACCCC AGGTCAGAGA    240

ACACAAGGCT TGCCACCATG TTGGAAGCAG CCCACCACCA TTTTGGAAGC GGCCCGCCAC    300

TATCTTGGGA GCTCTGGGAG CAAGGACCCC CAGGTAACAA TTTGGTGACC ACGAAGGGAC    360

CTGAATCCGC AACCATGAAG GGATCTCCAA AGCAATTGGA AATGTTCCTC CCAAGGCAAA    420

AATGCCCCTA AGATGTATTC TGGAGAATTG GGACCAATCT GACCCTCAGA CAGTAAGAAA    480

AAAAATGACT TATATTCTTC TGCAGTACCG CCTGGCCACG GATATCCTCT TCAAGGGGGA    540

GAAACCTGGC CTCCTGAGGG AAGTATAAAT TATAACACCA TCTTACAGCT AGACCTGTTT    600

TGTAGAAAAG GAGGCAAATG GAGTGAAGTG CCATATTTAC AAACTTTCTT TTCATTAAAA    660

GACAACTCGC AATTATGTAA ACAGTGTGAT TTGTGTCCTA CAGGAAGCCC TCAGATCTAC    720

CTCCCTACCC CGGCATCTCC CTGACTCCTT CCCCAACTAA TAAGGACCCA CTTCAGCCCA    780

AACAGTCCAA AAGGACATAG                                                800
```

(2) INFORMATION FOR SEQ ID NO: 128:

(i) SEQUENCE CHARACTERISTICS:
(A) LENGTH: 438 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 128:

```
GACTTGAGCC AGTCYTCATA CCTGGACAYT CTTGTCCTTC GGTACATGGA TGATTTACTT     60

TTAGCCACCC ATTCAGAAAC CTTGTGCCAT CAAGCCACCC AAGCACTCTT AAATTTCCTT    120

GCTACCTGTG GCTACAAGGT TTCCAAACCA AAGGCTCAGC TCTGCTCACA GCAGGTTAAA    180

TACTTAGGGC TAAAATTATC CAAAGGCACC AGAACCCTCA GTGAGGAACG TATCCAGCCT    240

ATACTGGGTT ATCCTCATCC CAAAACCCTA AAGCAACTAA CAGCGTTCCT TGGCATAACA    300

GGTTTCTGCC AAATATGGAT TCCCAGGTAC AGCAARRTAG CCAGACCATT AAATACACGA    360

ATTAAGGAAA CTCAAAAAGC CARTACCCAT TTAGTAAGAT GGACAYCTGA AGCAGAAGTG    420
```

-continued

GCTTTCCAGG CCCTAAAG 438

(2) INFORMATION FOR SEQ ID NO: 129:

(i) SEQUENCE CHARACTERISTICS:
(A) LENGTH: 438 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 129:

GACTTGAGCC AGTCCTCATA CCTGGACACT CTTGTCCTTC GGTACATGGA TGATTTACTT 60

TTAGCCACCC ATTCAGAAAC CTTGTGCCAT CAAGCCACCC AAGCACTCTT AAATTTCCTT 120

GCTACCTGTG GCTACAAGGT TTCCAAACCA AAGGCTCAGC TCTGCTCACA GCAGGTTAAA 180

TACTTAGGGC TAAAATTATC CAAAGGCACC AGAACCCTCA GTGAGGAACG TATCCAGCCT 240

ATACTGGGTT ATCCTCATCC CAAAACCCTA AAGCAACTAA CAGCGTTCCT TGGCATAACA 300

GGTTTCTGCC AAATATGGAT TCCCAGGTAC AGCAAGATAG CCAGACCATT AAATACACGA 360

ATTAAGGAAA CTCAAAAAGC CAATACCCAT TTAGTAAGAT GGACACCTGA AGCAGAAGTG 420

GCTTTCCAGG CCCTAAAG 438

(2) INFORMATION FOR SEQ ID NO: 130:

(i) SEQUENCE CHARACTERISTICS:
(A) LENGTH: 438 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 130:

GACTTGAGCC AGTCCTCATA CCTGGACACT CTTGTCCTTC GGTACATGGA TGATTTACTT 60

TTAGCCACCC ATTCAGAAAC CTTGTGCCAT CAAGCCACCC AAGCACTCTT AAATTTCCTT 120

GCTACCTGTG GCTACAAGGT TTCCAAACCA AAGGCTCAGC TCTGCTCACA GCAGGTTAAA 180

TACTTAGGGC TAAAATTATC CAAAGGCACC AGAACCCTCA GTGAGGAACG TATCCAGCCT 240

ATACTGGGTT ATCCTCATCC CAAAACCCTA AAGCAACTAA CAGCGTTCCT TGGCATAACA 300

GGTTTCTGCC AAATATGGAT TCCCAGGTAC AGCAAAGTAG CCAGACCATT AAATACACGA 360

ATTAAGGAAA CTCAAAAAGC CAGTACCCAT TTAGTAAGAT GGACACCTGA AGCAGAAGTG 420

GCTTTCCAGG CCCTAAAG 438

(2) INFORMATION FOR SEQ ID NO: 131:

(i) SEQUENCE CHARACTERISTICS:
(A) LENGTH: 438 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 131:

GACTTGAGCC AGTCYTCATA CCTGGACAYT CTTGTCCTTC GGTACATGGA TGATTTACTT 60

TTAGCCACCC ATTCAGAAAC CTTGTGCCAT CAAGCCACCC AAGCACTCTT AAATTTCCTT 120

GCTACCTGTG GCTACAAGGT TTCCAAACCA AAGGCTCAGC TCTGCTCACA GCAGGTTAAA 180

```
TACTTAGGGC TAAAATTATC CAAAGGCACC AGAACCCTCA GTGAGGAACG TATCCAGCCT    240

ATACTGGGTT ATCCTCATCC CAAAACCCTA AAGCAACTAA CAGCGTTCCT TGGCATAACA    300

GGTTTCTGCC AAATATGGAT TCCCAGGTAC AGCAAAATAG CCAGACCATT AAATACACGA    360

ATTAAGGAAA CTCAAAAAGC CAATACCCAT TTAGTAAGAT GGACATCTGA AGCAGAAGTG    420

GCTTTCCAGG CCCTAAAG                                                  438
```

```
(2) INFORMATION FOR SEQ ID NO: 132:

     (i) SEQUENCE CHARACTERISTICS:
          (A) LENGTH: 146 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 132:

Asp Leu Ser Gln Ser Ser Tyr Leu Asp Thr Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Gln Val Lys Tyr Leu Gly Leu
    50                  55                  60

Lys Leu Ser Lys Gly Thr Arg Thr Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
            100                 105                 110

Ile Ala Arg Pro Leu Asn Thr Arg Ile Lys Glu Thr Gln Lys Ala Asn
        115                 120                 125

Thr His Leu Val Arg Trp Thr Pro Glu Ala Glu Val Ala Phe Gln Ala
    130                 135                 140

Leu Lys
145
```

```
(2) INFORMATION FOR SEQ ID NO: 133:

     (i) SEQUENCE CHARACTERISTICS:
          (A) LENGTH: 146 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 133:

Asp Leu Ser Gln Ser Ser Tyr Leu Asp Thr Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Gln Val Lys Tyr Leu Gly Leu
    50                  55                  60
```

-continued

```
Lys Leu Ser Lys Gly Thr Arg Thr Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
            100                 105                 110

Val Ala Arg Pro Leu Asn Thr Arg Ile Lys Glu Thr Gln Lys Ala Ser
        115                 120                 125

Thr His Leu Val Arg Trp Thr Pro Glu Ala Glu Val Ala Phe Gln Ala
    130                 135                 140

Leu Lys
145
```

(2) INFORMATION FOR SEQ ID NO: 134:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 134:

```
Asp Leu Ser Gln Ser Ser Tyr Leu Asp Xaa Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Gln Val Lys Tyr Leu Gly Leu
    50                  55                  60

Lys Leu Ser Lys Gly Thr Arg Thr Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
            100                 105                 110

Ile Ala Arg Pro Leu Asn Thr Arg Ile Lys Glu Thr Gln Lys Ala Asn
        115                 120                 125

Thr His Leu Val Arg Trp Thr Ser Glu Ala Glu Val Ala Phe Gln Ala
    130                 135                 140

Leu Lys
145
```

(2) INFORMATION FOR SEQ ID NO: 135:

(i) SEQUENCE CHARACTERISTICS:
(A) LENGTH: 429 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 135:

```
GACTTGAGCC AGTCCTCATA CCTGGACATT CTTGTTCYTC AGTATRGGGA TGAYTTAATT     60

ATAGCCACCC ATTCAGAAAC CTTGTGGCAY CAAGCCACCC AAGYGCTCTT AAATTTCCTY    120

GCTACCTGTG GCTCCAAACA AARGGCTCAS CTCTGCTCAC ASCAGGTTAA ATACTTAGGG    180
```

-continued

```
CTAAAATTAT CCAAAGTCRC CAGGGCCCTC AGAGAGGAAC GTATCCAGCG TATACTGGYT    240

TATCCYCATC CCAWAACCYT AAAGCAACTA AGARGGTTCC TTGGCATAWC AGCCTTCTGC    300

CGAATATGGA TTCCCVGATA CAGYGAAATA GCCAGGCCAT TATGTACATT ADYTAAGGAA    360

ACTCAGAAAG CCAATACCCA TATAGTAAGA TGGACACCTG ARACAGAAGT GGCTTTCCAG    420

GCCCTAAAG                                                            429
```

(2) INFORMATION FOR SEQ ID NO: 136:

(i) SEQUENCE CHARACTERISTICS:
(A) LENGTH: 429 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 136:

```
GACTTGAGCC AGTCCTCATA CCTGGACATT CTTGTTCTTC AGTATGGGGA TGACTTAATT     60

ATAGCCACCC ATTCAGAAAC CTTGTGGCAT CAAGCCACCC AAGCGCTCTT AAATTTCCTT    120

GCTACCTGTG GCTCCAAACA AAAGGCTCAC CTCTGCTCAC ACCAGGTTAA ATACTTAGGG    180

CTAAAATTAT CCAAAGTCAC CAGGGCCCTC AGAGAGGAAC GTATCCAGCG TATACTGGCT    240

TATCCTCATC CCATAACCCT AAAGCAACTA AGAGGGTTCC TTGGCATATC AGCCTTCTGC    300

CGAATATGGA TTCCCGGATA CAGTGAAATA GCCAGGCCAT TATGTACATT AATTAAGGAA    360

ACTCAGAAAG CCAATACCCA TATAGTAAGA TGGACACCTG AAACAGAAGT GGCTTTCCAG    420

GCCCTAAAG                                                            429
```

(2) INFORMATION FOR SEQ ID NO: 137:

(i) SEQUENCE CHARACTERISTICS:
(A) LENGTH: 429 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 137:

```
GACTTGAGCC AGTCCTCATA CCTGGACATT CTTGTTCTTC AGTATAGGGA TGATTTAATT     60

ATAGCCACCC ATTCAGAAAC CTTGTGGCAT CAAGCCACCC AAGTGCTCTT AAATTTCCTC    120

GCTACCTGTG GCTCCAAACA AAGGGCTCAG CTCTGCTCAC AGCAGGTTAA ATACTTAGGG    180

CTAAAATTAT CCAAAGTCGC CAGGGCCCTC AGAGAGGAAC GTATCCAGCG TATACTGGAT    240

TATCCTCATC CCAAAACCAT AAAGCAACTA AGAGGGTTCC TTGGCATAAC AGCCTTCTGC    300

CGAATATGGA TTCCCCGATA CAGTGAAATA GCCAGGCCAT TATGTACATT AGTTAAGGAA    360

ACTCAGAAAG CCAATACCCA TATAGTAAGA TGGACACCTG AGACAGAAGT GGCTTTCCAG    420

GCCCTAAAG                                                            429
```

(2) INFORMATION FOR SEQ ID NO: 138:

(i) SEQUENCE CHARACTERISTICS:
(A) LENGTH: 429 base pairs
(B) TYPE: nucleic acid
(C) STRANDEDNESS: single
(D) TOPOLOGY: linear (ii) MOLECULE TYPE: cDNA -continued (xi) SEQUENCE DESCRIPTION: SEQ ID NO: 138:

GACTTGAGCC AGTCCTCATA CCTGGACATT CTTGTTCCTC AGTATGGGGA TGATTTAATT 60

ATAGCCACCC ATTCAGAAAC CTTGTGGCAC CAAGCCACCC AAGCGCTCTT AAATTTCCTC 120

GCTACCTGTG GCTCCAAACA AAAGGCTCAG CTCTGCTCAC AGCAGGTTAA ATACTTAGGG 180

CTAAAATTAT CCAAAGTCAC CAGGGCCCTC AGAGAGGAAC GTATCCAGCG TATACTGGCT 240

TATCCCCATC CCAAAACCCT AAAGCAACTA AGARGGTTCC TTGGCATAAC AGCCTTCTGC 300

CGAATATGGA TTCCCAGATA CAGCGAAATA GCCAGGCCAT TATGTACATT ATCTAAGGAA 360

ACTCAGAAAG CCAATACCCA TATAGTAAGA TGGACACCTG AAACAGAAGT GGCTTTCCAG 420

GCCCTAAAG 429

(2) INFORMATION FOR SEQ ID NO: 139:

(i) SEQUENCE CHARACTERISTICS:
(A) LENGTH: 143 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 139:

Asp Leu Ser Gln Ser Ser Tyr Leu Asp Ile Leu Val Leu Gln Tyr Gly
1 5 10 15

Asp Asp Leu Ile Ile Ala Thr His Ser Glu Thr Leu Trp His Gln Ala
20 25 30

Thr Gln Ala Leu Leu Asn Phe Leu Ala Thr Cys Gly Ser Lys Gln Lys
35 40 45

Ala His Leu Cys Ser His Gln Val Lys Tyr Leu Gly Leu Lys Leu Ser
50 55 60

Lys Val Thr Arg Ala Leu Arg Glu Glu Arg Ile Gln Arg Ile Leu Ala
65 70 75 80

Tyr Pro His Pro Ile Thr Leu Lys Gln Leu Arg Gly Phe Leu Gly Ile
85 90 95

Ser Ala Phe Cys Arg Ile Trp Ile Pro Gly Tyr Ser Glu Ile Ala Arg
100 105 110

Pro Leu Cys Thr Leu Ile Lys Glu Thr Gln Lys Ala Asn Thr His Ile
115 120 125

Val Arg Trp Thr Pro Glu Thr Glu Val Ala Phe Gln Ala Leu Lys
130 135 140

(2) INFORMATION FOR SEQ ID NO: 140:

(i) SEQUENCE CHARACTERISTICS:
(A) LENGTH: 143 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 140:

Asp Leu Ser Gln Ser Ser Tyr Leu Asp Ile Leu Val Leu Gln Tyr Arg
1 5 10 15

Asp Asp Leu Ile Ile Ala Thr His Ser Glu Thr Leu Trp His Gln Ala
20 25 30

Thr Gln Val Leu Leu Asn Phe Leu Ala Thr Cys Gly Ser Lys Gln Arg

-continued

```
        35                  40                  45

Ala Gln Leu Cys Ser Gln Gln Val Lys Tyr Leu Gly Leu Lys Leu Ser
    50                  55                  60

Lys Val Ala Arg Ala Leu Arg Glu Glu Arg Ile Gln Arg Ile Leu Asp
65                  70                  75                  80

Tyr Pro His Pro Lys Thr Ile Lys Gln Leu Arg Gly Phe Leu Gly Ile
                85                  90                  95

Thr Ala Phe Cys Arg Ile Trp Ile Pro Arg Tyr Ser Glu Ile Ala Arg
            100                 105                 110

Pro Leu Cys Thr Leu Val Lys Glu Thr Gln Lys Ala Asn Thr His Ile
        115                 120                 125

Val Arg Trp Thr Pro Glu Thr Glu Val Ala Phe Gln Ala Leu Lys
    130                 135                 140
```

(2) INFORMATION FOR SEQ ID NO: 141:

(i) SEQUENCE CHARACTERISTICS:
(A) LENGTH: 143 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 141:

```
Asp Leu Ser Gln Ser Ser Tyr Leu Asp Ile Leu Val Pro Gln Tyr Gly
1               5                   10                  15

Asp Asp Leu Ile Ile Ala Thr His Ser Glu Thr Leu Trp His Gln Ala
            20                  25                  30

Thr Gln Ala Leu Leu Asn Phe Leu Ala Thr Cys Gly Ser Lys Gln Lys
        35                  40                  45

Ala Gln Leu Cys Ser Gln Gln Val Lys Tyr Leu Gly Leu Lys Leu Ser
    50                  55                  60

Lys Val Thr Arg Ala Leu Arg Glu Glu Arg Ile Gln Arg Ile Leu Ala
65                  70                  75                  80

Tyr Pro His Pro Lys Thr Leu Lys Gln Leu Arg Xaa Phe Leu Gly Ile
                85                  90                  95

Thr Ala Phe Cys Arg Ile Trp Ile Pro Arg Tyr Ser Glu Ile Ala Arg
            100                 105                 110

Pro Leu Cys Thr Leu Ser Lys Glu Thr Gln Lys Ala Asn Thr His Ile
        115                 120                 125

Val Arg Trp Thr Pro Glu Thr Glu Val Ala Phe Gln Ala Leu Lys
    130                 135                 140
```

(2) INFORMATION FOR SEQ ID NO: 142:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 142:

```
GGCCAGGCAT CAGCCCAAGA CTTGA                                          25
```

(2) INFORMATION FOR SEQ ID NO: 143:

(i) SEQUENCE CHARACTERISTICS:

-continued (A) LENGTH: 22 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 143:

TGCAAGCTCA TCCCTSRGAC CT 22

(2) INFORMATION FOR SEQ ID NO: 144:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 144:

GACTTGAGCC AGTCCTCATA CCT 23

(2) INFORMATION FOR SEQ ID NO: 145:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 145:

CTTTAGGGCC TGGAAAGCCA CT 22

(2) INFORMATION FOR SEQ ID NO: 146:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 146:

Phe Cys Ile Pro Val Arg Pro Asp
1 5

(2) INFORMATION FOR SEQ ID NO: 147:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 147:

Arg Pro Asp Ser Gln Phe Leu Phe
1 5

(2) INFORMATION FOR SEQ ID NO: 148:

(i) SEQUENCE CHARACTERISTICS:
(A) LENGTH: 8 amino acids
(B) TYPE: amino acid

-continued (C) STRANDEDNESS: single
(D) TOPOLOGY: linear (ii) MOLECULE TYPE: peptide (xi) SEQUENCE DESCRIPTION: SEQ ID NO: 148:

Thr Val Leu Pro Gln Gly Phe Arg
1 5

(2) INFORMATION FOR SEQ ID NO: 149:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 149:

Leu Phe Gly Gln Ala Leu Ala Gln
1 5

(2) INFORMATION FOR SEQ ID NO: 150:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 150:

Asp Ala Phe Phe Cys Ile Pro Val
1 5

(2) INFORMATION FOR SEQ ID NO: 151:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 151:

Ala Phe Phe Cys Ile Pro Val Arg
1 5

(2) INFORMATION FOR SEQ ID NO: 152:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 152:

Phe Phe Cys Ile Pro Val Arg Pro
1 5

(2) INFORMATION FOR SEQ ID NO: 153:

(i) SEQUENCE CHARACTERISTICS:
(A) LENGTH: 8 amino acids

-continued (B) TYPE: amino acid
(C) STRANDEDNESS: single
(D) TOPOLOGY: linear (ii) MOLECULE TYPE: peptide (xi) SEQUENCE DESCRIPTION: SEQ ID NO: 153:

Cys Ile Pro Val Arg Pro Asp Ser
1 5

(2) INFORMATION FOR SEQ ID NO: 154:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 154:

Ile Pro Val Arg Pro Asp Ser Gln
1 5

(2) INFORMATION FOR SEQ ID NO: 155:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 155:

Pro Val Arg Pro Asp Ser Gln Phe
1 5

(2) INFORMATION FOR SEQ ID NO: 156:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 156:

Val Arg Pro Asp Ser Gln Phe Leu
1 5

(2) INFORMATION FOR SEQ ID NO: 157:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 157:

Pro Asp Ser Gln Phe Leu Phe Ala
1 5

(2) INFORMATION FOR SEQ ID NO: 158:

(i) SEQUENCE CHARACTERISTICS:

-continued (A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 158:

Asp Ser Gln Phe Leu Phe Ala Phe
1 5

(2) INFORMATION FOR SEQ ID NO: 159:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 159:

Ser Gln Phe Leu Phe Ala Phe Glu
1 5

(2) INFORMATION FOR SEQ ID NO: 160:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 160:

Gln Phe Leu Phe Ala Phe Glu Asp
1 5

(2) INFORMATION FOR SEQ ID NO: 161:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 161:

Phe Leu Phe Ala Phe Glu Asp Pro
1 5

(2) INFORMATION FOR SEQ ID NO: 162:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 162:

Ala Phe Glu Asp Pro Leu Asn Pro
1 5

(2) INFORMATION FOR SEQ ID NO: 163:

-continued (i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 163:

Phe Glu Asp Pro Leu Asn Pro Thr
1 5

(2) INFORMATION FOR SEQ ID NO: 164:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 164:

Glu Asp Pro Leu Asn Pro Thr Ser
1 5

(2) INFORMATION FOR SEQ ID NO: 165:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 165:

Asp Pro Leu Asn Pro Thr Ser Gln
1 5

(2) INFORMATION FOR SEQ ID NO: 166:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 166:

Pro Leu Asn Pro Thr Ser Gln Leu
1 5

(2) INFORMATION FOR SEQ ID NO: 167:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 167:

Leu Asn Pro Thr Ser Gln Leu Thr
1 5

(2) INFORMATION FOR SEQ ID NO: 168:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 168:

Asn Pro Thr Ser Gln Leu Thr Trp
1 5

(2) INFORMATION FOR SEQ ID NO: 169:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 169:

Pro Thr Ser Gln Leu Thr Trp Thr
1 5

(2) INFORMATION FOR SEQ ID NO: 170:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 170:

Thr Ser Gln Leu Thr Trp Thr Val
1 5

(2) INFORMATION FOR SEQ ID NO: 171:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 171:

Ser Gln Leu Thr Trp Thr Val Leu
1 5

(2) INFORMATION FOR SEQ ID NO: 172:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 172:

Gln Leu Thr Trp Thr Val Leu Pro
1 5

-continued (2) INFORMATION FOR SEQ ID NO: 173:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 173:

Leu Thr Trp Thr Val Leu Pro Gln
1 5

(2) INFORMATION FOR SEQ ID NO: 174:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 174:

Thr Trp Thr Val Leu Pro Gln Gly
1 5

(2) INFORMATION FOR SEQ ID NO: 175:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 175:

Trp Thr Val Leu Pro Gln Gly Phe
1 5

(2) INFORMATION FOR SEQ ID NO: 176:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 176:

Val Leu Pro Gln Gly Phe Arg Asp
1 5

(2) INFORMATION FOR SEQ ID NO: 177:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 177:

Leu Pro Gln Gly Phe Arg Asp Ser
1 5

(2) INFORMATION FOR SEQ ID NO: 178:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 178:

```
Pro Gln Gly Phe Arg Asp Ser Pro
1               5
```

(2) INFORMATION FOR SEQ ID NO: 179:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 179:

```
Gln Gly Phe Arg Asp Ser Pro His
1               5
```

(2) INFORMATION FOR SEQ ID NO: 180:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 180:

```
Gly Phe Arg Asp Ser Pro His Leu
1               5
```

(2) INFORMATION FOR SEQ ID NO: 181:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 181:

```
Phe Arg Asp Ser Pro His Leu Phe
1               5
```

(2) INFORMATION FOR SEQ ID NO: 182:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 182:

```
Arg Asp Ser Pro His Leu Phe Gln
1               5
```

(2) INFORMATION FOR SEQ ID NO: 183:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 183:

Asp Ser Pro His Leu Phe Gly Gln
1 5

(2) INFORMATION FOR SEQ ID NO: 184:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 184:

Ser Pro His Leu Phe Gly Gln Ala
1 5

(2) INFORMATION FOR SEQ ID NO: 185:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 185:

Pro His Leu Phe Gly Gln Ala Leu
1 5

(2) INFORMATION FOR SEQ ID NO: 186:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 186:

His Leu Phe Gly Gln Ala Leu Ala
1 5

(2) INFORMATION FOR SEQ ID NO: 187:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 187:

TGGAAAGTGT TACCCC 16

-continued (2) INFORMATION FOR SEQ ID NO: 188:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 188:

AGTGTTACCC CAAGG 15

(2) INFORMATION FOR SEQ ID NO: 189:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 189:

ATGTACCTAC TGTACGAC 18

(2) INFORMATION FOR SEQ ID NO: 190:

(i) SEQUENCE CHARACTERISTICS:
(A) LENGTH: 129 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 190:

TGGAAAGTAC TACCCCAAGG GTTTAAAAAT AGTCCCACCC TGTTCGAAAT GCAGCTGGCC 60

CATATCCTGC AGCCCATTCG GCAAGCTTTC CCCCAATGCA CTATTCTTCA GTACATGGAT 120

GACATTCTC 129

(2) INFORMATION FOR SEQ ID NO: 191:

(i) SEQUENCE CHARACTERISTICS:
(A) LENGTH: 129 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 191:

TACAATGTGC TTCCACAGGG ATGGAAAGGA TCACCAGCAA TATTCCAAAG TAGCATGACA 60

AAAATCTTAG AGCCTTTTAA AAAACAAAAT CCAGACATAG TTATCTATCA ATACATGGAT 120

GATTTGTAT 129

(2) INFORMATION FOR SEQ ID NO: 192:

(i) SEQUENCE CHARACTERISTICS:
(A) LENGTH: 129 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO: 192:

TGGACCAGAC TCCCACAGGG TTTCAAAAAC AGTCCCACCC TGTTTGATGA GGCACTGCAC 60

AGAGACCTAG CAGACTTCCG GATCCAGCAC CCAGACTTGA TCCTGCTACA GTACGTGGAT 120

GACTTACTG 129

(2) INFORMATION FOR SEQ ID NO: 193:

(i) SEQUENCE CHARACTERISTICS:
(A) LENGTH: 129 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 193:

TGGAAGGTTT TACCACAAGG TATGGCCAAC AGTCCTACCT TATGTCAAAA ATATGTGGCC 60

ACAGCCATAC ATAAGGTTAG ACATGCCTGG AAACAAATGT ATATTATACA TTACATGGAT 120

GACATCCTA 129

(2) INFORMATION FOR SEQ ID NO: 194:

(i) SEQUENCE CHARACTERISTICS:
(A) LENGTH: 123 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 194:

TGGATGGTCT TGCCCCAAGG GTTTAGGGAT AGCCCTCATC TGTTTGGTCA GGCCCTAGCC 60

AAAGATCTAG GCCACTTCTC AAGTCCAGGC ACTCTGGTCC TTCAATATGT GGATGATTTA 120

CTT 123

(2) INFORMATION FOR SEQ ID NO: 195:

(i) SEQUENCE CHARACTERISTICS:
(A) LENGTH: 85 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 195:

GTTCAGGGAT AGCCCCCATC TATTTGGCCA GGCATTAGCC CAAGACTTGA GCCAATTCTC 60

ATACCTGGAC ACTCTTGTCC TTCAG 85

(2) INFORMATION FOR SEQ ID NO: 196:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 196:

CATCTNTTTG GNCAGGCANT AGC 23

(2) INFORMATION FOR SEQ ID NO: 197:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 197:

CTTGAGCCAG TTCTCATACC TGGA 24

(2) INFORMATION FOR SEQ ID NO: 198:

(i) SEQUENCE CHARACTERISTICS:
(A) LENGTH: 683 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 198:

```
Ile Met Pro Glu Ser Pro Thr Pro Leu Leu Gly Arg Asp Ile Leu Ala
1               5                   10                  15

Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
        35                  40                  45

Glu Gly Gln Tyr Gly Gln Ala Lys Asn Ala Arg Pro Val Gln Val Lys
    50                  55                  60

Leu Lys Asp Ser Ala Ser Phe Pro Tyr Gln Arg Lys Tyr Pro Leu Arg
65                  70                  75                  80

Pro Glu Ala Leu Gln Gly Xaa Gln Lys Ile Val Lys Asp Leu Lys Ala
                85                  90                  95

Gln Gly Leu Val Lys Pro Cys Ser Ser Pro Cys Asn Thr Pro Ile Leu
            100                 105                 110

Gly Val Arg Lys Pro Asn Gly Gln Trp Arg Leu Val Gln Asp Leu Arg
        115                 120                 125

Ile Ile Asn Glu Ala Val Phe Pro Leu Tyr Pro Ala Val Ser Ser Pro
    130                 135                 140

Tyr Thr Leu Leu Ser Leu Ile Pro Glu Glu Ala Glu Trp Phe Thr Val
145                 150                 155                 160

Leu Asp Leu Lys Asp Ala Phe Phe Cys Ile Pro Val Arg Pro Asp Ser
                165                 170                 175

Gln Phe Leu Phe Ala Phe Glu Asp Pro Leu Asn Pro Thr Ser Gln Leu
            180                 185                 190

Thr Trp Thr Val Leu Pro Gln Gly Phe Arg Asp Ser Pro His Leu Phe
        195                 200                 205

Gly Gln Ala Leu Ala Gln Asp Leu Ser Gln Pro Ser Tyr Leu Asp Ile
    210                 215                 220

Leu Val Leu Gln Tyr Val Asp Asp Leu Leu Leu Val Ala Arg Ser Glu
225                 230                 235                 240

Thr Leu Cys His Gln Ala Thr Gln Glu Leu Leu Ile Phe Leu Thr Thr
                245                 250                 255

Cys Gly Tyr Lys Val Ser Lys Pro Lys Ala Arg Leu Cys Ser Gln Glu
            260                 265                 270
```

-continued

```
Ile Arg Tyr Leu Gly Leu Lys Leu Ser Lys Gly Thr Arg Ala Leu Ser
        275                 280                 285

Glu Glu Arg Ile Gln Pro Ile Leu Ala Tyr Pro His Pro Lys Thr Leu
    290                 295                 300

Lys Gln Leu Arg Gly Phe Leu Gly Ile Thr Gly Phe Cys Arg Lys Gln
305                 310                 315                 320

Ile Pro Arg Tyr Thr Pro Ile Ala Arg Pro Leu Tyr Thr Leu Ile Arg
                325                 330                 335

Glu Thr Gln Lys Ala Asn Thr Tyr Leu Val Arg Trp Thr Pro Thr Glu
            340                 345                 350

Val Ala Phe Gln Ala Leu Lys Lys Ala Leu Thr Gln Ala Pro Val Phe
        355                 360                 365

Ser Leu Pro Thr Gly Gln Asp Phe Ser Leu Tyr Ala Thr Glu Lys Thr
    370                 375                 380

Gly Ile Ala Leu Gly Val Leu Thr Gln Val Ser Gly Met Ser Leu Gln
385                 390                 395                 400

Pro Val Val Tyr Leu Ser Lys Glu Ile Asp Val Val Ala Lys Gly Trp
                405                 410                 415

Pro His Cys Leu Trp Val Met Ala Ala Val Ala Val Leu Val Ser Glu
            420                 425                 430

Ala Val Lys Ile Ile Gln Gly Arg Asp Leu Thr Val Trp Thr Ser His
        435                 440                 445

Asp Val Asn Gly Ile Leu Thr Ala Lys Gly Asp Leu Trp Leu Ser Asp
    450                 455                 460

Asn His Leu Leu Asn Tyr Gln Ala Leu Leu Leu Glu Glu Pro Val Leu
465                 470                 475                 480

Arg Leu Arg Thr Cys Ala Thr Leu Gln Pro Ala Thr Phe Leu Pro Asp
                485                 490                 495

Asn Glu Glu Gln Ile Glu His Asn Cys Gln Gln Val Ile Ala Gln Thr
            500                 505                 510

Tyr Ala Ala Arg Gly Asp Leu Leu Glu Val Pro Leu Thr Asp Pro Asp
        515                 520                 525

Leu Asn Leu Tyr Thr Asp Gly Ser Ser Leu Ala Glu Lys Gly Leu Arg
    530                 535                 540

Lys Ala Gly Tyr Ala Val Ile Ser Asp Asn Gly Ile Leu Glu Ser Asn
545                 550                 555                 560

Arg Leu Thr Pro Gly Thr Ser Ala His Leu Ala Glu Leu Ile Ala Leu
                565                 570                 575

Thr Trp Ala Leu Glu Leu Gly Glu Gly Lys Arg Val Asn Ile Tyr Ser
            580                 585                 590

Asp Ser Lys Tyr Ala Tyr Leu Val Leu His Ala His Ala Ala Ile Trp
        595                 600                 605

Arg Glu Arg Glu Phe Leu Thr Ser Glu Gly Thr Pro Ile Asn His Gln
    610                 615                 620

Glu Ala Ile Arg Arg Leu Leu Leu Ala Val Gln Lys Pro Lys Glu Val
625                 630                 635                 640

Ala Val Leu His Cys Gln Gly His Gln Glu Glu Glu Glu Arg Glu Ile
                645                 650                 655

Glu Gly Asn Arg Gln Ala Asp Ile Glu Ala Lys Lys Ala Ala Arg Gln
            660                 665                 670

Asp Ser Pro Leu Glu Met Leu Ile Glu Gly Pro
        675                 680
```

-continued (2) INFORMATION FOR SEQ ID NO: 199:

(i) SEQUENCE CHARACTERISTICS:
(A) LENGTH: 143 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 199:

```
Asp Leu Ser Gln Ser Ser Tyr Leu Asp Ile Leu Val Leu Gln Tyr Gly
1               5                   10                  15

Asp Asp Leu Ile Ile Ala Thr His Ser Glu Thr Leu Trp His Gln Ala
            20                  25                  30

Thr Gln Ala Leu Leu Asn Phe Leu Ala Thr Cys Gly Ser Lys Gln Lys
        35                  40                  45

Ala Gln Leu Cys Ser Gln Gln Val Lys Tyr Leu Gly Leu Lys Leu Ser
    50                  55                  60

Lys Val Thr Arg Ala Leu Arg Glu Glu Arg Ile Gln Arg Ile Leu Ala
65                  70                  75                  80

Tyr Pro His Pro Lys Thr Leu Lys Gln Leu Arg Gly Phe Leu Gly Ile
                85                  90                  95

Thr Ala Phe Cys Arg Ile Trp Ile Pro Arg Tyr Ser Glu Ile Ala Arg
            100                 105                 110

Pro Leu Cys Thr Leu Xaa Lys Glu Thr Gln Lys Ala Asn Thr His Ile
        115                 120                 125

Val Arg Trp Thr Pro Glu Thr Glu Val Ala Phe Gln Ala Leu Lys
    130                 135                 140
```

(2) INFORMATION FOR SEQ ID NO: 200:

(i) SEQUENCE CHARACTERISTICS:
(A) LENGTH: 683 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 200:

```
Ile Met Pro Glu Ser Pro Thr Pro Leu Leu Gly Arg Asp Ile Leu Ala
1               5                   10                  15

Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
        35                  40                  45

Glu Gly Gln Tyr Gly Gln Ala Lys Asn Ala Arg Pro Val Gln Val Lys
    50                  55                  60

Leu Lys Asp Ser Ala Ser Phe Pro Tyr Gln Arg Lys Tyr Pro Leu Arg
65                  70                  75                  80

Pro Glu Ala Leu Gln Gly Xaa Gln Lys Ile Val Lys Asp Leu Lys Ala
                85                  90                  95

Gln Gly Leu Val Lys Pro Cys Ser Ser Pro Cys Asn Thr Pro Ile Leu
            100                 105                 110

Gly Val Arg Lys Pro Asn Gly Gln Trp Arg Leu Val Gln Asp Leu Arg
        115                 120                 125

Ile Ile Asn Glu Ala Val Phe Pro Leu Tyr Pro Ala Val Ser Ser Pro
    130                 135                 140
```

-continued

```
Tyr Thr Leu Leu Ser Leu Ile Pro Glu Glu Ala Glu Trp Phe Thr Val
145                 150                 155                 160

Leu Asp Leu Lys Asp Ala Phe Phe Cys Ile Pro Val Arg Pro Asp Ser
                165                 170                 175

Gln Phe Leu Phe Ala Phe Glu Asp Pro Leu Asn Pro Thr Ser Gln Leu
            180                 185                 190

Thr Trp Thr Val Leu Pro Gln Gly Phe Arg Asp Ser Pro His Leu Phe
        195                 200                 205

Gly Gln Ala Leu Ala Gln Asp Leu Ser Gln Pro Ser Tyr Leu Asp Ile
    210                 215                 220

Leu Val Leu Gln Tyr Val Asp Asp Leu Leu Leu Val Ala Arg Ser Glu
225                 230                 235                 240

Thr Leu Cys His Gln Ala Thr Gln Glu Leu Leu Ile Phe Leu Thr Thr
                245                 250                 255

Cys Gly Tyr Lys Val Ser Lys Pro Lys Ala Arg Leu Cys Ser Gln Glu
            260                 265                 270

Ile Arg Tyr Leu Gly Leu Lys Leu Ser Lys Gly Thr Arg Ala Leu Ser
        275                 280                 285

Glu Glu Arg Ile Gln Pro Ile Leu Ala Tyr Pro His Pro Lys Thr Leu
    290                 295                 300

Lys Gln Leu Arg Gly Phe Leu Gly Ile Thr Gly Phe Cys Arg Lys Gln
305                 310                 315                 320

Ile Pro Arg Tyr Thr Pro Ile Ala Arg Pro Leu Tyr Thr Leu Ile Arg
                325                 330                 335

Glu Thr Gln Lys Ala Asn Thr Tyr Leu Val Arg Trp Thr Pro Thr Glu
            340                 345                 350

Val Ala Phe Gln Ala Leu Lys Lys Ala Leu Thr Gln Ala Pro Val Phe
        355                 360                 365

Ser Leu Pro Thr Gly Gln Asp Phe Ser Leu Tyr Ala Thr Glu Lys Thr
    370                 375                 380

Gly Ile Ala Leu Gly Val Leu Thr Gln Val Ser Gly Met Ser Leu Gln
385                 390                 395                 400

Pro Val Val Tyr Leu Ser Lys Glu Ile Asp Val Val Ala Lys Gly Trp
                405                 410                 415

Pro His Cys Leu Trp Val Met Ala Ala Val Ala Val Leu Val Ser Glu
            420                 425                 430

Ala Val Lys Ile Ile Gln Gly Arg Asp Leu Thr Val Trp Thr Ser His
        435                 440                 445

Asp Val Asn Gly Ile Leu Thr Ala Lys Gly Asp Leu Trp Leu Ser Asp
    450                 455                 460

Asn His Leu Leu Asn Tyr Gln Ala Leu Leu Leu Glu Glu Pro Val Leu
465                 470                 475                 480

Arg Leu Arg Thr Cys Ala Thr Leu Gln Pro Ala Thr Phe Leu Pro Asp
                485                 490                 495

Asn Glu Glu Gln Ile Glu His Asn Cys Gln Gln Val Ile Ala Gln Thr
            500                 505                 510

Tyr Ala Ala Arg Gly Asp Leu Leu Glu Val Pro Leu Thr Asp Pro Asp
        515                 520                 525

Leu Asn Leu Tyr Thr Asp Gly Ser Ser Leu Ala Glu Lys Gly Leu Arg
    530                 535                 540

Lys Ala Gly Tyr Ala Val Ile Ser Asp Asn Gly Ile Leu Glu Ser Asn
545                 550                 555                 560

Arg Leu Thr Pro Gly Thr Ser Ala His Leu Ala Glu Leu Ile Ala Leu
```

-continued

```
                565                 570                 575

Thr Trp Ala Leu Glu Leu Gly Glu Gly Lys Arg Val Asn Ile Tyr Ser
            580                 585                 590

Asp Ser Lys Tyr Ala Tyr Leu Val Leu His Ala His Ala Ala Ile Trp
        595                 600                 605

Arg Glu Arg Glu Phe Leu Thr Ser Glu Gly Thr Pro Ile Asn His Gln
    610                 615                 620

Glu Ala Ile Arg Arg Leu Leu Leu Ala Val Gln Lys Pro Lys Glu Val
625                 630                 635                 640

Ala Val Leu His Cys Gln Gly His Gln Glu Glu Glu Glu Arg Glu Ile
                645                 650                 655

Glu Gly Asn Arg Gln Ala Asp Ile Glu Ala Lys Lys Ala Ala Arg Gln
            660                 665                 670

Asp Ser Pro Leu Glu Met Leu Ile Glu Gly Pro
        675                 680
```

(2) INFORMATION FOR SEQ ID NO: 201:

(i) SEQUENCE CHARACTERISTICS:
(A) LENGTH: 438 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 201:

```
GACTTGAGCC AGTCYTCATA CCTGGACAYT CTTGTYCYTC RGTAYRKGGA TGAYTTAMTT     60

WTAGCCACCC ATTCAGAAAC CTTGTGSCAY CAAGCCACCC AAGYRCTCTT AAATTTCCTY    120

GCTACCTGTG GCTACAAGGT TTCCAAACMA ARGGCTCASC TCTGCTCACA SCAGGTTAAA    180

TACTTAGGGC TAAAATTATC CAAAGKCRCC AGRRCCCTCA GWGAGGAACG TATCCAGCST    240

ATACTGGVTT ATCCYCATCC CAWAACCMTA AAGCAACTAA SARSGTTCCT TGGCATAWCA    300

GSYTTCTGCC RAATATGGAT TCCCVGRTAC AGYRARRTAG CCAGRCCATT AWRTACAYKA    360

DYTAAGGAAA CTCARAAAGC CARTACCCAT WTAGTAAGAT GGACAYCTGA RRCAGAAGTG    420

GCTTTCCAGG CCCTAAAG                                                  438
```

(2) INFORMATION FOR SEQ ID NO: 202:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 202:

```
Asp Leu Ser Gln Ser Ser Tyr Leu Asp Thr Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Gln Val Lys Tyr Leu Gly Leu
    50                  55                  60

Lys Leu Ser Lys Gly Thr Arg Thr Leu Ser Glu Glu Arg Ile Gln Pro
65                  70                  75                  80
```

-continued

```
Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
            100                 105                 110

Ile Ala Arg Pro Leu Asn Thr Arg Ile Lys Glu Thr Gln Lys Ala Asn
        115                 120                 125

Thr His Leu Val Arg Trp Thr Pro Glu Ala Glu Val Ala Phe Gln Ala
    130                 135                 140

Leu Lys
145
```

(2) INFORMATION FOR SEQ ID NO: 203:

(i) SEQUENCE CHARACTERISTICS:
(A) LENGTH: 143 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 203:

```
Asp Leu Ser Gln Ser Ser Tyr Leu Asp Ile Leu Val Leu Gln Tyr Gly
1               5                   10                  15

Asp Asp Leu Ile Ile Ala Thr His Ser Glu Thr Leu Trp His Gln Ala
            20                  25                  30

Thr Gln Ala Leu Leu Asn Phe Leu Ala Thr Cys Gly Ser Lys Gln Lys
        35                  40                  45

Ala Gln Leu Cys Ser Gln Gln Val Lys Tyr Leu Gly Leu Lys Leu Ser
    50                  55                  60

Lys Val Thr Arg Ala Leu Arg Glu Glu Arg Ile Gln Arg Ile Leu Ala
65                  70                  75                  80

Tyr Pro His Pro Lys Thr Leu Lys Gln Leu Arg Gly Phe Leu Gly Ile
                85                  90                  95

Thr Ala Phe Cys Arg Ile Trp Ile Pro Arg Tyr Ser Glu Ile Ala Arg
            100                 105                 110

Pro Leu Cys Thr Leu Xaa Lys Glu Thr Gln Lys Ala Asn Thr His Ile
        115                 120                 125

Val Arg Trp Thr Pro Glu Thr Glu Val Ala Phe Gln Ala Leu Lys
    130                 135                 140
```

(2) INFORMATION FOR SEQ ID NO: 204:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 204:

```
Asp Leu Ser Gln Ser Ser Tyr Leu Asp Xaa Leu Val Leu Xaa Tyr Xaa
1               5                   10                  15

Asp Asp Leu Xaa Xaa Ala Thr His Ser Glu Thr Leu Xaa His Gln Ala
            20                  25                  30

Thr Gln Ala Leu Leu Asn Phe Leu Ala Thr Cys Gly Xaa Lys Xaa Xaa
        35                  40                  45

Xaa Xaa Lys Ala Gln Leu Cys Ser Gln Gln Val Lys Tyr Leu Gly Leu
```

-continued

```
    50                  55                  60

Lys Leu Ser Lys Xaa Thr Arg Xaa Leu Xaa Glu Glu Arg Ile Gln Xaa
65                  70                  75                  80

Ile Leu Xaa Tyr Pro His Pro Lys Thr Leu Lys Gln Leu Xaa Xaa Phe
                85                  90                  95

Leu Gly Ile Thr Xaa Phe Cys Xaa Ile Trp Ile Pro Arg Tyr Ser Xaa
            100                 105                 110

Ile Ala Arg Pro Leu Xaa Thr Xaa Xaa Lys Glu Thr Gln Lys Ala Asn
        115                 120                 125

Thr His Xaa Val Arg Trp Thr Pro Glu Xaa Glu Val Ala Phe Gln Ala
    130                 135                 140

Leu Lys
145
```

(2) INFORMATION FOR SEQ ID NO: 205:

(i) SEQUENCE CHARACTERISTICS:
(A) LENGTH: 1597 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 205:

```
ATTATGCCTG AAAGCCCCAC TCCCTTGTTA GGGAGAGACA TTTTAGCAAA AGCAGGGGCC     60

ATTATACACC TGAACATAGG AAAAGGAATA CCCATTTGCT GTCCCCTGCT TGAGGAAGGA    120

ATTAATCCTG AAGTCTGGGC AATAGAAGGA CAATATGGAC AAGCAAAGAA TGCCCGTCCT    180

GTTCAAGTTA AACTAAAGGA TTCTGCCTCC TTTCCCTACC AAAGGAAGTA CCCTCTTAGA    240

CCCGAGGCCC TACAAGGANC TCAAAAGATT GTTAAGGACC TAAAAGCCCA AGGCCTAGTA    300

AAACCATGCA GTAGCCCCTG CAATACTCCA ATTTTAGGAG TAAGGAAACC CAACGGACAG    360

TGGAGGTTAG TGCAAGAACT CAGGATTATC AATGAGGCTG TTGTTCCTCT ATACCCAGCT    420

GTACCTAACC CTTATACAGT GCTTTCCCAA ATACCAGAGG AAGCAGAGTG GTTTACAGTC    480

CTGGACCTTA AGGATGCCTT TTTCTGCATC CCTGTACGTC CTGACTCTCA ATTCTTGTTT    540

GCCTTTGAAG ATCCTTTGAA CCCAACGTCT CAACTCACCT GGACTGTTTT ACCCCAAGGG    600

TTCAGGGATA GCCCCCATCT ATTTGGCCAG GCATTAGCCC AAGACTTGAG TCAATTCTCA    660

TACCTGGACA CTCTTGTCCT TCAGTACATG GATGATTTAC TTTTAGTCGC CCGTTCAGAA    720

ACCTTGTGCC ATCAAGCCAC CCAAGAACTC TTAACTTTCC TCACTACCTG TGGCTACAAG    780

GTTTCCAAAC CAAAGGCTCG GCTCTGCTCA CAGGAGATTA GATACTNAGG GCTAAAATTA    840

TCCAAAGGCA CCAGGGCCCT CAGTGAGGAA CGTATCCAGC CTATACTGGC TTATCCTCAT    900

CCCAAAACCC TAAAGCAACT AAGAGGGTTC CTTGGCATAA CAGGTTTCTG CCGAAAACAG    960

ATTCCCAGGT ACASCCCAAT AGCCAGACCA TTATATACAC TAATTANGGA AACTCAGAAA   1020

GCCAATACCT ATTTAGTAAG ATGGACACCT ACAGAAGTGG CTTTCCAGGC CCTAAAGAAG   1080

GCCCTAACCC AAGCCCCAGT GTTCAGCTTG CCAACAGGGC AAGATTTTTC TTTATATGCC   1140

ACAGAAAAAA CAGGAATAGC TCTAGGAGTC CTTACGCAGG TCTCAGGGAT GAGCTTGCAA   1200

CCCGTGGTAT ACCTGAGTAA GGAAATTGAT GTAGTGGCAA AGGGTTGGCC TCATNGTTTA   1260

TGGGTAATGG NGGCAGTAGC AGTCTNAGTA TCTGAAGCAG TTAAAATAAT ACAGGGAAGA   1320

GATCTTNCTG TGTGGACATC TCATGATGTG AACGGCATAC TCACTGCTAA AGGAGACTTG   1380
```

-continued

```
TGGTTGTCAG ACAACCATTT ACTTAANTAT CAGGCTCTAT TACTTGAAGA GCCAGTGCTG   1440

NGACTGCGCA CTTGTGCAAC TCTTAAACCC GCCACATTTC TTCCAGACAA TGAAGAAAAG   1500

ATAGAACATA ACTGTCAACA AGTAATTGCT CAAACCTATG CTGCTCGAGG GGACCTTCTA   1560

GAGGTTCCCT TGACTGATCC CGACCTCAAC TTGTATA                            1597
```

(2) INFORMATION FOR SEQ ID NO: 206:

(i) SEQUENCE CHARACTERISTICS:
(A) LENGTH: 1600 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 206:

```
ATTATGCCTG AAAGCCCCAC TCCCTTGTTA GGGAGAGACA TTTTAGCAAA AGCAGGGGCC     60

ATTATACACC TGAACATAGG AAAAGGAATA CCCATTTGCT GTCCCCTGCT TGAGGAAGGA    120

ATTAATCCTG AAGTCTGGGC AATAGAAGGA CAATATGGAC AAGCAAAGAA TGCCCGTCCT    180

GTTCAAGTTA AACTAAAGGA TTCTGCCTCC TTTCCCTACC AAAGGAAGTA CCCTCTTAGA    240

CCCGAGGCCC TACAAGGANC TCAAAAGATT GTTAAGGACC TAAAAGCCCA AGGCCTAGTA    300

AAACCATGCA GTAGCCCCTG CAATACTCCA ATTTTAGGAG TAAGGAAACC CAACGGACAG    360

TGGAGGTTAG TGCAAGAACT CAGGATTATC AATGAGGCTG TTGTTCCTCT ATACCCAGCT    420

GTACCTAACC CTTATACAGT GCTTTCCCAA ATACCAGAGG AAGCAGAGTG GTTTACAGTC    480

CTGGACCTTA AGGATGCCTT TTTCTGCATC CCTGTACGTC CTGACTCTCA ATTCTTGTTT    540

GCCTTTGAAG ATCCTTTGAA CCCAACGTCT CAACTCACCT GGACTGTTTT ACCCCAAGGG    600

TTCAGGGATA GCCCCCATCT ATTTGGCCAG GCATTAGCCC AAGACTTGAG YCARTYCTCA    660

TACCTGGACA YTCTTGTYCY TCAGTAYRKG GATGAYTTAM TTWTAGYCRC CCRTTCAGAA    720

ACCTTGTGSC AMCAAGCCAC CCAAGHRCTC TTAAMTTTCC TYRCTACCTG TGGCTACAAG    780

GTTTCCAAAC MAARGGCTCR SCTCTGCTCA CASSAGRTTA RATACTNAGG GCTAAAATTA    840

TCCAAAGKCR CCAGGGCCCT CAGWGAGGAA CGTATCCAGC STATACTGGM TTATCCMCAT    900

CCCAWAACCM TAAAGCAACT AAGARGGTTC CTTGGCATAW CAGSYTTCTG CCGAAWAYRG    960

ATTCCCVGRT ACASYSMAAT AGCCAGRCCA TTATRTACAY TADYTARGGA AACTCAGAAA   1020

GCCAATACCY ATWTAGTAAG ATGGACACCT GARACAGAAG TGGCTTTCCA GGCCCTAAAG   1080

AAGGCCCTAA CCCAAGCCCC AGTGTTCAGC TTGCCAACAG GGCAAGATTT TTCTTTATAT   1140

GCCACAGAAA AAACAGGAAT AGCTCTAGGA GTCCTTACGC AGGTCTCAGG GATGAGCTTG   1200

CAACCCGTGG TATACCTGAG TAAGGAAATT GATGTAGTGG CAAAGGGTTG GCCTCATNGT   1260

TTATGGGTAA TGGNGGCAGT AGCAGTCTNA GTATCTGAAG CAGTTAAAAT AATACAGGGA   1320

AGAGATCTTN CTGTGTGGAC ATCTCATGAT GTGAACGGCA TACTCACTGC TAAAGGAGAC   1380

TTGTGGTTGT CAGACAACCA TTTACTTAAN TATCAGGCTC TATTACTTGA AGAGCCAGTG   1440

CTGNGACTGC GCACTTGTGC AACTCTTAAA CCCGCCACAT TTCTTCCAGA CAATGAAGAA   1500

AAGATAGAAC ATAACTGTCA ACAAGTAATT GCTCAAACCT ATGCTGCTCG AGGGGACCTT   1560

CTAGAGGTTC CCTTGACTGA TCCCGACCTC AACTTGTATA                         1600
```

(2) INFORMATION FOR SEQ ID NO: 207:

(i) SEQUENCE CHARACTERISTICS:

-continued (A) LENGTH: 1600 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 207:

```
ATTATGCCTG AAAGCCCCAC TCCCTTGTTA GGGAGAGACA TTTTAGCAAA AGCAGGGGCC     60
ATTATACACC TGAACATAGG AAAAGGAATA CCCATTTGCT GTCCCCTGCT TGAGGAAGGA    120
ATTAATCCTG AAGTCTGGGC AATAGAAGGA CAATATGGAC AAGCAAAGAA TGCCCGTCCT    180
GTTCAAGTTA AACTAAAGGA TTCTGCCTCC TTTCCCTACC AAAGGAAGTA CCCTCTTAGA    240
CCCGAGGCCC TACAAGGANC TCAAAAGATT GTTAAGGACC TAAAAGCCCA AGGCCTAGTA    300
AAACCATGCA GTAGCCCCTG CAATACTCCA ATTTTAGGAG TAAGGAAACC CAACGGACAG    360
TGGAGGTTAG TGCAAGAACT CAGGATTATC AATGAGGCTG TTGTTCCTCT ATACCCAGCT    420
GTACCTAACC CTTATACAGT GCTTTCCCAA ATACCAGAGG AAGCAGAGTG GTTTACAGTC    480
CTGGACCTTA AGGATGCCTT TTTCTGCATC CCTGTACGTC CTGACTCTCA ATTCTTGTTT    540
GCCTTTGAAG ATCCTTTGAA CCCAACGTCT CAACTCACCT GGACTGTTTT ACCCCAAGGG    600
TTCAGGGATA GCCCCCATCT ATTTGGCCAG GCATTAGCCC AAGACTTGAG YCARTYYTCA    660
TACCTGGACA YTCTTGTYCY TCRGTACRTG GATGATTTAC TTTTAGYCRC CCRTTCAGAA    720
ACCTTGTGCC ATCAAGCCAC CCAAGMACTC TTAAMTTTCC TYRCTACCTG TGGCTACAAG    780
GTTTCCAAAC CAAAGGCTCR GCTCTGCTCA CAGSAGRTTA RATACTTAGG GCTAAAATTA    840
TCCAAAGGCA CCAGRRCCCT CAGTGAGGAA CGTATCCAGC CTATACTGGS TTATCCTCAT    900
CCCAAAACCC TAAAGCAACT AASAGSGTTC CTTGGCATAA CAGGTTTCTG CCRAAWAYRG    960
ATTCCCAGGT ACASCMMRRT AGCCAGACCA TTAWATACAC KAATTARGGA AACTCARAAA   1020
GCCARTACCY ATTTAGTAAG ATGGACAYCT GAAGCAGAAG TGGCTTTCCA GGCCCTAAAG   1080
AAGGCCCTAA CCCAAGCCCC AGTGTTCAGC TTGCCAACAG GGCAAGATTT TTCTTTATAT   1140
GCCACAGAAA AAACAGGAAT AGCTCTAGGA GTCCTTACGC AGGTCTCAGG GATGAGCTTG   1200
CAACCCGTGG TATACCTGAG TAAGGAAATT GATGTAGTGG CAAAGGGTTG GCCTCATNGT   1260
TTATGGGTAA TGGNGGCAGT AGCAGTCTNA GTATCTGAAG CAGTTAAAAT AATACAGGGA   1320
AGAGATCTTN CTGTGTGGAC ATCTCATGAT GTGAACGGCA TACTCACTGC TAAAGGAGAC   1380
TTGTGGTTGT CAGACAACCA TTTACTTAAN TATCAGGCTC TATTACTTGA AGAGCCAGTG   1440
CTGNGACTGC GCACTTGTGC AACTCTTAAA CCCGCCACAT TTCTTCCAGA CAATGAAGAA   1500
AAGATAGAAC ATAACTGTCA ACAAGTAATT GCTCAAACCT ATGCTGCTCG AGGGGACCTT   1560
CTAGAGGTTC CCTTGACTGA TCCCGACCTC AACTTGTATA                         1600
```

(2) INFORMATION FOR SEQ ID NO: 208:

(i) SEQUENCE CHARACTERISTICS:
(A) LENGTH: 683 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 208:

```
Ile Met Pro Glu Ser Pro Thr Pro Leu Leu Gly Arg Asp Ile Leu Ala
1               5                   10                  15
```

-continued

```
Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
        35                  40                  45

Glu Gly Gln Tyr Gly Gln Ala Lys Asn Ala Arg Pro Val Gln Val Lys
    50                  55                  60

Leu Lys Asp Ser Ala Ser Phe Pro Tyr Gln Arg Lys Tyr Pro Leu Arg
65                  70                  75                  80

Pro Glu Ala Leu Gln Gly Xaa Gln Lys Ile Val Lys Asp Leu Lys Ala
                85                  90                  95

Gln Gly Leu Val Lys Pro Cys Ser Ser Pro Cys Asn Thr Pro Ile Leu
            100                 105                 110

Gly Val Arg Lys Pro Asn Gly Gln Trp Arg Leu Val Gln Asp Leu Arg
        115                 120                 125

Ile Ile Asn Glu Ala Val Phe Pro Leu Tyr Pro Ala Val Ser Ser Pro
    130                 135                 140

Tyr Thr Leu Leu Ser Leu Ile Pro Glu Glu Ala Glu Trp Phe Thr Val
145                 150                 155                 160

Leu Asp Leu Lys Asp Ala Phe Phe Cys Ile Pro Val Arg Pro Asp Ser
                165                 170                 175

Gln Phe Leu Phe Ala Phe Glu Asp Pro Leu Asn Pro Thr Ser Gln Leu
            180                 185                 190

Thr Trp Thr Val Leu Pro Gln Gly Phe Arg Asp Ser Pro His Leu Phe
        195                 200                 205

Gly Gln Ala Leu Ala Gln Asp Leu Ser Gln Pro Ser Tyr Leu Asp Thr
    210                 215                 220

Leu Val Leu Gln Tyr Val Asp Asp Leu Leu Leu Val Ala Arg Ser Glu
225                 230                 235                 240

Thr Leu Cys His Gln Ala Thr Gln Glu Leu Leu Ile Phe Leu Thr Thr
                245                 250                 255

Cys Gly Tyr Lys Val Ser Lys Pro Lys Ala Arg Leu Cys Ser Gln Glu
            260                 265                 270

Ile Arg Tyr Leu Gly Leu Lys Leu Ser Lys Gly Thr Arg Ala Leu Ser
        275                 280                 285

Glu Glu Arg Ile Gln Pro Ile Leu Ala Tyr Pro His Pro Lys Thr Leu
    290                 295                 300

Lys Gln Leu Arg Gly Phe Leu Gly Ile Thr Gly Phe Cys Arg Lys Gln
305                 310                 315                 320

Ile Pro Arg Tyr Thr Pro Ile Ala Arg Pro Leu Tyr Thr Leu Ile Arg
                325                 330                 335

Glu Thr Gln Lys Ala Asn Thr Tyr Leu Val Arg Trp Thr Pro Thr Glu
            340                 345                 350

Val Ala Phe Gln Ala Leu Lys Lys Ala Leu Thr Gln Ala Pro Val Phe
        355                 360                 365

Ser Leu Pro Thr Gly Gln Asp Phe Ser Leu Tyr Ala Thr Glu Lys Thr
    370                 375                 380

Gly Ile Ala Leu Gly Val Leu Thr Gln Val Ser Gly Met Ser Leu Gln
385                 390                 395                 400

Pro Val Val Tyr Leu Ser Lys Glu Ile Asp Val Val Ala Lys Gly Trp
                405                 410                 415

Pro His Cys Leu Trp Val Met Ala Ala Val Ala Val Leu Val Ser Glu
            420                 425                 430

Ala Val Lys Ile Ile Gln Gly Arg Asp Leu Thr Val Trp Thr Ser His
```

-continued

```
        435                 440                 445

Asp Val Asn Gly Ile Leu Thr Ala Lys Gly Asp Leu Trp Leu Ser Asp
    450                 455                 460

Asn His Leu Leu Asn Tyr Gln Ala Leu Leu Leu Glu Glu Pro Val Leu
465                 470                 475                 480

Arg Leu Arg Thr Cys Ala Thr Leu Gln Pro Ala Thr Phe Leu Pro Asp
                485                 490                 495

Asn Glu Glu Lys Ile Glu His Asn Cys Gln Gln Val Ile Ala Gln Thr
            500                 505                 510

Tyr Ala Ala Arg Gly Asp Leu Leu Glu Val Pro Leu Thr Asp Pro Asp
        515                 520                 525

Leu Asn Leu Tyr Thr Asp Gly Ser Ser Leu Ala Glu Lys Gly Leu Arg
    530                 535                 540

Lys Ala Gly Tyr Ala Val Ile Ser Asp Asn Gly Ile Leu Glu Ser Asn
545                 550                 555                 560

Arg Leu Thr Pro Gly Thr Ser Ala His Leu Ala Glu Leu Ile Ala Leu
                565                 570                 575

Thr Trp Ala Leu Glu Leu Gly Glu Gly Lys Arg Val Asn Ile Tyr Ser
            580                 585                 590

Asp Ser Lys Tyr Ala Tyr Leu Val Leu His Ala His Ala Ala Ile Trp
        595                 600                 605

Arg Glu Arg Glu Phe Leu Thr Ser Glu Gly Thr Pro Ile Asn His Gln
    610                 615                 620

Glu Ala Ile Arg Arg Leu Leu Leu Ala Val Gln Lys Pro Lys Glu Val
625                 630                 635                 640

Ala Val Leu His Cys Gln Gly His Gln Glu Glu Glu Glu Arg Glu Ile
                645                 650                 655

Glu Gly Asn Arg Gln Ala Asp Ile Glu Ala Lys Lys Ala Ala Arg Gln
            660                 665                 670

Asp Ser Pro Leu Glu Met Leu Ile Glu Gly Pro
        675                 680
```

(2) INFORMATION FOR SEQ ID NO: 209:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 209:

```
Asp Leu Ser Gln Ser Ser Tyr Leu Asp Ile Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Gln Val Lys Tyr Leu Gly Leu
    50                  55                  60

Lys Leu Ser Lys Gly Thr Arg Ile Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
```

-continued

```
            100                 105                 110

Ile Ala Arg Pro Leu Asn Thr Arg Ile Lys Glu Thr Gln Lys Ala Asn
        115                 120                 125

Thr His Leu Val Arg Trp Thr Pro Glu Ala Glu Val Ala Phe Gln Ala
    130                 135                 140

Leu Lys
145


(2) INFORMATION FOR SEQ ID NO: 210:

     (i) SEQUENCE CHARACTERISTICS:
          (A) LENGTH: 683 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 210:

Ile Met Pro Glu Ser Pro Thr Pro Leu Leu Gly Arg Asp Ile Leu Ala
1               5                   10                  15

Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
        35                  40                  45

Glu Gly Gln Tyr Gly Gln Ala Lys Asn Ala Arg Pro Val Gln Val Lys
    50                  55                  60

Leu Lys Asp Ser Ala Ser Phe Pro Tyr Gln Arg Lys Tyr Pro Leu Arg
65                  70                  75                  80

Pro Glu Ala Leu Gln Gly Xaa Gln Lys Ile Val Lys Asp Leu Lys Ala
                85                  90                  95

Gln Gly Leu Val Lys Pro Cys Ser Ser Pro Cys Asn Thr Pro Ile Leu
            100                 105                 110

Gly Val Arg Lys Pro Asn Gly Gln Trp Arg Leu Val Gln Asp Leu Arg
        115                 120                 125

Ile Ile Asn Glu Ala Val Phe Pro Leu Tyr Pro Ala Val Ser Ser Pro
    130                 135                 140

Tyr Thr Leu Leu Ser Leu Ile Pro Glu Glu Ala Glu Trp Phe Thr Val
145                 150                 155                 160

Leu Asp Leu Lys Asp Ala Phe Phe Cys Ile Pro Val Arg Pro Asp Ser
                165                 170                 175

Gln Phe Leu Phe Ala Phe Glu Asp Pro Leu Asn Pro Thr Ser Gln Leu
            180                 185                 190

Thr Trp Thr Val Leu Pro Gln Gly Phe Arg Asp Ser Pro His Leu Phe
        195                 200                 205

Gly Gln Ala Leu Ala Gln Asp Leu Ser Gln Pro Ser Tyr Leu Asp Thr
    210                 215                 220

Leu Val Leu Gln Tyr Val Asp Asp Leu Leu Leu Val Ala Arg Ser Glu
225                 230                 235                 240

Thr Leu Cys His Gln Ala Thr Gln Glu Leu Leu Ile Phe Leu Thr Thr
                245                 250                 255

Cys Gly Tyr Lys Val Ser Lys Pro Lys Ala Arg Leu Cys Ser Gln Glu
            260                 265                 270

Ile Arg Tyr Leu Gly Leu Lys Leu Ser Lys Gly Thr Arg Ala Leu Ser
        275                 280                 285

Glu Glu Arg Ile Gln Pro Ile Leu Ala Tyr Pro His Pro Lys Thr Leu
```

-continued

```
    290                 295                 300

Lys Gln Leu Arg Gly Phe Leu Gly Ile Thr Gly Phe Cys Arg Lys Gln
305                 310                 315                 320

Ile Pro Arg Tyr Thr Pro Ile Ala Arg Pro Leu Tyr Thr Leu Ile Arg
                325                 330                 335

Glu Thr Gln Lys Ala Asn Thr Tyr Leu Val Arg Trp Thr Pro Thr Glu
            340                 345                 350

Val Ala Phe Gln Ala Leu Lys Lys Ala Leu Thr Gln Ala Pro Val Phe
        355                 360                 365

Ser Leu Pro Thr Gly Gln Asp Phe Ser Leu Tyr Ala Thr Glu Lys Thr
    370                 375                 380

Gly Ile Ala Leu Gly Val Leu Thr Gln Val Ser Gly Met Ser Leu Gln
385                 390                 395                 400

Pro Val Val Tyr Leu Ser Lys Glu Ile Asp Val Val Ala Lys Gly Trp
                405                 410                 415

Pro His Cys Leu Trp Val Met Ala Ala Val Ala Val Leu Val Ser Glu
            420                 425                 430

Ala Val Lys Ile Ile Gln Gly Arg Asp Leu Thr Val Trp Thr Ser His
        435                 440                 445

Asp Val Asn Gly Ile Leu Thr Ala Lys Gly Asp Leu Trp Leu Ser Asp
    450                 455                 460

Asn His Leu Leu Asn Tyr Gln Ala Leu Leu Leu Glu Glu Pro Val Leu
465                 470                 475                 480

Arg Leu Arg Thr Cys Ala Thr Leu Gln Pro Ala Thr Phe Leu Pro Asp
                485                 490                 495

Asn Glu Glu Lys Ile Glu His Asn Cys Gln Gln Val Ile Ala Gln Thr
            500                 505                 510

Tyr Ala Ala Arg Gly Asp Leu Leu Glu Val Pro Leu Thr Asp Pro Asp
        515                 520                 525

Leu Asn Leu Tyr Thr Asp Gly Ser Ser Leu Ala Glu Lys Gly Leu Arg
    530                 535                 540

Lys Ala Gly Tyr Ala Val Ile Ser Asp Asn Gly Ile Leu Glu Ser Asn
545                 550                 555                 560

Arg Leu Thr Pro Gly Thr Ser Ala His Leu Ala Glu Leu Ile Ala Leu
                565                 570                 575

Thr Trp Ala Leu Glu Leu Gly Glu Gly Lys Arg Val Asn Ile Tyr Ser
            580                 585                 590

Asp Ser Lys Tyr Ala Tyr Leu Val Leu His Ala His Ala Ala Ile Trp
        595                 600                 605

Arg Glu Arg Glu Phe Leu Thr Ser Glu Gly Thr Pro Ile Asn His Gln
    610                 615                 620

Glu Ala Ile Arg Arg Leu Leu Leu Ala Val Gln Lys Pro Lys Glu Val
625                 630                 635                 640

Ala Val Leu His Cys Gln Gly His Gln Glu Glu Glu Glu Arg Glu Ile
                645                 650                 655

Glu Gly Asn Arg Gln Ala Asp Ile Glu Ala Lys Lys Ala Ala Arg Gln
            660                 665                 670

Asp Ser Pro Leu Glu Met Leu Ile Glu Gly Pro
        675                 680
```

(2) INFORMATION FOR SEQ ID NO: 211:

(i) SEQUENCE CHARACTERISTICS:
(A) LENGTH: 4 amino acids

-continued

```
        (B) TYPE: amino acid
        (C) STRANDEDNESS: not relevant
        (D) TOPOLOGY: linear

   (ii) MOLECULE TYPE: peptide

   (xi) SEQUENCE DESCRIPTION: SEQ ID NO: 211:

Leu Pro Gln Gly
1


(2) INFORMATION FOR SEQ ID NO: 212:

    (i) SEQUENCE CHARACTERISTICS:
        (A) LENGTH: 4 amino acids
        (B) TYPE: amino acid
        (C) STRANDEDNESS: not relevant
        (D) TOPOLOGY: linear

   (ii) MOLECULE TYPE: peptide

   (ix) FEATURE:
        (B) LOCATION: 2
        (D) OTHER INFORMATION: Xaa is unknown

   (xi) SEQUENCE DESCRIPTION: SEQ ID NO: 212:

Tyr Xaa Asp Asp
1
```